US009596856B2

United States Patent
Zhang et al.

(10) Patent No.: US 9,596,856 B2
(45) Date of Patent: Mar. 21, 2017

(54) MESOIONIC PESTICIDES

(71) Applicant: E I DU PONT DE NEMOURS AND COMPANY, Wilmington, DE (US)

(72) Inventors: Wenming Zhang, Newark, DE (US); Caleb William Holyoke, Jr., Newark, DE (US); Kenneth Andrew Hughes, Rising Sun, MD (US); George Philip Lahm, Wilmington, DE (US); Thomas Francis Pahutski, Jr., Elkton, MD (US); My-Hanh Thi Tong, Bear, DE (US); Ming Xu, Newark, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/934,336

(22) Filed: Nov. 6, 2015

(65) Prior Publication Data
US 2016/0066577 A1    Mar. 10, 2016

Related U.S. Application Data

(62) Division of application No. 14/219,079, filed on Mar. 19, 2014, now Pat. No. 9,210,932, which is a division
(Continued)

(51) Int. Cl.
| | |
|---|---|
| A01N 43/90 | (2006.01) |
| A61K 31/519 | (2006.01) |
| A01N 43/54 | (2006.01) |
| A01N 43/78 | (2006.01) |
| C07D 239/54 | (2006.01) |
| C07D 401/06 | (2006.01) |
| C07D 417/06 | (2006.01) |
| C07D 471/04 | (2006.01) |
| C07D 487/04 | (2006.01) |
| C07D 498/04 | (2006.01) |
| C07D 513/04 | (2006.01) |

(Continued)

(52) U.S. Cl.
CPC ............ *A01N 43/90* (2013.01); *A01N 25/00* (2013.01); *A01N 43/54* (2013.01); *A01N 43/78* (2013.01); *A61K 31/519* (2013.01); *C07D 239/54* (2013.01); *C07D 401/06* (2013.01); *C07D 417/06* (2013.01); *C07D 471/04* (2013.01); *C07D 487/04* (2013.01); *C07D 495/14* (2013.01); *C07D 498/04* (2013.01); *C07D 513/04* (2013.01)

(58) Field of Classification Search
None
See application file for complete search history.

(56) References Cited

U.S. PATENT DOCUMENTS

| | | |
|---|---|---|
| 5,089,501 A | 2/1992 | Molleyres |
| 5,151,427 A | 9/1992 | Molleyres |

(Continued)

FOREIGN PATENT DOCUMENTS

| | | |
|---|---|---|
| AU | 633661 B2 | 6/1991 |
| EP | 415889 A2 | 3/1991 |

(Continued)

OTHER PUBLICATIONS

Bottcher, A. et al., Journal of Organic Chemistry, vol. 50, No. 25, 1985, pp. 5050-5055.
Urban, R. et al., Helvetica Chimica Acta, vol. 53, No. 5, 1970, pp. 905-922.
Rogers, M. E. et al., Journal of Medicinal Chemistry, vol. 24, No. 11, 1981, pp. 1284-1287.
Glennon, R. A. et al., Journal of Pharmaceutical Sciences, vol. 67, No. 12, 1978, pp. 1762-1765.

(Continued)

Primary Examiner — Jeffrey H Murray
(74) Attorney, Agent, or Firm — Roman Kucharczyk

(57) ABSTRACT

Disclosed are compounds of Formula 1, N-oxides, and salts thereof,

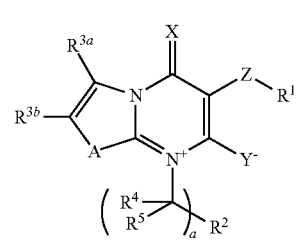

wherein
X is O or S;
Y is O or S;
A is O, S, $NR^{3e}$ or $C(R^{3c})=C(R^{3d})$;
Z is a direct bond, O, $S(O)_n$, $NR^6$, $C(R^7)_2O$, $OC(R^7)_2$, $C(=X^1)$, $C(=X^1)E$, $EC(=X^1)$, $C(=NOR^8)$ or $C(=NN(R^6)_2)$;
a is 1, 2 or 3;
and $R^1$, $R^2$, $R^{3a}$-$R^{3e}$, $R^4$, $R^5$, $R^6$, $R^7$, $R^8$, $X^1$ and E are as defined in the disclosure.

Also disclosed are compositions containing the compounds of Formula 1 and methods for controlling an invertebrate pest comprising contacting the invertebrate pest or its environment with a biologically effective amount of a compound or a composition of the invention.

3 Claims, No Drawings

Related U.S. Application Data of application No. 13/386,065, filed as application No. PCT/US2010/044274 on Aug. 3, 2010, now Pat. No. 8,722,690.

(60) Provisional application No. 61/231,464, filed on Aug. 5, 2009.

(51) Int. Cl.
*A01N 25/00* (2006.01)
*C07D 495/14* (2006.01)

(56) References Cited

U.S. PATENT DOCUMENTS

| 8,552,007 | B2 | 10/2013 | Holyoke, Jr. et al. |
| 8,697,707 | B2 | 4/2014 | Holyoke, Jr. et al. |
| 8,722,690 | B2 | 5/2014 | Zhang et al. |
| 8,895,738 | B2 | 11/2014 | Pahutski, Jr. |
| 2012/0122679 | A1 | 5/2012 | Zhang et al. |
| 2012/0122680 | A1 | 5/2012 | Holyoke, Jr. et al. |
| 2013/0338002 | A1 | 12/2013 | Holyoke, Jr. et al. |
| 2014/0187776 | A1 | 7/2014 | Holyoke, Jr. et al. |
| 2014/0206536 | A1 | 7/2014 | Zhang et al. |
| 2015/0038329 | A1 | 2/2015 | Pahutski, Jr. |
| 2015/0252040 | A1 | 9/2015 | Hoffmann et al. |

FOREIGN PATENT DOCUMENTS

| EP | 430883 A2 | 6/1991 | |
| EP | 430885 A2 | 6/1991 | |
| WO | WO2009/099929 | * 9/2009 | ........... C07D 239/54 |
| WO | 2012106495 A1 | 8/2012 | |

OTHER PUBLICATIONS

Giandinoto, S. et al., Journal of Heterocyclic Chemistry, vol. 33, No. 6, 1996, pp. 1839-1845.
Hellberg, M. et al., Bioorganic and Medicinal Chemistry, vol. 8, No. 8, 2000, pp. 1917-1923.
Glennon, R. A. et al., Journal of Heterocyclic Chemistry, vol. 17, No. 2, 1980, pp. 337-340.
Coburn, R. A. et al., Journal of Heterocyclic Chemistry, vol. 10, No. 4, 1973, pp. 487-494.
Schubert, E. M. et al., Journal of Heterocyclic Chemistry, vol. 22, No. 3, 1985, pp. 889-905.
Kappe, T., Encyclopedia of Reagents for Organic Synthesis, 2001, no page number available (carbon suboxide entry), John Wiley & Sons, Ltd.
Cesar, V. et al., Journal of the American Chemical Society, vol. 130, No. 34, 2008, pp. 11286-11287.
Jonas, U. et al., Tetrahedron, vol. 60, No. 44, 2004, pp. 10011-10018.
Ritter, H. et al., Macromolecules, vol. 36, No. 20, 2003, pp. 7520-7526.
Ritter, H. et al., Macromolecules, vol. 36, No. 20, 2003, pp. 7552-7559.
Ritter, H. et al., Macromolecular Chemistry and Physics, vol. 204, No. 10, 2003, pp. 1297-1304.
Ritter, H. et al., Macromolecular Chemistry and Physics, vol. 204, No. 8, 2003, pp. 1079-1084.
Ritter, H. et al., Designed Monomers and Polymers, vol. 4, No. 2, 2001, pp. 177-194.
Wentrup, C. et al., Journal of the Chemical Society, Perkin Trans. 2, No. 10, 2000, pp. 2096-2108.
Ritter, H. et al., Macromolecular Chemistry and Physics, vol. 201, No. 11, 2000, pp. 1200-1205.
Issac, Y., Bulletin of the Chemical Society of Japan, vol. 72, No. 3, 1999, pp. 503-509.
Ritter, H. et al., Macromolecular Rapid Communications, vol. 17, No. 10, 1996, pp. 723-730.
Ritter, H. et al., Macromolecular Rapid Communications, vol. 16, No. 6, 1995, pp. 407-415.
Kappe, T. et al., Heterocycles, vol. 40, No. 2, 1995, pp. 681-689.
Ritter, H. et al., Macromolecular Chemistry and Physics, vol. 195, No. 12, 1994, pp. 3823-3824.
Kappe, T. et al., Archiv der Pharmazie (Weinheim), vol. 324, No. 11, 1991, pp. 863-866.
Gotthardt, H. et al., Chemische Berichte, vol. 121, No. 6, 1988, pp. 1143-1146.
Gotthardt, H. et al., Chemische Berichte, vol. 119, No. 4, 1986, pp. 1315-1330.
Gotthardt, H. et al., Chemische Berichte, vol. 118, No. 11, 1985, pp. 4567-4577.
Gotthardt, H. et al., Chemische Berichte, vol. 118, No. 11, 1985, pp. 4578-4587.
Friedrichsen, W. et al., Zeitschrift fuer Naturforschung, vol. 37b2, 1982, pp. 222-233.
Friedrichsen, W. et al., Liebigs Annalen der Chemie, No. 3, 1981, pp. 521-531.
Moore, H. et al., Journal of the American Chemical Society, vol. 103, No. 7, 1981, pp. 1769-1777.
Kappe, T. et al., Chemische Berichte, vol. 112, No. 5, 1979, pp. 1584-1594.
Moore, H. et al., Heterocycles, vol. 12, No. 1, 1979, pp. 45-49.
Friedrichsen, W. et al., Liebigs Annalen der Chemie, No. 10, 1978, pp. 1655-1665.
Ziegler, E. et al., Zeitschrift fuer Naturforschung, vol. 32b, No. 10, 1977, pp. 1204-1208.
Huhn, M. et al., Tetrahedron, vol. 32, No. 17, 1976, pp. 2117-2120.
Kappe, T. et al., Chemische Berichte, vol. 109, No. 11, 1985, pp. 3668-3674.
Kappe, T. et al., Synthesis, No. 4, 1975, pp. 247-249.
Maki, Y. et al., Journal of the Chemical Society, Chemical Communications, No. 17, 1972, pp. 999-1000.
Kotarska, A. et al., Societatis Scientiarum Lodziensis, Acta Chimica, vol. 16, 1971, pp. 89-93.
Potts, K. et al., Journal of Organic Chemistry, vol. 37, No. 9, 1972, pp. 1422-1425.
Kappe, T. et al., Monatshefte fur Chemie, vol. 102, No. 3, 1971, pp. 781-787.
Kappe, T. et al., Monatshefte fur Chemie, vol. 102, No. 2, 1971, pp. 412-424.
Potts, K. et al., Journal of Organic Chemistry, vol. 36, No. 1, 1971, pp. 8-10.
Berre, A. et al., Bulletin de la Societe Chimique de France, vol. 9, 1969, pp. 3133-3138.
Ingalls, E. et al., Journal of Heterocyclic Chemistry, vol. 4, No. 4, 1967, pp. 523-526.
Prystas, M., Collection of Czechoslovak Chemical Communications, vol. 32, No. 12, 1967, pp. 4241-4259.
Prystas, M. et al., Collection of Czechoslovak Chemical Communications, vol. 32, No. 3, 1967, pp. 1298-1304.
Kheifets, G. et al., Doklady Akademii Nauk SSSR, vol. 166, No. 3, 1966, pp. 635-638.
Katritzky, A. et al., Journal of the Chemical Society, 1962, pp. 1544-1548.
Kheifets, G. et al., Zhurnal Organicheskoi Khimii, vol. 2, No. 8, 1966, pp. 1497-1502.
Glennon, R. et al., Journal of Medicinal Chemistry, vol. 27, 1984, pp. 1364-1367.
Glennon, R. et al., Journal of Medicinal Chemistry, vol. 24, 1981, pp. 658-661.
Bass, R. et al., Journal of Heterocyclic Chemistry, vol. 22, 1985, pp. 465-474.
Bass, R. et al., Organic Magnetic Resonance, vol. 21, No. 9, 1983, pp. 527-531.
Friedrichsen, W. et al., Heterocycles, vol. 19, No. 6, 1982, pp. 1083-1113.
XP002628604 (Gotthardt, H. et al., Chemische Berichte, vol. 120, No. 1, 1987, pp. 109-114).
XP002628606 (Katritzky, A. et al., Journal of the Chemical Society, 1962, pp. 1540-1544).

(56) References Cited

OTHER PUBLICATIONS

XP002628608 (Stoelting, D. et al., Journal of Heterocyclic Chemistry, vol. 39, No. 4, 2002, pp. 719-725).
XP002628612 (Prabhakar, Y. et al., Journal of Pharmacobio-Dynamics, vol. 7, No. 6, 1984, pp. 366-371).
XP002628614 (Coburn, R. et al., Journal of Heterocyclic Chemistry, vol. 10, No. 4, 1973, pp. 479-485).
XP002628617 (Siddiqi, S. et al., Nucleosides & Nucleotides, vol. 15, Nos. 1-3, 1996, pp. 693-717).
XP002628619 (Schindler, G. et al., Zeitschrift fuer Naturforschung, Teil B, vol. 31 B, No. 4, 1976, pp. 500-504).
XP002628622 (Szargan, R. et al., Recent Adv. Anal. Spectrosc., Proc. Int. Conf. At. Spectroscs., 9th, 1982 (Meeting date 1981), pp. 175-184).
XP002628623 (Gotthardt, H. et al., Chemische Berichte, vol. 118, No. 5, 1985, pp. 2079-2094).
XP002628625 (Rickborn, B., Organic Reactions, vol. 53, 1998, no pages given).
XP002628626 (Kappe, T. et al., Heterocycles, vol. 40, No. 2, 1995, pp. 681-689).

\* cited by examiner

MESOIONIC PESTICIDES

FIELD OF THE INVENTION

This invention relates to certain pyrimidinium compounds, their N-oxides, salts and their compositions suitable for agronomic, nonagronomic and animal health uses, methods of their use for controlling invertebrate pests such as arthropods in both agronomic and nonagronomic environments, and for treatment of parasite infections in animals or infestations in the general environment.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public health is also important. Many products are commercially available for these purposes, but the need continues for new compounds that are more effective, less costly, less toxic, environmentally safer or have different sites of action.

The control of animal parasites in animal health is essential, especially in the areas of food production and companion animals. Existing methods of treatment and parasite control are being compromised due to growing resistance to many current commercial parasiticides. The discovery of more effective ways to control animal parasites is therefore imperative.

U.S. Pat. No. 5,151,427 discloses mesoionic pyrimidinium compounds of Formula i as anthelmintics

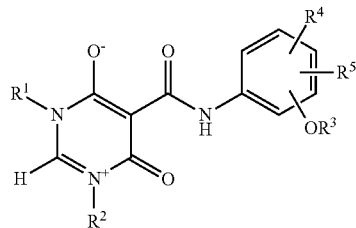

i wherein, inter alia, $R^1$ and $R^2$ are independently $C_1$-$C_6$ alkyl, $R^3$ is a heteroaromatic 6-membered ring, and $R^4$ and $R^5$ are independently hydrogen or $C_1$-$C_4$ alkyl.

The pyrimidinium compounds of the present invention are not disclosed in this publication.

SUMMARY OF THE INVENTION

This invention is directed to compounds of Formula 1 (including all stereoisomers), N-oxides, and salts thereof, and compositions containing them and their use for controlling invertebrate pests:

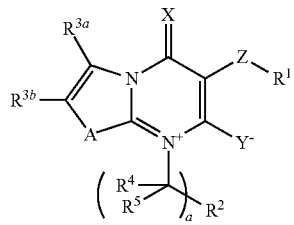

1 wherein
X is O or S;
Y is O or S;
A is O, S, $NR^{3e}$ or $C(R^{3c})$=$C(R^{3d})$, provided that the $C(R^{3c})$=$C(R^{3d})$ moiety is oriented so the carbon atom bonded to $R^{3d}$ is connected directly to the pyrimidinium ring of Formula 1;
Z is a direct bond, O, $S(O)_n$, $NR^6$, $C(R^7)_2O$, $OC(R^7)_2$, $C(=X^1)$, $C(=X^1)E$, $EC(=X^1)$, $C(=NOR^8)$ or $C(=NN(R^6)_2)$;
$X^1$ is O, S or $NR^9$;
E is O, S or $NR^{9a}$;
$R^1$ is H, halogen, cyano, CHO, C(=O)OH, C(=O)$NH_2$ or C(=S)$NH_2$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl or $C_3$-$C_6$ cycloalkenyl, each unsubstituted or substituted with at least one substituent independently selected from the group consisting of halogen, cyano, nitro, CHO, C(=O)OH, C(=O)$NH_2$, C(=O)$R^{10}$, C(=O)$OR^{11}$, C(=O)$NR^{12}R^{13}$, C(=O)$NR^{21}NR^{22}R^{23}$, $OR^{11}$, $S(O)_nR^{10}$, $SO_2NR^{12}R^{13}$, S(=O)(=$NR^{21}$)$R^{22}$, Si($R^{10}$)$_3$ and $Z^1Q^t$; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from $S(=O)_u(=NR^{24})_z$, each ring or ring system optionally substituted with up to 5 substituents independently selected from $R^{14}$; provided that when $R^1$ is halogen, then Z is a direct bond, S(=O), $S(=O)_2$, $OC(R^7)_2$, $C(=X^1)$, $EC(=X^1)$, $C(=NOR^8)$ or $C(=NN(R^6)_2)$;
$R^2$ is H, halogen, cyano, hydroxy, amino, nitro, OCN, SCN, CHO, C(=O)OH, C(=O)$NH_2$, C(=S)$NH_2$, $SO_2NH_2$, C(=O)$R^{18}$, C(=O)$OR^{18}$, $NHR^{18}$, $NR^{18}R^{19}$, C(=O)$NR^{21}R^{19}$, C(=S)$NR^{21}R^{19}$, $SO_2NR^{21}R^{19}$, OC(=O)$R^{21}$, OC(=O)$OR^{18}$, OC(=O)$NR^{21}R^{19}$, $N(R^{21})C(=O)R^{21}$, $N(R^{21})C(=O)OR^{19}$, $N(R^{21})C(=O)NR^{21}R^{22}$, $OSO_2R^{18}$, $OSO_2NR^{21}R^{22}$, $NR^{21}SO_2R^{18}$, $NR^{21}SO_2NR^{21}R^{22}$ or Si($R^{18}R^{19}R^{20}$); or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$ and Si(R$^{10}$)$_3$; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from S(=O)$_u$ (=NR$^{24}$)$_z$, each ring or ring system optionally substituted with up to 5 substituents independently selected from R$^{15}$;

R$^{3a}$, R$^{3b}$, R$^{3c}$ and R$^{3d}$ are independently H, halogen, cyano, hydroxy, amino, nitro, SF$_5$, OCN, SCN, CHO, C(=O)OH, C(=O)NH$_2$, C(=S)NH$_2$, SO$_2$NH$_2$, C(=O)R$^{18}$, C(=O)OR$^{18}$, NHR$^{18}$, NR$^{18}$R$^{19}$, C(=O)NR$^{21}$R$^{19}$, C(=S)NR$^{21}$R$^{19}$, SO$_2$NR$^{21}$R$^{19}$, OC(=O)R$^{21}$, OC(=O)OR$^{18}$, OC(=O)NR$^{21}$R$^{19}$, N(R$^{21}$)C(=O)R$^{21}$, N(R$^{21}$)C(=O)OR$^{19}$, N(R$^{21}$)C(=O)NR$^{21}$R$^{22}$, OSO$_2$R$^{18}$, OSO$_2$NR$^{21}$R$^{22}$, NR$^{21}$SO$_2$R$^{18}$, NR$^{21}$SO$_2$NR$^{21}$R$^{22}$, Si(R$^{18}$R$^{19}$R$^{20}$) or Z$^1$Q$^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from R$^{17}$; or R$^{3a}$ and R$^{3b}$, or R$^{3b}$ and R$^{3c}$, or R$^{3c}$ and R$^{3d}$ are taken together with the adjacent carbon atoms to which they are attached to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from S(=O)$_n$, each ring optionally substituted with up to 3 substituents independently selected from the group consisting of halogen, cyano, hydroxy, amino, nitro, C(=O)OH, C(=O)NH$_2$, SO$_2$NH$_2$, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_6$ alkoxy, $C_1$-$C_6$ haloalkoxy, $C_2$-$C_6$ alkoxycarbonyl, $C_2$-$C_6$ haloalkoxycarbonyl, $C_2$-$C_6$ alkylcarbonyl and $C_2$-$C_6$ haloalkylcarbonyl;

R$^{3e}$ is H, hydroxy, amino, CHO, C(=O)NH$_2$, C(=S)NH$_2$, SO$_2$NH$_2$, C(=O)R$^{18}$, C(=O)OR$^{18}$, NHR$^{18}$, NR$^{18}$R$^{19}$, C(=O)NR$^{21}$R$^{19}$, C(=S)NR$^{21}$R$^{19}$, SO$_2$NR$^{21}$R$^{19}$, OC(=O)R$^{21}$, OC(=O)OR$^{18}$, OC(=O)NR$^{21}$R$^{19}$, N(R$^{21}$)C(=O)R$^{21}$, N(R$^{21}$)C(=O)OR$^{19}$, N(R$^{21}$)C(=O)NR$^{21}$R$^{22}$, OSO$_2$R$^{18}$, OSO$_2$NR$^{21}$R$^{22}$, NR$^{21}$SO$_2$R$^{18}$, NR$^{21}$SO$_2$NR$^{21}$R$^{22}$, Si(R$^{18}$R$^{19}$R$^{20}$) or Z$^1$Q$^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylsulfinyl, $C_1$-$C_8$ alkylsulfonyl, $C_3$-$C_8$ cycloalkylsulfinyl, $C_3$-$C_8$ cycloalkylsulfonyl, $C_4$-$C_{10}$ cycloalkylalkylsulfinyl, $C_4$-$C_{10}$ cycloalkylalkylsulfonyl, $C_2$-$C_8$ alkenylsulfinyl, $C_2$-$C_8$ alkenylsulfonyl, $C_2$-$C_8$ alkynylsulfinyl or $C_2$-$C_8$ alkynylsulfonyl, each unsubstituted or substituted with at least one substituent independently selected from R$^{17}$; or R$^{3e}$ and R$^{3b}$ are taken together with the adjacent carbon atoms to which they are attached to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from S(=O)$_n$, each ring optionally substituted with up to 3 substituents independently selected from the group consisting of halogen, cyano, hydroxy, amino, nitro, C(=O)OH, C(=O)NH$_2$, SO$_2$NH$_2$, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_6$ alkoxy, $C_1$-$C_6$ haloalkoxy, $C_2$-$C_6$ alkoxycarbonyl, $C_2$-$C_6$ haloalkoxycarbonyl, $C_2$-$C_6$ alkylcarbonyl and $C_2$-$C_6$ haloalkylcarbonyl;

each R$^4$ and R$^5$ is independently H, halogen, cyano, hydroxy, amino, nitro, OCN, SCN, CHO, C(=O)OH, C(=O)NH$_2$, C(=S)NH$_2$ or SO$_2$NH$_2$; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{12}$ cycloalkylcycloalkyl, $C_5$-$C_8$ alkylcycloalkylalkyl, $C_3$-$C_6$ cycloalkenyl, $C_1$-$C_6$ alkoxy, $C_3$-$C_6$ cycloalkoxy, $C_4$-$C_8$ cycloalkylalkoxy, $C_2$-$C_6$ alkenyloxy or $C_2$-$C_6$ alkynyloxy, each unsubstituted or substituted with at least one substituent independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$ and Si(R$^{10}$)$_3$; or R$^4$ and R$^5$ are taken together with the carbon atom to which they are attached to form a 3- to 7-membered ring containing ring members selected from carbon atoms and up to 2 heteroatoms independently selected from one O, one S, and up to 2 N, wherein up to 2 carbon atom ring members are independently selected from C(=O) and C(=S) and the sulfur atom ring member is selected from S, S(O) or S(O)$_2$, said ring optionally substituted with up to 4 substituents independently selected from the group consisting of halogen, cyano and $C_1$-$C_4$ alkyl;

each R$^6$ is independently H; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, $C_2$-$C_6$ alkylcarbonyl or $C_2$-$C_6$ alkoxycarbonyl, each unsubstituted or substituted with at least one substituent independently selected from the group consisting of halogen, cyano, nitro, CHO, C(=O)OH, $C(=O)NH_2$, $C(=O)R^{10}$, $C(=O)OR^{11}$, $C(=O)NR^{12}R^{13}$, $OR^{11}$, $S(O)_nR^{10}$, $SO_2NR^{12}R^{13}$ and $Si(R^{10})_3$; or two $R^6$ substituents are taken together with the nitrogen atom to which they are attached to form a 3- to 7-membered ring containing ring members selected from carbon atoms and up to 2 heteroatoms independently selected from one O, one S, and up to 2 N, wherein up to 2 carbon atom ring members are independently selected from $C(=O)$ and $C(=S)$ and the sulfur atom ring member is selected from S, S(O) or $S(O)_2$, said ring optionally substituted with up to 4 substituents independently selected from the group consisting of halogen, cyano and $C_1$-$C_4$ alkyl;

each $R^7$ and $R^8$ is independently H; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, $C_2$-$C_6$ alkylcarbonyl or $C_2$-$C_6$ alkoxycarbonyl, each unsubstituted or substituted with at least one substituent independently selected from the group consisting of halogen, cyano, nitro, CHO, $C(=O)OH$, $C(=O)NH_2$, $C(=O)R^{10}$, $C(=O)OR^{11}$, $C(=O)NR^{12}R^{13}$, $OR^{11}$, $S(O)_nR^{10}$, $SO_2NR^{12}R^{13}$ and $Si(R^{10})_3$;

each $R^9$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, $C_2$-$C_6$ alkylcarbonyl or $C_2$-$C_6$ alkoxycarbonyl, each unsubstituted or substituted with at least one substituent independently selected from the group consisting of halogen, cyano, nitro, CHO, $C(=O)OH$, $C(=O)NH_2$, $C(=O)R^{10}$, $C(=O)OR^{11}$, $C(=O)NR^{12}R^{13}$, $OR^{11}$, $S(O)_nR^{10}$, $SO_2NR^{12}R^{13}$ and $Si(R^{10})_3$;

each $R^{9a}$ is independently H; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, $C_2$-$C_6$ alkylcarbonyl or $C_2$-$C_6$ alkoxycarbonyl, each unsubstituted or substituted with at least one substituent independently selected from the group consisting of halogen, cyano, nitro, CHO, $C(=O)OH$, $C(=O)NH_2$, $C(=O)R^{10}$, $C(=O)OR^{11}$, $C(=O)NR^{12}R^{13}$, $OR^{11}$, $S(O)_nR^{10}$, $SO_2NR^{12}R^{13}$ and $Si(R^{10})_3$;

each $R^{10}$ and $R^{11}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from the group consisting of halogen, cyano, nitro, CHO, $C(=O)OH$, $C(=O)NH_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl; or phenyl or a 5- or 6-membered heteroaromatic ring, each unsubstituted or substituted with at least one substituent independently selected from the group consisting of $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, halogen, cyano, nitro, CHO, $C(=O)OH$, $C(=O)NH_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl;

each $R^{12}$ and $R^{13}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from the group consisting of halogen, cyano, nitro, CHO, $C(=O)OH$, $C(=O)NH_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl; or $R^{12}$ and $R^{13}$ are taken together with the nitrogen atom to which they are attached to form a 3- to 7-membered ring containing ring members selected from carbon atoms and up to 2 heteroatoms independently selected from one O, one S, and up to 2 N, wherein up to 2 carbon atom ring members are independently selected from $C(=O)$ and $C(=S)$ and the sulfur atom ring member is selected from S, S(O) or $S(O)_2$, said ring optionally substituted with up to 4 substituents independently selected from the group consisting of halogen, cyano and $C_1$-$C_4$ alkyl;

each $R^{14}$ is independently halogen, cyano, hydroxy, amino, nitro, $SF_5$, OCN, SCN, CHO, $C(=O)OH$, $C(=O)NH_2$, $C(=S)NH_2$, $SO_2NH_2$, $C(=O)R^{18}$, $C(=O)OR^{18}$, $NHR^{18}$, $NR^{18}R^{19}$, $C(=O)NR^{21}R^{19}$, $C(=O)NR^{21}NR^{22}R^{23}$, $C(=S)NR^{21}R^{19}$, $SO_2NR^{21}R^{19}$, $OC(=O)R^{21}$, $OC(=O)OR^{18}$, $OC(=O)NR^{21}R^{19}$, $N(R^{21})C(=O)R^{21}$, $N(R^{21})C(=O)OR^{19}$, $N(R^{21})C(=O)NR^{21}R^{22}$, $OSO_2R^{18}$, $OSO_2NR^{21}R^{22}$, $NR^{21}SO_2R^{18}$, $NR^{21}SO_2NR^{21}R^{22}$, $Si(R^{18}R^{19}R^{20})$, $C(=NR^{21})R^{22}$, $C(=NOR^{21})R^{22}$, $C(=NNR^{21}R^{22})R^{23}$, $C(=NN(C(=O)R^{19})R^{21})R^{22}$, $C(=NN(C(=O)OR^{19})R^{21})R^{22}$, $ON=CR^{21}R^{22}$, $ONR^{21}R^{22}$, $S(=O)(=NR^{21})R^{22}$, $SO_2NR^{21}C(=O)NR^{22}R^{23}$, $P(=X^2)R^{18}R^{19}$, $OP(=X^2)R^{18}R^{19}$, $OP(=X^2)(OR^{18})R^{19}$, $OP(=X^2)(OR^{18})OR^{19}$, $N=CR^{21}R^{22}$, $NR^{21}N=CR^{22}R^{23}$, $NR^{21}NR^{22}R^{23}$, $NR^{21}C(=X^2)NR^{22}R^{23}$, $NR^{21}C(=NR^{21})NR^{22}R^{23}$, $NR^{21}NR^{21}C(=X^2)NR^{22}R^{23}$, $NR^{21}NR^{21}SO_2NR^{22}R^{23}$, $Z^1Q^t$ or $Z^1Q^iZ^1Q^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from $R^{17}$; or two $R^{14}$ substituents on adjacent ring atoms are taken together with the adjacent ring atoms to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from $C(=O)$ and $C(=S)$ and the sulfur atom ring members are independently selected from $S(=O)_n$, each ring optionally substituted with up to 3 substituents independently selected from the group consisting of halogen, cyano, hydroxy, amino, nitro, $C(=O)OH$, $C(=O)NH_2$, $SO_2NH_2$, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_6$ alkoxy, $C_1$-$C_6$ haloalkoxy, $C_2$-$C_6$ alkoxycarbonyl, $C_2$-$C_6$ haloalkoxycarbonyl, $C_2$-$C_6$ alkylcarbonyl and $C_2$-$C_6$ haloalkylcarbonyl;

each $X^2$ is independently O or S;

each $Z^1$ is independently a direct bond, O, $S(O)_n$, $NR^6$, $C(R^7)_2$, $C(R^7)=C(R^7)$, $C\equiv C$, $C(R^7)_2O$, $OC(R^7)_2$, $C(=X^1)$, $C(=X^1)E$, $EC(=X^1)$, $C(=NOR^8)$ or $C(=NN(R^6)_2)$;

each $Q^i$ is independently a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, each ring or ring system optionally substituted with up to 4 substituents independently selected from the group consisting of halogen, cyano, nitro, CHO, $C(=O)OH$, $C(=O)NH_2$, $C(=O)R^{10}$, $C(=O)OR^{11}$, $C(=O)NR^{12}R^{13}$, $OR^{11}$, $S(O)_nR^{10}$, $SO_2NR^{12}R^{13}$, $Si(R^{10})_3$ and $R^{16}$;

each $Q^t$ is independently a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, each ring or ring system optionally substituted with up to 5 substituents independently selected from the group consisting of halogen, cyano, nitro, CHO, $C(=O)OH$, $C(=O)NH_2$, $C(=O)R^{10}$, $C(=O)OR^{11}$, $C(=O)NR^{12}R^{13}$, $C(=O)NR^{21}NR^{22}R^{23}$, $OR^{11}$, $S(O)_nR^{10}$, $SO_2NR^{12}R^{13}$, $S(=O)(=NR^{21})R^{22}$, $Si(R^{10})_3$ and $R^{16}$;

each $R^{15}$ is independently halogen, cyano, hydroxy, amino, nitro, $SF_5$, OCN, SCN, CHO, $C(=O)OH$, $C(=O)NH_2$, $C(=S)NH_2$, $SO_2NH_2$, $C(=O)R^{18}$, $C(=O)OR^{18}$, $NHR^{18}$, $NR^{18}R^{19}$, $C(=O)NR^{21}R^{19}$, $C(=O)NR^{21}NR^{22}R^{23}$, $C(=S)NR^{21}R^{19}$, $SO_2NR^{21}R^{19}$, $S(=O)(=NR^{21})R^{22}$, $OC(=O)R^{21}$, $OC(=O)OR^{18}$, $OC(=O)NR^{21}R^{19}$, $N(R^{21})C(=O)R^{21}$, $N(R^{21})C(=O)OR^{19}$, $N(R^{21})C(=O)NR^{21}R^{22}$, $OSO_2R^{18}$, $OSO_2NR^{21}R^{22}$, $NR^{21}SO_2R^{18}$, $NR^{21}SO_2NR^{21}R^{22}$, $Si(R^{18}R^{19}R^{20})$ or $Z^1Q^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from $R^{17}$; or two $R^{15}$ substituents on adjacent ring atoms are taken together with the adjacent ring atoms to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from $C(=O)$ and $C(=S)$ and the sulfur atom ring members are independently selected from $S(=O)_n$, each ring optionally substituted with up to 3 substituents independently selected from the group consisting of halogen, cyano, hydroxy, amino, nitro, $C(=O)OH$, $C(=O)NH_2$, $SO_2NH_2$, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_6$ alkoxy, $C_1$-$C_6$ haloalkoxy, $C_2$-$C_6$ alkoxycarbonyl, $C_2$-$C_6$ haloalkoxycarbonyl, $C_2$-$C_6$ alkylcarbonyl and $C_2$-$C_6$ haloalkylcarbonyl;

each $R^{16}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from the group consisting of halogen, cyano, nitro, CHO, $C(=O)OH$, $C(=O)NH_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl; or phenyl or a 5- or 6-membered heteroaromatic ring, each unsubstituted or substituted with at least one substituent independently selected from the group consisting of $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, halogen, cyano, nitro, CHO, C(=O)OH, C(=O)NH$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl;

each $R^{17}$ is independently halogen, cyano, nitro, OH, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$, Si(R$^{10}$)$_3$ or Z$^1$Q$^t$;

each $R^{18}$, $R^{19}$ and $R^{20}$ is independently Q$^t$; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{17}$;

each $R^{21}$ is independently Q$^t$ or H; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{17}$;

each $R^{22}$ and $R^{23}$ is independently Q$^t$ or H; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{17}$; or $R^{22}$ and $R^{23}$ are taken together with the nitrogen atom to which they are attached to form a 3- to 7-membered ring containing ring members selected from carbon atoms and up to 2 heteroatoms independently selected from one O, one S, and up to 2 N, wherein up to 2 carbon atom ring members are independently selected from C(=O) and C(=S) and the sulfur atom ring member is selected from S, S(O) or S(O)$_2$, said ring optionally substituted with up to 4 substituents independently selected from the group consisting of halogen, cyano and $C_1$-$C_4$ alkyl;

each $R^{24}$ is independently H, cyano, OCN, SCN, CHO, C(=O)OH, C(=O)NH$_2$, C(=S)NH$_2$, SO$_2$NH$_2$, C(=O)R$^{18}$, C(=O)OR$^{18}$, NHR$^{18}$, NR$^{18}$R$^{19}$, C(=O)NR$^{21}$R$^{19}$, C(=S)NR$^{21}$R$^{19}$, SO$_2$NR$^{21}$R$^{19}$, OC(=O)R$^{21}$, OC(=O)OR$^{18}$, OC(=O)NR$^{21}$R$^{19}$, N(R$^{21}$)C(=O)R$^{21}$, N(R$^{21}$)C(=O)OR$^{19}$, N(R$^{21}$)C(=O)NR$^{21}$R$^{22}$, OSO$_2$R$^{18}$, OSO$_2$NR$^{21}$R$^{22}$, NR$^{21}$SO$_2$R$^{18}$, NR$^{21}$SO$_2$NR$^{21}$R$^{22}$, Si(R$^{18}$R$^{19}$R$^{20}$) or Z$^1$Q$^t$; or $C_1$-$C_8$ alkyl, $C_2$-$C_8$ alkenyl, $C_2$-$C_8$ alkynyl, $C_3$-$C_1$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from $R^{17}$;

a is 1, 2 or 3;

each n is independently 0, 1 or 2; and u and z in each instance of S(=O)$_u$(=NR$^{24}$)$_z$ are independently 0, 1 or 2, provided that the sum of u and z in each instance of S(=O)$_u$(=NR$^{24}$)$_z$ is 0, 1 or 2.

This invention is also directed to such compounds of Formula 1 (including all stereoisomers), N-oxides, and salts thereof, and compositions containing them and their use for controlling invertebrate pests as described above, and further herein, provided that when A is O, S, NCH$_3$ or C(R$^{3c}$)=C(R$^{3d}$), R$^{3c}$ is H or F, and R$^{3d}$ is H, F, CF$_2$H or CF$_3$, then at least one of R$^{3a}$ or R$^{3b}$ is other than H.

This invention also provides a composition comprising a compound of Formula 1, an N-oxide, or a salt thereof, and at least one additional component selected from the group consisting of surfactants, solid diluents and liquid diluents. In one embodiment, this invention also provides a composition for controlling an invertebrate pest comprising a compound of Formula 1, an N-oxide, or a salt thereof, and at least one additional component selected from the group consisting of surfactants, solid diluents and liquid diluents, said composition further comprising at least one additional biologically active compound or agent.

This invention provides a method for controlling an invertebrate pest comprising contacting the invertebrate pest or its environment with a biologically effective amount of a compound of Formula 1, an N-oxide, or a salt thereof (e.g., as a composition described herein). This invention also relates to such method wherein the invertebrate pest or its environment is contacted with a composition comprising a biologically effective amount of a compound of Formula 1, an N-oxide, or a salt thereof, and at least one additional component selected from the group consisting of surfactants, solid diluents and liquid diluents, said composition optionally further comprising a biologically effective amount of at least one additional biologically active compound or agent.

This invention also provides a method for controlling an invertebrate pest comprising contacting the invertebrate pest or its environment with a biologically effective amount of any of the aforesaid compositions wherein the environment is a plant.

This invention also provides a method for controlling an invertebrate pest comprising contacting the invertebrate pest or its environment with a biologically effective amount of any of the aforesaid compositions wherein the environment is an animal.

This invention also provides a method for controlling an invertebrate pest comprising contacting the invertebrate pest or its environment with a biologically effective amount of any of the aforesaid compositions wherein the environment is a seed.

This invention also provides a method for protecting a seed from an invertebrate pest comprising contacting the seed with a biologically effective amount of a compound of Formula 1, an N-oxide, or a salt thereof (e.g., as a composition described herein). This invention also relates to the treated seed.

This invention further provides a composition for protecting an animal from an invertebrate parasitic pest comprising a parasiticidally effective amount of a compound of Formula 1, an N-oxide, or a salt thereof, and at least one carrier.

This invention further provides a method for treating, preventing, inhibiting and/or killing ecto and/or endoparasites comprising administering to and/or on an animal a parasiticidally effective amount of a compound of Formula 1, an N-oxide, or a salt thereof (e.g., as a composition described herein). This invention also relates to such method wherein a parasiticidally effective amount of a compound of Formula 1, an N-oxide, or a salt thereof, (e.g., as a composition described herein) is administered to an environment (e.g., a stall or blanket) in which an animal resides.

DETAILS OF THE INVENTION

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising", it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" refers to a living organism of the Phylum Nematoda. The term "helminths" includes roundworms, heartworms, phytophagous nematodes (Nematoda), flukes (Tematoda), Acanthocephala and tapeworms (Cestoda).

In the context of this disclosure "invertebrate pest control" means inhibition of invertebrate pest development (including mortality, feeding reduction, and/or mating disruption), and related expressions are defined analogously.

The term "agronomic" refers to the production of field crops such as for food and fiber and includes the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from an invertebrate parasitic pest by administering a parasiticidally effective (i.e. biologically effective) amount of a compound of the invention, typically in the form of a composition formulated for veterinary use, to the animal to be protected. As referred to in the present disclosure and claims, the terms "parasiticidal" and "parasiticidally" refers to observable effects on an invertebrate parasite pest to provide protection of an animal from the pest. Parasiticidal effects typically relate to diminishing the occurrence or activity of the target invertebrate parasitic pest. Such effects on the pest include necrosis, death, retarded growth, diminished mobility or lessened ability to remain on or in the host animal, reduced feeding and inhibition of reproduction. These effects on invertebrate parasite pests provide control (including prevention, reduction or elimination) of parasitic infestation or infection of the animal.

In the above recitations, the term "alkyl", used either alone or in compound words such as "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. "Cycloalkenyl" includes groups such as cyclopentenyl and cyclohexenyl as well as groups with more than one double bond such as 1,3- and 1,4-cyclohexadienyl. The term "cycloalkoxy" denotes cycloalkyl attached to and linked through an oxygen atom such as cyclopentyloxy and cyclohexyloxy. "Alkylcycloalkylalkyl" denotes an alkyl group substituted with alkylcycloalkyl. Examples of "alkylcycloalkylalkyl" include 1-, 2-, 3- or 4-methyl or -ethyl cyclohexylmethyl. The term "cycloalkylcycloalkyl" denotes cycloalkyl substitution on another cycloalkyl ring, wherein each cycloalkyl ring independently has from 3 to 7 carbon atom ring members. Examples of cycloalkylcycloalkyl include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl). "Cycloalkylamino" denotes an NH radical substituted with cycloalkyl. Examples of "cycloalkylamino" include cyclopropylamino and cyclohexylamino. The term "cycloalkylaminoalkyl" denotes cycloalkylamino substitution on an alkyl group. Examples of "cycloalkylaminoalkyl" include cyclopropylaminomethyl, cyclopentylaminoethyl, and other cycloalkylamino moieties bonded to straight-chain or branched alkyl groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $CF_3$, $CH_2Cl$, $CH_2CF_3$ and $CCl_2CF_3$. The terms "haloalkenyl", "haloalkynyl" "haloalkoxy", "haloalkylthio", "haloalkylamino", "haloalkylsulfinyl", "haloalkylsulfonyl", "halocycloalkyl", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylamino" include $CF_3(CH_3)CHNH$, $(CF_3)_2CHNH$ and $CH_2ClCH_2NH$. Examples of "haloalkylsulfinyl" include $CF_3S(=O)$, $CCl_3S(=O)$, $CF_3CH_2S(=O)$ and $CF_3CF_2S(=O)$. Examples of "haloalkylsulfonyl" include $CF_3S(=O)_2$, $CCl_3S(=O)_2$, $CF_3CH_2S(=O)_2$ and $CF_3CF_2S(=O)_2$. Examples of "halocycloalkyl" include 2-chlorocyclopropyl, 2-fluorocyclobutyl, 3-bromocyclopentyl and 4-chlorocyclohexyl. The term "halodialkyl", either alone or in compound words such as "halodialkylamino", means at least one of the two alkyl groups is substituted with at least one halogen atom, and independently each halogenated alkyl group may be partially or fully substituted with halogen atoms which may be the same or different. Examples of "halodialkylamino" include $(BrCH_2CH_2)_2N$ and $BrCH_2CH_2(ClCH_2CH_2)N$.

"Alkoxy" includes, for example, methoxy, ethoxy, n-propoxy, isopropoxy and the different butoxy, pentoxy and hexyloxy isomers. "Alkoxyalkyl" denotes alkoxy substitution on alkyl. Examples of "alkoxyalkyl" include $CH_2OCH_3$, $CH_2CH_2OCH_3$, $CH_2OCH_2CH_3$, $CH_2OCH_2CH_2CH_3$ and $CH_2CH_2OCH_2CH_3$. "Alkenyloxy" includes straight-chain or branched alkenyl attached to and linked through an oxygen atom. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$.

The term "alkylthio" includes straight-chain or branched alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(=O)$, $CH_3CH_2S(=O)$, $CH_3CH_2CH_2S(=O)$, $(CH_3)_2CHS(=O)$ and the different butylsulfinyl, pentylsulfinyl and hexylsulfinyl isomers. Examples of "alkylsulfonyl" include $CH_3S(=O)_2$, $CH_3CH_2S(=O)_2$, $CH_3CH_2CH_2S(=O)_2$, $(CH_3)_2CHS(=O)_2$, and the different butylsulfonyl, pentylsulfonyl and hexylsulfonyl isomers. The chemical abbreviations $S(O)$ and $S(=O)$ as used herein represent a sulfinyl moiety. The chemical abbreviations $SO_2$, $S(O)_2$ and $S(=O)_2$ as used herein represent a sulfonyl moiety.

"Alkylamino" denotes an NH radical substituted with straight-chain or branched alkyl. Examples of "alkylamino" include $NHCH_2CH_3$, $NHCH_2CH_2CH_3$, and $NHCH_2CH(CH_3)_2$. "Dialkylamino" denotes an N radical substituted independently with two straight-chain or branched alkyl groups. Examples of "dialkylamino" include $N(CH_3)_2$, $N(CH_3CH_2CH_2)_2$ and $N(CH_3)CH_2CH_3$. "Halodialkylamino" denotes one straight-chain or branched alkyl moiety and one straight-chain or branched haloalkyl moiety bonded to an N radical, or two independent straight-chain or branched haloalkyl moieties bonded to an N radical, wherein "haloalkyl" is as defined above. Examples of "halodialkylamino" include $N(CH_2CH_3)(CH_2CH_2Cl)$ and $N(CF_2CF_3)_2$.

"Alkylcarbonyl" denotes a straight-chain or branched alkyl moiety bonded to a $C(O)$ moiety. The chemical abbreviations $C(O)$ and $C(=O)$ as used herein represent a carbonyl moiety. Examples of "alkylcarbonyl" include $C(O)CH_3$, $C(O)CH_2CH_2CH_3$ and $C(O)CH(CH_3)_2$. Examples of "haloalkylcarbonyl" include $C(O)CF_3$, $C(O)CCl_3$, $C(O)CH_2CF_3$ and $C(O)CF_2CF_3$.

"Alkoxycarbonyl" denotes a straight-chain or branched alkyl moiety bonded to a $CO_2$ moiety. The chemical abbreviations $CO_2$, $C(O)O$ and $C(=O)O$ as used herein represent an oxycarbonyl moiety. Examples of "alkoxycarbonyl" include $C(O)OCH_3$, $C(O)OCH_2CH_3$, $C(O)OCH_2CH_2CH_3$ and $C(O)OCH(CH_3)_2$.

"Alkylaminocarbonyl" denotes a straight-chain or branched alkyl moiety bonded to a $C(O)NH$ moiety. The chemical abbreviations $C(O)NH$, and $C(O)N$ as used herein represent an amide moiety (i.e. an aminocarbonyl group). Examples of "alkylaminocarbonyl" include $C(O)NHCH_3$, $C(O)NHCH_2CH_2CH_3$ and $C(O)NHCH(CH_3)_2$. "Dialkylaminocarbonyl" denotes two independent straight-chain or branched alkyl moieties bonded to a $C(O)N$ moiety. Examples of "dialkylaminocarbonyl" include $C(O)N(CH_3)_2$ and $C(O)N(CH_3)(CH_2CH_3)$.

"Trialkylsilyl" includes 3 branched and/or straight-chain alkyl radicals attached to and linked through a silicon atom, such as trimethylsilyl, triethylsilyl and tert-butyldimethylsilyl.

"CHO" means formyl, "OCN" means —O—C≡N, and "SCN" means —S—C≡N.

When A is $C(R^{3c})=C(R^{3d})$, the $C(R^{3c})=C(R^{3d})$ moiety is oriented so the carbon atom bonded to $R^{3d}$ is connected directly to the pyrimidinium ring of Formula 1 as shown below.

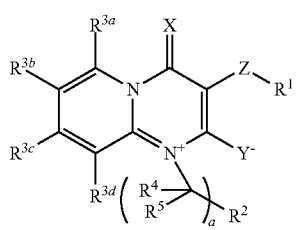

The total number of carbon atoms in a substituent group is indicated by the "$C_i$-$C_j$" prefix where i and j are numbers from 1 to 14. For example, $C_1$-$C_4$ alkyl designates methyl through butyl; $C_2$ alkoxyalkyl designates $CH_2OCH_3$; $C_3$ alkoxyalkyl designates, for example, $CH_3CH(OCH_3)$, $CH_2CH_2OCH_3$ or $CH_2OCH_2CH_3$; and $C_4$ alkoxyalkyl designates the various isomers of an alkyl group substituted with an alkoxy group containing a total of four carbon atoms, examples including $CH_2OCH_2CH_2CH_3$ and $CH_2CH_2OCH_2CH_3$.

When a group contains a substituent which can be hydrogen, for example $R^{3a}$, then when this substituent is taken as hydrogen, it is recognized that this is equivalent to said group being unsubstituted. When a variable group is shown to be optionally attached to a position, for example $(R^v)_r$ in U-36 of Exhibit 1 wherein r may be 0, then hydrogen can be at the position even if not recited in the variable group definition. When one or more positions on a group are said to be "not substituted" or "unsubstituted", then hydrogen atoms are attached to take up any free valency.

Unless otherwise indicated, a "ring" or "ring system" as a component of Formula 1 is carbocyclic or heterocyclic. The term "ring system" denotes two or more connected rings. The term "bicyclic ring system" denotes a ring system consisting of two rings sharing two or more common atoms.

A ring or a bicyclic ring system can be part of an extended ring system containing more than two rings wherein substituents on the ring or bicyclic ring system are taken together to form the additional rings, which may be in bicyclic relationships with other rings in the extended ring system.

The term "ring member" refers to an atom (e.g., C, O, N or S) or other moiety (e.g., $C(=O)$, $C(=S)$ or $S(=O)_u(=NR^{24})_z$) forming the backbone of a ring or ring system. The term "aromatic" indicates that each of the ring atoms is essentially in the same plane and has a p-orbital perpendicular to the ring plane, and that $(4n+2)\pi$ electrons, where n is a positive integer, are associated with the ring or ring system to comply with Hückel's rule.

"Partially saturated" and "partially unsaturated" with reference to a ring or ring system means that the ring or ring system contains at least one double bond but the ring or ring system is not aromatic. A ring system is aromatic if at least one component ring is aromatic.

The term "carbocyclic ring" denotes a ring wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic ring" refers to a ring having a backbone consisting of carbon atoms linked to one another by single bonds; unless otherwise specified, the remaining carbon valences are occupied by hydrogen atoms.

The terms "heterocyclic ring" or "heterocycle" denotes a ring wherein at least one of the atoms forming the ring backbone is other than carbon. Unless otherwise indicated, a heterocyclic ring can be a saturated, partially unsaturated, or fully unsaturated ring. "Saturated heterocyclic ring" refers to a heterocyclic ring containing only single bonds between ring members. "Partially saturated heterocyclic ring" refers a heterocyclic ring containing at least one double bond but which is not aromatic. The term "heteroaromatic ring" denotes a fully unsaturated aromatic ring in which at least one atom forming the ring backbone is not carbon. Typically a heteroaromatic ring contains no more than 4 nitrogens, no more than 1 oxygen and no more than 1 sulfur. Unless otherwise indicated, heteroaromatic rings can be attached through any available carbon or nitrogen by replacement of a hydrogen on said carbon or nitrogen. The term "heteroaromatic bicyclic ring system" denotes a ring system consisting of two fused rings, in which at least one of the two rings is a heteroaromatic ring as defined above.

When a radical (e.g., a 3- to 10-membered ring in the definition of $R^1$) is optionally substituted with listed substituents with the number of substituents stated (e.g., "up to 5"), then the radical may be unsubstituted or substituted with a number of substituents ranging up to the high number stated (e.g., "5"), and the attached substituents are independently selected from the substituents listed.

When a substituent (e.g., $R^1$) is a ring or ring system, it can be attached to the remainder of Formula 1 through any available ring member, unless otherwise described.

As noted above, $R^1$ is, inter alia, a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, each ring or ring system optionally substituted with up to 5 substituents independently selected from $R^{14}$. In this definition the ring members selected from up to 2 O, up to 2 S and up to 4 N are optional, because the number of heteroatom ring members may be zero. When no heteroatom ring members are present, the ring or ring system is carbocyclic. If at least one heteroatom ring member is present, the ring or ring system is heterocyclic. The definition of $S(=O)_u(=NR^{24})_z$ allows up to 2 sulfur ring members, which can be oxidized sulfur moieties (e.g., $S(=O)$ or $S(=O)_2$) or unoxidized sulfur atoms (i.e. when u and z are both zero). The nitrogen atom ring members may be oxidized as N-oxides, because compounds relating to Formula 1 also include N-oxide derivatives. The up to 3 carbon atom ring members selected from $C(=O)$ and $C(=S)$ are in addition to the up to 4 heteroatoms selected from up to 2 O, up to 2 S and up to 4 N atoms. As the $R^{14}$ substituents are optional, 0 to 5 substituents may be present, limited only by the number of available points of attachment.

The term "unsubstituted" in connection with a group such as a ring or ring system means the group does not have any substituents other than its one or more attachments to the remainder of Formula 1. The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 3.

The number of optional substituents may be restricted by an expressed limitation. For example, the phrase "optionally substituted with up to 5 substituents independently selected from $R^{15}$" means that 0, 1, 2, 3, 4 or 5 substituents can be present (if the number of potential connection points allows). When a range specified for the number of substituents exceeds the number of positions available for substituents on a ring, the actual higher end of the range is recognized to be the number of available positions.

When the number of optional substituents is not restricted by an expressed limitation (e.g., the phrases "optionally substituted with halogen" or "unsubstituted or substituted with at least one substituent independently selected from"), it is understood to mean that the number of optional substituents can range from 0 up to the number of positions available. One skilled in the art will appreciate that while some substituents such as halogen can be present at every available position (for example, the $C_2F_5$ substituent is a $C_2$ alkyl group substituted with the maximum number of 5 fluorine atoms), practical factors such as cost and synthetic accessibility can limit the number of occurrences of other substituents. These limitations are part of the general synthetic knowledge known to those skilled in the art. Of note are embodiments wherein in the absence of expressed limitation of number of optional substituents, the number of optional substituents is up to 3 (i.e. 0, 1, 2 or 3) if accommodated by the number of available positions.

As noted above, substituents such as $R^1$ can be (among others) a 5- or 6-membered heteroaromatic ring, optionally substituted with one or more substituents selected from a group of substituents as defined in the Summary of Invention. Examples of a 5- or 6-membered heteroaromatic ring optionally substituted with one or more substituents include the rings U-2 through U-61 illustrated in Exhibit 1 wherein $R^v$ is any substituent as defined in the Summary of the Invention (e.g., for $R^1$) and r is an integer from 0 to 5, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

U-1

U-2

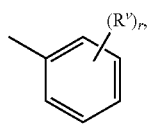

U-3

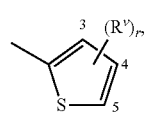

U-4

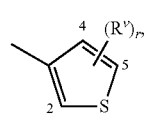

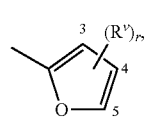

-continued

U-5

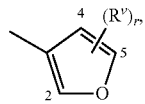

U-6

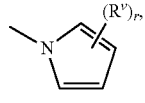

U-7

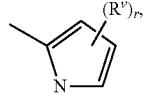

U-8

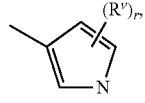

U-9

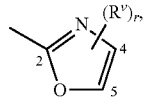

U-10

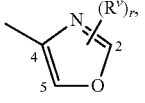

U-11

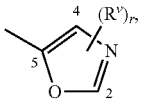

U-12

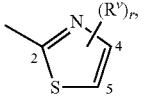

U-13

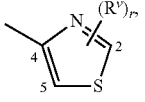

U-14

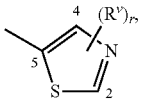

U-15

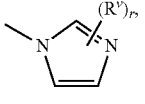

U-16

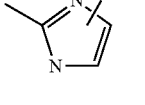

U-17

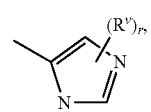 U-18
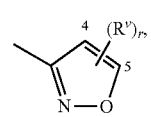 U-19
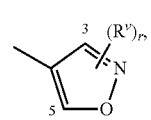 U-20
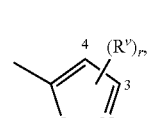 U-21
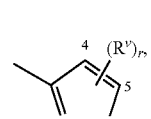 U-22
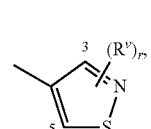 U-23
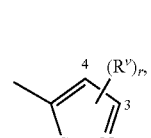 U-24
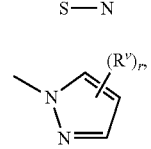 U-25
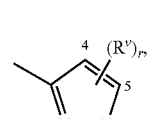 U-26
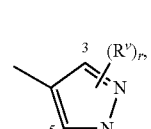 U-27
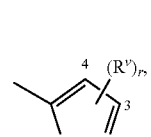 U-28
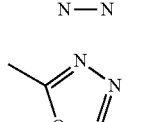 U-29
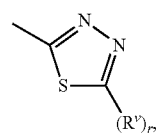 U-30
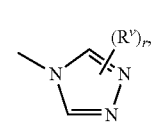 U-31
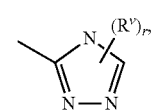 U-32
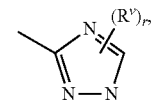 U-33
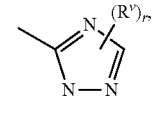 U-34
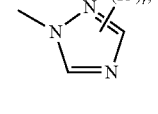 U-35
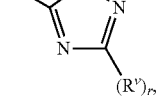 U-36
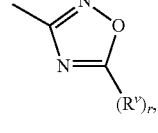 U-37
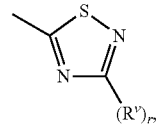 U-38
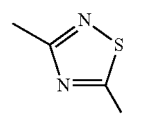 U-39
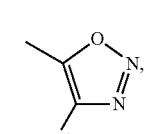 U-40
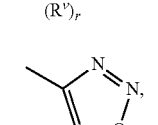 U-41

-continued

U-42 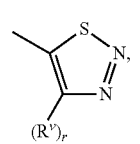

U-43 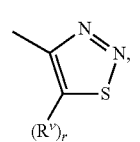

U-44 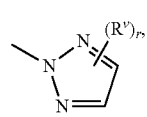

U-45 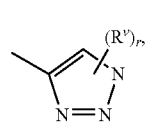

U-46 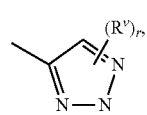

U-47 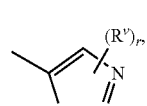

U-48 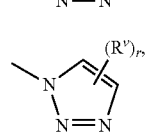

U-49 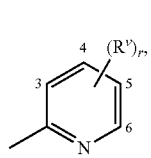

U-50 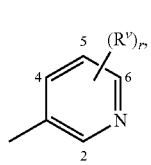

U-51 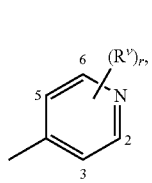

U-52 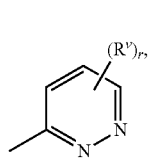

U-53 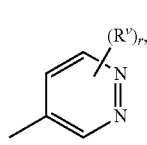

-continued

U-54 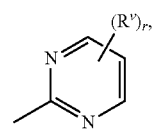

U-55 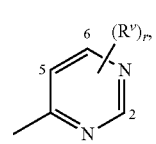

U-56 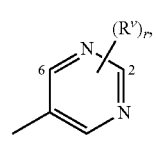

U-57 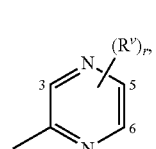

U-58 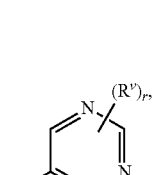

U-59 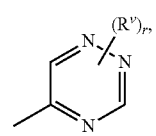

U-60 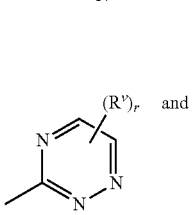

and

U-61 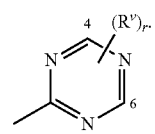

As noted above, substituents such as $R^1$ can be (among others) an 8-, 9- or 10-membered heteroaromatic bicyclic ring system optionally substituted with up to 5 substituents selected from a group of substituents as defined in the Summary of Invention. Examples of an 8-, 9- or 10-membered heteroaromatic bicyclic ring system optionally substituted with up to 5 substituents include the ring systems H-1 through H-23 illustrated in Exhibit 2 wherein $R^v$ is any substituent as defined in the Summary of the Invention (e.g., for $R^1$) and r is an integer from 0 to 5, limited by the number of available positions on each H group.

Exhibit 2

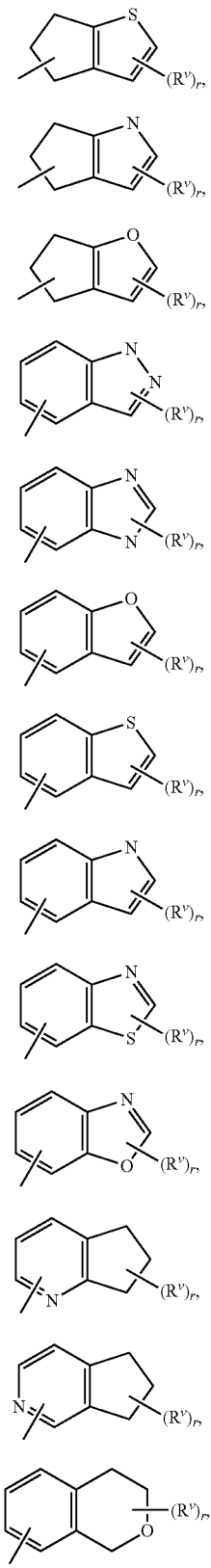
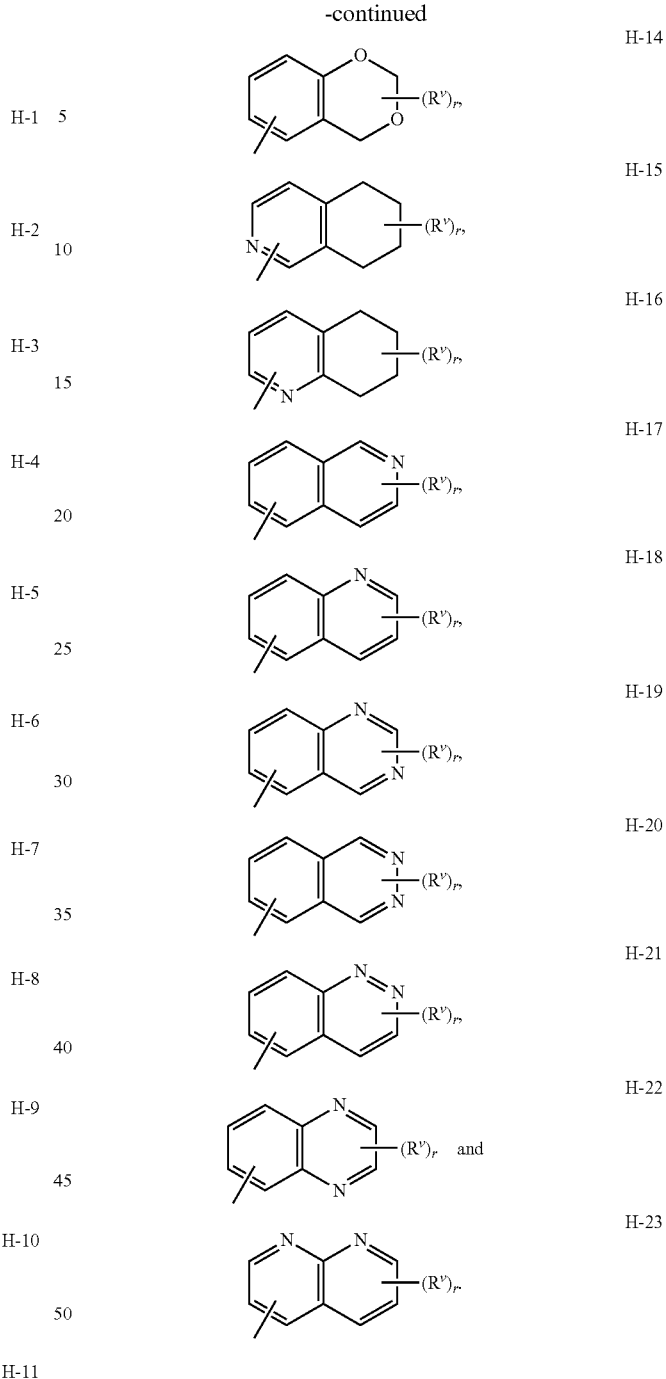

Although $R^v$ groups are shown in the structures U-1 through U-61 and H-1 through H-23, it is noted that they do not need to be present since they are optional substituents. The nitrogen atoms that require substitution to fill their valence are substituted with H or $R^v$. Note that when the attachment point between $(R^v)_r$ and the U or H group is illustrated as floating, $(R^v)_r$ can be attached to any available carbon atom or nitrogen atom of the U or H group. Note that when the attachment point on the U or H group is illustrated as floating, the U or H group can be attached to the remainder of Formula 1 through any available carbon or nitrogen of the U or H group by replacement of a hydrogen atom.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

The compounds of Formula 1 are mesoionic inner salts. "Inner salts", also known in the art as "zwitterions", are electrically neutral molecules but carry formal positive and negative charges on different atoms in each valence bond structure according to valence bond theory. Furthermore the molecular structure of the compounds of Formula 1 can be represented by the six valence bond structures shown below, each placing the formal positive and negative charges on different atoms. Because of this resonance, the compounds of Formula 1 are also described as "mesoionic". Although for sake of simplicity, the molecular structure of Formula 1 is depicted as a single valence bond structure herein, this particular valence bond structure is to be understood as representative of all six valence bond structures relevant to bonding in molecules of compounds of Formula 1. Therefore reference to Formula 1 herein relates to all six applicable valence bond structures and other (e.g., molecular orbital theory) structures unless otherwise specified.

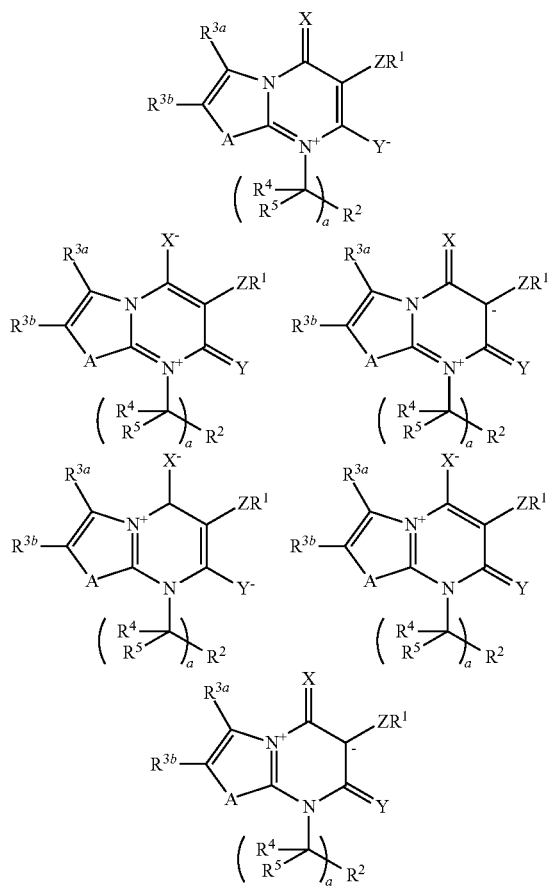

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of this invention can exist as one or more conformational isomers due to restricted bond rotation caused by steric hinderance. For example, a compound of Formula 1 wherein Z is a direct bond and $R^1$ is phenyl substituted in the ortho-position with a sterically demanding alkyl group (e.g., isopropyl) may exist as two rotamers due to restricted rotation about the $R^1$-pyrimidinium ring bond. This invention comprises mixtures of conformational isomers. In addition, this invention includes compounds that are enriched in one conformer relative to others.

Compounds selected from Formula 1 (including all stereoisomers, N-oxides, and salts thereof) typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and 3-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic*

*Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of invertebrate pests and animal parasites (i.e. are suitable for animal health use). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides, and salts thereof.

Embodiments of the present invention as described in the Summary of the Invention include those described below. In the following Embodiments Formula 1 includes stereoisomers, N-oxides, and salts thereof, and reference to "a compound of Formula 1" includes the definitions of substituents specified in the Summary of the Invention unless further defined in the Embodiments.

In the Embodiments that follow, recitation of the word "independently" before more than one variable being defined means that the definition can be applied to each variable independently of the other variables. For example, an Embodiment reciting "independently $R^{3a}$, $R^{3b}$ when taken alone, and $R^{3c}$ when taken alone are H or halogen" is equivalent to three Embodiments reciting: "$R^{3a}$ is H or halogen", "$R^{3b}$ when taken alone is H or halogen", and "$R^{3c}$ when taken alone is H or halogen", each of which can be independently used as basis to amend or add claims.

Embodiment 1. A compound of Formula 1 wherein X is O.

Embodiment 2. A compound of Formula 1 wherein X is S.

Embodiment 3. A compound of Formula 1 or Embodiments 1 or 2 wherein Y is O.

Embodiment 4. A compound of Formula 1 or Embodiments 1 or 2 wherein Y is S.

Embodiment 5. A compound of Formula 1 or any one of Embodiments 1-4 wherein A is S, $NR^{3e}$ or $C(R^{3c})=C(R^{3d})$.

Embodiment 5a. A compound of Embodiment 5 wherein A is S or $C(R^{3c})=C(R^{3d})$.

Embodiment 5b. A compound of Embodiment 5a wherein A is $C(R^{3c})=C(R^{3d})$.

Embodiment 5c. A compound of Embodiment 5a wherein A is S.

Embodiment 5d. A compound of Embodiment 5 wherein A is $C(R^{3c})=C(R^{3d})$ or $NR^{3e}$;

Embodiment 5e. A compound of Embodiment 5d wherein A is $NR^{3e}$.

Embodiment 6. A compound of Formula 1 or any one of Embodiments 1-5b wherein independently $R^{3a}$ when taken alone (i.e. when $R^{3a}$ is not taken together with $R^{3b}$ to form a ring), $R^{3b}$ when taken alone (i.e. when $R^{3b}$ is not taken together with $R^{3a}$, $R^{3c}$ or $R^{3e}$ to form a ring), $R^{3c}$ when taken alone (i.e. when $R^{3c}$ is not taken together with $R^{3b}$ or $R^{3d}$ to form a ring) and $R^{3d}$ when taken alone (i.e. when $R^{3d}$ is not taken together with $R^{3c}$ to form a ring) are H, halogen, cyano, hydroxy, amino, nitro, $SF_5$, OCN, SCN, CHO, $C(=O)OH$, $C(=O)NH_2$, $C(=S)NH_2$, $SO_2NH_2$, $C(=O)R^{18}$, $C(=O)OR^{18}$, $NHR^{18}$, $NR^{18}R^{19}$, $C(=O)NR^{21}R^{19}$, $C(=S)NR^{21}R^{19}$, $SO_2NR^{21}R^{19}$, $OC(=O)R^{21}$, $OC(=O)OR^{18}$, $OC(=O)NR^{21}R^{19}$, $N(R^{21})C(=O)R^{21}$, $N(R^{21})C(=O)OR^{19}$, $N(R^{21})C(=O)NR^{21}R^{22}$, $OSO_2R^{18}$, $OSO_2NR^{21}R^{22}$, $NR^{21}SO_2R^{18}$, $NR^{21}SO_2NR^{21}R^{22}$, $Si(R^{18}R^{19}R^{20})$ or $Z^1Q^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from $R^{17}$.

Embodiment 6a. A compound of Embodiment 6 wherein independently $R^{3a}$ when taken alone, $R^{3b}$ when taken alone, $R^{3c}$ when taken alone and $R^{3d}$ when taken alone are H, halogen, cyano, OCN, SCN, CHO, $SO_2NH_2$, $C(=O)R^{18}$, $C(=O)OR^{18}$, $C(=O)NR^{21}R^{19}$, $C(=S)NR^{21}R^{19}$, $SO_2NR^{21}R^{19}$, $OC(=O)R^{21}$, $OC(=O)OR^{18}$, $OC(=O)NR^{21}R^{19}$ or $Z^1Q^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_3$-$C_8$ cycloalkylthio, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio or $C_2$-$C_8$ alkynylthio, each unsubstituted or substituted with at least one substituent independently selected from $R^{17}$.

Embodiment 6b. A compound of Embodiment 6a wherein independently $R^{3a}$ when taken alone, $R^{3b}$ when taken alone, $R^{3c}$ when taken alone and $R^{3d}$ when taken alone are H or halogen; or $C_1$-$C_8$ alkyl, $C_2$-$C_8$ alkenyl, $C_2$-$C_8$ alkynyl, $C_3$-$C_{10}$ cycloalkyl, $C_1$-$C_8$ alkoxy, $C_3$-$C_8$ cycloalkoxy, $C_2$-$C_8$ alkenyloxy or $C_2$-$C_8$ alkynyloxy, each unsubstituted or substituted with at least one substituent independently selected from $R^{17}$.

Embodiment 6c. A compound of Embodiment 6b wherein independently $R^{3a}$ when taken alone, $R^{3b}$ when taken alone, $R^{3c}$ when taken alone and $R^{3d}$ when taken alone are H or halogen; or $C_1$-$C_8$ alkyl, $C_3$-$C_{10}$ cycloalkyl or $C_1$-$C_8$ alkoxy, each optionally substituted with halogen.

Embodiment 6d. A compound of Embodiment 6c wherein independently $R^{3a}$ when taken alone, $R^{3b}$ when taken alone, and $R^{3c}$ when taken alone are H or halogen.

Embodiment 6e. A compound of Embodiment 6d wherein independently $R^{3a}$ when taken alone, $R^{3b}$ when taken alone and $R^{3c}$ when taken alone are H.

Embodiment 7. A compound of Formula 1 or any one of Embodiments 1-6e wherein $R^{3d}$ when taken alone is H, halogen, $C_1$-$C_8$ alkyl or $C_1$-$C_8$ alkoxy.

Embodiment 7a. A compound of Embodiment 7 wherein $R^{3d}$ when taken alone is halogen, $C_1$-$C_8$ alkyl or $C_1$-$C_8$ alkoxy.

Embodiment 7a1. A compound of Formula 1 or any one of Embodiments 1-6e wherein $R^{3d}$ when taken alone is halogen, $C_1$-$C_8$ alkyl, $C_1$-$C_8$ alkoxy, $C_1$-$C_8$ haloalkyl or $C_1$-$C_8$ haloalkoxy.

Embodiment 7b. A compound of Embodiment 7a wherein $R^{3d}$ when taken alone is halogen, $C_1$-$C_4$ alkyl or $C_1$-$C_4$ alkoxy.

Embodiment 7c. A compound of Embodiment 7b wherein $R^{3d}$ when taken alone is F, Cl, Br, $CH_3$ or $OCH_3$.

Embodiment 7d. A compound of Embodiment 7c wherein $R^{3d}$ when taken alone is $CH_3$.

Embodiment 7e. A compound of Embodiment 7 wherein $R^{3d}$ when taken alone is H, halogen, $C_1$-$C_4$ alkyl or $C_1$-$C_4$ alkoxy.

Embodiment 7f. A compound of Embodiment 7e wherein $R^{3d}$ when taken alone is H or halogen.

Embodiment 7g. A compound of Embodiment 7e wherein $R^{3d}$ when taken alone is H, F, Cl, Br, $CH_3$ or $OCH_3$.

Embodiment 8. A compound of Formula 1 or any one of Embodiments 1-7g wherein $R^{3c}$ and $R^{3d}$ are taken alone.

Embodiment 9. A compound of Formula 1 or any one of Embodiments 1-7g wherein when $R^{3c}$ and $R^{3d}$ are taken together with the adjacent carbon atoms to which they are attached to form a 5- or 6-membered ring (which is understood to be optionally substituted with the substituents described in the Summary of the Invention).

Embodiment 9a. A compound of Embodiment 9 wherein the 5- or 6-membered ring formed is aromatic.

Embodiment 9b. A compound of Embodiment 9a wherein the 5- or 6-membered ring formed is 6-membered and carbocyclic (i.e. a fused benzene ring optionally substituted as described in Embodiment 9).

Embodiment 9d. A compound of Embodiment 9 wherein the 5- or 6-membered ring formed is partially unsaturated (and carbocyclic or heterocyclic).

Embodiment 9e. A compound of Formula 1 or any one of Embodiments 1-7g and 9-9d wherein $R^{3c}$ and $R^{3d}$ are taken together with the carbon atoms to which they are attached to form a ring (which is optionally substituted as described in Embodiment 9).

Embodiment 10. A compound of Formula 1 or any one of Embodiments 1-9d wherein $R^{3e}$ when taken alone (i.e. when $R^{3e}$ is not taken together with $R^{3b}$ to form a ring) is H, hydroxy, amino, CHO, $C(=O)NH_2$, $C(=S)NH_2$, $SO_2NH_2$, $C(=O)R^{18}$, $C(=O)OR^{18}$, $NHR^{18}$, $NR^{18}R^{19}$, $C(=O)NR^{21}R^{19}$, $C(=S)NR^{21}R^{19}$, $SO_2NR^{21}R^{19}$, $OC(=O)R^{21}$, $OC(=O)OR^{18}$, $OC(=O)NR^{21}R^{19}$, $N(R^{21})C(=O)R^{21}$, $N(R^{21})C(=O)OR^{19}$, $N(R^{21})C(=O)NR^{21}R^{22}$, $OSO_2R^{18}$, $OSO_2NR^{21}R^{22}$, $NR^{21}SO_2R^{18}$, $NR^{21}SO_2NR^{21}R^{22}$, $Si(R^{18}R^{19}R^{20})$ or $Z^1Q^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy or $C_2$-$C_8$ alkynyloxy, each unsubstituted or substituted with at least one substituent independently selected from $R^{17}$.

Embodiment 10a. A compound of Embodiment 10 wherein $R^{3e}$ when taken alone is H, CHO, $C(=O)R^{18}$, $C(=O)OR^{18}$, $C(=O)NR^{21}R^{19}$, $C(=S)NR^{21}R^{19}$, $SO_2NR^{21}R^{19}$, $C_1$-$C_8$ alkyl, $C_3$-$C_8$ cycloalkyl or $C_1$-$C_8$ alkoxy.

Embodiment 10b. A compound of Embodiment 10a wherein $R^{3e}$ when taken alone is H, $C_1$-$C_4$ alkyl, $C_3$-$C_4$ cycloalkyl or $C_1$-$C_4$ alkoxy.

Embodiment 10c. A compound of Embodiment 10b wherein $R^{3e}$ when taken alone is H or $C_1$-$C_4$ alkyl.

Embodiment 10d. A compound of Embodiment 10c wherein $R^{3e}$ when taken alone is $C_1$-$C_4$ alkyl.

Embodiment 10e. A compound of Embodiment 10d wherein $R^{3e}$ when taken alone is $CH_3$.

Embodiment 10f. A compound of Embodiment 10c wherein $R^{3e}$ when taken alone is H or $CH_3$.

Embodiment 10g. A compound of Embodiment 10f wherein $R^{3e}$ when taken alone is H.

Embodiment 11. A compound of Formula 1 or any one of Embodiments 1-10 wherein instances of $R^{17}$ in the definition of $R^{3e}$ are independently selected from $R^{17a}$; $R^{17a}$ is halogen, $OR^{11}$ or $Z^{1a}Q^t$; and $Z^{1a}$ is a direct bond.

Embodiment 12. A compound of Formula 1 or any one of Embodiments 1-11 wherein $R^{3b}$ and $R^{3e}$ are taken alone (i.e. $R^{3b}$ and $R^{3e}$ are not taken together to form a ring).

Embodiment 13. A compound of Formula 1 or any one of Embodiments 1-11 wherein when $R^{3e}$ and $R^{3b}$ are taken together with the adjacent carbon atoms to which they are attached to form a 5- or 6-membered ring (which is understood to be optionally substituted with the substituents described in the Summary of the Invention).

Embodiment 14. A compound of Embodiment 13 wherein the 5- or 6-membered ring formed is a fused pyridine ring (which is optionally substituted as described in Embodiment 13).

Embodiment 15. A compound of Formula 1 or any one of Embodiments 1-14 wherein Z is a direct bond, O, $NR^6$, $C(=X^1)$, $C(=X^1)E$, $EC(=X^1)$, $C(=NOR^8)$ or $C(=NN(R^6)_2)$.

Embodiment 15a. A compound of Embodiment 15 wherein Z is a direct bond, $C(=X^1)$, $C(=X^1)E$, $EC(=X^1)$, $C(=NOR^8)$ or $C(=NN(R^6)_2)$.

Embodiment 15b. A compound of Embodiment 15a wherein Z is a direct bond, $C(=X^1)$ or $C(=X^1)E$.

Embodiment 15c. A compound of Embodiment 15b wherein Z is $C(=X^1)E$.

Embodiment 15d. A compound of Embodiment 15b wherein Z is $C(=X^1)$.

Embodiment 15e. A compound of Embodiment 15b wherein Z is a direct bond.

Embodiment 16. A compound of Formula 1 or any one of Embodiments 1-15d wherein $X^1$ is O or S.

Embodiment 16a. A compound of Formula 1 or any one of Embodiments 1-15d wherein $X^1$ is $NR^9$.

Embodiment 16b. A compound of Embodiment 16 wherein $X^1$ is O.

Embodiment 16c. A compound of Embodiment 16 wherein $X^1$ is S.

Embodiment 17. A compound of Formula 1 or any one of Embodiments 1-15c wherein E is O.

Embodiment 17a. A compound of Formula 1 or any one of Embodiments 1-15c wherein E is S.

Embodiment 17b. A compound of Formula 1 or any one of Embodiments 1-15c wherein E is $NR^{9a}$.

Embodiment 18. A compound of Formula 1 or any one of Embodiments 1-15d and 16a wherein each $R^9$ is independently $C_1$-$C_6$ alkyl, $C_2$-$C_6$ alkylcarbonyl or $C_2$-$C_6$ alkoxycarbonyl.

Embodiment 18a. A compound of Embodiment 18 wherein each $R^9$ is independently $CH_3$, $C(=O)CH_3$ or $C(=O)OCH_3$.

Embodiment 19. A compound of Formula 1 or any one of Embodiments 1-15c, 16-16c and 17b wherein each $R^{9a}$ is independently H, $C_1$-$C_6$ alkyl, $C_2$-$C_6$ alkylcarbonyl or $C_2$-$C_6$ alkoxycarbonyl.

Embodiment 19a. A compound of Embodiment 19 wherein each $R^{9a}$ is independently H, $CH_3$, $C(=O)CH_3$ or $C(=O)OCH_3$.

Embodiment 20. A compound of Formula 1 or any one of Embodiments 1-19a wherein $R^1$ is H, halogen, cyano, CHO, $C(=O)OH$, $C(=O)NH_2$ or $C(=S)NH_2$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl or $C_3$-$C_6$ cycloalkenyl, each unsubstituted or substituted with at least one substituent independently selected from the group consisting of halogen, cyano, nitro, CHO, $C(=O)OH$, $C(=O)NH_2$, $C(=O)R^{10}$, $C(=O)OR^{11}$, $C(=O)NR^{12}R^{13}$, $OR^{11}$, $S(O)_nR^{10}$, $SO_2NR^{12}R^{13}$, $Si(R^{10})_3$ and $Z^1Q^t$; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, each ring or ring system optionally substituted with up to 5 substituents independently selected from $R^{14}$.

Embodiment 20a. A compound of Embodiment 20 wherein $R^1$ is H, halogen, cyano or CHO; or $C_1$-$C_8$ alkyl, $C_2$-$C_8$ alkenyl, $C_2$-$C_8$ alkynyl or $C_3$-$C_6$ cycloalkenyl, each unsubstituted or substituted with at least one substituent independently selected from the group consisting of halogen, cyano, nitro, CHO, $C(=O)OH$, $C(=O)NH_2$, $C(=O)R^{10}$, $C(=O)OR^{11}$, $C(=O)NR^{12}R^{13}$, $OR^{11}$, $S(O)_nR^{10}$, $SO_2NR^{12}R^{13}$, $Si(R^{10})_3$ and $Z^1Q^t$; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, each ring or ring system optionally substituted with up to 5 substituents independently selected from $R^{14}$.

Embodiment 20b. A compound of Embodiment 20a wherein $R^1$ is H, halogen or CHO; or $C_1$-$C_8$ alkyl unsubstituted or substituted with at least one substituent independently selected from the group consisting of halogen and $Z^1Q^t$; or $C_2$-$C_8$ alkenyl or $C_2$-$C_8$ alkynyl, each unsubstituted or substituted with at least one substituent independently selected from the group consisting of halogen, cyano, nitro, CHO, $C(=O)OH$, $C(=O)NH_2$, $C(=O)R^{10}$, $C(=O)OR^{11}$, $C(=O)NR^{12}R^{13}$, $OR^{11}$, $S(O)_nR^{10}$, $SO_2NR^{12}R^{13}$, $Si(R^{10})_3$ and $Z^1Q^t$; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, each ring or ring system optionally substituted with up to 5 substituents independently selected from $R^{14}$.

Embodiment 20c. A compound of Formula 1 or any one of Embodiments 1-20b wherein instances of $Z^1Q^t$ in the definition of $R^1$ are independently selected from $Z^{1b}Q^{tb}$; wherein $Z^{1b}$ is a direct bond; and $Q^{tb}$ is a 5- or 6-membered carbocyclic or heterocyclic ring unsubstituted or substituted with at least one substituent independently selected from the group consisting of halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl and $C_1$-$C_4$ haloalkylsulfinyl.

Embodiment 21. A compound of Embodiment 20b wherein $R^1$ is $C_1$-$C_8$ alkyl optionally substituted with halogen; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, each ring or ring system optionally substituted with up to 5 substituents independently selected from $R^{14}$.

Embodiment 21a. A compound of Embodiment 21 wherein $R^1$ is a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, each ring or ring system optionally substituted with up to 5 substituents independently selected from $R^{14}$.

Embodiment 21b. A compound of Formula 1 or any one of Embodiments 1-21a wherein the ring or ring system of $R^1$ is partially unsaturated or aromatic (including heteroaromatic).

Embodiment 21c. A compound of Embodiment 21b wherein the ring or ring system of $R^1$ is aromatic (including heteroaromatic).

Embodiment 21d. A compound of Formula 1 or any one of Embodiments 1-21c wherein the ring system of $R^1$ is bicyclic.

Embodiment 22. A compound of Formula 1 or any one of Embodiments 1-21c wherein $R^1$ is a 3- to 10-membered ring containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, and optionally substituted with up to 5 substituents independently selected from $R^{14}$.

Embodiment 22a. A compound of Embodiment 22 wherein the ring of $R^1$ is 5- or 6-membered.

Embodiment 22b. A compound of Embodiment 22 or 22a wherein the ring of $R^1$ is carbocyclic.

Embodiment 22c. A compound of Embodiment 22 or 22a wherein the ring of $R^1$ is heterocyclic.

Embodiment 22d. A compound of Embodiment 22a wherein the ring is phenyl optionally substituted with up to 5 substituents independently selected from $R^{14}$; a 5-membered heterocyclic ring optionally substituted with up to 3 substituents independently selected from $R^{14}$; or a 6-membered heterocyclic ring optionally substituted with up to 5 substituents independently selected from $R^{14}$.

Embodiment 22e. A compound of Embodiment 22d wherein $R^1$ is phenyl optionally substituted with up to 5 substituents independently selected from $R^{14}$; or pyridinyl optionally substituted with up to 4 substituents independently selected from $R^{14}$.

Embodiment 22f. A compound of Embodiment 22e wherein $R^1$ is phenyl optionally substituted with up to 3 substituents independently selected from $R^{14}$; or pyridinyl optionally substituted with up to 2 substituents independently selected from $R^{14}$.

Embodiment 22g. A compound of Embodiment 22f wherein $R^1$ is phenyl optionally substituted with up to 3 substituents independently selected from $R^{14}$.

Embodiment 22h. A compound of Embodiment 22f wherein $R^1$ is pyridinyl optionally substituted with up to 2 substituents independently selected from $R^{14}$.

Embodiment 22i. A compound of Formula 1 or any one of Embodiments 1-22h
wherein
$R^{14}$ when taken alone (i.e. when not taken together with another instance of $R^{14}$ on an adjacent ring atom to form a ring) is halogen, cyano, $SF_5$, CHO, C(=O)$R^{18}$, C(=O)O$R^{18}$, C(=O)N$R^{21}R^{19}$, $Z^1Q^t$ or $Z^1Q^{t'}Z^1Q^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_4$-$C_{10}$ cycloalkylalkylthio, $C_2$-$C_8$ alkenylthio, $C_2$-$C_8$ alkynylthio, each unsubstituted or substituted with at least one substituent independently selected from $R^{17a}$; and $R^{17a}$ is halogen, O$R^{11}$ or $Z^1Q^t$.

Embodiment 22j. A compound of Embodiment 22i wherein $R^{14}$ when taken alone is halogen or $Z^1Q^t$; or $C_1$-$C_8$ alkyl, $C_1$-$C_8$ alkoxy or $C_1$-$C_8$ alkylthio, each optionally substituted with halogen.

Embodiment 22k. A compound of Formula 1 or any one of Embodiments 1-22j wherein each instance of $R^{14}$ is taken alone (i.e. not taken together with another instance of $R^{14}$ on an adjacent ring atom to form a ring).

Embodiment 22m. A compound of Formula 1 or any one of Embodiments 1-22d wherein $R^1$ is phenyl or a 6-membered heteroaromatic ring, each optionally substituted with up to 3 substituents independently selected from $R^{14}$.

Embodiment 22m1. A compound of Formula 1 or any one of Embodiments 1-22d wherein $R^1$ is phenyl or a 5- or 6-membered heteroaromatic ring, each optionally substituted with up to 3 substituents independently selected from $R^{14}$.

Embodiment 22n. A compound of Embodiment 22m wherein $R^1$ is phenyl or pyridinyl, each optionally substituted with up to 3 substituents independently selected from $R^{14}$.

Embodiment 22o. A compound of Embodiments 22m or 22n wherein $R^{14}$ is halogen, cyano, C(=NO$R^{21}$)$R^{22}$ or $Z^1Q^t$; or $C_1$-$C_8$ alkyl, $C_1$-$C_8$ alkoxy or $C_1$-$C_8$ alkylthio, each optionally substituted with halogen.

Embodiment 22o1. A compound of Embodiments 22m, 22m1 or 22n wherein $R^{14}$ is halogen, cyano, C(=O)O$R^{18}$, C(=O)N$R^{21}R^{19}$, C(=NO$R^{21}$)$R^{22}$ or $Z^1Q^t$; or $C_1$-$C_8$ alkyl, $C_1$-$C_8$ alkoxy or $C_1$-$C_8$ alkylthio, each optionally substituted with halogen.

Embodiment 22p. A compound of Embodiment 22o wherein $R^{21}$ is $C_1$-$C_4$ alkyl.

Embodiment 22q. A compound of Embodiment 22o wherein $R^{22}$ is $C_1$-$C_4$ alkyl.

Embodiment 22 r. A compound of Embodiment 22o wherein one $R^{14}$ is $Z^1Q^t$; $Z^1$ is a direct bond; and $Q^t$ is phenyl, pyridinyl or pyrimidinyl, each optionally substituted with up to 5 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy.

Embodiment 23. A compound of Formula 1 or any one of Embodiments 1-22r wherein $R^2$ is H, halogen, cyano, CHO, C(=O)$R^{18}$, C(=O)O$R^{18}$, C(O)N$R^{21}R^{19}$, C(=S)N$R^{21}R^{19}$ or SO$_2$N$R^{21}R^{19}$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from the group consisting of halogen, cyano, nitro, CHO, C(=O)OH, C(=O)NH$_2$, C(=O)$R^{10}$, C(=O)O$R^{11}$, C(=O)N$R^{12}R^{13}$, O$R^{11}$, S(O)$_n R^{10}$, SO$_2$N$R^{12}R^{13}$ and Si($R^{10}$)$_3$; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from S(=O)$_u$(=N$R^{24}$)$_z$, each ring or ring system optionally substituted with up to 5 substituents independently selected from $R^{15}$.

Embodiment 23a. A compound of Embodiment 23 wherein $R^2$ is H, halogen, cyano, CHO, C(=O)$R^{18}$ or C(=O)O$R^{18}$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy or $C_2$-$C_8$ alkynyloxy, each unsubstituted or substituted with at least one substituent independently selected from the group consisting of halogen, cyano, nitro, CHO, C(=O)OH, C(=O)NH$_2$, C(=O)$R^{10}$, C(=O)O$R^{11}$, C(=O)N$R^{12}R^{13}$, O$R^{11}$, S(O)$_n R^{10}$, SO$_2$N$R^{12}R^{13}$ and Si($R^{10}$)$_3$; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from $S(=O)_u(=NR^{24})_z$, each ring or ring system optionally substituted with up to 5 substituents independently selected from $R^{15}$.

Embodiment 23b. A compound of Embodiment 23a wherein $R^2$ is H.

Embodiment 23c. A compound of Embodiment 23a wherein $R^2$ is halogen.

Embodiment 23d. A compound of Embodiment 23a wherein $R^2$ is cyano, CHO, $C(=O)R^{18}$ or $C(=O)OR^{18}$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_1$-$C_8$ alkoxy, $C_3$-$C_8$ cycloalkoxy or $C_4$-$C_{10}$ cycloalkylalkoxy, each unsubstituted or substituted with at least one substituent independently selected from the group consisting of halogen, cyano, nitro, CHO, C(=O)OH, $C(=O)NH_2$, $C(=O)R^{10}$, $C(=O)OR^{11}$, $C(=O)NR^{12}R^{13}$, $OR^{11}$, $S(O)_nR^{10}$, $SO_2NR^{12}R^{13}$ and $Si(R^{10})_3$; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from $S(=O)_u(=NR^{24})_z$, each ring or ring system optionally substituted with up to 5 substituents independently selected from $R^{15}$.

Embodiment 23e. A compound of Embodiment 23d wherein $R^2$ is $C(=O)OR^{18}$; or $C_1$-$C_8$ alkyl optionally substituted with halogen; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from $S(=O)_u(=NR^{24})_z$, each ring or ring system optionally substituted with up to 5 substituents independently selected from $R^{15}$.

Embodiment 23f. A compound of Formula 1 or any one of Embodiments 1-23e wherein instances of $R^{18}$ in the definition of $R^2$ are independently selected from $R^{18a}$; and $R^{18a}$ is $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{17a}$; $R^{17a}$ is halogen, $OR^{11}$ or $Z^{1c}Q^r$; and $Z^{1c}$ is a direct bond.

Embodiment 24. A compound of Embodiment 23e wherein $R^2$ is a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from $S(=O)_u(=NR^{24})_z$, each ring or ring system optionally substituted with up to 5 substituents independently selected from $R^{15}$.

Embodiment 24a. A compound of Embodiment 24 wherein $R^2$ is a 3- to 10-membered ring containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from $S(=O)_u(=NR^{24})_z$, and optionally substituted with up to 5 substituents independently selected from $R^{15}$.

Embodiment 24b. A compound of Embodiment 24a wherein the ring of $R^2$ is 5- or 6-membered.

Embodiment 24c. A compound of Embodiment 24b wherein the ring of $R^2$ is 5-membered and optionally substituted with up to 3 substituents independently selected from $R^{15}$.

Embodiment 24d. A compound of Embodiment 24b wherein the ring of $R^2$ is 6-membered.

Embodiment 24e. A compound of Formula 1 or any one of Embodiments 1-24d wherein the ring or ring system of $R^2$ is partially unsaturated or aromatic (including heteroaromatic).

Embodiment 24f. A compound of Embodiment 24e wherein the ring or ring system of $R^2$ is aromatic (including heteroaromatic).

Embodiment 24h. A compound of Formula 1 or any one of Embodiments 1-24f wherein the ring or ring system of $R^2$ is carbocyclic.

Embodiment 24i. A compound of Formula 1 or any one of Embodiments 1-24f wherein the ring or ring system of $R^2$ is heterocyclic.

Embodiment 25. A compound of Embodiment 24i wherein $R^2$ is pyridinyl, pyrimidinyl or thiazolyl, each optionally substituted with up to 3 substituents independently selected from the group consisting of halogen, cyano, $SF_5$, CHO, $C(=O)R^{18}$, $C(=O)OR^{18}$, $C(=O)NR^{21}R^{19}$ and $Z^1Q^r$, and $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_4$-$C_{10}$ cycloalkylalkylthio, $C_2$-$C_8$ alkenylthio and $C_2$-$C_8$ alkynylthio, each unsubstituted or substituted with at least one substituent independently selected from the group consisting of halogen, $OR^{11}$ and $Z^1Q^r$.

Embodiment 25a. A compound of Embodiment 24i wherein $R^2$ is pyridinyl, pyrimidinyl, oxazolyl or thiazolyl, each optionally substituted with up to 3 substituents independently selected from the group consisting of halogen and $C_1$-$C_4$ alkyl.

Embodiment 25b. A compound of Embodiment 25 wherein $R^2$ is pyridinyl, pyrimidinyl or thiazolyl, each optionally substituted with up to 3 substituents independently selected from the group consisting of halogen and $C_1$-$C_4$ alkyl.

Embodiment 25c. A compound of Embodiment 25b wherein $R^2$ is pyridinyl optionally substituted with at least one substituent independently selected from the group consisting of halogen and $C_1$-$C_4$ alkyl.

Embodiment 25d. A compound of Embodiment 25c wherein $R^2$ is pyridinyl optionally substituted with halogen.

Embodiment 25e. A compound of Embodiment 25d wherein $R^2$ is pyridinyl optionally substituted with Cl.

Embodiment 25f. A compound of Embodiment 25e wherein $R^2$ is 6-chloro-3-pyridinyl.

Embodiment 26. A compound of Embodiment 25b wherein $R^2$ is thiazolyl optionally substituted with at least one substituent independently selected from the group consisting of halogen or $C_1$-$C_4$ alkyl.

Embodiment 26a. A compound of Embodiment 26 wherein $R^2$ is thiazolyl optionally substituted with halogen.

Embodiment 26b. A compound of Embodiment 26a wherein $R^2$ is thiazolyl optionally substituted with Cl.

Embodiment 26c. A compound of Embodiment 26b wherein $R^2$ is 2-chloro-5-thiazolyl.

Embodiment 26d. A compound of Embodiment 25b wherein $R^2$ is pyrimidinyl optionally substituted with $C_1$-$C_4$ alkyl.

Embodiment 26e. A compound of Embodiment 24i wherein $R^2$ is N-methyl pyrazolyl optionally substituted with $C_1$-$C_4$ alkyl.

Embodiment 26f. A compound of Embodiment 25b wherein $R^2$ is 6-chloro-3-pyridinyl or 2-chloro-5-thiazolyl.

Embodiment 26g. A compound of Formula 1 or any one of Embodiments 1-26f wherein each $R^{15}$ is independently halogen, cyano, $SF_5$, CHO, $C(=O)R^{18}$, $C(=O)OR^{18}$, $C(=O)NR^{21}R^{19}$ or $Z^{1c}Q^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_4$-$C_{10}$ cycloalkylalkylthio, $C_2$-$C_8$ alkenylthio, $C_2$-$C_8$ alkynylthio, each unsubstituted or substituted with at least one substituent independently selected from $R^{17a}$; $R^{17a}$ is halogen, $OR^{11}$ or $Z^{1d}Q^t$; $Z^{1c}$ is a direct bond; and $Z^{1d}$ is a direct bond.

Embodiment 27. A compound of Formula 1 or any one of Embodiments 1-26g wherein each $R^4$ and $R^5$ is independently H, halogen, cyano, hydroxy, amino, nitro, OCN, SCN, CHO, $C(=O)OH$, $C(=O)NH_2$, $C(=S)NH_2$ or $SO_2NH_2$; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{12}$ cycloalkylcycloalkyl, $C_5$-$C_8$ alkylcycloalkylalkyl, $C_3$-$C_6$ cycloalkenyl, $C_1$-$C_6$ alkoxy, $C_3$-$C_6$ cycloalkoxy, $C_4$-$C_8$ cycloalkylalkoxy, $C_2$-$C_6$ alkenyloxy or $C_2$-$C_6$ alkynyloxy, each unsubstituted or substituted with at least one substituent independently selected from the group consisting of halogen, cyano, nitro, CHO, $C(=O)OH$, $C(=O)NH_2$, $C(=O)R^{10}$, $C(=O)OR^{11}$, $C(=O)NR^{12}R^{13}$, $OR^{11}$, $S(O)_nR^{10}$, $SO_2NR^{12}R^{13}$ and $Si(R^{10})_3$.

Embodiment 27a. A compound of Embodiment 27 where each $R^4$ and $R^5$ is independently H or halogen; or $C_1$-$C_6$ alkyl, $C_3$-$C_8$ cycloalkyl or $C_1$-$C_6$ alkoxy, each optionally substituted with halogen.

Embodiment 27b. A compound of Embodiment 27a where each $R^4$ and $R^5$ is independently H, halogen, $C_1$-$C_2$ alkyl or $C_1$-$C_2$ alkoxy.

Embodiment 27c. A compound of Embodiment 27b where each $R^4$ and $R^5$ is independently H, halogen or $CH_3$.

Embodiment 27d. A compound of Embodiment 27c wherein each $R^4$ and $R^5$ is independently H or halogen.

Embodiment 27e. A compound of Formula 1 or any one of Embodiments 1-27d wherein each $R^5$ is H.

Embodiment 27f. A compound of Embodiment 27e wherein each $R^4$ and $R^5$ is H.

Embodiment 28. A compound of Formula 1 or any one of Embodiments 1-27f wherein each $R^6$, $R^7$ and $R^8$ is independently H, $C_1$-$C_6$ alkyl, $C_2$-$C_6$ alkylcarbonyl or $C_2$-$C_6$ alkoxycarbonyl.

Embodiment 29. A compound of Embodiment 28 wherein each $R^6$, $R^7$ and $R^8$ is independently H, $CH_3$, $C(=O)CH_3$ or $C(=O)OCH_3$.

Embodiment 30. A compound of Formula 1 or any one of Embodiments 1-29 wherein each $Z^1$ is a direct bond.

Embodiment 30a. A compound of Formula 1 or any one of Embodiments 1-29 wherein each $Z^1$ is independently a direct bond or O.

Embodiment 31. A compound of Formula 1 or any one of Embodiments 1-30 wherein each $R^{16}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, each unsubstituted or substituted with at least one substituent independently selected from the group consisting of halogen, cyano, $C_1$-$C_4$ alkoxy, $C_1$-$C_4$ haloalkoxy, $C_1$-$C_4$ alkylthio, $C_1$-$C_4$ haloalkylthio, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy and $C_3$-$C_8$ dialkylaminocarbonyl.

Embodiment 32. A compound of Formula 1 or any one of Embodiments 1-31 wherein a is 1.

Embodiment 33. A compound of Formula 1 or any one of Embodiments 1-32 wherein each $R^{24}$ is independently H, cyano, $C_1$-$C_4$ alkyl or $C_1$-$C_4$ alkoxy.

Embodiment 34. A compound of Formula 1 or any one of Embodiments 1-33 wherein in each instance of $S(=O)_u(=NR^{24})_z$, when z is 1 then u is 1.

Embodiment 35. A compound of Formula 1 or any one of Embodiments 1-34 wherein each $Q^i$ and $Q^t$ is independently phenyl or pyridinyl, each optionally substituted with up to 5 substituents independently selected from halogen and $C_1$-$C_4$ haloalkyl.

Embodiment 35a. A compound of Formula 1 or any one of Embodiments 1-34 wherein each $Q^t$ is independently phenyl or a 5- or 6-membered heteroaromatic ring, each optionally substituted with up to 5 substituents independently selected from the group consisting of halogen, cyano, nitro, CHO, $C(=O)OH$, $C(=O)NH_2$, $C(=O)R^{10}$, $C(=O)OR^{11}$, $C(=O)NR^{12}R^{13}$, $C(=O)NR^{21}NR^{22}R^{23}$, $OR^{11}$, $S(O)_nR^{10}$, $SO_2NR^{12}R^{13}$, $S(=O)(=NR^{21})R^{22}$, $Si(R^{10})_3$ and $R^{16}$.

Embodiment 36. A compound of Formula 1 or any one of Embodiments 1-34 wherein each $Q^t$ is independently phenyl, pyridinyl or pyrimidinyl, each optionally substituted with up to 5 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy.

Of note are compounds of Formula 1 or any one of Embodiments 1-36 wherein X and Y are O, a composition comprising said compound, and its use for controlling an invertebrate pest.

Embodiments of this invention, including Embodiments 1-36 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-36 above as well as any other embodiments described herein, and any combination thereof, pertain to the compositions and methods of the present invention.

Combinations of Embodiments 1-36 are illustrated by:

Embodiment A. A compound of Formula 1 wherein
X is O;
Y is O;

Z is a direct bond, $C(=X^1)$ or $C(=X^1)E$;
$X^1$ is O;
E is O;
A is $C(R^{3c})=C(R^{3d})$ or $NR^{3e}$;
$R^1$ is $C_1$-$C_8$ alkyl optionally substituted with halogen; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, each ring or ring system optionally substituted with up to 5 substituents independently selected from $R^{14}$;
$R^2$ is $C(=O)OR^{18}$; or $C_1$-$C_8$ alkyl optionally substituted with halogen; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, each ring or ring system optionally substituted with up to 5 substituents independently selected from $R^{15}$;
$R^{3a}$, $R^{3b}$, $R^{3c}$ are independently H or halogen;
$R^{3d}$ is halogen, $C_1$-$C_8$ alkyl, $C_1$-$C_8$ alkoxy, $C_1$-$C_8$ haloalkyl or $C_1$-$C_8$ haloalkoxy; or $R^{3c}$ and $R^{3d}$ are taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from $C(=O)$ and $C(=S)$ and the sulfur atom ring members are independently selected from $S(=O)_n$, each ring optionally substituted with up to 3 substituents independently selected from the group consisting of halogen, cyano, hydroxy, amino, nitro, $C(=O)OH$, $C(=O)NH_2$, $SO_2NH_2$, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_6$ alkoxy, $C_1$-$C_6$ haloalkoxy, $C_2$-$C_6$ alkoxycarbonyl, $C_2$-$C_6$ haloalkoxycarbonyl, $C_2$-$C_6$ alkylcarbonyl and $C_2$-$C_6$ haloalkylcarbonyl;
$R^{3e}$ is $C_1$-$C_4$ alkyl;
$R^4$ and $R^5$ are H; and
a is 1.

Embodiment A1. A compound of Embodiment A wherein $R^{3d}$ is independently halogen, $C_1$-$C_8$ alkyl or $C_1$-$C_8$ alkoxy; or
$R^{3c}$ and $R^{3d}$ are taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from $C(=O)$ and $C(=S)$ and the sulfur atom ring members are independently selected from $S(=O)_n$, each ring optionally substituted with up to 3 substituents independently selected from the group consisting of halogen, cyano, hydroxy, amino, nitro, $C(=O)OH$, $C(=O)NH_2$, $SO_2NH_2$, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_6$ alkoxy, $C_1$-$C_6$ haloalkoxy, $C_2$-$C_6$ alkoxycarbonyl, $C_2$-$C_6$ haloalkoxycarbonyl, $C_2$-$C_6$ alkylcarbonyl and $C_2$-$C_6$ haloalkylcarbonyl.

Embodiment B. A compound of Embodiment A1 wherein $R^1$ is phenyl or a 5- or 6-membered heteroaromatic ring, each optionally substituted with up to 3 substituents independently selected from $R^{14}$;
$R^{14}$ is halogen, cyano, $C(=O)OR^{18}$, $C(=O)NR^{21}R^{19}$, $C(=NOR^{21})R^{22}$ or $Z^1Q^t$; or $C_1$-$C_8$ alkyl, $C_1$-$C_8$ alkoxy or $C_1$-$C_8$ alkylthio, each optionally substituted with halogen;
$R^{21}$ is $C_1$-$C_4$ alkyl;
$R^{22}$ is $C_1$-$C_4$ alkyl;
Z is a direct bond;
each $Z^1$ is independently a direct bond or O; and
each $Q^t$ is independently phenyl or a 5- or 6-membered heteroaromatic ring, each optionally substituted with up to 5 substituents independently selected from the group consisting of halogen, cyano, nitro, CHO, $C(=O)OH$, $C(=O)NH_2$, $C(=O)R^{10}$, $C(=O)OR^{11}$, $C(=O)NR^{12}R^{13}$, $C(=O)NR^{21}NR^{22}R^{23}$, $OR^{11}$, $S(O)_n R^{10}$, $SO_2NR^{12}R^{13}$, $S(=O)(=NR^{21})R^{22}$, $Si(R^{10})_3$ and $R^{16}$.

Embodiment B1. A compound of Embodiment B wherein $R^1$ is phenyl optionally substituted with up to 3 substituents independently selected from $R^{14}$;
$R^{14}$ is halogen, cyano, $SF_5$, CHO, $C(=O)R^{18}$, $C(=O)OR^{18}$, $C(=O)NR^{21}R^{19}$, $Z^1Q^t$ or $Z^1Q^tZ^1Q^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_4$-$C_{10}$ cycloalkylalkylthio, $C_2$-$C_8$ alkenylthio or $C_2$-$C_8$ alkynylthio, each unsubstituted or substituted with at least one substituent independently selected from $R^{17a}$;
$R^{17a}$ is halogen, $OR^{11}$ or $Z^1Q^t$;
$R^2$ is pyridinyl, pyrimidinyl or thiazolyl, each optionally substituted with up to 3 substituents independently selected from halogen, cyano, $SF_5$, CHO, $C(=O)R^{18}$, $C(=O)OR^{18}$, $C(=O)NR^{21}R^{19}$, $Z^1Q^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_4$-$C_{10}$ cycloalkylalkylthio, $C_2$-$C_8$ alkenylthio and $C_2$-$C_8$ alkynylthio, each unsubstituted or substituted with at least one substituent independently selected from the group consisting of halogen, $OR^{11}$ and $Z^1Q^t$;
each $Z^1$ is a direct bond; and
each $Q^i$ and $Q^t$ is independently phenyl or pyridinyl, each optionally substituted with up to 5 substituents independently selected from the group consisting of halogen and $C_1$-$C_4$ haloalkyl.

Embodiment C. A compound of Embodiment B1 wherein A is $C(R^{3c})=C(R^{3d})$;
Z is a direct bond;

R¹⁴ is halogen or $Z^1Q^t$; or $C_1$-$C_8$ alkyl, $C_1$-$C_8$ alkoxy or $C_1$-$C_8$ alkylthio, each optionally substituted with halogen; and R² is pyridinyl, pyrimidinyl or thiazolyl, each optionally substituted with up to 3 substituents independently selected from the group consisting of halogen and $C_1$-$C_4$ alkyl.

Embodiment D. A compound of Embodiment C wherein $R^{3a}$, $R^{3b}$ and $R^{3c}$ are H; and $R^{3d}$ is halogen, $C_1$-$C_4$ alkyl or $C_1$-$C_4$ alkoxy.

Embodiment E. A compound of Embodiment A wherein

R¹ is phenyl or a 6-membered heteroaromatic ring, each optionally substituted with up to 3 substituents independently selected from R¹⁴;

R¹⁴ is halogen, cyano, C(=NOR²¹)R²² or $Z^1Q^t$; or $C_1$-$C_8$ alkyl, $C_1$-$C_8$ alkoxy or $C_1$-$C_8$ alkylthio, each optionally substituted with halogen;

R²¹ is $C_1$-$C_4$ alkyl;

R²² is $C_1$-$C_4$ alkyl;

Z is a direct bond; and each $Z^1$ is a direct bond.

Embodiment F. A compound of Embodiment B wherein

R² is pyridinyl, pyrimidinyl, oxazolyl or thiazolyl, each optionally substituted with up to 3 substituents independently selected from the group consisting of halogen and $C_1$-$C_4$ alkyl.

Embodiment G. A compound of Embodiment F wherein

R¹ is phenyl or pyridinyl, each optionally substituted with up to 3 substituents independently selected from R¹⁴; and each $Q^t$ is independently phenyl, pyridinyl or pyrimidinyl, each optionally substituted with up to 5 substituents independently selected from the group consisting of halogen, cyano, $C_1$-$C_4$ alkyl, $C_1$-$C_4$ haloalkyl, $C_1$-$C_4$ alkoxy and $C_1$-$C_4$ haloalkoxy.

Embodiment H. A compound of Embodiment G wherein

A is $C(R^{3c})=C(R^{3d})$;

$R^{3a}$, $R^{3b}$ and $R^{3c}$ are H; and $R^{3d}$ is halogen, $C_1$-$C_4$ alkyl or $C_1$-$C_4$ alkoxy.

Specific embodiments include compounds of Formula 1 selected from the group consisting of:

9-bromo-1-[(2-chloro-5-thiazolyl)methyl]-2-hydroxy-4-oxo-3-[3-(trifluoromethoxy)phenyl]-4H-pyrido[1,2-a]pyrimidinium inner salt;

9-bromo-1-[(2-chloro-5-thiazolyl)methyl]-2-hydroxy-4-oxo-3-[3-(trifluoromethyl)phenyl]-4H-pyrido[1,2-a]pyrimidinium inner salt;

9-bromo-3-(3-bromophenyl)-1-[(2-chloro-5-thiazolyl)methyl]-2-hydroxy-4-oxo-4H-pyrido[1,2-a]pyrimidinium inner salt;

9-bromo-1-[(2-chloro-5-thiazolyl)methyl]-3-[3-chloro-5-(trifluoromethyl)phenyl]-2-hydroxy-4-oxo-4H-pyrido[1,2-a]pyrimidinium inner salt;

9-bromo-3-[3-chloro-2-fluoro-5-(trifluoromethyl)phenyl]-1-[(2-chloro-5-thiazolyl)methyl]-2-hydroxy-4-oxo-4H-pyrido[1,2-a]pyrimidinium inner salt;

9-chloro-1-[(2-chloro-5-thiazolyl)methyl]-2-hydroxy-4-oxo-3-[3-(trifluoromethoxy)phenyl]-4H-pyrido[1,2-a]pyrimidinium inner salt;

1-[(2-chloro-5-thiazolyl)methyl]-2-hydroxy-9-methyl-4-oxo-3-[3-(trifluoromethoxy)phenyl]-4H-pyrido[1,2-a]pyrimidinium inner salt;

1-[(2-chloro-5-thiazolyl)methyl]-2-hydroxy-9-methyl-4-oxo-3-[3-(trifluoromethyl)phenyl]-4H-pyrido[1,2-a]pyrimidinium inner salt;

1-[(2-chloro-5-thiazolyl)methyl]-3-(2-fluorophenyl)-2-hydroxy-9-methyl-4-oxo-4H-pyrido[1,2-a]pyrimidinium inner salt;

9-bromo-1-[(2-chloro-5-thiazolyl)methyl]-3-[3-chloro-5-(trifluoromethoxy)phenyl]-2-hydroxy-4-oxo-4H-pyrido[1,2-a]pyrimidinium inner salt;

1-[(2-chloro-5-thiazolyl)methyl]-3-[3-chloro-5-(trifluoromethoxy)phenyl]-2-hydroxy-9-methyl-4-oxo-4H-pyrido[1,2-a]pyrimidinium inner salt;

1-[(2-chloro-5-thiazolyl)methyl]-3-(2,6-difluorophenyl)-2-hydroxy-9-methyl-4-oxo-4H-pyrido[1,2-a]pyrimidinium inner salt;

1-[(2-chloro-5-thiazolyl)methyl]-2-hydroxy-9-methyl-4-oxo-3-[3-[(trifluoromethyl)thio]phenyl]-4H-pyrido[1,2-a]pyrimidinium inner salt;

3-(2-fluorophenyl)-2-hydroxy-9-methyl-4-oxo-1-(5-pyrimidinylmethyl)-4H-pyrido[1,2-a]pyrimidinium inner salt;

1-[(2-chloro-5-thiazolyl)methyl]-2-hydroxy-9-methyl-4-oxo-3-phenyl-4H-pyrido[1,2-a]pyrimidinium inner salt;

1-[(2-chloro-5-thiazolyl)methyl]-3-[2-fluoro-5-(trifluoromethyl)phenyl]-2-hydroxy-9-methyl-4-oxo-4H-pyrido[1,2-a]pyrimidinium inner salt;

1-[(2-chloro-5-thiazolyl)methyl]-3-(4-fluorophenyl)-2-hydroxy-9-methyl-4-oxo-4H-pyrido[1,2-a]pyrimidinium inner salt;

1-[(2-chloro-5-thiazolyl)methyl]-2-hydroxy-9-methoxy-4-oxo-3-[3-(trifluoromethoxy)phenyl]-4H-pyrido[1,2-a]pyrimidinium inner salt;

1-[(2-chloro-5-thiazolyl)methyl]-3-[2-fluoro-5-(trifluoromethyl)phenyl]-2-hydroxy-9-methoxy-4-oxo-4H-pyrido[1,2-a]pyrimidinium inner salt;

1-[(2-chloro-5-thiazolyl)methyl]-2-hydroxy-3-[2-methoxy-5-(trifluoromethoxy)phenyl]-9-methyl-4-oxo-4H-pyrido[1,2-a]pyrimidinium inner salt;

1-[(2-chloro-5-thiazolyl)methyl]-2-hydroxy-3-(2-methoxyphenyl)-9-methyl-4-oxo-4H-pyrido[1,2-a]pyrimidinium inner salt;

3-[3-chloro-2-fluoro-5-(trifluoromethyl)phenyl]-1-[(2-chloro-5-thiazolyl)methyl]-2-hydroxy-9-methyl-4-oxo-4H-pyrido[1,2-a]pyrimidinium inner salt;

1-[(2-chloro-5-thiazolyl)methyl]-2-hydroxy-9-methyl-4-oxo-3-[4-[(trifluoromethyl)thio]phenyl]-4H-pyrido[1,2-a]pyrimidinium inner salt;

1-[(2-chloro-5-thiazolyl)methyl]-3-(2,4-difluorophenyl)-2-hydroxy-9-methyl-4-oxo-4H-pyrido[1,2-a]pyrimidinium inner salt;

3-(3-chloro-2-fluorophenyl)-1-[(2-chloro-5-thiazolyl)methyl]-2-hydroxy-9-methyl-4-oxo-4H-pyrido[1,2-a]pyrimidinium inner salt;

1-[(2-chloro-5-thiazolyl)methyl]-2-hydroxy-3-(3-methoxyphenyl)-9-methyl-4-oxo-4H-pyrido[1,2-a]pyrimidinium inner salt;

7-bromo-1-[(2-chloro-5-thiazolyl)methyl]-3-[2-fluoro-3-(trifluoromethyl)phenyl]-2-hydroxy-9-methyl-4-oxo-4H-pyrido[1,2-a]pyrimidinium inner salt;

1-[(2-chloro-5-thiazolyl)methyl]-2-hydroxy-3-(3-iodophenyl)-9-methyl-4-oxo-4H-pyrido[1,2-a]pyrimidinium inner salt;

2-hydroxy-9-methyl-1-[(2-methyl-5-thiazolyl)methyl]-4-oxo-3-[3-(trifluoromethoxy)phenyl]-4H-pyrido[1,2-a]pyrimidinium inner salt;

2-hydroxy-9-methyl-1-[(2-methyl-5-thiazolyl)methyl]-4-oxo-3-[3-(trifluoromethyl)phenyl]-4H-pyrido[1,2-a]pyrimidinium inner salt;

3-(2-fluorophenyl)-2-hydroxy-9-methyl-1-[(2-methyl-5-thiazolyl)methyl]-4-oxo-4H-pyrido[1,2-a]pyrimidinium inner salt;

3-[3-bromo-5-(trifluoromethyl)phenyl]-1-[(2-chloro-5-thiazolyl)methyl]-2-hydroxy-9-methyl-4-oxo-4H-pyrido[1,2-a]pyrimidinium inner salt;

3-[3-bromo-5-(trifluoromethoxy)phenyl]-1-[(2-chloro-5-thiazolyl)methyl]-2-hydroxy-9-methyl-4-oxo-4H-pyrido[1,2-a]pyrimidinium inner salt;

1-[(2-chloro-5-thiazolyl)methyl]-3-[3-chloro-5-(trifluoromethyl)phenyl]-2-hydroxy-9-methyl-4-oxo-4H-pyrido[1,2-a]pyrimidinium inner salt;

1-[(2-chloro-5-thiazolyl)methyl]-3-[3-fluoro-5-(trifluoromethyl)phenyl]-2-hydroxy-9-methyl-4-oxo-4H-pyrido[1,2-a]pyrimidinium inner salt;

1-[(2-chloro-5-thiazolyl)methyl]-2-hydroxy-3-(3-iodo-5-methoxyphenyl)-9-methyl-4-oxo-4H-pyrido[1,2-a]pyrimidinium inner salt;

3-(3-bromophenyl)-1-[(2-chloro-5-thiazolyl)methyl]-2-hydroxy-9-methyl-4-oxo-4H-pyrido[1,2-a]pyrimidinium inner salt;

1-[(2-chloro-5-thiazolyl)methyl]-2-hydroxy-9-methyl-4-oxo-3-[3'-(trifluoromethoxy)[1,1'-biphenyl]-3-yl]-4H-pyrido[1,2-a]pyrimidinium inner salt;

1-[(2-chloro-5-thiazolyl)methyl]-3-(2',5'-difluoro[1,1'-biphenyl]-3-yl)-2-hydroxy-9-methyl-4-oxo-4H-pyrido[1,2-a]pyrimidinium inner salt;

3-[3-(6-chloro-3-pyridinyl)-5-(trifluoromethoxy)phenyl]-1-[(2-chloro-5-thiazolyl)methyl]-2-hydroxy-9-methyl-4-oxo-4H-pyrido[1,2-a]pyrimidinium inner salt;

1-[(2-chloro-5-thiazolyl)methyl]-3-(2',4'-dichloro[1,1'-biphenyl]-3-yl)-2-hydroxy-9-methyl-4-oxo-4H-pyrido[1,2-a]pyrimidinium inner salt;

1-[(2-chloro-5-thiazolyl)methyl]-2-hydroxy-4-oxo-3-phenyl-4H-pyrimido[2,1-a]isoquinolinium inner salt; and 1-[(2-chloro-5-thiazolyl)methyl]-3-(3-ethenylphenyl)-2-hydroxy-9-methyl-4-oxo-4H-pyrido[1,2-a]pyrimidinium inner salt;

Further specific embodiments include compounds of Formula 1 selected from the group consisting of compound numbers 113, 118, 125, 137, 183, 190, 191, 196, 229, 231, 254, 257, 272, 289, 296, 299, 307, 308, 315, 343, 344, 352, 363, 364, 368, 381, 385, 421, 433, 435, 448, 449, 450, 451, 462, 482, 490 and 493, wherein the compound number refers to compounds in Index Tables A-E.

An embodiment of this invention is directed to compounds of Formula 1 (including all stereoisomers), N-oxides, and salts thereof, and compositions containing them and their use for controlling invertebrate pests:

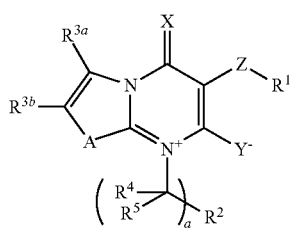

1 wherein
X is O or S;
Y is O or S;
A is O, S, $NR^{3e}$ or $C(R^{3c})=C(R^{3d})$, provided that the $C(R^{3c})=C(R^{3d})$ moiety is oriented so the carbon atom bonded to $R^{3d}$ is connected directly to the pyrimidinium ring of Formula 1;

Z is a direct bond, O, $S(O)_n$, $NR^6$, $C(R^7)_2O$, $OC(R^7)_2$, $C(=X^1)$, $C(=X^1)E$, $EC(=X^1)$, $C(=NOR^8)$ or $C(=NN(R^6)_2)$;

$X^1$ is O, S or $NR^9$;

E is O, S or $NR^{9a}$;

$R^1$ is H, halogen, cyano, CHO, $C(=O)OH$, $C(=O)NH_2$ or $C(=S)NH_2$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl or $C_3$-$C_6$ cycloalkenyl, each unsubstituted or substituted with at least one substituent independently selected from the group consisting of halogen, cyano, nitro, CHO, $C(=O)OH$, $C(=O)NH_2$, $C(=O)R^{10}$, $C(=O)OR^{11}$, $C(O)NR^{12}R^{13}$, $C(=O)NR^{21}NR^{22}R^{23}$, $OR^{11}$, $S(O)_nR^{10}$, $SO_2NR^{12}R^{13}$, $S(=O)(=NR^{21})R^{22}$, $Si(R^{10})_3$ and $Z^1Q^t$; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, each ring or ring system optionally substituted with up to 5 substituents independently selected from $R^{14}$; provided that when $R^1$ is halogen, then Z is a direct bond, $S(=O)$, $S(=O)_2$, $OC(R^7)_2$, $C(=X^1)$, $EC(=X^1)$, $C(=NOR^8)$ or $C(=NN(R^6)_2)$;

$R^2$ is H, halogen, cyano, hydroxy, amino, nitro, OCN, SCN, CHO, $C(=O)OH$, $C(=O)NH_2$, $C(=S)NH_2$, $SO_2NH_2$, $C(=O)R^{18}$, $C(=O)OR^{18}$, $NHR^{18}$, $NR^{18}R^{19}$, $C(=O)NR^{21}R^{19}$, $C(=S)NR^{21}R^{19}$, $SO_2NR^{21}R^{19}$, $OC(=O)R^{21}$, $OC(=O)OR^{18}$, $OC(=O)NR^{21}R^{19}$, $N(R^{21})C(=O)R^{21}$, $N(R^{21})C(=O)OR^{19}$, $N(R^{21})C(=O)NR^{21}R^{22}$, $OSO_2R^{18}$, $OSO_2NR^{21}R^{22}$, $NR^{21}SO_2R^{18}$, $NR^{21}SO_2NR^{21}R^{22}$ or $Si(R^{18}R^{19}R^{20})$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from the group consisting of halogen, cyano, nitro, CHO, $C(=O)OH$, $C(=O)NH_2$, $C(=O)R^{10}$, $C(=O)OR^{11}$, $C(=O)NR^{12}R^{13}$, $OR^{11}$, $S(O)_nR^{10}$, $SO_2NR^{12}R^{13}$ and $Si(R^{10})_3$; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from $C(=O)$ and $C(=S)$ and the sulfur atom ring members are independently selected from $S(=O)_u(=NR^{24})_z$, each ring or ring system optionally substituted with up to 5 substituents independently selected from $R^{15}$;

$R^{3a}$, $R^{3b}$, $R^{3c}$ and $R^{3d}$ are independently H, halogen, cyano, hydroxy, amino, nitro, $SF_5$, OCN, SCN, CHO, C(=O)OH, C(=O)NH$_2$, C(=S)NH$_2$, SO$_2$NH$_2$, C(=O)R$^{18}$, C(=O)OR$^{18}$, NHR$^{18}$, NR$^{18}$R$^{19}$, C(=O) NR$^{21}$R$^{19}$, C(=S)NR$^{21}$R$^{19}$, SO$_2$NR$^{21}$R$^{19}$, OC(=O) R$^{21}$, OC(=O)OR$^{18}$, OC(=O)NR$^{21}$R$^{19}$, N(R$^{21}$)C (=O)R$^{21}$, N(R$^{21}$)C(=O)OR$^{19}$, N(R$^{21}$)C(=O) NR$^{21}$R$^{22}$, OSO$_2$R$^{18}$, OSO$_2$NR$^{21}$R$^{22}$, NR$^{21}$SO$_2$R$^{18}$, NR$^{21}$SO$_2$NR$^{21}$R$^{22}$, Si(R$^{18}$R$^{19}$R$^{20}$) or Z$^1$Q$^t$; or C$_1$-C$_8$ alkyl, C$_2$-C$_8$ alkenyl, C$_2$-C$_8$ alkynyl, C$_3$-C$_{10}$ cycloalkyl, C$_4$-C$_{10}$ alkylcycloalkyl, C$_4$-C$_{10}$ cycloalkylalkyl, C$_6$-C$_{14}$ cycloalkylcycloalkyl, C$_5$-C$_{10}$ alkylcycloalkylalkyl, C$_3$-C$_8$ cycloalkenyl, C$_1$-C$_8$ alkoxy, C$_3$-C$_8$ cycloalkoxy, C$_4$-C$_{10}$ cycloalkylalkoxy, C$_2$-C$_8$ alkenyloxy, C$_2$-C$_8$ alkynyloxy, C$_1$-C$_8$ alkylthio, C$_1$-C$_8$ alkylsulfinyl, C$_1$-C$_8$ alkylsulfonyl, C$_3$-C$_8$ cycloalkylthio, C$_3$-C$_8$ cycloalkylsulfinyl, C$_3$-C$_8$ cycloalkylsulfonyl, C$_4$-C$_{10}$ cycloalkylalkylthio, C$_4$-C$_{10}$ cycloalkylalkylsulfinyl, C$_4$-C$_{10}$ cycloalkylalkylsulfonyl, C$_2$-C$_8$ alkenylthio, C$_2$-C$_8$ alkenylsulfinyl, C$_2$-C$_8$ alkenylsulfonyl, C$_2$-C$_8$ alkynylthio, C$_2$-C$_8$ alkynylsulfinyl or C$_2$-C$_8$ alkynylsulfonyl, each unsubstituted or substituted with at least one substituent independently selected from R$^{17}$; or R$^{3a}$ and R$^{3b}$, or R$^{3b}$ and R$^{3c}$, or R$^{3c}$ and R$^{3d}$ are taken together with the adjacent carbon atoms to which they are attached to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from S(=O)$_n$, each ring optionally substituted with up to 3 substituents independently selected from the group consisting of halogen, cyano, hydroxy, amino, nitro, C(=O)OH, C(=O)NH$_2$, SO$_2$NH$_2$, C$_1$-C$_4$ alkyl, C$_1$-C$_4$ haloalkyl, C$_2$-C$_4$ alkenyl, C$_2$-C$_4$ haloalkenyl, C$_2$-C$_4$ alkynyl, C$_2$-C$_4$ haloalkynyl, C$_3$-C$_7$ cycloalkyl, C$_3$-C$_7$ halocycloalkyl, C$_4$-C$_8$ alkylcycloalkyl, C$_4$-C$_8$ haloalkylcycloalkyl, C$_4$-C$_8$ cycloalkylalkyl, C$_4$-C$_8$ halocycloalkylalkyl, C$_1$-C$_6$ alkoxy, C$_1$-C$_6$ haloalkoxy, C$_2$-C$_6$ alkoxycarbonyl, C$_2$-C$_6$ haloalkoxycarbonyl, C$_2$-C$_6$ alkylcarbonyl and C$_2$-C$_6$ haloalkylcarbonyl;

R$^{3e}$ is H, hydroxy, amino, CHO, C(=O)NH$_2$, C(=S) NH$_2$, SO$_2$NH$_2$, C(=O)R$^{18}$, C(=O)OR$^{18}$, NHR$^{18}$, NR$^{18}$R$^{19}$, C(=O)NR$^{21}$R$^{19}$, C(=S)NR$^{21}$R$^{19}$, SO$_2$NR$^{21}$R$^{19}$, OC(=O)R$^{21}$, OC(=O)OR$^{18}$, OC(=O) NR$^{21}$R$^{19}$, N(R$^{21}$)C(=O)R$^{21}$, N(R$^{21}$)C(=O)OR$^{19}$, N(R$^{21}$)C(=O)NR$^{21}$R$^{22}$, OSO$_2$R$^{18}$, OSO$_2$NR$^{21}$R$^{22}$, NR$^{21}$SO$_2$R$^{18}$, NR$^{21}$SO$_2$NR$^{21}$R$^{22}$, Si(R$^{18}$R$^{19}$R$^{20}$) or Z$^1$Q$^t$; or C$_1$-C$_8$ alkyl, C$_2$-C$_8$ alkenyl, C$_2$-C$_8$ alkynyl, C$_3$-C$_{10}$ cycloalkyl, C$_4$-C$_{10}$ alkylcycloalkyl, C$_4$-C$_{10}$ cycloalkylalkyl, C$_6$-C$_{14}$ cycloalkylcycloalkyl, C$_5$-C$_{10}$ alkylcycloalkylalkyl, C$_3$-C$_8$ cycloalkenyl, C$_1$-C$_8$ alkoxy, C$_3$-C$_8$ cycloalkoxy, C$_4$-C$_{10}$ cycloalkylalkoxy, C$_2$-C$_8$ alkenyloxy, C$_2$-C$_8$ alkynyloxy, C$_1$-C$_8$ alkylsulfinyl, C$_1$-C$_8$ alkylsulfonyl, C$_3$-C$_8$ cycloalkylsulfinyl, C$_3$-C$_8$ cycloalkylsulfonyl, C$_4$-C$_{10}$ cycloalkylalkylsulfinyl, C$_4$-C$_{10}$ cycloalkylalkylsulfonyl, C$_2$-C$_8$ alkenylsulfinyl, C$_2$-C$_8$ alkenylsulfonyl, C$_2$-C$_8$ alkynylsulfinyl or C$_2$-C$_8$ alkynylsulfonyl, each unsubstituted or substituted with at least one substituent independently selected from R$^{17}$; or R$^{3e}$ and R$^{3b}$ are taken together with the adjacent carbon atoms to which they are attached to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from S(=O)$_n$, each ring optionally substituted with up to 3 substituents independently selected from the group consisting of halogen, cyano, hydroxy, amino, nitro, C(=O)OH, C(=O)NH$_2$, SO$_2$NH$_2$, C$_1$-C$_4$ alkyl, C$_1$-C$_4$ haloalkyl, C$_2$-C$_4$ alkenyl, C$_2$-C$_4$ haloalkenyl, C$_2$-C$_4$ alkynyl, C$_2$-C$_4$ haloalkynyl, C$_3$-C$_7$ cycloalkyl, C$_3$-C$_7$ halocycloalkyl, C$_4$-C$_8$ alkylcycloalkyl, C$_4$-C$_8$ haloalkylcycloalkyl, C$_4$-C$_8$ cycloalkylalkyl, C$_4$-C$_8$ halocycloalkylalkyl, C$_1$-C$_6$ alkoxy, C$_1$-C$_6$ haloalkoxy, C$_2$-C$_6$ alkoxycarbonyl, C$_2$-C$_6$ haloalkoxycarbonyl, C$_2$-C$_6$ alkylcarbonyl and C$_2$-C$_6$ haloalkylcarbonyl;

each R$^4$ and R$^5$ is independently H, halogen, cyano, hydroxy, amino, nitro, OCN, SCN, CHO, C(=O)OH, C(=O)NH$_2$, C(=S)NH$_2$ or SO$_2$NH$_2$; or C$_1$-C$_6$ alkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{12}$ cycloalkylcycloalkyl, C$_5$-C$_8$ alkylcycloalkylalkyl, C$_3$-C$_6$ cycloalkenyl, C$_1$-C$_6$ alkoxy, C$_3$-C$_6$ cycloalkoxy, C$_4$-C$_8$ cycloalkylalkoxy, C$_2$-C$_6$ alkenyloxy or C$_2$-C$_6$ alkynyloxy, each unsubstituted or substituted with at least one substituent independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$ and Si(R$^{10}$)$_3$;

each R$^6$, R$^7$ and R$^8$ is independently H; or C$_1$-C$_6$ alkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl, C$_3$-C$_6$ cycloalkenyl, C$_2$-C$_6$ alkylcarbonyl or C$_2$-C$_6$ alkoxycarbonyl, each unsubstituted or substituted with at least one substituent independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$ and Si(R$^{10}$)$_3$;

each R$^9$ is independently C$_1$-C$_6$ alkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl, C$_3$-C$_6$ cycloalkenyl, C$_2$-C$_6$ alkylcarbonyl or C$_2$-C$_6$ alkoxycarbonyl, each unsubstituted or substituted with at least one substituent independently selected from the group consisting of halogen, cyano, nitro, CHO, C(=O)OH, C(=O)NH$_2$, C(=O)R$^{10}$, C(=O)OR$^{11}$, C(=O) NR$^{12}$R$^{13}$, OR$^{11}$, S(O)$_n$R$^{10}$, SO$_2$NR$^{12}$R$^{13}$ and Si(R$^{10}$)$_3$;

each R$^{9a}$ is independently H; or C$_1$-C$_6$ alkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl, C$_3$-C$_6$ cycloalkenyl, C$_2$-C$_6$ alkylcarbonyl or C$_2$-C$_6$ alkoxycarbonyl, each unsubstituted or substituted with at least one substituent independently selected from the group consisting of halogen, cyano, nitro, CHO, C(=O)OH, C(=O)NH$_2$, C(=O)R$^{10}$, C(=O)OR$^{11}$, C(=O) NR$^{12}$R$^{13}$, OR$^{11}$, S(O)$_n$R$^{10}$, SO$_2$NR$^{12}$R$^{13}$ and Si(R$^{10}$)$_3$;

each R$^{10}$, R$^{11}$, R$^{12}$ and R$^{13}$ is independently C$_1$-C$_6$ alkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl or C$_3$-C$_6$ cycloalkenyl, each unsubstituted or substituted with at least one substituent independently selected from the group consisting of halogen, cyano, nitro, CHO, C(=O)OH, C(=O)NH$_2$, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl and C$_3$-C$_6$ trialkylsilyl; or phenyl or a 5- or 6-membered heteroaromatic ring, each unsubstituted or substituted with at least one substituent independently selected from the group consisting of C$_1$-C$_6$ alkyl, C$_1$-C$_6$ haloalkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl, C$_3$-C$_6$ cycloalkenyl, halogen, cyano, nitro, CHO, C(=O)OH, C(=O)NH$_2$, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl and C$_3$-C$_6$ trialkylsilyl;

each R$^{14}$ is independently halogen, cyano, hydroxy, amino, nitro, SF$_5$, OCN, SCN, CHO, C(=O)OH, C(=O)NH$_2$, C(=S)NH$_2$, SO$_2$NH$_2$, C(=O)R$^{18}$, C(=O)OR$^{18}$, NHR$^{18}$, NR$^{18}$R$^{19}$, C(=O)NR$^{21}$R$^{19}$, C(=O)NR$^{21}$NR$^{22}$R$^{23}$, C(=S)NR$^{21}$R$^{19}$, SO$_2$NR$^{21}$R$^{19}$, OC(=O)R$^{21}$, OC(=O)OR$^{18}$, OC(=O)NR$^{21}$R$^{19}$, N(R$^{21}$)C(=O)R$^{21}$, N(R$^{21}$)C(=O)OR$^{19}$, N(R$^{21}$)C(=O)NR$^{21}$R$^{22}$, OSO$_2$R$^{18}$, OSO$_2$NR$^{21}$R$^{22}$, NR$^{21}$SO$_2$R$^{18}$, NR$^{21}$SO$_2$NR$^{21}$R$^{22}$, Si(R$^{18}$R$^{19}$R$^{20}$), C(=NR$^{21}$)R$^{22}$, C(=NOR$^{21}$)R$^{22}$, C(=NNR$^{21}$R$^{22}$)R$^{23}$, C(=NN(C(=O)R$^{19}$)R$^{21}$)R$^{22}$, C(=NN(C(=O)OR$^{19}$)R$^{21}$)R$^{22}$, ON=CR$^{21}$R$^{22}$, ONR$^{21}$R$^{22}$, S(=O)(=NR$^{21}$)R$^{22}$, SO$_2$NR$^{21}$C(=O)NR$^{22}$R$^{23}$, P(=X$^2$)R$^{18}$R$^{19}$, OP(=X$^2$)R$^{18}$R$^{19}$, OP(=X$^2$)(OR$^{18}$)R$^{19}$, OP(=X$^2$)(OR$^{18}$)OR$^{19}$, N=CR$^{21}$R$^{22}$, NR$^{21}$N=CR$^{22}$R$^{23}$, NR$^{21}$NR$^{22}$R$^{23}$, NR$^{21}$C(=X$^2$)NR$^{22}$R$^{23}$, NR$^{21}$C(=NR$^{21}$)NR$^{22}$R$^{23}$, NR$^{21}$NR$^{21}$C(=X$^2$)NR$^{22}$R$^{23}$, NR$^{21}$NR$^{21}$SO$_2$NR$^{22}$R$^{23}$, Z$^1$Q$^t$ or Z$^1$Q$^i$Z$^1$Q$^t$; or C$_1$-C$_8$ alkyl, C$_2$-C$_8$ alkenyl, C$_2$-C$_8$ alkynyl, C$_3$-C$_{10}$ cycloalkyl, C$_4$-C$_{10}$ alkylcycloalkyl, C$_4$-C$_{10}$ cycloalkylalkyl, C$_6$-C$_{14}$ cycloalkylcycloalkyl, C$_5$-C$_{10}$ alkylcycloalkylalkyl, C$_3$-C$_8$ cycloalkenyl, C$_1$-C$_8$ alkoxy, C$_3$-C$_8$ cycloalkoxy, C$_4$-C$_{10}$ cycloalkylalkoxy, C$_2$-C$_8$ alkenyloxy, C$_2$-C$_8$ alkynyloxy, C$_1$-C$_8$ alkylthio, C$_1$-C$_8$ alkylsulfinyl, C$_1$-C$_8$ alkylsulfonyl, C$_3$-C$_8$ cycloalkylthio, C$_3$-C$_8$ cycloalkylsulfinyl, C$_3$-C$_8$ cycloalkylsulfonyl, C$_4$-C$_{10}$ cycloalkylalkylthio, C$_4$-C$_{10}$ cycloalkylalkylsulfinyl, C$_4$-C$_{10}$ cycloalkylalkylsulfonyl, C$_2$-C$_8$ alkenylthio, C$_2$-C$_8$ alkenylsulfinyl, C$_2$-C$_8$ alkenylsulfonyl, C$_2$-C$_8$ alkynylthio, C$_2$-C$_8$ alkynylsulfinyl or C$_2$-C$_8$ alkynylsulfonyl, each unsubstituted or substituted with at least one substituent independently selected from R$^{17}$; or two R$^{14}$ substituents on adjacent ring atoms are taken together with the adjacent ring atoms to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from S(=O)$_n$, each ring optionally substituted with up to 3 substituents independently selected from the group consisting of halogen, cyano, hydroxy, amino, nitro, C(=O)OH, C(=O)NH$_2$, SO$_2$NH$_2$, C$_1$-C$_4$ alkyl, C$_1$-C$_4$ haloalkyl, C$_2$-C$_4$ alkenyl, C$_2$-C$_4$ haloalkenyl, C$_2$-C$_4$ alkynyl, C$_2$-C$_4$ haloalkynyl, C$_3$-C$_7$ cycloalkyl, C$_3$-C$_7$ halocycloalkyl, C$_4$-C$_8$ alkylcycloalkyl, C$_4$-C$_8$ haloalkylcycloalkyl, C$_4$-C$_8$ cycloalkylalkyl, C$_4$-C$_8$ halocycloalkylalkyl, C$_1$-C$_6$ alkoxy, C$_1$-C$_6$ haloalkoxy, C$_2$-C$_6$ alkoxycarbonyl, C$_2$-C$_6$ haloalkoxycarbonyl, C$_2$-C$_6$ alkylcarbonyl and C$_2$-C$_6$ haloalkylcarbonyl;

each X$^2$ is independently O or S;

each Z$^1$ is independently a direct bond, O, S(O)$_n$, NR$^6$, C(R$^7$)$_2$, C(R$^7$)=C(R$^7$), C≡C, C(R$^7$)$_2$O, OC(R$^7$)$_2$, C(=X$^1$), C(=X$^1$)E, EC(=X$^1$), C(=NOR$^8$) or C(=NN(R$^6$)$_2$);

each Q$^i$ is independently a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from S(=O)$_u$(=NR$^{24}$)$_z$, each ring or ring system optionally substituted with up to 4 substituents independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$, Si(R$^{10}$)$_3$ and R$^{16}$;

each Q$^t$ is independently a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from S(=O)$_u$(=NR$^{24}$)$_z$, each ring or ring system optionally substituted with up to 5 substituents independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, C(=O)NR$^{21}$NR$^{22}$R$^{23}$, OR$^{11}$, S(O)$_n$R$^{10}$, SO$_2$NR$^{12}$R$^{13}$, S(=O)(=NR$^{21}$)R$^{22}$, Si(R$^{10}$)$_3$ and R$^{16}$;

each R$^{15}$ is independently halogen, cyano, hydroxy, amino, nitro, SF$_5$, OCN, SCN, CHO, C(=O)OH, C(=O)NH$_2$, C(=S)NH$_2$, SO$_2$NH$_2$, C(=O)R$^{18}$, C(=O)OR$^{18}$, NHR$^{18}$, NR$^{18}$R$^{19}$, C(=O)NR$^{21}$R$^{19}$, C(=O)NR$^{21}$NR$^{22}$R$^{23}$, C(=S)NR$^{21}$R$^{19}$, SO$_2$NR$^{21}$R$^{19}$, S(=O)(=NR$^{21}$)R$^{22}$, OC(=O)R$^{21}$, OC(=O)OR$^{18}$, OC(=O)NR$^{21}$R$^{19}$, N(R$^{21}$)C(=O)R$^{21}$, N(R$^{21}$)C(=O)OR$^{19}$, N(R$^{21}$)C(=O)NR$^{21}$R$^{22}$, OSO$_2$R$^{18}$, OSO$_2$NR$^{21}$R$^{22}$, NR$^{21}$SO$_2$R$^{18}$, NR$^{21}$SO$_2$NR$^{21}$R$^{22}$, Si(R$^{18}$R$^{19}$R$^{20}$) or Z$^1$Q$^t$; or C$_1$-C$_8$ alkyl, C$_2$-C$_8$ alkenyl, C$_2$-C$_8$ alkynyl, C$_3$-C$_{10}$ cycloalkyl, C$_4$-C$_{10}$ alkylcycloalkyl, C$_4$-C$_{10}$ cycloalkylalkyl, C$_6$-C$_{14}$ cycloalkylcycloalkyl, C$_5$-C$_{10}$ alkylcycloalkylalkyl, C$_3$-C$_8$ cycloalkenyl, C$_1$-C$_8$ alkoxy, C$_3$-C$_8$ cycloalkoxy, C$_4$-C$_{10}$ cycloalkylalkoxy, C$_2$-C$_8$ alkenyloxy, C$_2$-C$_8$ alkynyloxy, C$_1$-C$_8$ alkylthio, C$_1$-C$_8$ alkylsulfinyl, C$_1$-C$_8$ alkylsulfonyl, C$_3$-C$_8$ cycloalkylthio, C$_3$-C$_8$ cycloalkylsulfinyl, C$_3$-C$_8$ cycloalkylsulfonyl, C$_4$-C$_{10}$ cycloalkylalkylthio, C$_4$-C$_{10}$ cycloalkylalkylsulfinyl, C$_4$-C$_{10}$ cycloalkylalkylsulfonyl, C$_2$-C$_8$ alkenylthio, C$_2$-C$_8$ alkenylsulfinyl, C$_2$-C$_8$ alkenylsulfonyl, C$_2$-C$_8$ alkynylthio, C$_2$-C$_8$ alkynylsulfinyl or C$_2$-C$_8$ alkynylsulfonyl, each unsubstituted or substituted with at least one substituent independently selected from $R^{17}$; or two $R^{15}$ substituents on adjacent ring atoms are taken together with the adjacent ring atoms to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from $S(=O)_n$, each ring optionally substituted with up to 3 substituents independently selected from the group consisting of halogen, cyano, hydroxy, amino, nitro, C(=O)OH, C(=O)NH$_2$, SO$_2$NH$_2$, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_6$ alkoxy, $C_1$-$C_6$ haloalkoxy, $C_2$-$C_6$ alkoxycarbonyl, $C_2$-$C_6$ haloalkoxycarbonyl, $C_2$-$C_6$ alkylcarbonyl and $C_2$-$C_6$ haloalkylcarbonyl;

each $R^{16}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from the group consisting of halogen, cyano, nitro, CHO, C(=O)OH, C(=O)NH$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl; or phenyl or a 5- or 6-membered heteroaromatic ring, each unsubstituted or substituted with at least one substituent independently selected from the group consisting of $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, halogen, cyano, nitro, CHO, C(=O)OH, C(=O)NH$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl;

each $R^{17}$ is independently halogen, cyano, nitro, OH, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$, Si(R$^{10}$)$_3$ or $Z^1Q^t$;

each $R^{18}$, $R^{19}$ and $R^{20}$ is independently $Q^t$; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{17}$;

each $R^{21}$, $R^{22}$ and $R^{23}$ is independently $Q^t$ or H; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{17}$;

each $R^{24}$ is independently H, cyano, OCN, SCN, CHO, C(=O)OH, C(=O)NH$_2$, C(=S)NH$_2$, SO$_2$NH$_2$, C(=O)R$^{18}$, C(=O)OR$^{18}$, NHR$^{18}$, NR$^{18}$R$^{19}$, C(=O)NR$^{21}$R$^{19}$, C(=S)NR$^{21}$R$^{19}$, SO$_2$NR$^{21}$R$^{19}$, OC(=O)R$^{21}$, OC(=O)OR$^{18}$, OC(=O)NR$^{21}$R$^{19}$, N(R$^{21}$)C(=O)R$^{21}$, N(R$^{21}$)C(=O)OR$^{19}$, N(R$^{21}$)C(=O)NR$^{21}$R$^{22}$, OSO$_2$R$^{18}$, OSO$_2$NR$^{21}$R$^{22}$, NR$^{21}$SO$_2$R$^{18}$, NR$^{21}$SO$_2$NR$^{21}$R$^{22}$, Si(R$^{18}$R$^{19}$R$^{20}$) or $Z^1Q^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from $R^{17}$;

a is 1, 2 or 3;

each n is independently 0, 1 or 2; and u and z in each instance of $S(=O)_u(=NR^{24})_z$ are independently 0, 1 or 2, provided that the sum of u and z in each instance of $S(=O)_u(=NR^{24})_z$ is 0, 1 or 2;

provided that when A is O, S, NCH$_3$ or C(R$^{3c}$)=C(R$^{3d}$), R$^{3c}$ is H or F, and R$^{3d}$ is H, F, CF$_2$H or CF$_3$, then at least one of R$^{3a}$ or R$^{3b}$ is other than H.

Of note is that compounds of this invention are characterized by favorable metabolic and/or soil residual patterns and exhibit activity controlling a spectrum of agronomic and nonagronomic invertebrate pests.

Of particular note, for reasons of invertebrate pest control spectrum and economic importance, protection of agronomic crops from damage or injury caused by invertebrate pests by controlling invertebrate pests are embodiments of the invention. Compounds of this invention because of their favorable translocation properties or systemicity in plants also protect foliar or other plant parts which are not directly contacted with a compound of Formula 1 or a composition comprising the compound.

Also noteworthy as embodiments of the present invention are compositions comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent.

Further noteworthy as embodiments of the present invention are compositions for controlling an invertebrate pest comprising a compound (i.e. in a biologically effective amount) of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent (i.e. in a biologically effective amount).

Embodiments of the invention also include a composition for protecting an animal comprising a compound (i.e. in a parasiticidally effective amount) of any of the preceding Embodiments and a carrier.

Embodiments of the invention further include methods for controlling an invertebrate pest comprising contacting the invertebrate pest or its environment with a biologically effective amount of a compound of any of the preceding Embodiments (e.g., as a composition described herein). Of particular note is a method for protecting an animal comprising administering to the animal a parasiticidally effective amount of a compound of any of the preceding Embodiments (e.g., as a composition described herein).

Embodiments of the invention also include a composition comprising a compound of any of the preceding Embodiments in the form of a soil drench liquid formulation. Embodiments of the invention further include methods for controlling an invertebrate pest comprising contacting the soil with a liquid composition as a soil drench comprising a biologically effective amount of a compound of any of the preceding Embodiments.

Embodiments of the invention also include a spray composition for controlling an invertebrate pest comprising a compound (i.e. in a biologically effective amount) of any of the preceding Embodiments and a propellant. Embodiments of the invention further include a bait composition for controlling an invertebrate pest comprising a compound (i.e. in a biologically effective amount) of any of the preceding Embodiments, one or more food materials, optionally an attractant, and optionally a humectant. Embodiments of the invention also include a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

Embodiments of the invention also include a method for protecting a seed from an invertebrate pest comprising contacting the seed with a biologically effective amount of a compound of any of the preceding Embodiments (e.g., as a composition described herein).

Embodiments of the invention also include methods for protecting an animal from an invertebrate parasitic pest comprising administering to the animal a parasiticidally effective amount of a compound of any of the preceding Embodiments.

Embodiments of the invention also include methods for controlling an invertebrate pest comprising contacting the invertebrate pest or its environment with a biologically effective amount of a compound of Formula 1, an N-oxide, or a salt thereof, (e.g., as a composition described herein), provided that the methods are not methods of medical treatment of a human or animal body by therapy.

This invention also relates to such methods wherein the invertebrate pest or its environment is contacted with a composition comprising a biologically effective amount of a compound of Formula 1, an N-oxide, or a salt thereof, and at least one additional component selected from the group consisting of surfactants, solid diluents and liquid diluents, said composition optionally further comprising a biologically effective amount of at least one additional biologically active compound or agent, provided that the methods are not methods of medical treatment of a human or animal body by therapy.

One or more of the following methods and variations as described in Schemes 1-13 can be used to prepare the compounds of Formula 1. The definitions of $R^1$, $R^2$, $R^{3a}$, $R^{3b}$, $R^4$, $R^5$, X, Y, Z and A in the compounds of Formulae 1-13 below are as defined above in the Summary of the Invention unless otherwise noted. Formulae 1a-1e are various subsets of Formula 1, and all substituents for Formulae 1a-1e are as defined above for Formula 1 unless otherwise indicated. Ambient or room temperature is defined as about 20-25° C.

Compounds of Formula 1a (i.e. Formula 1 wherein X and Y are 0) can be prepared by condensation of appropriately substituted compounds of Formula 2 with optionally substituted malonic acids (3a) in the presence of condensing agents as shown in Scheme 1. Condensing agents can be carbodiimides such as dicyclohexyl carbodiimide (see, for example, Koch, A. et al. *Tetrahedron* 2004, 60, 10011-10018) or other agents well known in the art to form amide bonds with or without activating agents such as N-hydroxybenzotriazole as described in *Science of Synthesis* 2005, 21, 17-25 and *Tetrahedron* 2005, 61, 10827-10852. This reaction is typically carried out in an inert organic solvent, such as dichloromethane or 1,2-dichloroethane, at temperatures from about 0 to about 80° C. for a period of 10 min to several days.

Scheme 1

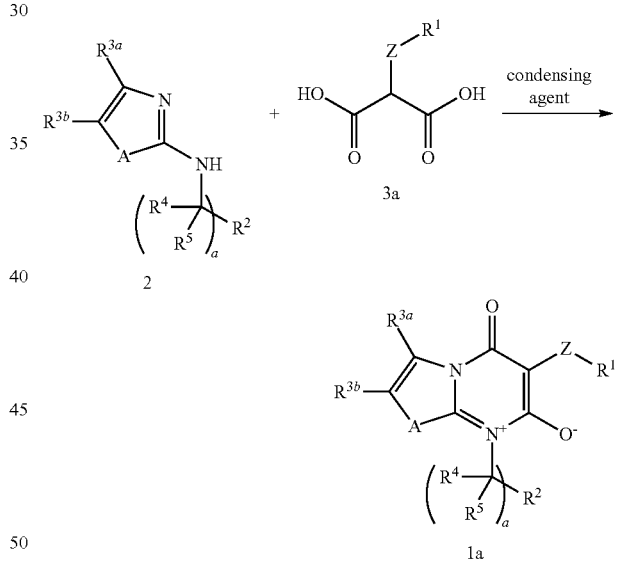

Compounds of Formula 1a can also be prepared by the condensation of compounds of Formula 2 with malonic acid esters (3b) wherein R is a $C_1$-$C_5$ alkyl group as shown in Scheme 2. These reactions can be performed neat or in the presence of inert solvents as described in *Bulletin of the Chemical Society of Japan* 1999, 72(3), 503-509. Inert solvents include, but are not limited to, high boiling hydrocarbons such as mesitylene, tetralin or cymene, or high boiling ethers such as diphenyl ether. Typical temperatures range from 50 to 250° C. Of note are temperatures from 150 to 200° C., which typically provide rapid reaction times and high yields. These reactions can also be performed in microwave reactors within the same temperature ranges. Typical reaction times range from 5 minutes to several hours.

Scheme 2

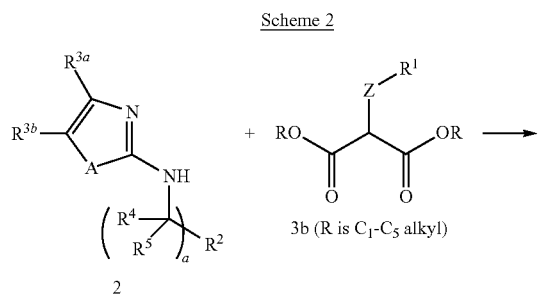

Compounds of Formula 3a can be prepared by a variety of methods known in the art, for example by base hydrolysis of compounds of Formula 3b.

Compounds of Formula 3b wherein Z is a direct bond and $R^1$ is an optionally substituted aromatic (including heteroaromatic) ring or ring system can be prepared by arylation of malonate esters (using compounds of formula $R^1X^1$ wherein $X^1$ is Cl, Br or I, examples of which are found in Tables I-24a-24c) catalyzed by palladium (*J. Org. Chem* 2002, 67, 541-555) or copper (*Org. Lett.* 2002, 4, 269-272 and *Org. Lett.* 2005, 7, 4693-4695). Alternatively, compounds of Formula 3b can be prepared by the method shown in Scheme 2a (see, for example, *J. Med. Chem* 1982, 25(6), 745-747).

Scheme 2a

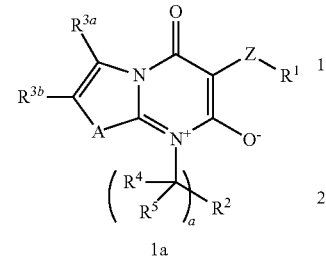

Esters of Formula 4 can be prepared from the corresponding acids by methods well known in the art. Many of the acids of Formula 4 where R is H are commercially available or readily prepared by methods known in the art (examples are listed in Table I-1).

Compounds of Formula 3b can also be prepared by the method shown in Scheme 2b. Reaction of nitriles of Formula 3g with dialkyl carbonates yields nitrile esters of Formula 3h, and subsequent acidic hydrolysis in the presence of an alcohol provides the compounds of Formula 3b (see, for example, *Helvetica Chimica Acta* 1991, 74(2), 309-314). Many of the nitriles of Formula 3g are commercially available or readily prepared by methods known in the art.

Scheme 2b

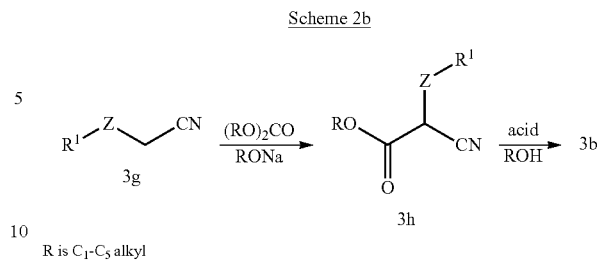

R is $C_1$-$C_5$ alkyl

Compounds of Formula 1a can also be prepared by treatment of compounds of Formula 2 with activated esters of Formula 3c wherein LvO is an activated leaving group as shown in Scheme 3. Examples of Lv preferred for ease of synthesis or reactivity are phenyl, 4-nitrophenyl or halogen-substituted phenyl (e.g., 2,4,6-trichlorophenyl, pentachlorophenyl or pentafluorophenyl) as described in *Archiv der Pharmazie* (Weinheim, Germany) 1991, 324, 863-866. Other activated esters are well known in the art and include, but are not limited to, N-hydroxysuccinimide esters (see, for example, *J. Am. Chem. Soc.* 2002, 124, 6872-6878). Typical temperatures range from 50 to 200° C. Of note are temperatures from 50 to 150° C., which typically provide rapid reaction times and high yields. These reactions can be performed with or without solvent, such as toluene, and in microwave reactors within the same temperature ranges. Typical reaction times range from 5 minutes to 2 hours.

Scheme 3

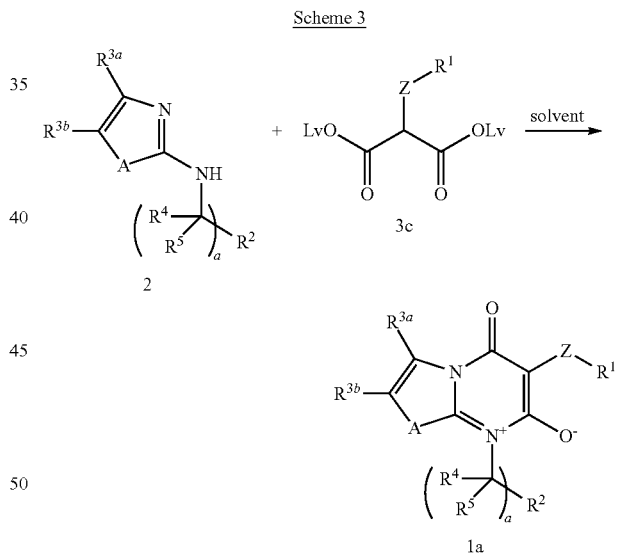

Compounds of the Formula 3c can be prepared, for example, from compounds of Formula 3a (see, for example, *J. Het. Chem.* 1980, 17, 337).

Compounds of Formula 1a can also be prepared by condensation of compounds of Formula 2 with compounds of Formula 3d or 3e, or by condensation of compounds of Formula 2 with mixtures of compounds of Formulae 3d and 3e as shown in Scheme 4. These reactions are typically performed in an inert solvent, such as dichloromethane, and optionally in the presence of two or more equivalents of an acid acceptor (see, for example, *Zeitschrift für Naturforschung, Teil B: Anorganische Chemie, Organische Chemie* 1982, 37B(2), 222-233). Typical acid acceptors include, but are not limited to, triethylamine, N,N-diisopropylethylamine, pyridine and substituted pyridines, and metal hydroxides, carbonates and bicarbonates.

Scheme 4

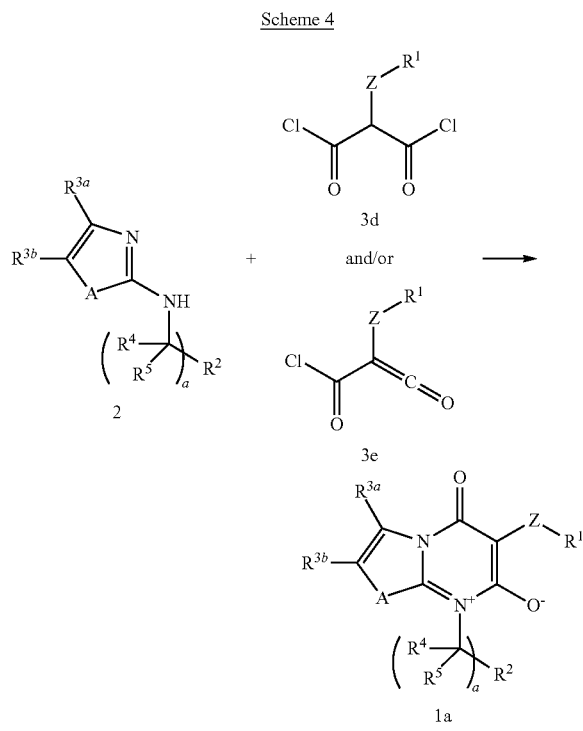

Compounds of Formula 1b (i.e. Formula 1a wherein Z is a direct bond and $R^1$ is H) can be prepared by condensation of compounds of Formula 2 with carbon suboxide (3f) (see, for example, *J. Org. Chem.* 1972, 37(9), 1422-1425) as shown in Scheme 5. The reactions are typically performed in an inert solvent such as ether and can include the use of a catalyst such as $AlCl_3$.

Scheme 5

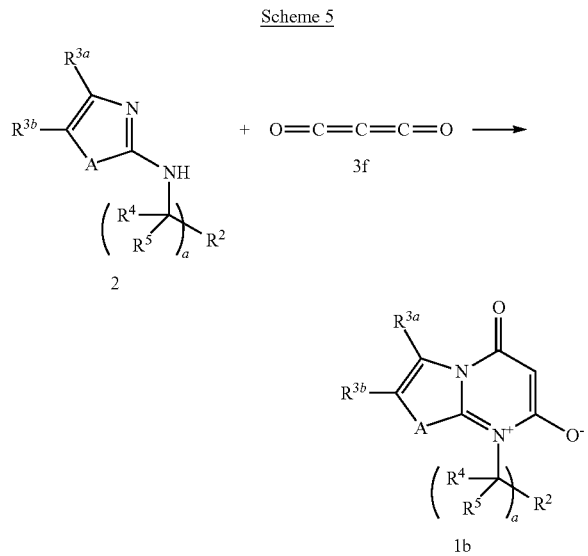

Compounds of Formula 2 can be prepared in a variety of ways known in the art; see, for example, Patai, S. *The Chemistry of Functional Groups: The Chemistry of Amidines and Imidates*; Wiley: Chichester, UK, 1975; *The Chemistry of Amidines and Imidates*; Patai, S.; Rappoport, Z., Eds.; Wiley: Chichester, UK, 1991; Vol. 2; Mega, T. et al. *Bulletin of the Chemical Society of Japan* 1988, 61(12), 4315-4321; Ife, R. et al. *European Journal of Medicinal Chemistry* 1989, 24(3), 249-257; Wagaw, S.; Buchwald, S. *Journal of Organic Chemistry* 1996, 61(21), 7240-7241; Shen, Q. et al. *Angewandte Chemie, International Edition* 2005, 44(9), 1371-1375; and Okano, K. et al. *Organic Letters* 2003, 5(26), 4987-4990.

One skilled in the art will recognize that the compounds of Formula 2 can also be used as their acid-addition salts (e.g., hydrochloric salts, acetic acid salts) in the coupling methods of Schemes 1-5.

Compounds of Formula 1a wherein Z is a direct bond and $R^1$ is $C_2$-$C_8$ alkenyl or an optionally substituted aromatic ring or ring system, can be prepared from compounds of Formula 1c (i.e. Formula 1 wherein X and Y are O, Z is a direct bond and $R^1$ is Cl, Br or I, preferably Br or I) and compounds of Formula 5 wherein $R^1$ is $C_2$-$C_8$ alkenyl or an optionally substituted aromatic ring or ring system, and M with Z—$R^1$ forms a boronic acid, boronic acid ester or trifluoroborate salt, or M is trialkylstannyl or zinc and Z is a direct bond, as shown in Scheme 6.

Scheme 6

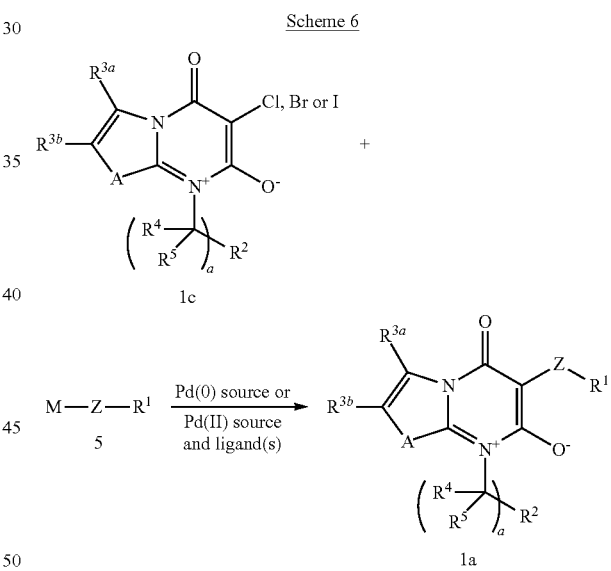

In a similar manner, compounds of Formula 1 wherein a substituent (e.g., $R^1$ or $R^2$) consists of two directly bonded aromatic rings or ring systems (e.g., a phenyl ring bonded to a second phenyl ring, a phenyl ring bonded to a pyridinyl ring, or a pyridinyl ring bonded to a second pyridinyl ring) can be prepared by palladium-catalyzed coupling of the two appropriately substituted aromatic rings or ring systems. These palladium-catalyzed couplings between an aromatic chloride, bromide or iodide and an aromatic boronic acid or ester, or an aromatic tin or zinc reagent, are well known and have been extensively described in the art. For example, see Scheme 6a, wherein a compound of Formula 13a or 13b is coupled with an appropriately substituted phenyl ring to provide the biphenyl compound of Formula 13c. M is as defined above for Scheme 6.

Scheme 6a

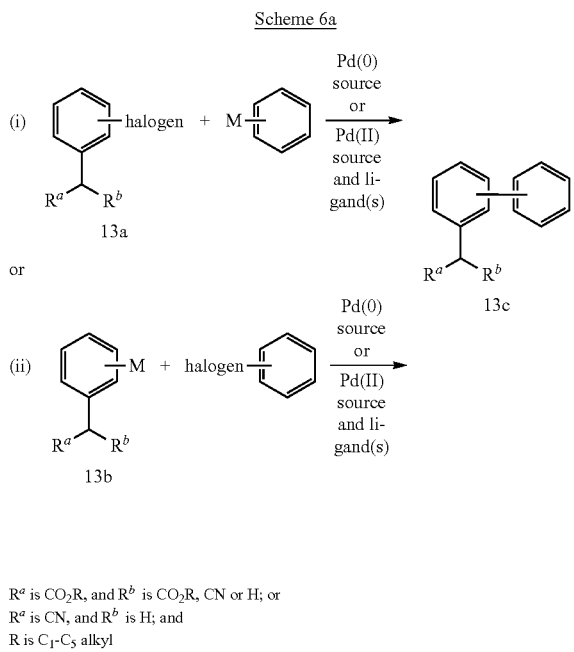

$R^a$ is $CO_2R$, and $R^b$ is $CO_2R$, CN or H; or
$R^a$ is CN, and $R^b$ is H; and
R is $C_1$-$C_5$ alkyl Scheme 7

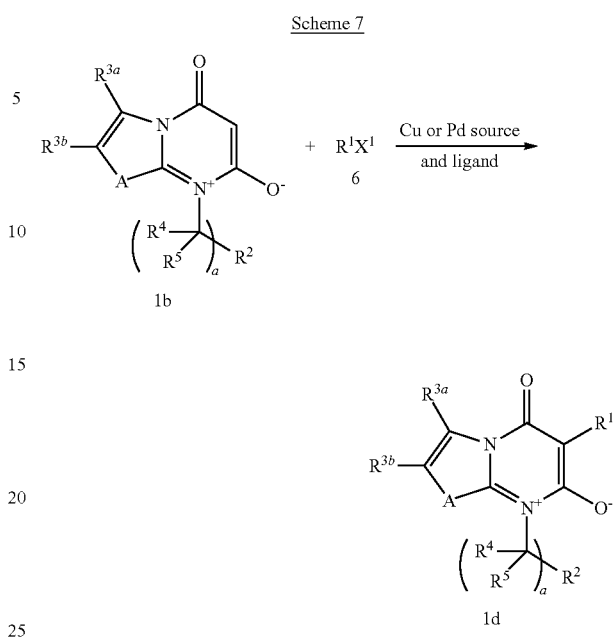

These coupling reactions are typically carried out in the presence of a palladium catalyst and a base optionally under an inert atmosphere. The palladium catalysts used for these coupling reactions typically comprises palladium in a formal oxidation state of either 0 (i.e. Pd(0)) or 2 (i.e. Pd(II)). A wide variety of such palladium-containing compounds and complexes are useful as catalysts for these reactions. Examples of palladium-containing compounds and complexes useful as catalysts in the methods include $PdCl_2$ $(PPh_3)_2$ (bis(triphenylphosphine)palladium (II) dichloride), $Pd(PPh_3)_4$ (tetrakis(triphenylphosphine)-palladium(0)), $Pd(C_5H_7O_2)_2$ (palladium(II) acetylacetonate), $Pd_2(dba)_3$ (tris(dibenzylidene-acetone)dipalladium(0)), and [1,1'-bis (diphenylphosphino)ferrocene]dichloropalladium(II). These coupling methods are generally conducted in a liquid phase, and therefore the palladium catalyst preferably has good solubility in the liquid phase. Useful solvents include, for example, water, ethers such as 1,2-dimethoxyethane, amides such as N,N-dimethylacetamide, and non-halogenated aromatic hydrocarbons such as toluene.

The coupling methods can be conducted over a wide range of temperatures, ranging from about 25 to about 200° C. Of note are temperatures from about 60 to about 150° C., which typically provide fast reaction times and high product yields. The general methods and procedures for Stille, Negishi and Suzuki couplings with aryl iodides, bromides or chlorides and an aryl tin, aryl zinc or aryl boronic acid respectively are well known in the literature; see, for example, E. Negishi, *Handbook of Organopalladium Chemistry for Organic Synthesis*, Wiley-Interscience, 2002, New York, N.Y.

Compounds of Formula 1d (i.e. Formula 1 wherein X and Y are O and Z is a direct bond) wherein $R^1$ is an optionally substituted aromatic ring or ring system can be prepared from compounds of Formula 1a (i.e. Formula 1a wherein Z is a direct bond and $R^1$ is H) and compounds of Formula 6 wherein $X^1$ is Cl, Br or I (preferably Br or I) as shown in Scheme 7.

These reactions are typically carried out in the presence of a copper or palladium catalyst preferably under an inert atmosphere. The copper catalysts used for the present method typically comprise copper in metallic form (e.g., as a powder) or copper in a formal oxidation state of 1 (i.e. Cu(I)). Examples of copper-containing compounds useful as catalysts in the method of Scheme 7 include Cu, CuI, CuBr, CuCl. Examples of palladium-containing compounds useful as catalysts in the method of Scheme 7 include $Pd(OAc)_2$. Useful solvents for the method of Scheme 7 include, for example, ethers such as 1,4-dioxane, amides such as N,N-dimethylacetamide and dimethyl sulfoxide.

The method of Scheme 7 can be conducted over a wide range of temperatures from 25 to 200° C. Of note are temperatures from 40 to 150° C. The method of Scheme 7 can be conducted in the presence of a ligand. A wide variety of copper-binding compounds are useful as ligands for the present method. Examples of useful ligands include, but are not limited to, 1,10-phenanthroline, N,N-dimethylethylenediamine, L-proline and 2-picolinic acid. The general methods and procedures for copper-catalyzed Ullmann-type coupling reactions are well known in the literature; see, for example, Xie, Ma, et al. *Org. Lett.* 2005, 7, 4693-4695.

Compounds of Formula 1a wherein Z is $S(O)_n$, $C(=X^1)$ or $C(=X^1)E$ can be prepared from compounds of Formula 1b by treatment with compounds of Formula 7, optionally in the presence of a Lewis acid catalyst (e.g., $FeCl_3$), as shown in Scheme 8. Examples of compounds of Formula 7 useful in the method of Scheme 8 include, but are not limited to, sulfenyl and sulfonyl halides, carboxylic acids, acid anhydrides, acid halides, chloroformates, aminocarbonyl halides, isocyanates and isothiocyanates. Typically the reaction is performed in an inert solvent, more typically a polar solvent such as N,N-dimethylacetamide or 1-methyl-2-pyrrolidinone. The reaction is typically performed at temperatures from 0 to 180° C., more typically at ambient temperature to 150° C. Microwave irradiation can be advantageous in heating the reaction mixture.

Scheme 8

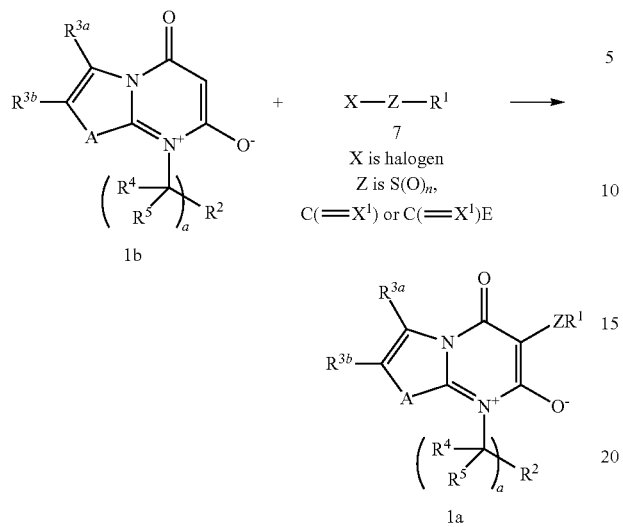

Scheme 10

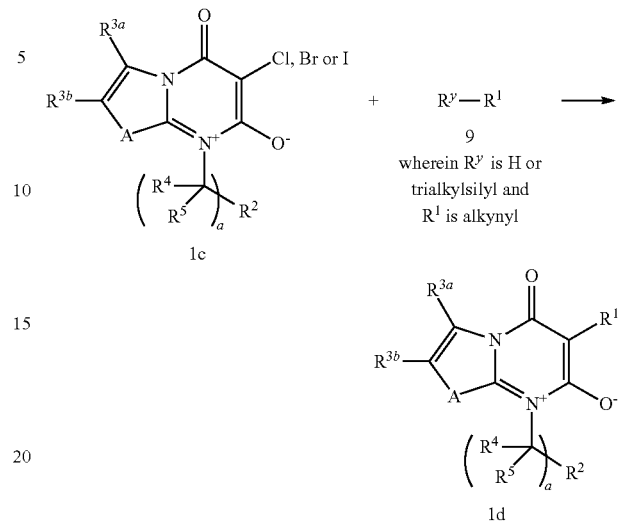

Compounds of the Formula 1e (i.e. Formula 1a wherein Z is C(=NOR⁸) or C(=NN(R⁶)₂) can be prepared by reacting compounds of Formula 1a wherein Z is C(=O) with an alkoxyamine or hydrazine salt of Formula 8, where X³ is a counterion such as halide or oxalate, as shown in Scheme 9. The reaction can be run in an alcoholic solvent such as ethanol or propanol at temperatures ranging from 80° C. to the reflux temperature of the solvent in 3 to 24 hours.

Compounds of Formula 1c can be prepared from compounds of Formula 1b by halogenation using, for example, liquid bromine or N-halosuccinimides (10) as shown in Scheme 11. Typically the reaction is performed in an inert solvent, more typically a halogenated solvent such as methylene chloride or 1,2-dichloroethane. The reaction is typically performed at temperatures from 0 to 80° C., more typically at ambient temperature.

Scheme 9

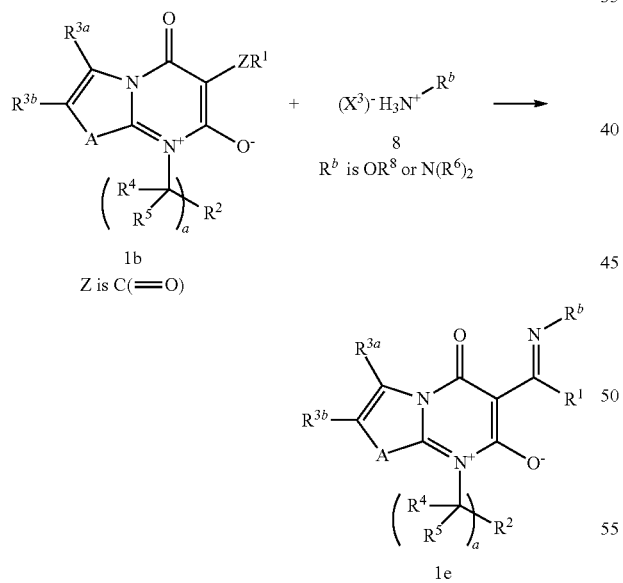

Scheme 11

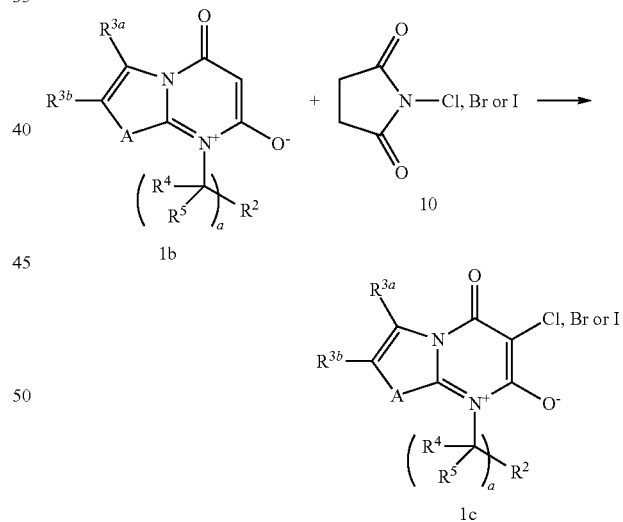

Compounds of Formula 1d wherein R¹ is $C_2$-$C_8$ alkynyl, can be prepared from compounds of Formula 1c and substituted alkynes of Formula 9 by a Sonogashira coupling reaction as shown in Scheme 10. Sonogashira couplings are well known in the literature. See, for example, K. Sonogashira, *Sonogashira Alkyne Synthesis* Vol 2, p. 493 in E. Negishi, *Handbook of Organopalladium Chemistry for Organic Synthesis*, Wiley-Interscience, 2002, New York, N.Y.

Compounds of Formula 1a can also be prepared by alkylation of compounds of Formula 11 using appropriately substituted alkylating agents and bases such as potassium carbonate as shown in Scheme 12 (see, for example, Kappe, T. et al. *Monatschefte fur Chemie* 1971, 102, 412-424 and Urban, M. G.; Arnold, W. *Helvetica Chimica Acta* 1970, 53, 905-922). Alkylating agents include, but are not limited to, alkyl chlorides, bromides, iodides and sulfonate esters. A wide variety of bases and solvents can be employed in the method of Scheme 12, and these bases and solvents are well known in the art.

Scheme 12

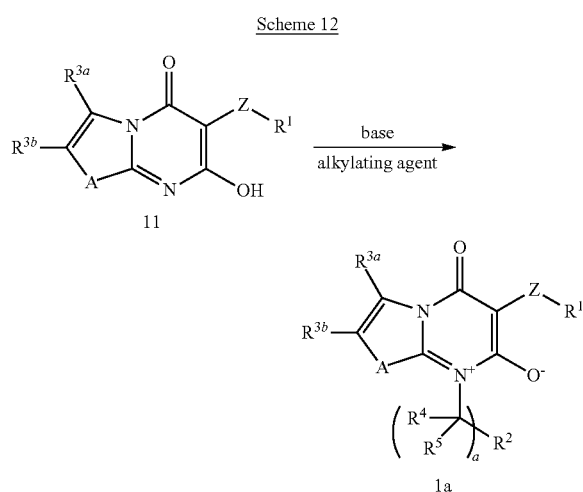

Compounds of Formula 11 can be prepared from compounds of Formula 2a by methods analogous to those shown in Schemes 1 through 5 wherein the compound of Formula 2 is replaced by a compound of Formula 2a. Compounds of Formula 2a are commercially available or can be prepared by general methods well known in the art.

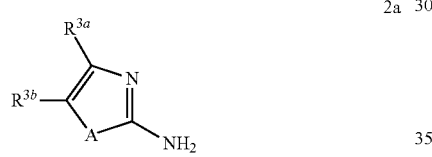

A particularly useful method for the preparation of compounds of Formula 2 is shown in Scheme 13. In the method of Scheme 13, compounds of Formula 2a are protected with suitable protecting groups such as, but not limited to, tert-butoxycarbonyl, acetyl or formyl to form the intermediate of Formula 2b wherein PG is a protecting group. The compound of Formula 2b is then alkylated with an appropriate reagent of Formula 12 (wherein at least one of $R^4$ or $R^5$ is hydrogen and X is a leaving group such as a halogen) to give an intermediate of Formula 2c. The protecting group is removed to provide a compound of Formula 2. Conditions for the formation and removal of protecting groups on an amine function are known in the literature (see, for example, Greene, T. W.; Wuts, P. G. M. *Protective Groups in Organic Synthesis,* 2nd ed.; Wiley: New York, 1991).

Examples of particularly useful compounds of Formula 2 are shown in Tables I-27 to I-27g and I-29. Some examples of compounds of Formula 2a are shown in Tables I-28 to I-28g.

An alternative method for the preparation of compounds of Formula 2 is by the reductive amination of appropriate carbonyl compounds. This method is shown in Steps B and C of Synthesis Example 1, and Step A of Synthesis Example 5.

Another alternative method for the preparation of compounds of Formula 2 is by the reaction of appropriately substituted amines with halogen-substituted heteroaromatic compounds analogous to the compounds of Formula 2a (i.e. compounds of Formula 2a wherein the amino group is replaced with halogen) in the presence of a copper or palladium catalyst. This method is shown in Step A of Synthesis Example 2.

Compounds of Formula 2 can also be prepared in a variety of ways known in the art; see, for example, Patai, S. *The Chemistry of Functional Groups: The Chemistry of Amidines and Imidates*; Wiley: Chichester, UK, 1975; *The Chemistry of Amidines and Imidates*; Patai, S.; Rappoport, Z., Eds.; Wiley: Chichester, UK, 1991; Vol. 2; Mega, T. et al. *Bulletin of the Chemical Society of Japan* 1988, 61(12), 4315-4321; Ife, R. et al. *European Journal of Medicinal Chemistry* 1989, 24(3), 249-257; Wagaw, S.; Buchwald, S. *Journal of Organic Chemistry* 1996, 61(21), 7240-7241; Shen, Q. et al. *Angewandte Chemie, International Edition* 2005, 44(9), 1371-1375; and Okano, K. et al. *Organic Letters* 2003, 5(26), 4987-4990.

Scheme 13

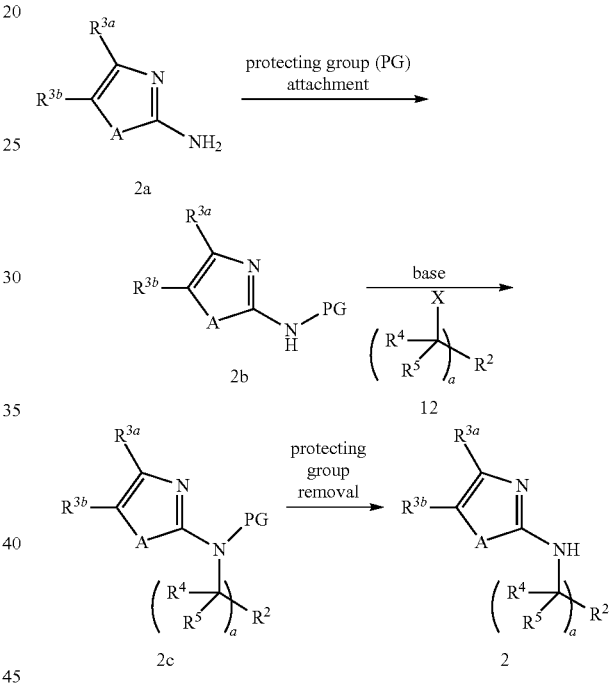

Compounds of Formula 1a wherein Z is O can be prepared by reaction of appropriately substituted alcohols (e.g., alkyl alcohols or phenols) with compounds of Formula 1c in the presence of a Cu source (the Ullmann reaction; for example, see Hayashi, S.; Nakanishi, W. *Bulletin of the Chemical Society of Japan* 2008, 81(12), 1605-1615). This Cu-catalyzed reaction is typically performed at room temperature to 200° C., more typically at 100 to 150° C., and in a solvent such as N,N-dimethylformamide or N-methylpyrrolidinone. Alternatively, this method can be performed in the presence of a Pd source (for example, see Buchwald, S. et al. *Angew. Chem. Int. Ed.* 2006, 45, 1-7. This Pd-catalyzed reaction is typically performed at room temperature to 200° C., more typically at 100 to 150° C., and in the presence of a base such as $K_3PO_4$, and in the presence of a ligand such as 2-di-tert-butylphosphino-2',4',6'-triisopropylbiphenyl (i.e. di-t-BuXphos) in an inert solvent such as toluene.

Compounds of Formula 1a wherein Z is $NR^6$ can be prepared by reaction of appropriately substituted amines (e.g., alkyl amines or anilines) with compounds of Formula 1c in the presence of a Cu source (the Ullmann reaction; for example, see Xu, H.; Yin, K.; Huang, W. *Chemistry—A European Journal* 2007, 13(36), 10281-10293). This Cu-catalyzed reaction is typically performed at room temperature to 200° C., more typically at 100 to 150° C., and in a solvent such as N,N-dimethylformamide or N-methylpyrrolidinone. Alternatively, this method can be performed in the presence of a Pd source (for example, see Uchiyama, M. et al. *J. Am. Chem. Soc.* 2004, 126(28), 8755-8759). This Pd-catalyzed reaction is typically performed at room temperature to 200° C., more typically at 100 to 150° C., in an inert solvent such as toluene, and in the presence of a base such as NaO-t-Bu.

Compounds of Formula 1 wherein X and/or Y are S can be prepared from corresponding compounds of Formula 1a by general methods known in the art involving treatment with thionating reagents such as $P_4S_{10}$ or Lawessen's Reagent (2,4-bis-(4-methoxyphenyl)-1,3-dithia-2,4-diphosphetane 2,4-disulfide). Alternatively, malonic acids of Formula 3a can be treated with $P_2S_6(CH_3)_2$ as described in *J. Am. Chem. Soc.* 1988, 110 (4), 1316-1318. The resulting malonic acid sulfur derivatives can then be used to prepare the compounds of Formula 1 wherein X and/or Y are S by the method of Scheme 1.

Schemes 1 through 13 illustrate methods to prepare compounds of Formula 1 having a variety of substituents noted for $R^1$, $R^2$, $R^{3a}$, $R^{3b}$, $R^4$, $R^5$, X, Y, Z and A. Compounds of Formula 1 having $R^1$, $R^2$, $R^{3a}$, $R^{3b}$, $R^4$, $R^5$, X, Y, Z and A substituents other than those particularly noted for Schemes 1 through 13 can be prepared by general methods known in the art of synthetic organic chemistry, including methods analogous to those described for Schemes 1 to 13.

Examples of intermediates useful in the preparation of compounds of this invention are shown in Tables I-1 through I-30. The following abbreviations are used in the Tables which follow: Me means methyl, Et means ethyl, Pr means propyl, Ph means phenyl, C(O)O(2,4,6-trichlorophenyl) means

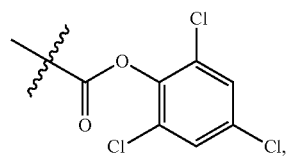

C(O)O(4-nitrophenyl) means

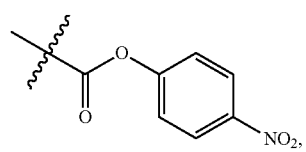 [SMILES: *C(=O)Oc1ccc([N+](=O)[O-])cc1]

and
C(O)(3-methyl-2-pyridinylamino) means

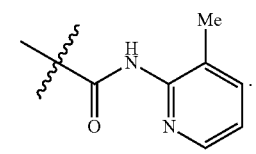 [SMILES: *C(=O)Nc1ncccc1C]

TABLE I-1

$R^x$ is C(O)OH; $R^y$ is H; $R^b$, $R^c$, $R^d$ and $R^e$ are H

| $R^a$ | $R^a$ | $R^a$ | $R^a$ |
|---|---|---|---|
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O-n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N-Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE I-1-continued

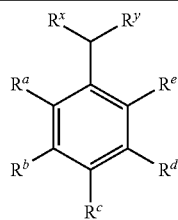

| R$^x$ is C(O)OH; R$^y$ is H; R$^a$, R$^c$, R$^d$ and R$^e$ are H | | | |
|---|---|---|---|
| R$^b$ | R$^b$ | R$^b$ | R$^b$ |
| H | O—i-Pr | 3-(CF$_3$)phenyl | 2-fluoro-4-cyanophenyl |
| F | OCH$_2$CH═CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(═NOMe)Me | 3-chloro-5-fluorophenyl | N-Me-4-pyrazolyl |
| CH═CH$_2$ | C(═NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| R$^x$ is C(O)OH; R$^y$ is H; R$^a$, R$^b$, R$^d$ and R$^e$ are H | | | |
|---|---|---|---|
| R$^c$ | R$^c$ | R$^c$ | R$^c$ |
| H | O—i-Pr | 3-(CF$_3$)phenyl | 2-fluoro-4-cyanophenyl |
| F | OCH$_2$CH═CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(═NOMe)Me | 3-chloro-5-fluorophenyl | N-Me-4-pyrazolyl |
| CH═CH$_2$ | C(═NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| R$^x$ is C(O)OH; R$^y$ is H; R$^a$ is F; R$^c$, R$^d$ and R$^e$ are H | | | |
|---|---|---|---|
| R$^b$ | R$^b$ | R$^b$ | R$^b$ |
| H | O—i-Pr | 3-(CF$_3$)phenyl | 2-fluoro-4-cyanophenyl |
| F | OCH$_2$CH═CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |

TABLE I-1-continued

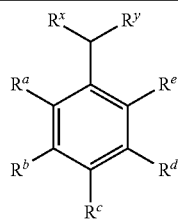

| | | | |
|---|---|---|---|
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

R$^x$ is C(O)OH; R$^y$ is H; R$^a$ is F; R$^b$, R$^d$ and R$^e$ are H

| R$^c$ | R$^c$ | R$^c$ | R$^c$ |
|---|---|---|---|
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

R$^x$ is C(O)OH; R$^y$ is H; R$^a$ is F; R$^b$, R$^c$ and R$^e$ are H

| R$^d$ | R$^d$ | R$^d$ | R$^d$ |
|---|---|---|---|
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

R$^x$ is C(O)OH; R$^y$ is H; R$^a$ is F; R$^b$, R$^c$ and R$^d$ are H

| R$^e$ | R$^e$ | R$^e$ | R$^e$ |
|---|---|---|---|
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |

TABLE I-1-continued

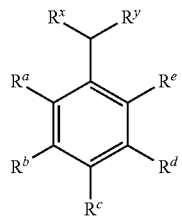

| | | | |
|---|---|---|---|
| I | OCF₃ | 4-fluorophenyl | 2,4-bis(CF₃)phenyl |
| Me | OCHF₂ | 4-chlorophenyl | 2-fluoro-4-bromophenyl |
| Et | OCH₂CF₃ | 4-(CF₃)phenyl | 2-chloro-4-fluorophenyl |
| Pr | SCF₃ | 4-cyanophenyl | 2-(CF₃)-4-fluorophenyl |
| i-Pr | SCF₃ | 4-bromophenyl | 2-methyl-4-(CF₃)phenyl |
| c-Pr | SCHF₂ | 6-chloro-3-pyridinyl | 2-chloro-4-(CF₃)phenyl |
| t-Bu | S(O)CF₃ | 6-fluoro-3-pyridinyl | 2-(CF₃)-4-chlorophenyl |
| CF₃ | SO₂CF₃ | 6-(CF₃)-3-pyridinyl | 2,5-difluorophenyl |
| CH₂F | CO₂Me | 4,6-dichloro-3-pyridinyl | 2-fluoro-5-(CF₃)phenyl |
| CHF₂ | CO₂Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF₃)phenyl |
| O-n-Pr | C(O)NMe₂ | 3-bromo-5-fluorophenyl | 2-chloro-5-(CF₃)phenyl |
| OPh | C(=NOMe)Me | 3-chloro-5-fluorophenyl | N-Me-4-pyrazolyl |
| CH=CH₂ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^a$ is Cl; $R^c$, $R^d$ and $R^e$ are H | | | |
|---|---|---|---|
| $R^b$ | $R^b$ | $R^b$ | $R^b$ |
| H | O—i-Pr | 3-(CF₃)phenyl | 2-fluoro-4-cyanophenyl |
| F | OCH₂CH=CH2 | 3-fluorophenyl | 2-fluoro-4-chlorophenyl |
| Cl | OCH₂C≡CH | 3-cyanophenyl | 2-methyl-4-chlorophenyl |
| Br | O—c-Pr | 3-(OCF₃)phenyl | 2-fluoro-4-(CF₃)phenyl |
| I | OCF₃ | 4-fluorophenyl | 2,4-bis(CF₃)phenyl |
| Me | OCHF₂ | 4-chlorophenyl | 2-fluoro-4-bromophenyl |
| Et | OCH₂CF₃ | 4-(CF₃)phenyl | 2-chloro-4-fluorophenyl |
| Pr | SCF₃ | 4-cyanophenyl | 2-(CF₃)-4-fluorophenyl |
| i-Pr | SCF₃ | 4-bromophenyl | 2-methyl-4-(CF₃)phenyl |
| c-Pr | SCHF₂ | 6-chloro-3-pyridinyl | 2-chloro-4-(CF₃)phenyl |
| t-Bu | S(O)CF₃ | 6-fluoro-3-pyridinyl | 2-(CF₃)-4-chlorophenyl |
| CF₃ | SO₂CF₃ | 6-(CF₃)-3-pyridinyl | 2,5-difluorophenyl |
| CH₂F | CO₂Me | 4,6-dichloro-3-pyridinyl | 2-fluoro-5-(CF₃)phenyl |
| CHF₂ | CO₂Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF₃)phenyl |
| O-n-Pr | C(O)NMe₂ | 3-bromo-5-fluorophenyl | 2-chloro-5-(CF₃)phenyl |
| OPh | C(=NOMe)Me | 3-chloro-5-fluorophenyl | N-Me-4-pyrazolyl |
| CH=CH₂ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^a$ is Cl; $R^b$, $R^d$ and $R^e$ are H | | | |
|---|---|---|---|
| $R^c$ | $R^c$ | $R^c$ | $R^c$ |
| H | O—i-Pr | 3-(CF₃)phenyl | 2-fluoro-4-cyanophenyl |
| F | OCH₂CH=CH2 | 3-fluorophenyl | 2-fluoro-4-chlorophenyl |
| Cl | OCH₂C≡CH | 3-cyanophenyl | 2-methyl-4-chlorophenyl |
| Br | O—c-Pr | 3-(OCF₃)phenyl | 2-fluoro-4-(CF₃)phenyl |
| I | OCF₃ | 4-fluorophenyl | 2,4-bis(CF₃)phenyl |
| Me | OCHF₂ | 4-chlorophenyl | 2-fluoro-4-bromophenyl |
| Et | OCH₂CF₃ | 4-(CF₃)phenyl | 2-chloro-4-fluorophenyl |
| Pr | SCF₃ | 4-cyanophenyl | 2-(CF₃)-4-fluorophenyl |
| i-Pr | SCF₃ | 4-bromophenyl | 2-methyl-4-(CF₃)phenyl |
| c-Pr | SCHF₂ | 6-chloro-3-pyridinyl | 2-chloro-4-(CF₃)phenyl |
| t-Bu | S(O)CF₃ | 6-fluoro-3-pyridinyl | 2-(CF₃)-4-chlorophenyl |
| CF₃ | SO₂CF₃ | 6-(CF₃)-3-pyridinyl | 2,5-difluorophenyl |
| CH₂F | CO₂Me | 4,6-dichloro-3-pyridinyl | 2-fluoro-5-(CF₃)phenyl |
| CHF₂ | CO₂Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF₃)phenyl |
| O-n-Pr | C(O)NMe₂ | 3-bromo-5-fluorophenyl | 2-chloro-5-(CF₃)phenyl |
| OPh | C(=NOMe)Me | 3-chloro-5-fluorophenyl | N-Me-4-pyrazolyl |
| CH=CH₂ | C(=NOEt)Me | 3-fluoro-4-chlorophenyl | 3-Me-5-isoxazolyl |

TABLE I-1-continued

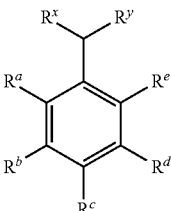

| | | | |
|---|---|---|---|
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^a$ is Cl; $R^b$, $R^c$ and $R^e$ are H | | | |
|---|---|---|---|
| $R^d$ | $R^d$ | $R^d$ | $R^d$ |
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^a$ is Cl; $R^b$, $R^c$ and $R^d$ are H | | | |
|---|---|---|---|
| $R^e$ | $R^e$ | $R^e$ | $R^e$ |
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^a$ is OMe; $R^c$, $R^d$ and $R^e$ are H | | | |
|---|---|---|---|
| $R^b$ | $R^b$ | $R^b$ | $R^b$ |
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |

TABLE I-1-continued

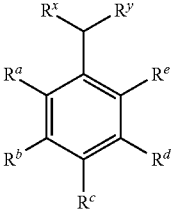

| | | | |
|---|---|---|---|
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^a$ is OMe; $R^b$, $R^d$ and $R^e$ are H | | | |
|---|---|---|---|
| $R^c$ | $R^c$ | $R^c$ | $R^c$ |
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^a$ is OMe; $R^b$, $R^c$ and $R^e$ are H | | | |
|---|---|---|---|
| $R^d$ | $R^d$ | $R^d$ | $R^d$ |
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE I-1-continued

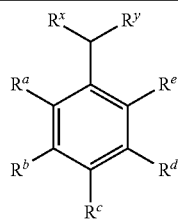

| $R^x$ is C(O)OH; $R^y$ is H; $R^a$ is OMe; $R^b$, $R^c$ and $R^d$ are H ||||
|---|---|---|---|
| $R^e$ | $R^e$ | $R^e$ | $R^e$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O-n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N-Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^a$ is Me; $R^c$, $R^d$ and $R^e$ are H ||||
|---|---|---|---|
| $R^b$ | $R^b$ | $R^b$ | $R^b$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O-n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N-Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^a$ is Me; $R^b$, $R^d$ and $R^e$ are H ||||
|---|---|---|---|
| $R^c$ | $R^c$ | $R^c$ | $R^c$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |

TABLE I-1-continued

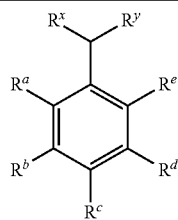

| | | | |
|---|---|---|---|
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| R$^x$ is C(O)OH; R$^y$ is H; R$^a$ is Me; R$^b$, R$^c$ and R$^e$ are H | | | |
|---|---|---|---|
| R$^d$ | R$^d$ | R$^d$ | R$^d$ |
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| R$^x$ is C(O)OH; R$^y$ is H; R$^a$ is Me; R$^b$, R$^c$ and R$^d$ are H | | | |
|---|---|---|---|
| R$^e$ | R$^e$ | R$^e$ | R$^e$ |
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| R$^x$ is C(O)OH; R$^y$ is H; R$^d$ is Cl; R$^a$, R$^c$ and R$^e$ are H | | | |
|---|---|---|---|
| R$^b$ | R$^b$ | R$^b$ | R$^b$ |
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |

TABLE I-1-continued

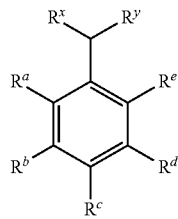

| | | | |
|---|---|---|---|
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

R$^x$ is C(O)OH; R$^y$ is H; R$^d$ is CF$_3$; R$^a$, R$^c$ and R$^e$ are H

| R$^b$ | R$^b$ | R$^b$ | R$^b$ |
|---|---|---|---|
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

R$^x$ is C(O)OH; R$^y$ is H; R$^b$ is Br; R$^a$, R$^c$ and R$^e$ are H

| R$^d$ | R$^d$ | R$^d$ | R$^d$ |
|---|---|---|---|
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |

TABLE I-1-continued

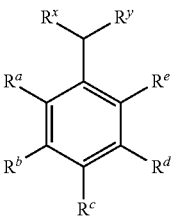

| | | | |
|---|---|---|---|
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^b$ is OCF$_3$; $R^a$, $R^c$ and $R^e$ are H | | | |
|---|---|---|---|
| $R^d$ | $R^d$ | $R^d$ | $R^d$ |
| H | O—i-Pr | 3-(CF$_3$)phenyl | 2-fluoro-4-cyanophenyl |
| F | OCH$_2$CH═CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(═NOMe)Me | 3-chloro-5-fluorophenyl | N-Me-4-pyrazolyl |
| CH═CH$_2$ | C(═NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^b$ is OMe; $R^a$, $R^c$ and $R^e$ are H | | | |
|---|---|---|---|
| $R^d$ | $R^d$ | $R^d$ | $R^d$ |
| H | O—i-Pr | 3-(CF$_3$)phenyl | 2-fluoro-4-cyanophenyl |
| F | OCH$_2$CH═CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(═NOMe)Me | 3-chloro-5-fluorophenyl | N-Me-4-pyrazolyl |
| CH═CH$_2$ | C(═NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^b$ is F; $R^a$, $R^c$ and $R^e$ are H | | | |
|---|---|---|---|
| $R^d$ | $R^d$ | $R^d$ | $R^d$ |
| H | O—i-Pr | 3-(CF$_3$)phenyl | 2-fluoro-4-cyanophenyl |
| F | OCH$_2$CH═CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |

TABLE I-1-continued

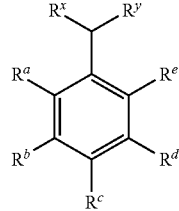

| | | | |
|---|---|---|---|
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| R$^x$ is C(O)OH; R$^y$ is H; R$^b$ is CN; R$^a$, R$^c$ and R$^e$ are H | | | |
|---|---|---|---|
| R$^d$ | R$^d$ | R$^d$ | R$^d$ |
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| R$^x$ is C(O)OH; R$^y$ is H; R$^b$ is Me; R$^a$, R$^c$ and R$^e$ are H | | | |
|---|---|---|---|
| R$^d$ | R$^d$ | R$^d$ | R$^d$ |
| H | O—i-Pr | 3-(CF$_3$)phenyl | 2-fluoro-4-cyanophenyl |
| F | OCH$_2$CH=CH2 | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O-n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N-Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE I-1-continued

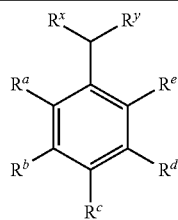

| $R^x$ is C(O)OH; $R^y$ is H; $R^b$ is I; $R^a$, $R^c$ and $R^e$ are H | | | |
|---|---|---|---|
| $R^d$ | $R^d$ | $R^d$ | $R^d$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O-n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N-Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^a$ and $R^b$ are F; $R^c$ and $R^e$ are H | | | |
|---|---|---|---|
| $R^d$ | $R^d$ | $R^d$ | $R^d$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O-n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N-Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^a$ is F; $R^b$ is Cl; $R^c$ and $R^e$ are H | | | |
|---|---|---|---|
| $R^d$ | $R^d$ | $R^d$ | $R^d$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |

TABLE I-1-continued

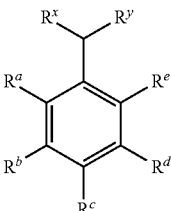

| | | | |
|---|---|---|---|
| CHF₂ | CO₂Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF₃)phenyl |
| O-n-Pr | C(O)NMe₂ | 3-bromo-5-fluorophenyl | 2-chloro-5-(CF₃)phenyl |
| OPh | C(=NOMe)Me | 3-chloro-5-fluorophenyl | N-Me-4-pyrazolyl |
| CH=CH₂ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

$R^x$ is C(O)OH; $R^y$ is H; $R^c$ is OMe; $R^a$, $R^b$ and $R^e$ are H

| $R^d$ | $R^d$ | $R^d$ | $R^d$ |
|---|---|---|---|
| H | O—i-Pr | 3-(CF₃)phenyl | 2-fluoro-4-cyanophenyl |
| F | OCH₂CH=CH2 | 3-fluorophenyl | 2-fluoro-4-chlorophenyl |
| Cl | OCH₂C≡CH | 3-cyanophenyl | 2-methyl-4-chlorophenyl |
| Br | O—c-Pr | 3-(OCF₃)phenyl | 2-fluoro-4-(CF₃)phenyl |
| I | OCF₃ | 4-fluorophenyl | 2,4-bis(CF₃)phenyl |
| Me | OCHF₂ | 4-chlorophenyl | 2-fluoro-4-bromophenyl |
| Et | OCH₂CF₃ | 4-(CF₃)phenyl | 2-chloro-4-fluorophenyl |
| Pr | SCF₃ | 4-cyanophenyl | 2-(CF₃)-4-fluorophenyl |
| i-Pr | SCF₃ | 4-bromophenyl | 2-methyl-4-(CF₃)phenyl |
| c-Pr | SCHF₂ | 6-chloro-3-pyridinyl | 2-chloro-4-(CF₃)phenyl |
| t-Bu | S(O)CF₃ | 6-fluoro-3-pyridinyl | 2-(CF₃)-4-chlorophenyl |
| CF₃ | SO₂CF₃ | 6-(CF₃)-3-pyridinyl | 2,5-difluorophenyl |
| CH₂F | CO₂Me | 4,6-dichloro-3-pyridinyl | 2-fluoro-5-(CF₃)phenyl |
| CHF₂ | CO₂Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF₃)phenyl |
| O-n-Pr | C(O)NMe₂ | 3-bromo-5-fluorophenyl | 2-chloro-5-(CF₃)phenyl |
| OPh | C(=NOMe)Me | 3-chloro-5-fluorophenyl | N-Me-4-pyrazolyl |
| CH=CH₂ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

$R^x$ is C(O)OH; $R^y$ is H; $R^c$ is Me; $R^a$, $R^b$ and $R^e$ are H

| $R^d$ | $R^d$ | $R^d$ | $R^d$ |
|---|---|---|---|
| H | O—i-Pr | 3-(CF₃)phenyl | 2-fluoro-4-cyanophenyl |
| F | OCH₂CH=CH2 | 3-fluorophenyl | 2-fluoro-4-chlorophenyl |
| Cl | OCH₂C≡CH | 3-cyanophenyl | 2-methyl-4-chlorophenyl |
| Br | O—c-Pr | 3-(OCF₃)phenyl | 2-fluoro-4-(CF₃)phenyl |
| I | OCF₃ | 4-fluorophenyl | 2,4-bis(CF₃)phenyl |
| Me | OCHF₂ | 4-chlorophenyl | 2-fluoro-4-bromophenyl |
| Et | OCH₂CF₃ | 4-(CF₃)phenyl | 2-chloro-4-fluorophenyl |
| Pr | SCF₃ | 4-cyanophenyl | 2-(CF₃)-4-fluorophenyl |
| i-Pr | SCF₃ | 4-bromophenyl | 2-methyl-4-(CF₃)phenyl |
| c-Pr | SCHF₂ | 6-chloro-3-pyridinyl | 2-chloro-4-(CF₃)phenyl |
| t-Bu | S(O)CF₃ | 6-fluoro-3-pyridinyl | 2-(CF₃)-4-chlorophenyl |
| CF₃ | SO₂CF₃ | 6-(CF₃)-3-pyridinyl | 2,5-difluorophenyl |
| CH₂F | CO₂Me | 4,6-dichloro-3-pyridinyl | 2-fluoro-5-(CF₃)phenyl |
| CHF₂ | CO₂Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF₃)phenyl |
| O-n-Pr | C(O)NMe₂ | 3-bromo-5-fluorophenyl | 2-chloro-5-(CF₃)phenyl |
| OPh | C(=NOMe)Me | 3-chloro-5-fluorophenyl | N-Me-4-pyrazolyl |
| CH=CH₂ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

$R^x$ is C(O)OH; $R^y$ is H; $R^c$ is F; $R^a$, $R^b$ and $R^e$ are H

| $R^d$ | $R^d$ | $R^d$ | $R^d$ |
|---|---|---|---|
| H | O—i-Pr | 3-(CF₃)phenyl | 2-fluoro-4-cyanophenyl |
| F | OCH₂CH=CH2 | 3-fluorophenyl | 2-fluoro-4-chlorophenyl |
| Cl | OCH₂C≡CH | 3-cyanophenyl | 2-methyl-4-chlorophenyl |
| Br | O—c-Pr | 3-(OCF₃)phenyl | 2-fluoro-4-(CF₃)phenyl |

TABLE I-1-continued

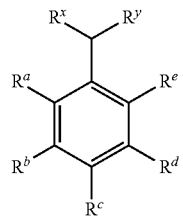

| | | | |
|---|---|---|---|
| I | OCF₃ | 4-fluorophenyl | 2,4-bis(CF₃)phenyl |
| Me | OCHF₂ | 4-chlorophenyl | 2-fluoro-4-bromophenyl |
| Et | OCH₂CF₃ | 4-(CF₃)phenyl | 2-chloro-4-fluorophenyl |
| Pr | SCF₃ | 4-cyanophenyl | 2-(CF₃)-4-fluorophenyl |
| i-Pr | SCF₃ | 4-bromophenyl | 2-methyl-4-(CF₃)phenyl |
| c-Pr | SCHF₂ | 6-chloro-3-pyridinyl | 2-chloro-4-(CF₃)phenyl |
| t-Bu | S(O)CF₃ | 6-fluoro-3-pyridinyl | 2-(CF₃)-4-chlorophenyl |
| CF₃ | SO₂CF₃ | 6-(CF₃)-3-pyridinyl | 2,5-difluorophenyl |
| CH₂F | CO₂Me | 4,6-dichloro-3-pyridinyl | 2-fluoro-5-(CF₃)phenyl |
| CHF₂ | CO₂Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF₃)phenyl |
| O-n-Pr | C(O)NMe₂ | 3-bromo-5-fluorophenyl | 2-chloro-5-(CF₃)phenyl |
| OPh | C(=NOMe)Me | 3-chloro-5-fluorophenyl | N-Me-4-pyrazolyl |
| CH=CH₂ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^c$ is Cl; $R^a$, $R^b$ and $R^e$ are H | | | |
|---|---|---|---|
| $R^d$ | $R^d$ | $R^d$ | $R^d$ |
| H | O—i-Pr | 3-(CF₃)phenyl | 2-fluoro-4-cyanophenyl |
| F | OCH₂CH=CH2 | 3-fluorophenyl | 2-fluoro-4-chlorophenyl |
| Cl | OCH₂C≡CH | 3-cyanophenyl | 2-methyl-4-chlorophenyl |
| Br | O—c-Pr | 3-(OCF₃)phenyl | 2-fluoro-4-(CF₃)phenyl |
| I | OCF₃ | 4-fluorophenyl | 2,4-bis(CF₃)phenyl |
| Me | OCHF₂ | 4-chlorophenyl | 2-fluoro-4-bromophenyl |
| Et | OCH₂CF₃ | 4-(CF₃)phenyl | 2-chloro-4-fluorophenyl |
| Pr | SCF₃ | 4-cyanophenyl | 2-(CF₃)-4-fluorophenyl |
| i-Pr | SCF₃ | 4-bromophenyl | 2-methyl-4-(CF₃)phenyl |
| c-Pr | SCHF₂ | 6-chloro-3-pyridinyl | 2-chloro-4-(CF₃)phenyl |
| t-Bu | S(O)CF₃ | 6-fluoro-3-pyridinyl | 2-(CF₃)-4-chlorophenyl |
| CF₃ | SO₂CF₃ | 6-(CF₃)-3-pyridinyl | 2,5-difluorophenyl |
| CH₂F | CO₂Me | 4,6-dichloro-3-pyridinyl | 2-fluoro-5-(CF₃)phenyl |
| CHF₂ | CO₂Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF₃)phenyl |
| O-n-Pr | C(O)NMe₂ | 3-bromo-5-fluorophenyl | 2-chloro-5-(CF₃)phenyl |
| OPh | C(=NOMe)Me | 3-chloro-5-fluorophenyl | N-Me-4-pyrazolyl |
| CH=CH₂ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^x$ is C(O)OH; $R^y$ is H; $R^a$ and $R^e$ are F; $R^c$ and $R^d$ are H | | | |
|---|---|---|---|
| $R^b$ | $R^b$ | $R^b$ | $R^b$ |
| H | O—i-Pr | 3-(CF₃)phenyl | 2-fluoro-4-cyanophenyl |
| F | OCH₂CH=CH2 | 3-fluorophenyl | 2-fluoro-4-chlorophenyl |
| Cl | OCH₂C≡CH | 3-cyanophenyl | 2-methyl-4-chlorophenyl |
| Br | O—c-Pr | 3-(OCF₃)phenyl | 2-fluoro-4-(CF₃)phenyl |
| I | OCF₃ | 4-fluorophenyl | 2,4-bis(CF₃)phenyl |
| Me | OCHF₂ | 4-chlorophenyl | 2-fluoro-4-bromophenyl |
| Et | OCH₂CF₃ | 4-(CF₃)phenyl | 2-chloro-4-fluorophenyl |
| Pr | SCF₃ | 4-cyanophenyl | 2-(CF₃)-4-fluorophenyl |
| i-Pr | SCF₃ | 4-bromophenyl | 2-methyl-4-(CF₃)phenyl |
| c-Pr | SCHF₂ | 6-chloro-3-pyridinyl | 2-chloro-4-(CF₃)phenyl |
| t-Bu | S(O)CF₃ | 6-fluoro-3-pyridinyl | 2-(CF₃)-4-chlorophenyl |
| CF₃ | SO₂CF₃ | 6-(CF₃)-3-pyridinyl | 2,5-difluorophenyl |
| CH₂F | CO₂Me | 4,6-dichloro-3-pyridinyl | 2-fluoro-5-(CF₃)phenyl |
| CHF₂ | CO₂Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF₃)phenyl |
| O-n-Pr | C(O)NMe₂ | 3-bromo-5-fluorophenyl | 2-chloro-5-(CF₃)phenyl |
| OPh | C(=NOMe)Me | 3-chloro-5-fluorophenyl | N-Me-4-pyrazolyl |
| CH=CH₂ | C(=NOEt)Me | 3-fluoro-4-chlorophenyl | 3-Me-5-isoxazolyl |

TABLE I-1-continued

| | | | |
|---|---|---|---|
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

Table I-2

Table I-2 is identical to Table I-1, except that $R^x$ is C(O)OMe.

Table I-3

Table I-3 is identical to Table I-1, except that $R^x$ is C(O)OEt.

Table I-4

Table I-4 is identical to Table I-1, except that $R^x$ is C(O)OPh.

Table I-5

Table I-5 is identical to Table I-1, except that $R^x$ is C(O)OC(CH₃)₃.

Table I-5a

Table I-5a is identical to Table I-1, except that $R^x$ is C(O)O(2,4,6-trichlorophenyl).

Table I-5b

Table I-5b is identical to Table I-1, except that $R^x$ is C(O)O(4-nitrophenyl).

Table I-6

Table I-6 is identical to Table I-1, except that $R^x$ is C(O)OH and $R^y$ is C(O)OH.

Table I-7

Table I-7 is identical to Table I-1, except that $R^x$ is C(O)OH and $R^y$ is C(O)OMe.

Table I-8

Table I-8 is identical to Table I-1, except that $R^x$ is C(O)OH and $R^y$ is C(O)OEt.

Table I-9

Table I-9 is identical to Table I-1, except that $R^x$ is C(O)OH and $R^y$ is C(O)OC(CH₃)₃.

Table I-10

Table I-10 is identical to Table I-1, except that $R^x$ is C(O)OH and $R^y$ is C(O)OPh.

Table I-10a

Table I-10a identical to Table I-1, except that $R^x$ is C(O)OH and $R^y$ is C(O)O(2,4,6-trichlorophenyl).

Table I-10b

Table I-10b identical to Table I-1, except that $R^x$ is C(O)OH and $R^y$ is C(O)O(4-nitrophenyl).

Table I-11

Table I-11 is identical to Table I-1, except that $R^x$ is C(O)OPh and $R^y$ is C(O)OMe.

Table I-12

Table I-12 is identical to Table I-1, except that $R^x$ is C(O)OPh and $R^y$ is C(O)OEt.

Table I-13

Table I-13 is identical to Table I-1, except that $R^x$ is C(O)OPh and $R^y$ is C(O)OC(CH₃)₃.

Table I-14

Table I-14 is identical to Table I-1, except that $R^x$ is C(O)OPh and $R^y$ is C(O)OPh.

Table I-14a

Table I-14a is identical to Table I-1, except that $R^x$ is C(O)OPh and $R^y$ is C(O)O(2,4,6-trichlorophenyl).

Table I-14b

Table I-14b is identical to Table I-1, except that $R^x$ is C(O)OPh and $R^y$ is C(O)O(4-nitrophenyl).

Table I-15

Table I-15 is identical to Table I-1, except that $R^x$ is C(O)Cl and $R^y$ is C(O)Cl.

Table I-16

Table I-16 is identical to Table I-1, except that $R^x$ is C(O)OMe and $R^y$ is C(O)OMe.

Table I-17

Table I-17 is identical to Table I-1, except that $R^x$ is C(O)OEt and $R^y$ is C(O)OEt.

Table I-18

Table I-18 is identical to Table I-1, except that $R^x$ is C(O)OC(CH$_3$)$_3$ and $R^y$ is C(O)OC(CH$_3$)$_3$.

Table I-19

Table I-19 is identical to Table I-1, except that $R^x$ is C(O)O(2,4,6-trichlorophenyl) and $R^y$ is C(O)O(2,4,6-trichlorophenyl).

Table I-19a

Table I-19a is identical to Table I-1, except that $R^x$ is C(O)O(4-nitrophenyl) and $R^y$ is C(O)O(4-nitrophenyl).

Table I-20

Table I-20 is identical to Table I-1, except that $R^x$ is C(O)(3-methyl-2-pyridinylamino) and $R^y$ is C(O)OH.

Table I-21

Table I-21 is identical to Table I-1, except that $R^x$ is C(O)(3-methyl-2-pyridinylamino) and $R^y$ is C(O)OMe.

Table I-22

Table I-22 is identical to Table I-1, except that $R^x$ is C(O)(3-methyl-2-pyridinylamino) and $R^y$ is C(O)OEt.

Table I-23

Table I-23 is identical to Table I-1, except that $R^x$ is C(O)(3-methyl-2-pyridinylamino) and $R^y$ is C(O)OPh.

Table I-23a

Table 1-23a is identical to Table I-1, except that $R^x$ is C(O)(3-methyl-2-pyridinylamino) and $R^y$ is C(O)O(2,4,6-trichlorophenyl).

Table I-23b

Table I-23b is identical to Table I-1, except that $R^x$ is C(O)(3-methyl-2-pyridinylamino) and $R^y$ is C(O)O(4-nitrophenyl).

Table I-24

Table I-24 is identical to Table I-1, except that $R^x$ is C(O)(3-methyl-2-pyridinylamino) and $R^y$ is C(O)OC(CH$_3$)$_3$.

Table I-24a

Table I-24a is identical to Table I-1, except that the chemical structure under the Table I-24a heading is replaced with the following structure, and R is Cl. The groups $R^x$ and $R^y$ found in Table I-1 are not relevant to Table I-24a, as the CH($R^x$)($R^y$) moiety in the structure of Table I-1 is replaced with a R group in the structure of Table I-24a.

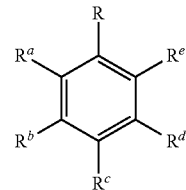

For example, the first compound in Table I-24a is the structure shown immediately above wherein $R^a$, $R^b$, $R^c$, $R^d$ and $R^e$ are H, and R is Cl.

Table I-24b

Table I-24b is identical to Table I-24a, except that R is Br.

Table I-24c

Table I-24c is identical to Table I-24a, except that R is I.

Table I-24d

Table I-24d is identical to Table I-24a, except that R is CH$_2$OH.

Table I-24e

Table I-24e is identical to Table I-24a, except that R is CH$_2$CN.

Table I-24f

Table I-24f is identical to Table I-24a, except that R is CH$_2$Cl.

Table I-24g

Table I-24g is identical to Table I-24a, except that R is CH(CN)CO$_2$Me.

Table I-24h

Table I-24h is identical to Table I-24a, except that R is CH(CN)CO$_2$Et.

TABLE I-25

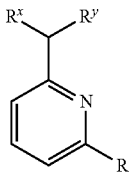

| $R^x$ | $R^y$ |
|---|---|
| R is CF$_3$ | |
| H | C(O)O(2,4,6-trichlorophenyl) |
| H | C(O)O(4-nitrophenyl) |
| C(O)OH | C(O)O(4-nitrophenyl) |

TABLE I-25-continued

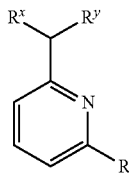

| $R^x$ | $R^y$ |
|---|---|
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is H | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is Cl | |
| H | C(O)O(2,4,6-trichlorophenyl) |
| H | C(O)O(4-nitrophenyl) |

TABLE I-25-continued

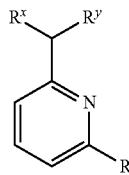

| $R^x$ | $R^y$ |
|---|---|
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is Br | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |

TABLE I-25-continued

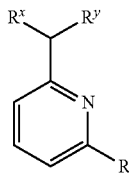

| $R^x$ | $R^y$ |
|---|---|
| R is I | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is NH$_2$ | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is 2-chloro-4-(trifluoromethyl)phenyl | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is 2-fluoro-5-(trifluoromethyl)phenyl | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |

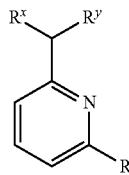

TABLE I-25-continued

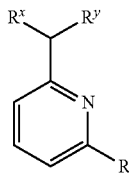

| $R^x$ | $R^y$ |
|---|---|
| H | C(O)OEt |
| H | C(O)OPh |
| H | C(O)OC(CH$_3$)$_3$ |
| R is 2-chloro-4-cyanophenyl | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is 2-fluoro-4-cyanophenyl | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |

TABLE I-25-continued

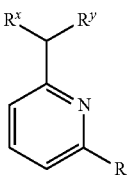

| $R^x$ | $R^y$ |
|---|---|
| H | C(O)OMe |
| H | C(O)OEt |
| H | C(O)OPh |
| H | C(O)OC(CH$_3$)$_3$ |

TABLE I-26

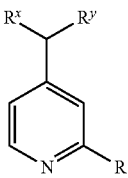

| $R^x$ | $R^y$ |
|---|---|
| R is H | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is CF$_3$ | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |

TABLE I-26-continued

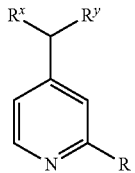

| $R^x$ | $R^y$ |
|---|---|
| C(O)OC(CH₃)₃ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH₃)₃ |
| C(O)Cl | C(O)Cl |
| C(O)OMe | C(O)OMe |
| C(O)OEt | C(O)OEt |
| C(O)OPh | C(O)OPh |
| C(O)OC(CH₃)₃ | C(O)OC(CH₃)₃ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH₃)₃ |

R is F

| H | C(O)O(2,4,6-trichlorophenyl) |
|---|---|
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH₃)₃ | C(O)OPh |
| C(O)OC(CH₃)₃ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH₃)₃ |
| C(O)Cl | C(O)Cl |
| C(O)OMe | C(O)OMe |
| C(O)OEt | C(O)OEt |
| C(O)OPh | C(O)OPh |
| C(O)OC(CH₃)₃ | C(O)OC(CH₃)₃ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH₃)₃ |

R is Cl

| H | C(O)O(2,4,6-trichlorophenyl) |
|---|---|
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |

TABLE I-26-continued

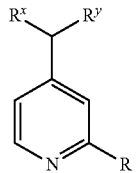

| $R^x$ | $R^y$ |
|---|---|
| C(O)OC(CH₃)₃ | C(O)OPh |
| C(O)OC(CH₃)₃ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH₃)₃ |
| C(O)Cl | C(O)Cl |
| C(O)OMe | C(O)OMe |
| C(O)OEt | C(O)OEt |
| C(O)OPh | C(O)OPh |
| C(O)OC(CH₃)₃ | C(O)OC(CH₃)₃ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH₃)₃ |

R is Br

| H | C(O)O(2,4,6-trichlorophenyl) |
|---|---|
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH₃)₃ | C(O)OPh |
| C(O)OC(CH₃)₃ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH₃)₃ |
| C(O)Cl | C(O)Cl |
| C(O)OMe | C(O)OMe |
| C(O)OEt | C(O)OEt |
| C(O)OPh | C(O)OPh |
| C(O)OC(CH₃)₃ | C(O)OC(CH₃)₃ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH₃)₃ |

R is I

| H | C(O)O(2,4,6-trichlorophenyl) |
|---|---|
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |

TABLE I-26-continued

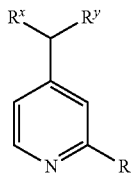

| $R^x$ | $R^y$ |
|---|---|
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is NH$_2$ | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is 2-chloro-4-(trifluoromethyl)phenyl | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |

TABLE I-26-continued

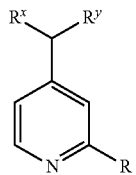

| $R^x$ | $R^y$ |
|---|---|
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is 2-fluoro-5-(trifluoromethyl)phenyl | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH$_3$)$_3$ | C(O)OPh |
| C(O)OC(CH$_3$)$_3$ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH$_3$)$_3$ |
| C(O)Cl | C(O)Cl |
| C(O)OMe | C(O)OMe |
| C(O)OEt | C(O)OEt |
| C(O)OPh | C(O)OPh |
| C(O)OC(CH$_3$)$_3$ | C(O)OC(CH$_3$)$_3$ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH$_3$)$_3$ |
| R is 2-chloro-4-cyanophenyl | |
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |

TABLE I-26-continued

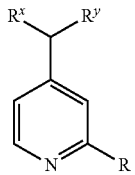

| Rˣ | Rʸ |
|---|---|
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH₃)₃ | C(O)OPh |
| C(O)OC(CH₃)₃ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH₃)₃ |
| C(O)Cl | C(O)Cl |
| C(O)OMe | C(O)OMe |
| C(O)OEt | C(O)OEt |
| C(O)OPh | C(O)OPh |
| C(O)OC(CH₃)₃ | C(O)OC(CH₃)₃ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH₃)₃ |

R is 2-fluoro-4-cyanophenyl

| Rˣ | Rʸ |
|---|---|
| H | C(O)O(2,4,6-trichlorophenyl) |
| H | C(O)O(4-nitrophenyl) |
| C(O)OH | C(O)O(4-nitrophenyl) |
| C(O)OH | C(O)O(2,4,6-trichlorophenyl) |
| C(O)OH | C(O)(3-methyl-2-pyridinylamino) |
| C(O)OMe | C(O)(3-methyl-2-pyridinylamino) |
| C(O)OEt | C(O)(3-methyl-2-pyridinylamino) |
| C(O)OPh | C(O)O(4-nitrophenyl) |
| C(O)OPh | C(O)O(2,4,6-trichlorophenyl) |
| C(O)OPh | C(O)(3-methyl-2-pyridinylamino) |
| C(O)OC(CH₃)₃ | C(O)OPh |
| C(O)OC(CH₃)₃ | C(O)(3-methyl-2-pyridinylamino) |
| C(O)O(4-nitrophenyl) | C(O)O(4-nitrophenyl) |
| C(O)O(4-nitrophenyl) | C(O)(3-methyl-2-pyridinylamino) |
| C(O)O(2,4,6-trichlorophenyl) | C(O)O(2,4,6-trichlorophenyl) |
| C(O)O(2,4,6-trichlorophenyl) | C(O)(3-methyl-2-pyridinylamino) |
| C(O)OH | C(O)OH |
| C(O)OH | C(O)OMe |
| C(O)OH | C(O)OEt |
| C(O)OH | C(O)OPh |
| C(O)OH | C(O)OC(CH₃)₃ |
| C(O)Cl | C(O)Cl |
| C(O)OMe | C(O)OMe |
| C(O)OEt | C(O)OEt |
| C(O)OPh | C(O)OPh |
| C(O)OC(CH₃)₃ | C(O)OC(CH₃)₃ |
| C(O)OMe | C(O)OPh |
| C(O)OEt | C(O)OPh |
| H | C(O)OH |
| H | C(O)OMe |
| H | C(O)OEt |
| H | C(O)OPh |
| H | C(O)OC(CH₃)₃ |

TABLE I-27

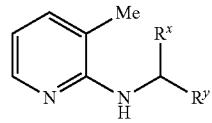

| Rˣ | Rʸ |
|---|---|
| H | CF₃ |
| Me | CF₃ |
| H | Et |
| Me | Et |
| H | 3-pyridinyl |
| Me | 3-pyridinyl |
| H | 6-fluoro-3-pyridinyl |
| Me | 6-fluoro-3-pyridinyl |
| H | 6-bromo-3-pyridinyl |
| Me | 6-bromo-3-pyridinyl |
| H | 2-methyl-5-thiazolyl |
| Me | 2-methyl-5-thiazolyl |
| H | CH₂CHFCF₂Cl |
| Me | CH₂CHFCF₂Cl |
| H | cyclopropyl |
| Me | cyclopropyl |
| H | 6-methyl-3-pyridinyl |
| Me | 6-methyl-3-pyridinyl |
| H | 6-chloro-3-pyridinyl |
| Me | 6-chloro-3-pyridinyl |
| H | 5-thiazolyl |
| Me | 5-thiazolyl |
| H | 2-fluoro-5-thiazolyl |
| Me | 2-fluoro-5-thiazolyl |
| H | 2-chloro-5-thiazolyl |
| Me | 2-chloro-5-thiazolyl |
| H | 1-methyl-4-pyrazolyl |
| Me | 1-methyl-4-pyrazolyl |
| H | 5-pyrimidinyl |
| Me | 5-pyrimidinyl |
| H | 2-bromo-5-thiazolyl |
| Me | 2-bromo-5-thiazolyl |
| H | 3-methyl-5-isoxazolyl |
| Me | 3-methyl-5-isoxazolyl |
| H | 2-methyl-5-pyrimidinyl |
| Me | 2-methyl-5-pyrimidinyl |

TABLE I-27a

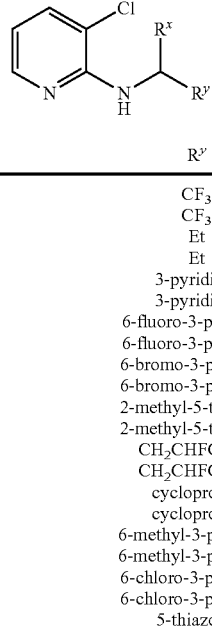

| Rˣ | Rʸ |
|---|---|
| H | CF₃ |
| Me | CF₃ |
| H | Et |
| Me | Et |
| H | 3-pyridinyl |
| Me | 3-pyridinyl |
| H | 6-fluoro-3-pyridinyl |
| Me | 6-fluoro-3-pyridinyl |
| H | 6-bromo-3-pyridinyl |
| Me | 6-bromo-3-pyridinyl |
| H | 2-methyl-5-thiazolyl |
| Me | 2-methyl-5-thiazolyl |
| H | CH₂CHFCF₂Cl |
| Me | CH₂CHFCF₂Cl |
| H | cyclopropyl |
| Me | cyclopropyl |
| H | 6-methyl-3-pyridinyl |
| Me | 6-methyl-3-pyridinyl |
| H | 6-chloro-3-pyridinyl |
| Me | 6-chloro-3-pyridinyl |
| H | 5-thiazolyl |

TABLE I-27a-continued

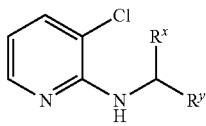

| R$^x$ | R$^y$ |
|---|---|
| Me | 5-thiazolyl |
| H | 2-fluoro-5-thiazolyl |
| Me | 2-fluoro-5-thiazolyl |
| H | 2-chloro-5-thiazolyl |
| Me | 2-chloro-5-thiazolyl |
| H | 1-methyl-4-pyrazolyl |
| Me | 1-methyl-4-pyrazolyl |
| H | 5-pyrimidinyl |
| Me | 5-pyrimidinyl |
| H | 2-bromo-5-thiazolyl |
| Me | 2-bromo-5-thiazolyl |
| H | 3-methyl-5-isoxazolyl |
| Me | 3-methyl-5-isoxazolyl |
| H | 2-methyl-5-pyrimidinyl |
| Me | 2-methyl-5-pyrimidinyl |

TABLE I-27b

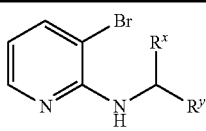

| R$^x$ | R$^y$ |
|---|---|
| H | CF$_3$ |
| Me | CF$_3$ |
| H | Et |
| Me | Et |
| H | 3-pyridinyl |
| Me | 3-pyridinyl |
| H | 6-fluoro-3-pyridinyl |
| Me | 6-fluoro-3-pyridinyl |
| H | 6-bromo-3-pyridinyl |
| Me | 6-bromo-3-pyridinyl |
| H | 2-methyl-5-thiazolyl |
| Me | 2-methyl-5-thiazolyl |
| H | CH$_2$CHFCF$_2$Cl |
| Me | CH$_2$CHFCF$_2$Cl |
| H | cyclopropyl |
| Me | cyclopropyl |
| H | 6-methyl-3-pyridinyl |
| Me | 6-methyl-3-pyridinyl |
| H | 6-chloro-3-pyridinyl |
| Me | 6-chloro-3-pyridinyl |
| H | 5-thiazolyl |
| Me | 5-thiazolyl |
| H | 2-fluoro-5-thiazolyl |
| Me | 2-fluoro-5-thiazolyl |
| H | 2-chloro-5-thiazolyl |
| Me | 2-chloro-5-thiazolyl |
| H | 1-methyl-4-pyrazolyl |
| Me | 1-methyl-4-pyrazolyl |
| H | 5-pyrimidinyl |
| Me | 5-pyrimidinyl |
| H | 2-bromo-5-thiazolyl |
| Me | 2-bromo-5-thiazolyl |
| H | 3-methyl-5-isoxazolyl |
| Me | 3-methyl-5-isoxazolyl |
| H | 2-methyl-5-pyrimidinyl |
| Me | 2-methyl-5-pyrimidinyl |

TABLE I-27c

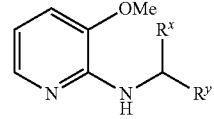

| R$^x$ | R$^y$ |
|---|---|
| H | CF$_3$ |
| Me | CF$_3$ |
| H | Et |
| Me | Et |
| H | 3-pyridinyl |
| Me | 3-pyridinyl |
| H | 6-fluoro-3-pyridinyl |
| Me | 6-fluoro-3-pyridinyl |
| H | 6-bromo-3-pyridinyl |
| Me | 6-bromo-3-pyridinyl |
| H | 2-methyl-5-thiazolyl |
| Me | 2-methyl-5-thiazolyl |
| H | CH$_2$CHFCF$_2$Cl |
| Me | CH$_2$CHFCF$_2$Cl |
| H | cyclopropyl |
| Me | cyclopropyl |
| H | 6-methyl-3-pyridinyl |
| Me | 6-methyl-3-pyridinyl |
| H | 6-chloro-3-pyridinyl |
| Me | 6-chloro-3-pyridinyl |
| H | 5-thiazolyl |
| Me | 5-thiazolyl |
| H | 2-fluoro-5-thiazolyl |
| Me | 2-fluoro-5-thiazolyl |
| H | 2-chloro-5-thiazolyl |
| Me | 2-chloro-5-thiazolyl |
| H | 1-methyl-4-pyrazolyl |
| Me | 1-methyl-4-pyrazolyl |
| H | 5-pyrimidinyl |
| Me | 5-pyrimidinyl |
| H | 2-bromo-5-thiazolyl |
| Me | 2-bromo-5-thiazolyl |
| H | 3-methyl-5-isoxazolyl |
| Me | 3-methyl-5-isoxazolyl |
| H | 2-methyl-5-pyrimidinyl |
| Me | 2-methyl-5-pyrimidinyl |

TABLE I-27d

| R$^x$ | R$^y$ |
|---|---|
| H | CF$_3$ |
| Me | CF$_3$ |
| H | Et |
| Me | Et |
| H | 3-pyridinyl |
| Me | 3-pyridinyl |
| H | 6-fluoro-3-pyridinyl |
| Me | 6-fluoro-3-pyridinyl |
| H | 6-bromo-3-pyridinyl |
| Me | 6-bromo-3-pyridinyl |
| H | 2-methyl-5-thiazolyl |
| Me | 2-methyl-5-thiazolyl |
| H | CH$_2$CHFCF$_2$Cl |
| Me | CH$_2$CHFCF$_2$Cl |
| H | cyclopropyl |
| Me | cyclopropyl |
| H | 6-methyl-3-pyridinyl |
| Me | 6-methyl-3-pyridinyl |

TABLE I-27d-continued

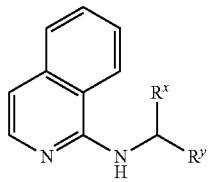

| R$^x$ | R$^y$ |
|---|---|
| H | 6-chloro-3-pyridinyl |
| Me | 6-chloro-3-pyridinyl |
| H | 5-thiazolyl |
| Me | 5-thiazolyl |
| H | 2-fluoro-5-thiazolyl |
| Me | 2-fluoro-5-thiazolyl |
| H | 2-chloro-5-thiazolyl |
| Me | 2-chloro-5-thiazolyl |
| H | 1-methyl-4-pyrazolyl |
| Me | 1-methyl-4-pyrazolyl |
| H | 5-pyrimidinyl |
| Me | 5-pyrimidinyl |
| H | 2-bromo-5-thiazolyl |
| Me | 2-bromo-5-thiazolyl |
| H | 3-methyl-5-isoxazolyl |
| Me | 3-methyl-5-isoxazolyl |
| H | 2-methyl-5-pyrimidinyl |
| Me | 2-methyl-5-pyrimidinyl |

TABLE I-27e

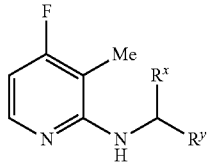

| R$^x$ | R$^y$ |
|---|---|
| H | CF$_3$ |
| Me | CF$_3$ |
| H | Et |
| Me | Et |
| H | 3-pyridinyl |
| Me | 3-pyridinyl |
| H | 6-fluoro-3-pyridinyl |
| Me | 6-fluoro-3-pyridinyl |
| H | 6-bromo-3-pyridinyl |
| Me | 6-bromo-3-pyridinyl |
| H | 2-methyl-5-thiazolyl |
| Me | 2-methyl-5-thiazolyl |
| H | CH$_2$CHFCF$_2$Cl |
| Me | CH$_2$CHFCF$_2$Cl |
| H | cyclopropyl |
| Me | cyclopropyl |
| H | 6-methyl-3-pyridinyl |
| Me | 6-methyl-3-pyridinyl |
| H | 6-chloro-3-pyridinyl |
| Me | 6-chloro-3-pyridinyl |
| H | 5-thiazolyl |
| Me | 5-thiazolyl |
| H | 2-fluoro-5-thiazolyl |
| Me | 2-fluoro-5-thiazolyl |
| H | 2-chloro-5-thiazolyl |
| Me | 2-chloro-5-thiazolyl |
| H | 1-methyl-4-pyrazolyl |
| Me | 1-methyl-4-pyrazolyl |
| H | 5-pyrimidinyl |
| Me | 5-pyrimidinyl |
| H | 2-bromo-5-thiazolyl |
| Me | 2-bromo-5-thiazolyl |
| H | 3-methyl-5-isoxazolyl |
| Me | 3-methyl-5-isoxazolyl |

TABLE I-27e-continued

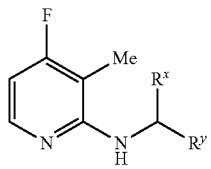

| R$^x$ | R$^y$ |
|---|---|
| H | 2-methyl-5-pyrimidinyl |
| Me | 2-methyl-5-pyrimidinyl |

TABLE I-27f

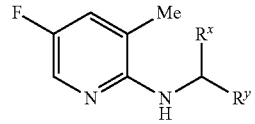

| R$^x$ | R$^y$ |
|---|---|
| H | CF$_3$ |
| Me | CF$_3$ |
| H | Et |
| Me | Et |
| H | 3-pyridinyl |
| Me | 3-pyridinyl |
| H | 6-fluoro-3-pyridinyl |
| Me | 6-fluoro-3-pyridinyl |
| H | 6-bromo-3-pyridinyl |
| Me | 6-bromo-3-pyridinyl |
| H | 2-methyl-5-thiazolyl |
| Me | 2-methyl-5-thiazolyl |
| H | CH$_2$CHFCF$_2$Cl |
| Me | CH$_2$CHFCF$_2$Cl |
| H | cyclopropyl |
| Me | cyclopropyl |
| H | 6-methyl-3-pyridinyl |
| Me | 6-methyl-3-pyridinyl |
| H | 6-chloro-3-pyridinyl |
| Me | 6-chloro-3-pyridinyl |
| H | 5-thiazolyl |
| Me | 5-thiazolyl |
| H | 2-fluoro-5-thiazolyl |
| Me | 2-fluoro-5-thiazolyl |
| H | 2-chloro-5-thiazolyl |
| Me | 2-chloro-5-thiazolyl |
| H | 1-methyl-4-pyrazolyl |
| Me | 1-methyl-4-pyrazolyl |
| H | 5-pyrimidinyl |
| Me | 5-pyrimidinyl |
| H | 2-bromo-5-thiazolyl |
| Me | 2-bromo-5-thiazolyl |
| H | 3-methyl-5-isoxazolyl |
| Me | 3-methyl-5-isoxazolyl |
| H | 2-methyl-5-pyrimidinyl |
| Me | 2-methyl-5-pyrimidinyl |

TABLE I-27g

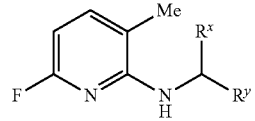

| R$^x$ | R$^y$ |
|---|---|
| H | CF$_3$ |
| Me | CF$_3$ |
| H | Et |

TABLE I-27g-continued

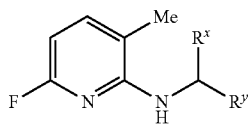

| $R^x$ | $R^y$ |
|---|---|
| Me | Et |
| H | 3-pyridinyl |
| Me | 3-pyridinyl |
| H | 6-fluoro-3-pyridinyl |
| Me | 6-fluoro-3-pyridinyl |
| H | 6-bromo-3-pyridinyl |
| Me | 6-bromo-3-pyridinyl |
| H | 2-methyl-5-thiazolyl |
| Me | 2-methyl-5-thiazolyl |
| H | $CH_2CHFCF_2Cl$ |
| Me | $CH_2CHFCF_2Cl$ |
| H | cyclopropyl |
| Me | cyclopropyl |
| H | 6-methyl-3-pyridinyl |
| Me | 6-methyl-3-pyridinyl |
| H | 6-chloro-3-pyridinyl |
| Me | 6-chloro-3-pyridinyl |
| H | 5-thiazolyl |
| Me | 5-thiazolyl |
| H | 2-fluoro-5-thiazolyl |
| Me | 2-fluoro-5-thiazolyl |
| H | 2-chloro-5-thiazolyl |
| Me | 2-chloro-5-thiazolyl |
| H | 1-methyl-4-pyrazolyl |
| Me | 1-methyl-4-pyrazolyl |
| H | 5-pyrimidinyl |
| Me | 5-pyrimidinyl |
| H | 2-bromo-5-thiazolyl |
| Me | 2-bromo-5-thiazolyl |
| H | 3-methyl-5-isoxazolyl |
| Me | 3-methyl-5-isoxazolyl |
| H | 2-methyl-5-pyrimidinyl |
| Me | 2-methyl-5-pyrimidinyl |

TABLE I-28

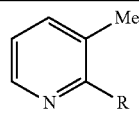

| R |
|---|
| F |
| NHCHO |
| Cl |
| $NHC(O)CH_3$ |
| Br |
| $NHCO_2CH_2Ph$ |
| I |
| $NHCO_2CH_3$ |
| $NH_2$ |
| $NHCO_2CH_2CH_3$ |
| $NH(CO_2\text{—}t\text{-Bu})$ |
| $NH(CO_2\text{—}i\text{-Pr})$ |

TABLE I-28a

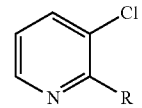

| R |
|---|
| F |
| NHCHO |
| Cl |
| $NHC(O)CH_3$ |
| Br |
| $NHCO_2CH_2Ph$ |
| I |
| $NHCO_2CH_3$ |
| $NH_2$ |
| $NHCO_2CH_2CH_3$ |
| $NH(CO_2\text{—}t\text{-Bu})$ |
| $NH(CO_2\text{—}i\text{-Pr})$ |

TABLE I-28b

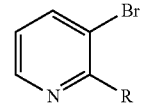

| R |
|---|
| F |
| NHCHO |
| Cl |
| $NHC(O)CH_3$ |
| Br |
| $NHCO_2CH_2Ph$ |
| I |
| $NHCO_2CH_3$ |
| $NH_2$ |
| $NHCO_2CH_2CH_3$ |
| $NH(CO_2\text{—}t\text{-Bu})$ |
| $NH(CO_2\text{—}i\text{-Pr})$ |

TABLE I-28c

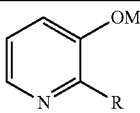

| R |
|---|
| F |
| NHCHO |
| Cl |
| $NHC(O)CH_3$ |
| Br |
| $NHCO_2CH_2Ph$ |
| I |
| $NHCO_2CH_3$ |
| $NH_2$ |
| $NHCO_2CH_2CH_3$ |
| $NH(CO_2\text{—}t\text{-Bu})$ |
| $NH(CO_2\text{—}i\text{-Pr})$ |

TABLE I-28d

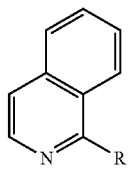

| R |
|---|
| F |
| NHCHO |
| Cl |
| NHC(O)CH$_3$ |
| Br |
| NHCO$_2$CH$_2$Ph |
| I |
| NHCO$_2$CH$_3$ |
| NH$_2$ |
| NHCO$_2$CH$_2$CH$_3$ |
| NH(CO$_2$—t-Bu) |
| NH(CO$_2$—i-Pr) |

TABLE I-28e

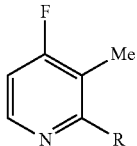

| R |
|---|
| F |
| NHCHO |
| Cl |
| NHC(O)CH$_3$ |
| Br |
| NHCO$_2$CH$_2$Ph |
| I |
| NHCO$_2$CH$_3$ |
| NH$_2$ |
| NHCO$_2$CH$_2$CH$_3$ |
| NH(CO$_2$—t-Bu) |
| NH(CO$_2$—i-Pr) |

TABLE I-28f

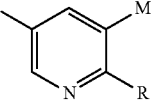

| R |
|---|
| F |
| NHCHO |
| Cl |
| NHC(O)CH$_3$ |
| Br |
| NHCO$_2$CH$_2$Ph |
| I |
| NHCO$_2$CH$_3$ |
| NH$_2$ |
| NHCO$_2$CH$_2$CH$_3$ |
| NH(CO$_2$—t-Bu) |
| NH(CO$_2$—i-Pr) |

TABLE I-28g

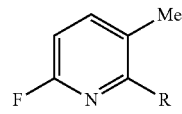

| R |
|---|
| F |
| NHCHO |
| Cl |
| NHC(O)CH$_3$ |
| Br |
| NHCO$_2$CH$_2$Ph |
| I |
| NHCO$_2$CH$_3$ |
| NH$_2$ |
| NHCO$_2$CH$_2$CH$_3$ |
| NH(CO$_2$—t-Bu) |
| NH(CO$_2$—i-Pr) |

TABLE I-29

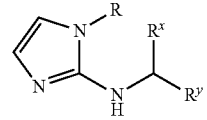

| $R^x$ | $R^y$ |
|---|---|
| R is Et | |
| H | CF$_3$ |
| Me | CF$_3$ |
| H | Et |
| Me | Et |
| H | 3-pyridinyl |
| Me | 3-pyridinyl |
| H | 6-fluoro-3-pyridinyl |
| Me | 6-fluoro-3-pyridinyl |
| H | 6-bromo-3-pyridinyl |
| Me | 6-bromo-3-pyridinyl |
| H | 2-methyl-5-thiazolyl |
| Me | 2-methyl-5-thiazolyl |
| H | 2-chloro-5-thiazolyl |
| Me | 2-chloro-5-thiazolyl |
| H | 1-methyl-4-pyrazolyl |
| Me | 1-methyl-4-pyrazolyl |
| H | 5-pyrimidinyl |
| Me | 5-pyrimidinyl |
| H | CH$_2$CHFCF$_2$Cl |
| Me | CH$_2$CHFCF$_2$Cl |
| H | cyclopropyl |
| Me | cyclopropyl |
| H | 6-methyl-3-pyridinyl |
| Me | 6-methyl-3-pyridinyl |
| H | 6-chloro-3-pyridinyl |
| Me | 6-chloro-3-pyridinyl |
| H | 5-thiazolyl |
| Me | 5-thiazolyl |
| H | 2-fluoro-5-thiazolyl |
| Me | 2-fluoro-5-thiazolyl |
| H | 2-bromo-5-thiazolyl |
| Me | 2-bromo-5-thiazolyl |
| H | 3-methyl-5-isoxazolyl |
| Me | 3-methyl-5-isoxazolyl |
| H | 2-methyl-5-pyrimidinyl |
| Me | 2-methyl-5-pyrimidinyl |
| R is CH$_2$CHF$_2$ | |
| H | CF$_3$ |
| Me | CF$_3$ |
| H | Et |
| Me | Et |
| H | 3-pyridinyl |
| Me | 3-pyridinyl |

TABLE I-29-continued

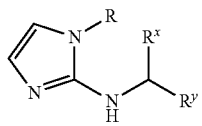

| $R^x$ | $R^y$ |
|---|---|
| H | 6-fluoro-3-pyridinyl |
| Me | 6-fluoro-3-pyridinyl |
| H | 6-bromo-3-pyridinyl |
| Me | 6-bromo-3-pyridinyl |
| H | 2-methyl-5-thiazolyl |
| Me | 2-methyl-5-thiazolyl |
| H | 2-chloro-5-thiazolyl |
| Me | 2-chloro-5-thiazolyl |
| H | 1-methyl-4-pyrazolyl |
| Me | 1-methyl-4-pyrazolyl |
| H | 5-pyrimidinyl |
| Me | 5-pyrimidinyl |
| H | $CH_2CHFCF_2Cl$ |
| Me | $CH_2CHFCF_2Cl$ |
| H | cyclopropyl |
| Me | cyclopropyl |
| H | 6-methyl-3-pyridinyl |
| Me | 6-methyl-3-pyridinyl |
| H | 6-chloro-3-pyridinyl |
| Me | 6-chloro-3-pyridinyl |
| H | 5-thiazolyl |
| Me | 5-thiazolyl |
| H | 2-fluoro-5-thiazolyl |
| Me | 2-fluoro-5-thiazolyl |
| H | 2-bromo-5-thiazolyl |
| Me | 2-bromo-5-thiazolyl |
| H | 3-methyl-5-isoxazolyl |
| Me | 3-methyl-5-isoxazolyl |
| H | 2-methyl-5-pyrimidinyl |
| Me | 2-methyl-5-pyrimidinyl |

TABLE I-30

| | |
|---|---|
| 2-chloro-6-(trifluoromethyl)pyridine | 4-chloro-2-(trifluoromethyl)pyridine |
| 2-bromo-6-(trifluoromethyl)pyridine | 4-bromo-2-(trifluoromethyl)pyridine |
| 2-iodo-6-(trifluoromethyl)pyridine | 4-iodo-2-(trifluoromethyl)pyridine |
| 4-chloro-2-fluoropyridine | 2,4-dichloropyridine |
| 4-bromo-2-fluoropyridine | 4-bromo-2-chloropyridine |
| 2-fluoro-4-iodopyridine | 2-chloro-4-iodopyridine |
| 2-bromo-4-chloropyridine | |
| 2,4-dibromopyridine | |
| 2-bromo-4-iodopyridine | |

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. Ambient or room temperature is defined as about 20-25° C. Percentages are by weight except for chromatographic solvent mixtures or where otherwise indicated. Parts and percentages for chromatographic solvent mixtures are by volume unless otherwise indicated. MPLC refers to medium pressure liquid chromatography on silica gel. $^1$H NMR spectra are reported in ppm downfield from tetramethylsilane; "s" means singlet, "d" means doublet, "dd" means doublet of doublets, "ddd" means doublet of doublet of doublets, "t" means triplet, "m" means multiplet, and "br s" means broad singlet. For mass spectral data, the numerical value reported is the molecular weight of the parent molecular ion (M) formed by addition of H$^+$ (molecular weight of 1) to the molecule to give a M+1 peak observed by mass spectrometry using atmospheric pressure chemical ionization (AP$^+$).

Synthesis Example 1

Preparation of 1-[(2-chloro-5-thiazolyl)methyl]-2-hydroxy-4-oxo-9-phenyl-3-[3-(trifluoromethoxy)phenyl]-4H-pyrido[1,2-a]pyrimidinium inner salt (compound number 68)

Step A: Preparation of 2-amino-3-phenylpyridine

A microwave vial was charged with 2-amino-3-bromopyridine (0.5 g, 2.9 mmol), phenylboronic acid (0.52 g, 4.3 mmol), sodium bicarbonate (0.31 g, 2.9 mmol), dichlorobis(triphenylphosphine)palladium(II) (0.1 g, 0.14 mmol), dioxane (5 mL) and water (1 mL). The vial was capped, and the reaction mixture was heated at 150° C. for 10 min. The reaction mixture was then cooled, quenched with water (10 mL), and extracted twice with ethyl acetate. The combined organic phases were dried (MgSO$_4$) and concentrated to leave a black oil. The crude product was purified by chromatography on silica gel using 10-40% ethyl acetate/hexanes as eluant to provide the title compound as a white solid (0.35 g).

$^1$H NMR (CDCl$_3$) δ 8.10 (d, 1H), 7.46 (m, 4H), 7.38 (m, 2H), 6.75 (m, 1H), 4.50-4.55 (br s, 2H).

Step B: Preparation of N-[(2-chloro-5-thiazolyl)methylene]-3-phenyl-2-pyridinamine 2-Amino-3-phenylpyridine (i.e. the product of Step A, 0.342 g, 2.01 mmol) was added to 2-chloro-1,3-thiazole-5-carbaldehyde (0.296 g, 2.01 mmol) in dichloromethane (10 mL) at room temperature. The suspension was stirred for 10 min and then concentrated to dryness under vacuum. The resulting residue was heated to 90° C. for 20 min on a rotary evaporator with a non-returning bump trap to facilitate water removal. The residual yellow solid was again dissolved in dichloromethane (10 mL) and heated to 90° C. on a rotory evaporator for an additional 20 min. At this time the yellow solid was checked by NMR to verify reaction completion. The title compound was obtained as a yellow solid and used in the next step without further purification.

$^1$H NMR (CDCl$_3$) δ 9.29 (s, 1H), 8.45 (m, 1H), 7.92 (s, 1H), 7.80 (dd, 1H), 7.50-7.35 (m, 5H), 7.30-7.25 (m, 1H).

Step C: Preparation of N-[(2-chloro-5-thiazolyl) methyl]-3-phenyl-2-pyridinamine N-[(2-chloro-5-thiazolyl)methylene]-3-phenyl-2-pyridinamine (i.e. the product of Step B) was added portionwise to a stirred excess of sodium borohydride (0.379 g, 10.0 mmol) in methanol (8 mL). After addition was complete, the reaction mixture was allowed to stir for 5 min at ambient temperature. The excess reducing agent was quenched by adding glacial acetic acid until gas evolution ceased. Water (20 mL) was added, and the reaction mixture was concentrated to remove methanol. The resulting aqueous phase was extracted twice with ethyl acetate, and the combined organic phases were dried (MgSO$_4$) and concentrated to give the title compound as a yellow solid (0.659 g).

$^1$H NMR (CDCl$_3$) δ 8.2 (d, 1H), 7.5-7.3 (m, 7H), 6.8-6.7 (m, 1H), 5.0-4.9 (br s, 1H), 4.68 (d, 2H).

Step D: Preparation of 1-[(2-chloro-5-thiazolyl) methyl]-2-hydroxy-4-oxo-9-phenyl-3-[3-(trifluoromethoxy)phenyl]-4H-pyrido[1,2-a]pyrimidinium inner salt N-[(2-chloro-5-thiazolyl)methyl]-3-phenyl-2-pyridinamine (i.e. the product of Step C, 100 mg, 0.33 mmol) and 1,3-bis(2,4,6-trichlorophenyl)-2-[3-(trifluoromethoxy)phenyl]propanedioate (246 mg, 0.398 mmol) were dissolved in toluene (10 mL) and heated at 85° C. overnight. The reaction mixture was then poured onto a silica gel column which was eluted with 50-100% ethyl acetate in hexanes to provide the title compound, a compound of the present invention, as a yellow solid (63 mg).

$^1$H NMR (CDCl$_3$) δ 9.60 (d, 1H), 8.05 (d, 1H), 7.85-7.75 (m, 2), 7.55 (m, 3H), 7.5-7.4 (m, 4H), 7.1 (dd, 1H), 6.84 (s, 1H), 5.1-5.25 (br s, 2H).

Synthesis Example 2

Preparation of 1-[(2-chloro-5-thiazolyl)methyl]-3-(2-fluorophenyl)-2-hydroxy-9-methyl-4-oxo-4H-pyrido[1,2-a]pyrimidinium inner salt (compound number 30)

Step A: Preparation of N-[(2-chloro-5-thiazolyl) methyl]-3-methyl-2-pyridinamine A mixture of 2-amino-3-methylpyridine (2.16 g, 20 mmol) and 2-chloro-5-(chloromethyl)thiazole (1.68 g, 10 mmol) in N-methylpyrrolidinone (10 mL) was heated at 180° C. in a microwave reactor for 10 min. The cooled reaction mixture was poured into a saturated aqueous sodium bicarbonate solution and extracted with ethyl acetate. The organic layer was separated, washed with saturated aqueous sodium bicarbonate solution, dried over Na$_2$SO$_4$, and concentrated under reduced pressure. The residue was purified by chromatography on silica gel eluted with 10% ethyl acetate in hexanes to provide the title compound as an oil (2.0 g).

$^1$H NMR (CDCl$_3$) δ 8.07 (d, 1H), 7.43 (s, 1H), 7.26 (d, 1H), 6.63 (dd, 1H), 4.77 (d, 2H), 4.54 (br s, 1H).

Step B: Preparation of 1,3-bis(2,4,6-trichlorophenyl) 2-(2-fluorophenyl)propanedioate To a solution of 2-(2-fluorophenyl)propanedioic acid (0.60 g, 3 mmol, prepared by the method described in *Eur. J. Biochem.* 1992, 210, 475) in dichloromethane (5 mL) was added oxalyl chloride (0.65 mL, 7.5 mmol) and one drop of N,N-dimethylformamide. The reaction mixture was stirred for 1 h at room temperature. 2,4,6-Trichlorophenol (1.47 g, 7.5 mmol) was then added, and the reaction mixture was stirred at room temperature overnight. The reaction mixture was concentrated under reduced pressure, and the crude residue was triturated with a small amount of cold methanol to yield the title compound as a white solid (1.1 g).

$^1$H NMR (CDCl$_3$) δ 7.73 (m, 1H), 7.42 (m, 1H), 7.37 (s, 2H), 7.24 (m, 1H), 7.19 (t, 1H), 5.72 (s, 1H).

Step C: Preparation of 1-[(2-chloro-5-thiazolyl) methyl]-3-(2-fluorophenyl)-2-hydroxy-9-methyl-4-oxo-4H-pyrido[1,2-a]pyrimidinium inner salt A solution of N-[(2-chloro-5-thiazolyl)methyl]-3-methyl-2-pyridinamine (i.e. the product of Step A, 100 mg, 0.4 mmol) and 1,3-bis(2,4,6-trichlorophenyl) 2-(2-fluorophenyl)propanedioate (i.e. the product of Step B, 300 mg, 0.5 mmol) in toluene (1 mL) was heated at 70° C. for 1 h. The reaction mixture was then cooled and filtered, and the filtered solid was triturated with a small amount of diethyl ether to yield the title product, a compound of the present invention, as a yellow solid (60 mg).

$^1$H NMR (CDCl$_3$) δ 9.52 (d, 1H), 8.01 (dd, 1H), 7.58 (t, 1H), 7.37 (t, 1H), 7.1-7.35 (m, 4H), 5.62 (s, 2H), 2.84 (s, 3H).

Synthesis Example 2a

Alternative preparation of 1-[(2-chloro-5-thiazolyl)methyl]-3-(2-fluorophenyl)-2-hydroxy-9-methyl-4-oxo-4H-pyrido[1,2-a]pyrimidinium inner salt (compound number 30)

Step A: Preparation of methyl α-cyano-2-fluorobenzeneacetate

Sodium methoxide (51.84 g) was added to dry toluene (815 mL) in a 1 L reactor under a nitrogen atmosphere. The reaction mixture was heated to 75° C., and then a mixture of 2-fluorobenzeneacetonitrile (100 g) in dimethyl carbonate (131.64 g) was added at 70-74° C. over a period of 45 minutes. The reaction mixture was further maintained at this temperature (70-75° C.) for an additional 4.5 hours. The reaction mixture was then cooled to 25-30° C. and added to a mixture of HCl (110 g, 35.2 wt %) diluted with water (300 mL) at 10-15° C. using an addition funnel. The resulting layers were separated, and the aqueous layer was extracted with ethyl acetate (2×200 mL). The combined organic layers were washed with water (2×200 mL), dried over sodium sulfate, and concentrated under reduced pressure to provide the title compound as a brown oily liquid (138.8 g, 94.8% yield).

Step B: Preparation of 1,3-dimethyl 2-(2-fluorophenyl)propanedioate

Methyl α-cyano-2-fluorobenzeneacetate (135 g) was added to methanol (675 g) in a 1 L reactor under nitrogen atmosphere. The reaction mixture was cooled to 0° C. and thionyl chloride (240.47 g) was added slowly over a period of 45 minutes. The reaction mixture was heated to 45° C. for 19 hours, and the progress of the reaction was monitored by HPLC. The reaction mixture was then cooled to 30° C., and concentrated under reduced pressure at 45-47° C. The residue was dissolved in water (300 mL) and extracted with ethyl acetate (2×300 mL). The combined organic layers were washed with water (2×300 mL), dried over sodium sulfate, and concentrated under reduced pressure to dryness to give the title compound (152.2 g, 95.9% yield).

Step C: Preparation of 2-(2-fluorophenyl)propanedioic acid

Sodium hydroxide (117.11 g of a 50% aqueous solution) was added to water (160.5 g), and the solution was cooled to 10-15° C. Tetramethylammonium chloride (4.88 g) was added, followed by the dropwise addition of 1,3-dimethyl 2-(2-fluorophenyl)propanedioate (150 g) over a period of 30 minutes at 10-15° C. The temperature of the reaction was slowly raised to 30° C. after the addition and maintained at 27-32° C. The reaction mass became a thick slurry, and water (25 g) was added to improve stirring. The progress of the reaction was monitored by HPLC. After stirring for 2 hours, the reaction mixture was added to a solution of HCl (231 g) and water (150 mL) over a period of 30 minutes at 5-10° C. The pH of the mixture was adjusted to <2, and the reaction mixture was stirred at 5-10° C. for half an hour. The reaction mixture was then filtered to isolate a solid product that was air dried, and then further dried under reduced pressure at 35° C. for 3 hours. The dried solid was slurried with petroleum ether, and the slurry was filtered to reisolated the solid. The solid was then dried under reduced pressure at 35° C. for 3 hours to give the title product (115.5 g, 93.97%).

Step D: Preparation of 1,3-bis(4-nitrophenyl) 2-(2-fluorophenyl)propanedioate

To a 1 L flask was added toluene (500 mL), 2-(2-fluorophenyl)propanedioic acid (100 g, 0.479 moles) and N,N-dimethylformamide (6.92 g) at 25° C. under a nitrogen atmosphere. The reaction mixture was initially heated to 30° C. and thionyl chloride (127.53 g, 1.071 moles) was added dropwise over a period of 20 minutes at 25-30° C. After the addition, the reaction mixture was heated to 48-50° C. and this temperature maintained for 3.5 hours. Toluene (300 mL) was then added to the reaction mixture in one portion, followed by the addition of solid 4-nitrophenol (148.09 g total, 1.064 moles) in ten portions over a period of 15 minutes. After the addition, the reaction mixture was maintained at 49-55° C. for 1.5 hours. The reaction mixture was then concentrated under reduced pressure at 40-45° C. to remove toluene. The resulting residue was triturated using cold methanol (300 mL, approximately 5° C.) to yield an off-white solid which was isolated by filtration, washed with cold methanol (2×150 mL, approximately 5° C.) and dried under reduced pressure at 45° C. to give the title compound (163.8 g, 71.6%).

Step E: Preparation of 1-[(2-chloro-5-thiazolyl) methyl]-3-(2-fluorophenyl)-2-hydroxy-9-methyl-4-oxo-4H-pyrido[1,2-a]pyrimidinium inner salt N-[(2-chloro-5-thiazolyl)methyl]-3-methyl-2-pyridinamine (i.e. the product of Example 2 Step A, 60.0 g, 0.247 mol), 1,3-bis(4-nitrophenyl) 2-(2-fluorophenyl)propanedioate (142 g, 0.297 mol), imidazole (6.74 g, 99 mmol), and ethyl acetate (300 mL) were added to a reactor, and the reaction mixture was heated to 72-77° C. for 2.0 hours. The reaction mixture was then cooled to 40° C., and water (460 mL) was added. The resulting slurry was cooled to 10° C. and further maintained at that temperature for 15 minutes. The slurry was then filtered to isolate a wet solid which was washed with methanol (360 mL). The crude product was air dried, and then dried further under reduced pressure at 45-50° C. for 3 hours to provide the title compound, a compound of this invention, as a solid (93.7 g, 93.1% yield).
$^1$H NMR (dmso-d$_6$) δ 9.26 (d, 1H), 8.27 (d, 1H), 7.78 (s, 1H), 7.57-7.46 (m, 2H), 7.33-7.29 (m, 1H), 7.21-7.15 (m, 2H), 5.44 (s, 2H), 2.72 (s, 3H).

Synthesis Example 3

Preparation of 1-[(2-chloro-5-thiazolyl)methyl]-3-(2',3'-dichloro[1,1'-biphenyl]-3-yl)-2-hydroxy-9-methyl-4-oxo-4H-pyrido[1,2-a]pyrimidinium inner salt (compound number 88)

Step A: Preparation of 2',3'-dichloro-[1,1'-biphenyl]-3-acetic acid ethyl ester

A mixture of 3-iodobenzeneacetic acid ethyl ester (0.87 g, 3 mmol, prepared by the method described in J. Chem. Soc. 1963, 5437), 2,3-dichlorophenylboronic acid (0.85 g, 4.5 mmol), bis(triphenylphosphine)palladium dichloride (0.10 g, 0.15 mmol) and 2 N aqueous sodium bicarbonate solution (3 mL) in p-dioxane (6 mL) was heated at 160 OC in a microwave reactor for 5 min. The reaction mixture was cooled, poured into water, and extracted with ethyl acetate. The organic layer was separated, washed with brine, dried over Na$_2$SO$_4$, and concentrated under reduced pressure. The residue was purified by chromatography on silica gel eluted with ethyl acetate in hexanes to provide the title product (0.48 g).
$^1$H NMR (CDCl$_3$) δ 8.07 (d, 1H), 7.43 (s, 1H), 7.26 (d, 1H), 6.63 (dd, 1H), 4.77 (d, 2H), 4.54 (br s, 1H).

Step B: Preparation of 2-(2',3'-dichloro-[1,1'-biphenyl]-3-yl)propanedioic acid 1,3-diethyl ester To a solution of 2',3'-dichloro-[1,1'-biphenyl]-3-acetic acid ethyl ester (i.e. the product of Step A, 0.45 g, 1.45 mmol) and diethyl carbonate (5 mL) was added sodium hydride (60% dispersion in oil, 0.23 g, 5.8 mmol). The reaction mixture was stirred overnight at room temperature, and then quenched with saturated aqueous ammonium chloride solution. The reaction mixture was then extracted with ethyl acetate, and the organic layer was dried over sodium sulfate and concentrated under reduced pressure to yield the title compound (0.50 g).
$^1$H NMR (CDCl$_3$) δ 7.35-7.5 (m, 5H), 7.25 (t, 2H), 5.30 (s, 1H), 4.20 (q, 4H), 1.26 (t, 6H).

Step C: Preparation of 2-(2',3'-dichloro[1,1'-biphenyl]-3-yl)propanedioic acid 2-(2',3'-Dichloro-[1,1'-biphenyl]-3-yl)propanedioic acid 1,3-diethyl ester (i.e. the product of Step B, 0.30 g, 0.79 mmol) was added to 2% aqueous sodium hydroxide (5 mL), and the reaction mixture was heated at 70 OC for 20 min. The reaction mixture was cooled, quenched with 6 N aqueous hydrochloric acid, and extracted with ethyl acetate. The organic layer was separated, washed with brine, dried over sodium sulfate, and concentrated under reduced pressure to yield the title compound (0.20 g).

$^1$H NMR (CDCl$_3$) δ 7.4-7.5 (m, 5H), 7.20-7.25 (m, 2H), 4.74 (s, 1H).

Step D: Preparation of 1-[(2-chloro-5-thiazolyl)methyl]-3-(2',3'-dichloro[1,1'-biphenyl]-3-yl)-2-hydroxy-9-methyl-4-oxo-4H-pyrido[1,2-a]pyrimidinium inner salt To a solution of 2-(2',3'-dichloro[1,1'-biphenyl]-3-yl)propanedioic acid (i.e. the product of Step C, 200 mg, 0.62 mmol) in dichloromethane (3 mL) was added one drop of N,N-dimethylformamide and oxalyl chloride (0.3 mL, 3.5 mmol). The reaction mixture was stirred at room temperature for 30 min, and concentrated under reduced pressure. The residue was redissolved in dichloromethane (3 mL), and this solution was added to an ice-cooled solution of N-[(2-chloro-5-thiazolyl)methyl]-3-methyl-2-pyridinamine (i.e. the product of Synthesis Example 2 Step A, 100 mg, 0.44 mmol) and triethylamine (0.3 mL, 2.2 mmol) in dichloromethane (2 mL). The reaction mixture was stirred with cooling for 15 min and then concentrated in the presence of a small amount of Celite® diatomaceous filter aid. The crude residue was purified by MPLC to yield 88 mg of the title compound, a compound of the present invention.

$^1$H NMR (CDCl$_3$) δ 9.52 (d, 1H), 8.04 (dd, 1H), 7.76 (d, 1H), 7.2-7.45 (m, 6H), 5.95 (m, 1H), 5.34 (d, 1H), 5.30 (d, 1H), 5.01 (d, 2H).

Synthesis Example 4

Preparation of 1-[(2-chloro-5-thiazolyl)methyl]-2-hydroxy-4-oxo-3-phenyl-4H-pyrimido[2,1-a]isoquinolinium inner salt (compound number 99)

Step A: Preparation of N-[(2-chloro-5-thiazolyl)methyl]-1-isoquinolinamine

A mixture of 1-aminoisoquinoline (0.56 g, 3.9 mmol) and 2-chloro-5-(chloromethyl)thiazole (0.50 g, 3.0 mmol) in N-methylpyrrolidinone (3 mL) was heated to 220° C. in a microwave reactor for 10 min. The reaction mixture was cooled to room temperature, diluted with water (20 mL), and extracted with diethyl ether (5×20 mL). The combined organic extracts were concentrated under reduced pressure, and the resulting residue was purified by chromatography on silica gel eluted with 20-50% ethyl acetate/hexane to give the title compound as a pale yellow solid (0.09 g).

$^1$H NMR (CDCl$_3$) δ 8.07 (d, 1H), 7.70-7.75 (m, 2H), 7.62 (t, 1H), 7.50 (t, 1H), 7.05 (d, 1H), 5.60 (br s, 1H), 4.91 (d, 2H), 1.58 (br s, NH+H$_2$O).

Step B: Preparation of 1-[(2-chloro-5-thiazolyl)methyl]-2-hydroxy-4-oxo-3-phenyl-4H-pyrimido[2,1-a]isoquinolinium inner salt To a solution of phenylmalonic acid (0.44 g, 2.4 mmol) in dichloromethane (10 mL) was added two drops of N,N-dimethylformamide and oxalyl chloride (1.1 mL, 12 mmol). The reaction mixture was stirred at room temperature for 30 min, concentrated under reduced pressure, and then redissolved in dichloromethane (2.4 mL). A portion of the resulting solution (0.4 mL, 0.4 mmol) was added to an ice-cooled solution of N-[(2-chloro-5-thiazolyl)methyl]-1-isoquinolinamine (i.e. the product of Step A, 50 mg, 0.18 mmol) and triethylamine (0.08 mL) in dichloromethane (2 mL). The reaction mixture was allowed to warm to room temperature and stirred overnight. The reaction mixture was then concentrated, and the crude residue was purified by MPLC (80-100% ethyl acetate/hexane as eluant) to yield 17.4 mg of the title compound, a compound of the present invention.

$^1$H NMR (CDCl$_3$) δ 9.26 (d, 1H), 8.65 (d, 1H), 7.97-8.02 (m, 2H), 7.84 (d, 2H), 7.78-7.82 (m, 1H), 7.68 (s, 1H), 7.60 (d, 1H), 7.42-7.48 (m, 3H), 5.64 (br s, 2H).

Synthesis Example 5

Preparation of 2-hydroxy-9-methyl-4-oxo-1-(5-pyrimidinylmethyl)-3-[3-(trifluoromethoxy)phenyl]-4H-pyrido[1,2-a]pyrimidinium inner salt (compound number 43)

Step A: Preparation of N-(5-pyrimidinylmethyl)-3-methyl-2-pyridinamine

To a solution of 5-pyrimidinecarboxaldehyde (5.0 g, 46 mmol) in toluene (100 mL) was added 2-amino-3-picoline (5.0 g, 46 mmol). The reaction mixture was heated to 80° C. on a rotary evaporator while under reduced pressure. After 10 min an additional 200 mL of toluene was added. Continued heating under reduced pressure resulted in a white solid which was dissolved in methanol (200 mL). This solution was stirred vigorously under a nitrogen atmosphere, and granular sodium borohydride (10.0 g, 265 mmol) was added portionwise, resulting in vigorous bubbling. The reaction was allowed to stir for 1 h at room temperature after completion of the sodium borohydride addition. Acetic acid (1 mL) was then added, and the reaction mixture was stirred for 5 min, followed by the addition of water (100 mL). The volatiles were removed under reduced pressure, and the aqueous suspension was extracted with dichloromethane (2×100 mL). The organic layers were combined and dried over MgSO$_4$, filtered, and the solvent was removed under reduced pressure to yield an off-white solid. The crude solid was adsorbed onto Celite® and purified by column chromatography (gradient of 100% hexanes to 100% ethyl acetate over 30 minutes) to yield 8.848 g of a white solid.

$^1$H NMR (CDCl$_3$) δ 9.11 (s, 1H), 8.77 (s, 2H), 8.00 (d, 1H), 7.26 (s, 1H), 6.60 (dd, 1H), 4.73 (d, 2H), 4.59 (br s, NH), 2.12 (s, 3H).

Step B: Preparation of 2-hydroxy-9-methyl-4-oxo-1-(5-pyrimidinylmethyl)-3-[3-(trifluoromethoxy)phenyl]-4H-pyrido[1,2-a]pyrimidinium inner salt To a solution of 1,3-bis(2,4,6-trichlorophenyl)-2-[3-(trifluoromethoxy)phenyl]-propanedioic acid ester (100 mg, 0.16 mmoles) in toluene (10 mL) was added N-(5-pyrimidinylmethyl)-3-methyl-2-pyridinamine (i.e. the product of Step A, 32 mg, 0.16 mmoles). The reaction mixture was heated to 80° C. for 18 h. Cooling of the reaction vessel to 0° C. resulted in the precipitation of a yellow solid which was isolated by filtration to provide 13.2 mg of the title compound, a compound of the present invention, as a yellow solid.

$^1$H NMR (CD$_3$C(O)CD$_3$) δ 9.46 (d, 1H), 9.05 (s, 1H), 8.83 (s, 2H) 8.27 (d, 1H), 8.04 (d, 1H), 8.02 (s, 1H), 7.57 (t, 1H), 7.38 (t, 1H), 7.07 (d, 1H), 5.66 (s, 2H), 2.69 (s, 3H).

By the procedures described herein together with methods known in the art, the following compounds of Tables 1 to 32 can be prepared. The following abbreviations are used in Tables 1 to 32 which follow: Me means methyl, Et means ethyl, Pr means propyl and Ph means phenyl.

Tables 1-15 pertain to the structure of Formula T-1 shown below.

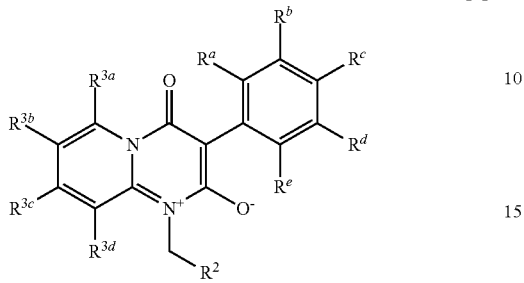

T-1

TABLE 1

| $R^b$, $R^c$, $R^d$, $R^e$, $R^{3a}$, $R^{3b}$ and $R^{3c}$ are H; $R^{3d}$ is Me; $R^2$ is 2-chloro-5-thiazolyl | | | |
|---|---|---|---|
| $R^a$ | $R^a$ | $R^a$ | $R^a$ |
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^a$, $R^c$, $R^d$, $R^e$, $R^{3a}$, $R^{3b}$ and $R^{3c}$ are H; $R^{3d}$ is Me; $R^2$ is 2-chloro-5-thiazolyl | | | |
|---|---|---|---|
| $R^b$ | $R^b$ | $R^b$ | $R^b$ |
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE 1-continued $R^a$, $R^b$, $R^d$, $R^e$, $R^{3a}$, $R^{3b}$ and $R^{3c}$ are H; $R^{3d}$ is Me; $R^2$ is 2-chloro-5-thiazolyl

| $R^c$ | $R^c$ | $R^c$ | $R^c$ |
|---|---|---|---|
| H | O—i-Pr | 3-(CF$_3$)phenyl | 2-fluoro-4-cyanophenyl |
| F | OCH$_2$CH═CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(═NOMe)Me | 3-chloro-5-fluorophenyl | N—Me-4-pyrazolyl |
| CH═CH$_2$ | C(═NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

$R^a$ is F; $R^c$, $R^d$, $R^e$, $R^{3a}$, $R^{3b}$ and $R^{3c}$ are H; $R^{3d}$ is Me; $R^2$ is 2-chloro-5-thiazolyl

| $R^b$ | $R^b$ | $R^b$ | $R^b$ |
|---|---|---|---|
| H | O—i-Pr | 3-(CF$_3$)phenyl | 2-fluoro-4-cyanophenyl |
| F | OCH$_2$CH═CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(═NOMe)Me | 3-chloro-5-fluorophenyl | N—Me-4-pyrazolyl |
| CH═CH$_2$ | C(═NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

$R^a$ is F; $R^b$, $R^d$, $R^e$, $R^{3a}$, $R^{3b}$ and $R^{3c}$ are H; $R^{3d}$ is Me; $R^2$ is 2-chloro-5-thiazolyl

| $R^c$ | $R^c$ | $R^c$ | $R^c$ |
|---|---|---|---|
| H | O—i-Pr | 3-(CF$_3$)phenyl | 2-fluoro-4-cyanophenyl |
| F | OCH$_2$CH═CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(═NOMe)Me | 3-chloro-5-fluorophenyl | N—Me-4-pyrazolyl |
| CH═CH$_2$ | C(═NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE 1-continued

| | $R^a$ is F; $R^b$, $R^c$, $R^e$, $R^{3a}$, $R^{3b}$ and $R^{3c}$ are H; $R^{3d}$ is Me; $R^2$ is 2-chloro-5-thiazolyl |

| $R^d$ | $R^d$ | $R^d$ | $R^d$ |
|---|---|---|---|
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| | $R^a$ is F; $R^b$, $R^c$, $R^d$, $R^{3a}$, $R^{3b}$ and $R^{3c}$ are H; $R^{3d}$ is Me; $R^2$ is 2-chloro-5-thiazolyl |

| $R^e$ | $R^e$ | $R^e$ | $R^e$ |
|---|---|---|---|
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| | $R^a$ is Cl; $R^c$, $R^d$, $R^e$, $R^{3a}$, $R^{3b}$ and $R^{3c}$ are H; $R^{3d}$ is Me; $R^2$ is 2-chloro-5-thiazolyl |

| $R^b$ | $R^b$ | $R^b$ | $R^b$ |
|---|---|---|---|
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE 1-continued

| | | | |
|---|---|---|---|
| $R^a$ is Cl; $R^b$, $R^d$, $R^e$, $R^{3a}$, $R^{3b}$ and $R^{3c}$ are H; $R^{3d}$ is Me; $R^2$ is 2-chloro-5-thiazolyl | | | |

| $R^c$ | $R^c$ | $R^c$ | $R^c$ |
|---|---|---|---|
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| | | | |
|---|---|---|---|
| $R^a$ is Cl; $R^b$, $R^c$, $R^e$, $R^{3a}$, $R^{3b}$ and $R^{3c}$ are H; $R^{3d}$ is Me; $R^2$ is 2-chloro-5-thiazolyl | | | |

| $R^d$ | $R^d$ | $R^d$ | $R^d$ |
|---|---|---|---|
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| | | | |
|---|---|---|---|
| $R^a$ is Cl; $R^b$, $R^c$, $R^d$, $R^{3a}$, $R^{3b}$ and $R^{3c}$ are H; $R^{3d}$ is Me; $R^2$ is 2-chloro-5-thiazolyl | | | |

| $R^e$ | $R^e$ | $R^e$ | $R^e$ |
|---|---|---|---|
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE 1-continued

| $R^a$ is OMe; $R^c$, $R^d$, $R^e$, $R^{3a}$, $R^{3b}$ and $R^{3c}$ are H; $R^{3d}$ is Me; $R^2$ is 2-chloro-5-thiazolyl ||||
|---|---|---|---|
| $R^b$ | $R^b$ | $R^b$ | $R^b$ |
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^a$ is OMe; $R^b$, $R^d$, $R^e$, $R^{3a}$, $R^{3b}$ and $R^{3c}$ are H; $R^{3d}$ is Me; $R^2$ is 2-chloro-5-thiazolyl ||||
|---|---|---|---|
| $R^c$ | $R^c$ | $R^c$ | $R^c$ |
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^a$ is OMe; $R^b$, $R^c$, $R^e$, $R^{3a}$, $R^{3b}$ and $R^{3c}$ are H; $R^{3d}$ is Me; $R^2$ is 2-chloro-5-thiazolyl ||||
|---|---|---|---|
| $R^d$ | $R^d$ | $R^d$ | $R^d$ |
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE 1-continued

| $R^a$ is OMe; $R^b$, $R^c$, $R^d$, $R^{3a}$, $R^{3b}$ and $R^{3c}$ are H; $R^{3d}$ is Me; $R^2$ is 2-chloro-5-thiazolyl | | | |
|---|---|---|---|
| $R^e$ | $R^e$ | $R^e$ | $R^e$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O—n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N—Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^a$ is Me; $R^c$, $R^d$, $R^e$, $R^{3a}$, $R^{3b}$ and $R^{3c}$ are H; $R^{3d}$ is Me; $R^2$ is 2-chloro-5-thiazolyl | | | |
|---|---|---|---|
| $R^b$ | $R^b$ | $R^b$ | $R^b$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O—n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N—Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^a$ is Me; $R^b$, $R^d$, $R^e$, $R^{3a}$, $R^{3b}$ and $R^{3c}$ are H; $R^{3d}$ is Me; $R^2$ is 2-chloro-5-thiazolyl | | | |
|---|---|---|---|
| $R^c$ | $R^c$ | $R^c$ | $R^c$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O—n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N—Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE 1-continued

| $R^a$ is Me; $R^b$, $R^c$, $R^e$, $R^{3a}$, $R^{3b}$ and $R^{3c}$ are H; $R^{3d}$ is Me; $R^2$ is 2-chloro-5-thiazolyl ||||
|---|---|---|---|
| $R^d$ | $R^d$ | $R^d$ | $R^d$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O—n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N—Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^a$ is Me; $R^b$, $R^c$, $R^d$, $R^{3a}$, $R^{3b}$ and $R^{3c}$ are H; $R^{3d}$ is Me; $R^2$ is 2-chloro-5-thiazolyl ||||
|---|---|---|---|
| $R^e$ | $R^e$ | $R^e$ | $R^e$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O—n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N—Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

| $R^d$ is Cl; $R^a$, $R^c$, $R^e$, $R^{3a}$, $R^{3b}$ and $R^{3c}$ are H; $R^{3d}$ is Me; $R^2$ is 2-chloro-5-thiazolyl ||||
|---|---|---|---|
| $R^b$ | $R^b$ | $R^b$ | $R^b$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O—n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N—Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE 1-continued

$R^d$ is $CF_3$; $R^a$, $R^c$, $R^e$, $R^{3a}$, $R^{3b}$ and $R^{3c}$ are H; $R^{3d}$ is Me; $R^2$ is 2-chloro-5-thiazolyl

| $R^b$ | $R^b$ | $R^b$ | $R^b$ |
|---|---|---|---|
| H | O—i-Pr | 3-($CF_3$)phenyl | 2-fluoro-4-cyanophenyl |
| F | $OCH_2CH$=$CH_2$ | 3-fluorophenyl | 2-fluoro-4-chlorophenyl |
| Cl | $OCH_2C$≡CH | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O—n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N—Me-4-pyrazolyl |
| CH=$CH_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

$R^b$ is Br; $R^a$, $R^c$, $R^e$, $R^{3a}$, $R^{3b}$ and $R^{3c}$ are H; $R^{3d}$ is Me; $R^2$ is 2-chloro-5-thiazolyl

| $R^d$ | $R^d$ | $R^d$ | $R^d$ |
|---|---|---|---|
| H | O—i-Pr | 3-($CF_3$)phenyl | 2-fluoro-4-cyanophenyl |
| F | $OCH_2CH$=$CH_2$ | 3-fluorophenyl | 2-fluoro-4-chlorophenyl |
| Cl | $OCH_2C$≡CH | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O—n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N—Me-4-pyrazolyl |
| CH=$CH_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

$R^b$ is $OCF_3$; $R^a$, $R^c$, $R^e$, $R^{3a}$, $R^{3b}$ and $R^{3c}$ are H; $R^{3d}$ is Me; $R^2$ is 2-chloro-5-thiazolyl

| $R^d$ | $R^d$ | $R^d$ | $R^d$ |
|---|---|---|---|
| H | O—i-Pr | 3-($CF_3$)phenyl | 2-fluoro-4-cyanophenyl |
| F | $OCH_2CH$=$CH_2$ | 3-fluorophenyl | 2-fluoro-4-chlorophenyl |
| Cl | $OCH_2C$≡CH | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O—n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N—Me-4-pyrazolyl |
| CH=$CH_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE 1-continued

| | $R^b$ is OMe; $R^a$, $R^c$, $R^e$, $R^{3a}$, $R^{3b}$ and $R^{3c}$ are H; $R^{3d}$ is Me; $R^2$ is 2-chloro-5-thiazolyl |
|---|---|---|---|
| $R^d$ | $R^d$ | $R^d$ | $R^d$ |
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| | $R^b$ is F; $R^a$, $R^c$, $R^e$, $R^{3a}$, $R^{3b}$ and $R^{3c}$ are H; $R^{3d}$ is Me; $R^2$ is 2-chloro-5-thiazolyl |
|---|---|---|---|
| $R^d$ | $R^d$ | $R^d$ | $R^d$ |
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| | $R^b$ is CN; $R^a$, $R^c$, $R^e$, $R^{3a}$, $R^{3b}$ and $R^{3c}$ are H; $R^{3d}$ is Me; $R^2$ is 2-chloro-5-thiazolyl |
|---|---|---|---|
| $R^d$ | $R^d$ | $R^d$ | $R^d$ |
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE 1-continued $R^b$ is Me; $R^a$, $R^c$, $R^e$, $R^{3a}$, $R^{3b}$ and $R^{3c}$ are H; $R^{3d}$ is Me; $R^2$ is 2-chloro-5-thiazolyl

| $R^d$ | $R^d$ | $R^d$ | $R^d$ |
|---|---|---|---|
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

$R^b$ is I; $R^a$, $R^c$, $R^e$, $R^{3a}$, $R^{3b}$ and $R^{3c}$ are H; $R^{3d}$ is Me; $R^2$ is 2-chloro-5-thiazolyl

| $R^d$ | $R^d$ | $R^d$ | $R^d$ |
|---|---|---|---|
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

$R^a$ and $R^b$ are F; $R^c$, $R^e$, $R^{3a}$, $R^{3b}$ and $R^{3c}$ are H; $R^{3d}$ is Me; $R^2$ is 2-chloro-5-thiazolyl

| $R^d$ | $R^d$ | $R^d$ | $R^d$ |
|---|---|---|---|
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE 1-continued

| | $R^a$ is F; $R^b$ is Cl; $R^c$, $R^e$, $R^{3a}$, $R^{3b}$ and $R^{3c}$ are H; $R^{3d}$ is Me; $R^2$ is 2-chloro-5-thiazolyl |
| --- | --- | --- | --- |
| $R^d$ | $R^d$ | $R^d$ | $R^d$ |
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| | $R^a$ and $R^e$ are F; $R^c$, $R^d$, $R^{3a}$, $R^{3b}$ and $R^{3c}$ are H; $R^{3d}$ is Me; $R^2$ is 2-chloro-5-thiazolyl |
| --- | --- | --- | --- |
| $R^b$ | $R^b$ | $R^b$ | $R^b$ |
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

| | $R^c$ is OMe $R^a$, $R^b$, $R^e$, $R^{3a}$, $R^{3b}$ and $R^{3c}$ are H; $R^{3d}$ is Me; $R^2$ is 2-chloro-5-thiazolyl |
| --- | --- | --- | --- |
| $R^d$ | $R^d$ | $R^d$ | $R^d$ |
| H | O—i-Pr | 3-(CF$_3$)phenyl | 2-fluoro-4-cyanophenyl |
| F | OCH$_2$CH=CH$_2$ | 3-fluorophenyl | 2-fluoro-4-chlorophenyl |
| Cl | OCH$_2$C≡CH | 3-cyanophenyl | 2-methyl-4-chlorophenyl |
| Br | O—c-Pr | 3-(OCF$_3$)phenyl | 2-fluoro-4-(CF$_3$)phenyl |
| I | OCF$_3$ | 4-fluorophenyl | 2,4-bis(CF$_3$)phenyl |
| Me | OCHF$_2$ | 4-chlorophenyl | 2-fluoro-4-bromophenyl |
| Et | OCH$_2$CF$_3$ | 4-(CF$_3$)phenyl | 2-chloro-4-fluorophenyl |
| Pr | SCF$_3$ | 4-cyanophenyl | 2-(CF$_3$)-4-fluorophenyl |
| i-Pr | SCF$_3$ | 4-bromophenyl | 2-methyl-4-(CF$_3$)phenyl |
| c-Pr | SCHF$_2$ | 6-chloro-3-pyridinyl | 2-chloro-4-(CF$_3$)phenyl |
| t-Bu | S(O)CF$_3$ | 6-fluoro-3-pyridinyl | 2-(CF$_3$)-4-chlorophenyl |
| CF$_3$ | SO$_2$CF$_3$ | 6-(CF$_3$)-3-pyridinyl | 2,5-difluorophenyl |
| CH$_2$F | CO$_2$Me | 4,6-dichloro-3-pyridinyl | 2-fluoro-5-(CF$_3$)phenyl |
| CHF$_2$ | CO$_2$Et | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-(OCF$_3$)phenyl |
| O—n-Pr | C(O)NMe$_2$ | 3-bromo-5-fluorophenyl | 2-chloro-5-(CF$_3$)phenyl |
| OPh | C(=NOMe)Me | 3-chloro-5-fluorophenyl | N—Me-4-pyrazolyl |
| CH=CH$_2$ | C(=NOEt)Me | 3-fluoro-4-chlorophenyl | 3-Me-5-isoxazolyl |
| C≡CH | 2-fluorophenyl | 2,4-dichlorophenyl | 6-(6-Cl-3-pyridinyl)-3-pyridinyl |
| phenyl | 3-chlorophenyl | 2,4-difluorophenyl | |

TABLE 1-continued

| | $R^c$ is Me; $R^a$, $R^b$, $R^e$, $R^{3a}$, $R^{3b}$ and $R^{3c}$ are H; $R^{3d}$ is Me; $R^2$ is 2-chloro-5-thiazolyl | | |
|---|---|---|---|
| $R^d$ | $R^d$ | $R^d$ | $R^d$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O—n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N—Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

| | $R^c$ is F; $R^a$, $R^b$, $R^e$, $R^{3a}$, $R^{3b}$ and $R^{3c}$ are H; $R^{3d}$ is Me; $R^2$ is 2-chloro-5-thiazolyl | | |
|---|---|---|---|
| $R^d$ | $R^d$ | $R^d$ | $R^d$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O—n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N—Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

| | $R^c$ is Cl; $R^a$, $R^b$, $R^e$, $R^{3a}$, $R^{3b}$ and $R^{3c}$ are H; $R^{3d}$ is Me; $R^2$ is 2-chloro-5-thiazolyl | | |
|---|---|---|---|
| $R^d$ | $R^d$ | $R^d$ | $R^d$ |
| H | O—i-Pr | 3-($CF_3$)phenyl | 2-fluoro-4-cyanophenyl |
| F | $OCH_2CH=CH_2$ | 3-fluorophenyl | 2-fluoro-4-chlorophenyl |
| Cl | $OCH_2C\equiv CH$ | 3-cyanophenyl | 2-methyl-4-chlorophenyl |
| Br | O—c-Pr | 3-($OCF_3$)phenyl | 2-fluoro-4-($CF_3$)phenyl |
| I | $OCF_3$ | 4-fluorophenyl | 2,4-bis($CF_3$)phenyl |
| Me | $OCHF_2$ | 4-chlorophenyl | 2-fluoro-4-bromophenyl |
| Et | $OCH_2CF_3$ | 4-($CF_3$)phenyl | 2-chloro-4-fluorophenyl |
| Pr | $SCF_3$ | 4-cyanophenyl | 2-($CF_3$)-4-fluorophenyl |
| i-Pr | $SCF_3$ | 4-bromophenyl | 2-methyl-4-($CF_3$)phenyl |
| c-Pr | $SCHF_2$ | 6-chloro-3-pyridinyl | 2-chloro-4-($CF_3$)phenyl |
| t-Bu | $S(O)CF_3$ | 6-fluoro-3-pyridinyl | 2-($CF_3$)-4-chlorophenyl |
| $CF_3$ | $SO_2CF_3$ | 6-($CF_3$)-3-pyridinyl | 2,5-difluorophenyl |
| $CH_2F$ | $CO_2Me$ | 4,6-dichloro-3-pyridinyl | 2-fluoro-5-($CF_3$)phenyl |
| $CHF_2$ | $CO_2Et$ | 2-fluoro-6-chloro-3-pyridinyl | 2-fluoro-5-chlorophenyl |
| OMe | cyano | 2,6-dichloro-3-pyridinyl | 2,5-dichlorophenyl |
| OEt | C(O)NHMe | 2-bromo-5-chloro-4-pyridinyl | 2-fluoro-5-($OCF_3$)phenyl |
| O—n-Pr | $C(O)NMe_2$ | 3-bromo-5-fluorophenyl | 2-chloro-5-($CF_3$)phenyl |
| OPh | C(=NOMe)Me | 3-chloro-5-fluorophenyl | N—Me-4-pyrazolyl |
| $CH=CH_2$ | C(=NOEt)Me | 3-fluoro-4-chlorophenyl | 3-Me-5-isoxazolyl |
| $C\equiv CH$ | 2-fluorophenyl | 2,4-dichlorophenyl | 6-(6-Cl-3-pyridinyl)-3-pyridinyl |
| phenyl | 3-chlorophenyl | 2,4-difluorophenyl | |

Table 2

Table 2 is identical to Table 1, except that $R^{3d}$ is OMe. For example, the first compound in Table 2 is the compound of Formula T-1 wherein $R^a$, $R^b$, $R^c$, $R^d$, $R^e$, $R^{3a}$, $R^{3b}$ and $R^{3c}$ are H; $R^{3d}$ is OMe; and $R^2$ is 2-chloro-5-thiazolyl.

Table 2a

Table 2a is identical to Table 1, except that $R^{3d}$ is Et. For example, the first compound in Table 2a is the compound of Formula T-1 wherein $R^a$, $R^b$, $R^c$, $R^d$, $R^e$, $R^{3a}$, $R^{3b}$ and $R^{3c}$ are H; $R^{3d}$ is Et; and $R^2$ is 2-chloro-5-thiazolyl.

Table 3

Table 3 is identical to Table 1, except that $R^{3d}$ is Cl. For example, the first compound in Table 3 is the compound of Formula T-1 wherein $R^a$, $R^b$, $R^c$, $R^d$, $R^e$, $R^{3a}$, $R^{3b}$ and $R^{3c}$ are H; $R^{3d}$ is Cl; and $R^2$ is 2-chloro-5-thiazolyl.

Table 4

Table 4 is identical to Table 1, except that $R^{3c}$ is F. For example, the first compound in Table 4 is the compound of Formula T-1 wherein $R^a$, $R^b$, $R^c$, $R^d$, $R^e$, $R^{3a}$ and $R^{3b}$ are H; $R^{3c}$ is F; $R^{3d}$ is Me; and $R^2$ is 2-chloro-5-thiazolyl.

Table 5

Table 5 is identical to Table 1, except that $R^{3b}$ is F. For example, the first compound in Table 5 is the compound of Formula T-1 wherein $R^a$, $R^b$, $R^c$, $R^d$, $R^e$, $R^{3a}$ and $R^{3c}$ are H; $R^{3b}$ is F; $R^{3d}$ is Me; and $R^2$ is 2-chloro-5-thiazolyl.

Table 6

Table 6 is identical to Table 1, except that $R^{3a}$ is F. For example, the first compound in Table 6 is the compound of Formula T-1 wherein $R^a$, $R^b$, $R^c$, $R^d$, $R^e$, $R^{3b}$ and $R^{3c}$ are H; $R^{3a}$ is F; $R^{3d}$ is Me; and $R^2$ is 2-chloro-5-thiazolyl.

Table 7

Table 7 is identical to Table 1, except that $R^{3d}$ is Br. For example, the first compound in Table 7 is the compound of Formula T-1 wherein $R^a$, $R^b$, $R^c$, $R^d$, $R^e$, $R^{3a}$, $R^{3b}$ and $R^{3c}$ are H; $R^{3d}$ is Br, and $R^2$ is 2-chloro-5-thiazolyl.

Table 8

Table 8 is identical to Table 1, except that $R^2$ is 6-chloro-3-pyridinyl. For example, the first compound in Table 8 is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is 6-chloro-3-pyridinyl.

Table 8a

Table 8a is identical to Table 1, except that $R^2$ is 6-bromo-3-pyridinyl. For example, the first compound in Table 8a is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is 6-bromo-3-pyridinyl.

Table 8b

Table 8b is identical to Table 1, except that $R^2$ is 6-methyl-3-pyridinyl. For example, the first compound in Table 8b is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is 6-methyl-3-pyridinyl.

Table 8c

Table 8c is identical to Table 1, except that $R^2$ is 3-pyridinyl. For example, the first compound in Table 8c is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is 3-pyridinyl.

Table 9

Table 9 is identical to Table 1, except that $R^2$ is 5-thiazolyl. For example, the first compound in Table 9 is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is 5-thiazolyl.

Table 10

Table 10 is identical to Table 1, except that $R^2$ is 2-methyl-5-thiazolyl. For example, the first compound in Table 10 is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is 2-methyl-5-thiazolyl.

Table 10a

Table 10a is identical to Table 1, except that $R^2$ is 2-methyl-5-oxazolyl. For example, the first compound in Table 10a is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is 2-methyl-5-oxazolyl.

Table 11

Table 11 is identical to Table 1, except that $R^2$ is 6-fluoro-3-pyridinyl. For example, the first compound in Table 11 is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is 6-fluoro-3-pyridinyl.

Table 12

Table 12 is identical to Table 1, except that $R^2$ is 2-bromo-5-thiazolyl. For example, the first compound in Table 12 is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is 2-bromo-5-thiazolyl.

Table 12a

Table 12a is identical to Table 1, except that $R^2$ is 2-fluoro-5-thiazolyl. For example, the first compound in Table 12a is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is 2-fluoro-5-thiazolyl.

Table 13

Table 13 is identical to Table 1, except that $R^2$ is 4-pyrimidinyl. For example, the first compound in Table 13 is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is 4-pyrimidinyl.

Table 13a

Table 13a is identical to Table 1, except that $R^2$ is 2-methyl-4-pyrimidinyl. For example, the first compound in

149

Table 13a is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is 2-methyl-4-pyrimidinyl.

Table 14

Table 14 is identical to Table 1, except that $R^2$ is N-methyl-4-pyrazolyl. For example, the first compound in Table 14 is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is N-methyl-4-pyrazolyl.

Table 15

Table 15 is identical to Table 1, except that $R^2$ is $CF_3$. For example, the first compound in Table 15 is the compound of Formula T-1 wherein $R^a$, $R^b$, $R^c$, $R^d$, $R^e$, $R^{3a}$, $R^{3b}$ and $R^{3c}$ are H; $R^{3d}$ is Me; and $R^2$ is $CF_3$.

Table 16

Table 16 is identical to Table 1, except that $R^{3c}$ and $R^{3d}$ are taken together to form a phenyl ring. For example, the first compound in Table 16 is the compound shown immediately below wherein $R^a$, $R^b$, $R^c$, $R^d$, $R^e$, $R^{3a}$ and $R^{3b}$ are H; and $R^2$ is 2-chloro-5-thiazolyl.

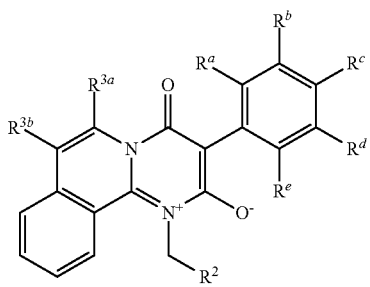

Table 17

Table 17 is identical to Table 1, except that the chemical structure under the Table 17 heading is replaced with the following structure:

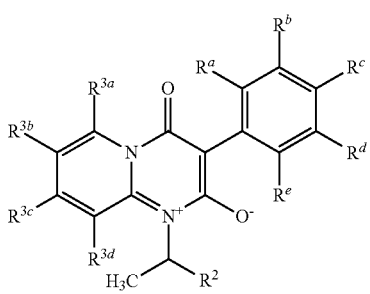

For example, the first compound in Table 17 is the structure shown immediately above wherein $R^a$, $R^b$, $R^c$, $R^d$, $R^e$, $R^{3a}$, $R^{3b}$ and $R^{3c}$ are H; $R^{3d}$ is Me; and $R^2$ is 2-chloro-5-thiazolyl.

TABLE 17a

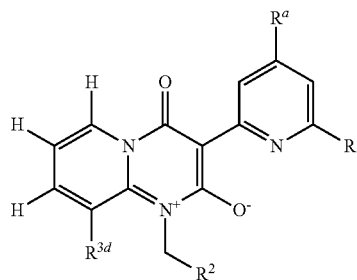

| $R^a$ | R |
|---|---|
| $R^2$ is 2-chloro-5-thiazolyl; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 2-chloro-5-thiazolyl; $R^{3d}$ is OMe | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 2-chloro-5-thiazolyl; $R^{3d}$ is Cl | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |

TABLE 17a-continued

[Structure: pyrido-pyrimidinone with substituents $R^a$, $R$, $R^{3d}$, $R^2$]

| $R^a$ | R |
|---|---|
| cyano | 2-chloro-4-(trifluoromethyl)phenyl |
| cyano | 2-fluoro-4-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

$R^2$ is 2-chloro-5-thiazolyl; $R^{3d}$ is Br

| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

$R^2$ is 2-bromo-5-thiazolyl; $R^{3d}$ is Me

| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

$R^2$ is 2-fluoro-5-thiazolyl; $R^{3d}$ is Me

| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

$R^2$ is 5-thiazolyl; $R^{3d}$ is Me

| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

TABLE 17a-continued

[Structure: pyrido-pyrimidinone core with substituents $R^a$, $R$, $R^2$, $R^{3d}$]

| $R^a$ | R |
|---|---|
| $R^2$ is 2-methyl-5-thiazolyl; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 6-chloro-3-pyridinyl; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 6-fluoro-3-pyridinyl; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 6-bromo-3-pyridinyl; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| $CH_3$ | 4-chloro-2-fluorophenyl |
| $CH_3$ | 2-fluoro-4-(trifluoromethyl)phenyl |
| $CH_3$ | 2-chloro-4-(trifluoromethyl)phenyl |
| $CH_3$ | 2-fluoro-5-(trifluoromethyl)phenyl |
| $CH_3$ | 2-fluoro-5-(trifluoromethoxy)phenyl |
| $OCH_3$ | 2-chloro-4-(trifluoromethyl)phenyl |
| $OCH_3$ | 2-fluoro-5-(trifluoromethyl)phenyl |
| $OCH_3$ | 2-fluoro-5-(trifluoromethoxy)phenyl |
| $R^2$ is 6-methyl-3-pyridinyl; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| $OCH_3$ | 4-chloro-2-fluorophenyl |
| $OCH_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |

TABLE 17a-continued

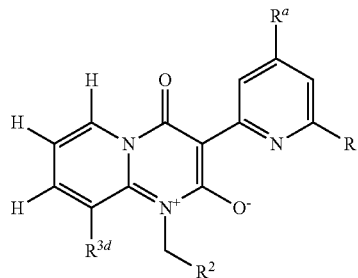

| $R^a$ | R |
|---|---|
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| $R^2$ is 3-pyridinyl; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| $R^2$ is 4-pyrimidinyl; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

TABLE 17a-continued

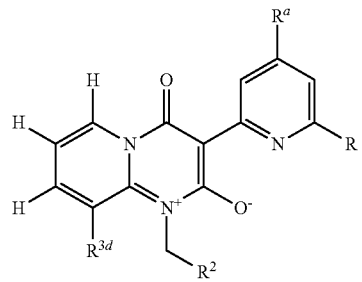

| $R^a$ | R |
|---|---|
| $R^2$ is 2-methyl-4-pyrimidinyl; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| $R^2$ is N-methyl-4-pyrazolyl; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |
| $R^2$ is CF₃; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |

TABLE 17a-continued

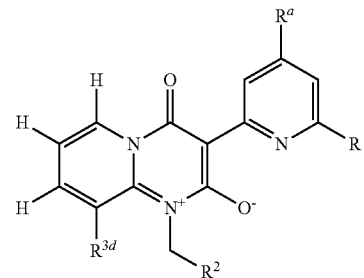

| $R^a$ | R |
|---|---|
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| $R^2$ is CH$_2$CF$_3$; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| $R^2$ is CH$_2$CFClCHF$_2$; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |

TABLE 17a-continued

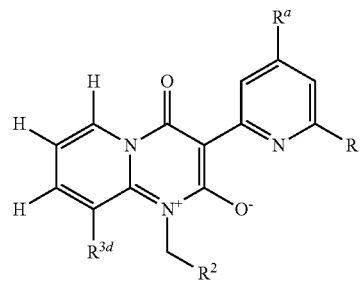

| $R^a$ | R |
|---|---|
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

TABLE 17b

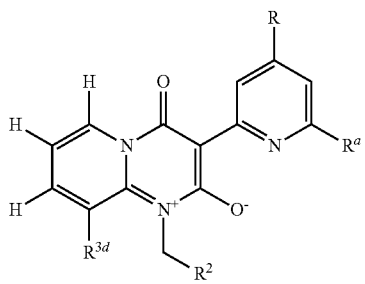

| $R^a$ | R |
|---|---|
| $R^2$ is 2-chloro-5-thiazolyl; $R^{3d}$ is Me | |
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |
| $R^2$ is 2-chloro-5-thiazolyl; $R^{3d}$ is OMe | |
| H | 4-chloro-2-fluorophenyl |
| H | 2-fluoro-4-(trifluoromethyl)phenyl |

TABLE 17b-continued

[Structure: pyrido-pyrimidinone with R, Rᵃ, R², R³ᵈ substituents]

| Rᵃ | R |
|---|---|
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

R² is 2-chloro-5-thiazolyl; R³ᵈ is Cl

| Rᵃ | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

R² is 2-chloro-5-thiazolyl; R³ᵈ is Br

| Rᵃ | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |

TABLE 17b-continued

[Structure: pyrido-pyrimidinone with R, Rᵃ, R², R³ᵈ substituents]

| Rᵃ | R |
|---|---|
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

R² is 2-bromo-5-thiazolyl; R³ᵈ is Me

| Rᵃ | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-4-(trifluoromethyl)phenyl |
| OCH₃ | 2-fluoro-5-(trifluoromethoxy)phenyl |

R² is 2-fluoro-5-thiazolyl; R³ᵈ is Me

| Rᵃ | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |

TABLE 17b-continued

[Structure: pyrido-pyrimidinone core with substituents R, R^a, R^2, R^{3d}]

| R^a | R |
|---|---|
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

R² is 5-thiazolyl; R^{3d} is Me

| R^a | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

R² is 2-methyl-5-thiazolyl; R^{3d} is Me

| R^a | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

R² is 6-chloro-3-pyridinyl; R^{3d} is Me

| R^a | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

R² is 6-fluoro-3-pyridinyl; R^{3d} is Me

| R^a | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

R² is 6-bromo-3-pyridinyl; R^{3d} is Me

| R^a | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |

TABLE 17b-continued

[Structure: pyrido-pyrimidinone core with substituents R, R$^a$, R$^{3d}$, R$^2$]

| R$^a$ | R |
|---|---|
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

R$^2$ is 6-methyl-3-pyridinyl; R$^{3d}$ is Me

| R$^a$ | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

R$^2$ is 3-pyridinyl; R$^{3d}$ is Me

| R$^a$ | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |

TABLE 17b-continued

[Structure: pyrido-pyrimidinone core with substituents R, R$^a$, R$^{3d}$, R$^2$]

| R$^a$ | R |
|---|---|
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

R$^2$ is 4-pyrimidinyl; R$^{3d}$ is Me

| R$^a$ | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

R$^2$ is 2-methyl-4-pyrimidinyl; R$^{3d}$ is Me

| R$^a$ | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH$_3$ | 4-chloro-2-fluorophenyl |
| OCH$_3$ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH$_3$ | 4-chloro-2-fluorophenyl |
| CH$_3$ | 2-fluoro-4-(trifluoromethyl)phenyl |
| CH$_3$ | 2-chloro-4-(trifluoromethyl)phenyl |
| CH$_3$ | 2-fluoro-5-(trifluoromethyl)phenyl |
| CH$_3$ | 2-fluoro-5-(trifluoromethoxy)phenyl |
| OCH$_3$ | 2-chloro-4-(trifluoromethyl)phenyl |
| OCH$_3$ | 2-fluoro-5-(trifluoromethyl)phenyl |
| OCH$_3$ | 2-fluoro-5-(trifluoromethoxy)phenyl |

R$^2$ is N-methyl-4-pyrazolyl; R$^{3d}$ is Me

| R$^a$ | R |
|---|---|
| H | 4-chloro-2-fluorophenyl |
| H | 2-fluoro-4-(trifluoromethyl)phenyl |

TABLE 17b-continued

[Structure: pyrido-pyrimidinone with R on pyridine, R^a on pyridine, R^{3d} on ring, N^+-CH2-R^2, O^-]

R² is CF₃; R³ᵈ is Me

| Rᵃ | R |
|---|---|
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

R² is CH₂CF₃; R³ᵈ is Me

| Rᵃ | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

| Rᵃ | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |

TABLE 17b-continued

[Structure: pyrido-pyrimidinone with R on pyridine, R^a on pyridine, R^{3d} on ring, N^+-CH2-R^2, O^-]

| Rᵃ | R |
|---|---|
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

R² is CH₂CFClCHF₂; R³ᵈ is Me

| Rᵃ | R |
|---|---|
| H | 4-chloro-2-fluorophenyl |
| H | 2-fluoro-4-(trifluoromethyl)phenyl |
| H | 2-chloro-4-(trifluoromethyl)phenyl |
| H | 2-fluoro-5-(trifluoromethyl)phenyl |
| H | 2-fluoro-5-(trifluoromethoxy)phenyl |
| cyano | 4-chloro-2-fluorophenyl |
| cyano | 2-fluoro-4-(trifluoromethyl)phenyl |
| cyano | 2-chloro-4-(trifluoromethyl)phenyl |
| cyano | 2-fluoro-5-(trifluoromethyl)phenyl |
| cyano | 2-fluoro-5-(trifluoromethoxy)phenyl |
| OCH₃ | 4-chloro-2-fluorophenyl |
| OCH₃ | 2-fluoro-4-(trifluoromethyl)phenyl |
| F | 4-chloro-2-fluorophenyl |
| F | 2-fluoro-4-(trifluoromethyl)phenyl |
| F | 2-chloro-4-(trifluoromethyl)phenyl |
| F | 2-fluoro-5-(trifluoromethyl)phenyl |
| F | 2-fluoro-5-(trifluoromethoxy)phenyl |
| CH₃ | 4-chloro-2-fluorophenyl |
| CH₃ | 2-fluoro-4-(trifluoromethyl)phenyl |
| CH₃ | 2-chloro-4-(trifluoromethyl)phenyl |
| CH₃ | 2-fluoro-5-(trifluoromethyl)phenyl |
| CH₃ | 2-fluoro-5-(trifluoromethoxy)phenyl |
| OCH₃ | 2-chloro-4-(trifluoromethyl)phenyl |
| OCH₃ | 2-fluoro-5-(trifluoromethyl)phenyl |
| OCH₃ | 2-fluoro-5-(trifluoromethoxy)phenyl |

TABLE 17c

[Structure: pyrido-pyrimidine N-oxide with R group on pyridine, R³ᵈ on ring, R² on CH₂ substituent]

R

| $R^2$ is 2-chloro-5-thiazolyl; $R^{3d}$ is Me |
|---|
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |
| $R^2$ is 2-chloro-5-thiazolyl; $R^{3d}$ is OMe |
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |
| $R^2$ is 2-chloro-5-thiazolyl; $R^{3d}$ is Cl |
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |
| $R^2$ is 2-chloro-5-thiazolyl; $R^{3d}$ is Br |
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |
| $R^2$ is 2-bromo-5-thiazolyl; $R^{3d}$ is Me |
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |
| $R^2$ is 2-fluoro-5-thiazolyl; $R^{3d}$ is Me |
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |
| $R^2$ is 5-thiazolyl; $R^{3d}$ is Me |
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |

TABLE 17c-continued

R

| |
|---|
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |
| $R^2$ is 2-methyl-5-thiazolyl; $R^{3d}$ is Me |
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |
| $R^2$ is 6-chloro-3-pyridinyl; $R^{3d}$ is Me |
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |
| $R^2$ is 6-fluoro-3-pyridinyl; $R^{3d}$ is Me |
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |
| $R^2$ is 6-bromo-3-pyridinyl; $R^{3d}$ is Me |
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |
| $R^2$ is 6-methyl-3-pyridinyl; $R^{3d}$ is Me |
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |
| $R^2$ is 3-pyridinyl; $R^{3d}$ is Me |
| 4-chloro-2-fluorophenyl |
| 2-fluoro-4-(trifluoromethyl)phenyl |
| 4-cyano-2-fluorophenyl |
| 2-chloro-4-(trifluoromethyl)phenyl |
| 2-fluoro-5-(trifluoromethyl)phenyl |
| 2-fluoro-5-(trifluoromethoxy)phenyl |
| 2-chloro-4-cyanophenyl |
| 4-chloro-2-methylphenyl |

TABLE 17c-continued

R² is 4-pyrimidinyl; R³ᵈ is Me 4-chloro-2-fluorophenyl
2-fluoro-4-(trifluoromethyl)phenyl
4-cyano-2-fluorophenyl
2-chloro-4-(trifluoromethyl)phenyl
2-fluoro-5-(trifluoromethyl)phenyl
2-fluoro-5-(trifluoromethoxy)phenyl
2-chloro-4-cyanophenyl
4-chloro-2-methylphenyl R² is 2-methyl-4-pyrimidinyl; R³ᵈ is Me 4-chloro-2-fluorophenyl
2-fluoro-4-(trifluoromethyl)phenyl
4-cyano-2-fluorophenyl
2-chloro-4-(trifluoromethyl)phenyl
2-fluoro-5-(trifluoromethyl)phenyl
2-fluoro-5-(trifluoromethoxy)phenyl
2-chloro-4-cyanophenyl
4-chloro-2-methylphenyl R² is N-methyl-4-pyrazolyl; R³ᵈ is Me 4-chloro-2-fluorophenyl
2-fluoro-4-(trifluoromethyl)phenyl
4-cyano-2-fluorophenyl
2-chloro-4-(trifluoromethyl)phenyl
2-fluoro-5-(trifluoromethyl)phenyl
2-fluoro-5-(trifluoromethoxy)phenyl
2-chloro-4-cyanophenyl
4-chloro-2-methylphenyl

TABLE 17c-continued

R² is CF₃; R³ᵈ is Me 4-chloro-2-fluorophenyl
2-fluoro-4-(trifluoromethyl)phenyl
4-cyano-2-fluorophenyl
2-chloro-4-(trifluoromethyl)phenyl
2-fluoro-5-(trifluoromethyl)phenyl
2-fluoro-5-(trifluoromethoxy)phenyl
2-chloro-4-cyanophenyl
4-chloro-2-methylphenyl R² is CH₂CF₃; R³ᵈ is Me 4-chloro-2-fluorophenyl
2-fluoro-4-(trifluoromethyl)phenyl
4-cyano-2-fluorophenyl
2-chloro-4-(trifluoromethyl)phenyl
2-fluoro-5-(trifluoromethyl)phenyl
2-fluoro-5-(trifluoromethoxy)phenyl
2-chloro-4-cyanophenyl
4-chloro-2-methylphenyl R² is CH₂CFClCHF₂; R³ᵈ is Me 4-chloro-2-fluorophenyl
2-fluoro-4-(trifluoromethyl)phenyl
4-cyano-2-fluorophenyl
2-chloro-4-(trifluoromethyl)phenyl
2-fluoro-5-(trifluoromethyl)phenyl
2-fluoro-5-(trifluoromethoxy)phenyl
2-chloro-4-cyanophenyl
4-chloro-2-methylphenyl

TABLE 18

| ZR¹ | ZR¹ | ZR¹ | ZR¹ |
|---|---|---|---|
| R² is 2-chloro-5-thiazolyl; R³ᵈ is Me | | | |
| 4-CF₃-2-pyridinyl | 2-CN-4-pyridinyl | 6-CF₃-2-pyridinyl | 4-CN-2-pyridinyl |
| 2-Cl-4-pyridinyl | 2-CF₃-4-pyridinyl | 6-OCF₃-2-pyridinyl | 4-Cl-2-pyridinyl |
| 2-F-4-pyridinyl | 2-OCF₃-4-pyridinyl | 4-OCF₃-2-pyridinyl | 6-CH₃-2-pyridinyl |
| 2-Br-4-pyridinyl | 2-OCH₃-4-pyridinyl | 4-CH₃-2-pyridinyl | 6-CN-2-pyridinyl |
|  | 6-OCH₃-2-pyridinyl | 4-OCH₃-2-pyridinyl | 6-Cl-2-pyridinyl |
| R² is 2-chloro-5-thiazolyl; R³ᵈ is OMe | | | |
| 4-CF₃-2-pyridinyl | 2-CN-4-pyridinyl | 6-CF₃-2-pyridinyl | 4-CN-2-pyridinyl |
| 2-Cl-4-pyridinyl | 2-CF₃-4-pyriidnyl | 6-OCF₃-2-pyridinyl | 4-Cl-2-pyridinyl |
| 2-F-4-pyridinyl | 2-OCF₃-4-pyridinyl | 4-OCF₃-2-pyridinyl | 6-CH₃-2-pyridinyl |
| 2-Br-4-pyridinyl | 2-OCH₃-4-pyridinyl | 4-CH₃-2-pyridinyl | 6-CN-2-pyridinyl |
|  | 6-OCH₃-2-pyridinyl | 4-OCH₃-2-pyridinyl | 4-Cl-2-pyridinyl |

TABLE 18-continued

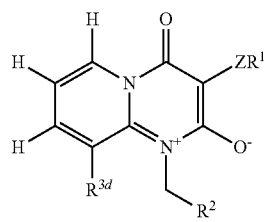

| ZR¹ | ZR¹ | ZR¹ | ZR¹ |
|---|---|---|---|
| R² is 2-chloro-5-thiazolyl; R$^{3d}$ is Cl | | | |
| 4-CF$_3$-2-pyridinyl | 2-CN-4-pyridinyl | 6-CF$_3$-2-pyridinyl | 4-CN-2-pyridinyl |
| 2-Cl-4-pyridinyl | 2-CF$_3$-4-pyridinyl | 6-OCF$_3$-2-pyridinyl | 4-Cl-2-pyridinyl |
| 2-F-4-pyridinyl | 2-OCF$_3$-4-pyridinyl | 4-OCF$_3$-2-pyridinyl | 6-CH$_3$-2-pyridinyl |
| 2-Br-4-pyridinyl | 2-OCH$_3$-4-pyridinyl | 4-CH$_3$-2-pyridinyl | 6-CN-2-pyridinyl |
| | 6-OCH$_3$-2-pyridinyl | 4-OCH$_3$-2-pyridinyl | 6-Cl-2-pyridinyl |
| R² is 2-chloro-5-thiazolyl; R$^{3d}$ is Br | | | |
| 4-CF$_3$-2-pyridinyl | 2-CN-4-pyridinyl | 6-CF$_3$-2-pyridinyl | 4-CN-2-pyridinyl |
| 2-Cl-4-pyridinyl | 2-CF$_3$-4-pyridinyl | 6-OCF$_3$-2-pyridinyl | 4-Cl-2-pyridinyl |
| 2-F-4-pyridinyl | 2-OCF$_3$-4-pyridinyl | 4-OCF$_3$-2-pyridinyl | 6-CH$_3$-2-pyridinyl |
| 2-Br-4-pyridinyl | 2-OCH$_3$-4-pyridinyl | 4-CH$_3$-2-pyridinyl | 6-CN-2-pyridinyl |
| | 6-OCH$_3$-2-pyridinyl | 4-OCH$_3$-2-pyridinyl | 6-Cl-2-pyridinyl |
| R² is 2-bromo-5-thiazolyl; R$^{3d}$ is Me | | | |
| 4-CF$_3$-2-pyridinyl | 2-CN-4-pyridinyl | 6-CF$_3$-2-pyridinyl | 4-CN-2-pyridinyl |
| 2-Cl-4-pyridinyl | 2-CF$_3$-4-pyridinyl | 6-OCF$_3$-2-pyridinyl | 4-Cl-2-pyridinyl |
| 2-F-4-pyridinyl | 2-OCF$_3$-4-pyridinyl | 4-OCF$_3$-2-pyridinyl | 6-CH$_3$-2-pyridinyl |
| 2-Br-4-pyridinyl | 2-OCH$_3$-4-pyridinyl | 4-CH$_3$-2-pyridinyl | 6-CN-2-pyridinyl |
| | 6-OCH$_3$-2-pyridinyl | 4-OCH$_3$-2-pyridinyl | 6-Cl-2-pyridinyl |
| R² is 2-fluoro-5-thiazolyl; R$^{3d}$ is Me | | | |
| 4-CF$_3$-2-pyridinyl | 2-CN-4-pyridinyl | 6-CF$_3$-2-pyridinyl | 4-CN-2-pyridinyl |
| 2-Cl-4-pyridinyl | 2-CF$_3$-4-pyridinyl | 6-OCF$_3$-2-pyridinyl | 4-Cl-2-pyridinyl |
| 2-F-4-pyridinyl | 2-OCF$_3$-4-pyridinyl | 4-OCF$_3$-2-pyridinyl | 6-CH$_3$-2-pyridinyl |
| 2-Br-4-pyridinyl | 2-OCH$_3$-4-pyridinyl | 4-CH$_3$-2-pyridinyl | 6-CN-2-pyridinyl |
| | 6-OCH$_3$-2-pyridinyl | 4-OCH$_3$-2-pyridinyl | 6-Cl-2-pyridinyl |
| R² is 5-thiazolyl; R$^{3d}$ is Me | | | |
| 4-CF$_3$-2-pyridinyl | 2-CN-4-pyridinyl | 6-CF$_3$-2-pyridinyl | 4-CN-2-pyridinyl |
| 2-Cl-4-pyridinyl | 2-CF$_3$-4-pyridinyl | 6-OCF$_3$-2-pyridinyl | 4-Cl-2-pyridinyl |
| 2-F-4-pyridinyl | 2-OCF$_3$-4-pyridinyl | 4-OCF$_3$-2-pyridinyl | 6-CH$_3$-2-pyridinyl |
| 2-Br-4-pyridinyl | 2-OCH$_3$-4-pyridinyl | 4-CH$_3$-2-pyridinyl | 6-CN-2-pyridinyl |
| | 6-OCH$_3$-2-pyridinyl | 4-OCH$_3$-2-pyridinyl | 6-Cl-2-pyridinyl |
| R² is 2-methyl-5-thiazolyl; R$^{3d}$ is Me | | | |
| 4-CF$_3$-2-pyridinyl | 2-CN-4-pyridinyl | 6-CF$_3$-2-pyridinyl | 4-CN-2-pyridinyl |
| 2-Cl-4-pyridinyl | 2-CF$_3$-4-pyridinyl | 6-OCF$_3$-2-pyridinyl | 4-Cl-2-pyridinyl |
| 2-F-4-pyridinyl | 2-OCF$_3$-4-pyridinyl | 4-OCF$_3$-2-pyridinyl | 6-CH$_3$-2-pyridinyl |
| 2-Br-4-pyridinyl | 2-OCH$_3$-4-pyridinyl | 4-CH$_3$-2-pyridinyl | 6-CN-2-pyridinyl |
| | 6-OCH$_3$-2-pyridinyl | 4-OCH$_3$-2-pyridinyl | 6-Cl-2-pyridinyl |
| R² is 6-chloro-3-pyridinyl; R$^{3d}$ is Me | | | |
| 4-CF$_3$-2-pyridinyl | 2-CN-4-pyriidnyl | 6-CF$_3$-2-pyridinyl | 4-CN-2-pyridinyl |
| 2-Cl-4-pyridinyl | 2-CF$_3$-4-pyridinyl | 6-OCF$_3$-2-pyridinyl | 4-Cl-2-pyridinyl |
| 2-F-4-pyridinyl | 2-OCF$_3$-4-pyridinyl | 4-OCF$_3$-2-pyridinyl | 6-CH$_3$-2-pyridinyl |
| 2-Br-4-pyridinyl | 2-OCH$_3$-4-pyridinyl | 4-CH$_3$-2-pyridinyl | 6-CN-2-pyridinyl |
| | 6-OCH$_3$-2-pyridinyl | 4-OCH$_3$-2-pyridinyl | 6-Cl-2-pyridinyl |
| R² is 6-fluoro-3-pyridinyl; R$^{3d}$ is Me | | | |
| 4-CF$_3$-2-pyridinyl | 2-CN-4-pyridinyl | 6-CF$_3$-2-pyridinyl | 4-CN-2-pyridinyl |
| 2-Cl-4-pyridinyl | 2-CF$_3$-4-pyridinyl | 6-OCF$_3$-2-pyridinyl | 4-Cl-2-pyridinyl |
| 2-F-4-pyridinyl | 2-OCF$_3$-4-pyridinyl | 4-OCF$_3$-2-pyridinyl | 6-CH$_3$-2-pyridinyl |
| 2-Br-4-pyridinyl | 2-OCH$_3$-4-pyridinyl | 4-CH$_3$-2-pyridinyl | 6-CN-2-pyridinyl |
| | 6-OCH$_3$-2-pyridinyl | 4-OCH$_3$-2-pyridinyl | 6-Cl-2-pyridinyl |
| R² is 6-bromo-3-pyridinyl; R$^{3d}$ is Me | | | |
| 4-CF$_3$-2-pyridinyl | 2-CN-4-pyridinyl | 6-CF$_3$-2-pyridinyl | 4-CN-2-pyridinyl |
| 2-Cl-4-pyridinyl | 2-CF$_3$-4-pyridinyl | 6-OCF$_3$-2-pyridinyl | 4-Cl-2-pyridinyl |
| 2-F-4-pyridinyl | 2-OCF$_3$-4-pyridinyl | 4-OCF$_3$-2-pyridinyl | 6-CH$_3$-2-pyridinyl |
| 2-Br-4-pyridinyl | 2-OCH$_3$-4-pyridinyl | 4-CH$_3$-2-pyridinyl | 6-CN-2-pyridinyl |
| | 6-OCH$_3$-2-pyridinyl | 4-OCH$_3$-2-pyridinyl | 6-Cl-2-pyridinyl |

TABLE 18-continued

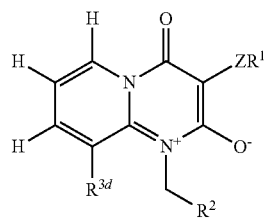

| ZR¹ | ZR¹ | ZR¹ | ZR¹ |
|---|---|---|---|
| \multicolumn{4}{c}{R² is 6-methyl-3-pyridinyl; R³ᵈ is Me} ||||
| 4-CF₃-2-pyridinyl | 2-CN-4-pyridinyl | 6-CF₃-2-pyridinyl | 4-CN-2-pyridinyl |
| 2-Cl-4-pyridinyl | 2-CF₃-4-pyridinyl | 6-OCF₃-2-pyridinyl | 4-Cl-2-pyridinyl |
| 2-F-4-pyridinyl | 2-OCF₃-4-pyridinyl | 4-OCF₃-2-pyridinyl | 6-CH₃-2-pyridinyl |
| 2-Br-4-pyridinyl | 2-OCH₃-4-pyridinyl | 4-CH₃-2-pyridinyl | 6-CN-2-pyridinyl |
|  | 6-OCH₃-2-pyridinyl | 4-OCH₃-2-pyridinyl | 6-Cl-2-pyridinyl |
| \multicolumn{4}{c}{R² is 3-pyridinyl; R³ᵈ is Me} ||||
| 4-CF₃-2-pyridinyl | 2-CN-4-pyridinyl | 6-CF₃-2-pyridinyl | 4-CN-2-pyridinyl |
| 2-Cl-4-pyridinyl | 2-CF₃-4-pyridinyl | 6-OCF₃-2-pyridinyl | 4-Cl-2-pyridinyl |
| 2-F-4-pyridinyl | 2-OCF₃-4-pyridinyl | 4-OCF₃-2-pyridinyl | 6-CH₃-2-pyridinyl |
| 2-Br-4-pyridinyl | 2-OCH₃-4-pyridinyl | 4-CH₃-2-pyridinyl | 6-CN-2-pyridinyl |
|  | 6-OCH₃-2-pyridinyl | 4-OCH₃-2-pyridinyl | 6-Cl-2-pyridinyl |
| \multicolumn{4}{c}{R² is 4-pyrimidinyl; R³ᵈ is Me} ||||
| 4-CF₃-2-pyridinyl | 2-CN-4-pyridinyl | 6-CF₃-2-pyridinyl | 4-CN-2-pyridinyl |
| 2-Cl-4-pyridinyl | 2-CF₃-4-pyridinyl | 6-OCF₃-2-pyridinyl | 4-Cl-2-pyridinyl |
| 2-F-4-pyridinyl | 2-OCF₃-4-pyridinyl | 4-OCF₃-2-pyridinyl | 6-CH₃-2-pyridinyl |
| 2-Br-4-pyridinyl | 2-OCH₃-4-pyridinyl | 4-CH₃-2-pyridinyl | 6-CN-2-pyridinyl |
|  | 6-OCH₃-2-pyridinyl | 4-OCH₃-2-pyridinyl | 6-Cl-2-pyridinyl |
| \multicolumn{4}{c}{R² is 2-methyl-4-pyrimidinyl; R³ᵈ is Me} ||||
| 4-CF₃-2-pyridinyl | 2-CN-4-pyridinyl | 6-CF₃-2-pyridinyl | 4-CN-2-pyridinyl |
| 2-Cl-4-pyridinyl | 2-CF₃-4-pyridinyl | 6-OCF₃-2-pyridinyl | 4-Cl-2-pyridinyl |
| 2-F-4-pyridinyl | 2-OCF₃-4-pyridinyl | 4-OCF₃-2-pyridinyl | 6-CH₃-2-pyridinyl |
| 2-Br-4-pyridinyl | 2-OCH₃-4-pyridinyl | 4-CH₃-2-pyridinyl | 6-CN-2-pyridinyl |
|  | 6-OCH₃-2-pyridinyl | 4-OCH₃-2-pyridinyl | 6-Cl-2-pyridinyl |
| \multicolumn{4}{c}{R² is N-methyl-4-pyrazolyl; R³ᵈ is Me} ||||
| 4-CF₃-2-pyridinyl | 2-CN-4-pyridinyl | 6-CF₃-2-pyridinyl | 4-CN-2-pyridinyl |
| 2-Cl-4-pyridinyl | 2-CF₃-4-pyridinyl | 6-OCF₃-2-pyridinyl | 4-Cl-2-pyridinyl |
| 2-F-4-pyridinyl | 2-OCF₃-4-pyridinyl | 4-OCF₃-2-pyridinyl | 6-CH₃-2-pyridinyl |
| 2-Br-4-pyridinyl | 2-OCH₃-4-pyridinyl | 4-CH₃-2-pyridinyl | 6-CN-2-pyridinyl |
|  | 6-OCH₃-2-pyridinyl | 4-OCH₃-2-pyridinyl | 6-Cl-2-pyridinyl |
| \multicolumn{4}{c}{R² is CF₃; R³ᵈ is Me} ||||
| 4-CF₃-2-pyridinyl | 2-CN-4-pyridinyl | 6-CF₃-2-pyridinyl | 4-CN-2-pyridinyl |
| 2-Cl-4-pyridinyl | 2-CF₃-4-pyridinyl | 6-OCF₃-2-pyridinyl | 4-Cl-2-pyridinyl |
| 2-F-4-pyridinyl | 2-OCF₃-4-pyridinyl | 4-OCF₃-2-pyridinyl | 6-CH₃-2-pyridinyl |
| 2-Br-4-pyridinyl | 2-OCH₃-4-pyridinyl | 4-CH₃-2-pyridinyl | 6-CN-2-pyridinyl |
|  | 6-OCH₃-2-pyridinyl | 4-OCH₃-2-pyridinyl | 6-Cl-2-pyridinyl |
| \multicolumn{4}{c}{R² is CH₂CF₃; R³ᵈ is Me} ||||
| 4-CF₃-2-pyridinyl | 2-CN-4-pyridinyl | 6-CF₃-2-pyridinyl | 4-CN-2-pyridinyl |
| 2-Cl-4-pyridinyl | 2-CF₃-4-pyridinyl | 6-OCF₃-2-pyridinyl | 4-Cl-2-pyridinyl |
| 2-F-4-pyridinyl | 2-OCF₃-4-pyridinyl | 4-OCF₃-2-pyridinyl | 6-CH₃-2-pyridinyl |
| 2-Br-4-pyridinyl | 2-OCH₃-4-pyridinyl | 4-CH₃-2-pyridinyl | 6-CN-2-pyridinyl |
|  | 6-OCH₃-2-pyridinyl | 4-OCH₃-2-pyridinyl | 6-Cl-2-pyridinyl |
| \multicolumn{4}{c}{R² is CH₂CFClCHF₂; R³ᵈ is Me} ||||
| 4-CF₃-2-pyridinyl | 2-CN-4-pyriidnyl | 6-CF₃-2-pyridinyl | 4-CN-2-pyridinyl |
| 2-Cl-4-pyridinyl | 2-CF₃-4-pyridinyl | 6-OCF₃-2-pyridinyl | 4-Cl-2-pyridinyl |
| 2-F-4-pyridinyl | 2-OCF₃-4-pyridinyl | 4-OCF₃-2-pyridinyl | 6-CH₃-2-pyridinyl |
| 2-Br-4-pyridinyl | 2-OCH₃-4-pyridinyl | 4-CH₃-2-pyridinyl | 6-CN-2-pyridinyl |
|  | 6-OCH₃-2-pyridinyl | 4-OCH₃-2-pyridinyl | 6-Cl-2-pyridinyl |

TABLE 19

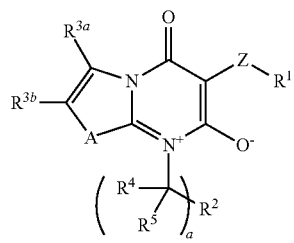

Z—R$^1$ is phenyl; R$^{3b}$ is H; A is CH=CMe; R$^4$ and R$^5$ are H; a is 1; R$^2$ is 2-chloro-5-thiazolyl

| R$^{3a}$ | R$^{3a}$ | R$^{3a}$ | R$^{3a}$ | R$^{3a}$ | R$^{3a}$ | R$^{3a}$ |
|---|---|---|---|---|---|---|
| H | CHO | Me | OMe | CH=CH$_2$ | OPh | 3-F-2-pyridinyl |
| Cl | C(O)Me | Et | OEt | C≡CH | NMe$_2$ | 4-Me-3-pyridinyl |
| Br | CO$_2$Et | i-Pr | OCF$_3$ | CF$_3$ | NHCHO | 2-cyano-4-pyridinyl |
| cyano | C(O)NMe$_2$ | c-Pr | SMe | Ph | | |

Z—R$^1$ is phenyl; R$^{3a}$ is H; A is CH=CMe; R$^4$ and R$^5$ are H; a is 1; R$^2$ is 2-chloro-5-thiazolyl

| R$^{3b}$ | R$^{3b}$ | R$^{3b}$ | R$^{3b}$ | R$^{3b}$ | R$^{3b}$ | R$^{3b}$ |
|---|---|---|---|---|---|---|
| Cl | CHO | Me | OMe | CH=CH$_2$ | OPh | 3-F-2-pyridinyl |
| Br | C(O)Me | Et | OEt | C≡CH | NMe$_2$ | 4-Me-3-pyridinyl |
| cyano | CO$_2$Et | i-Pr | OCF$_3$ | CF$_3$ | NHCHO | 2-cyano-4-pyriidnyl |
| Ph | C(O)NMe$_2$ | c-Pr | SMe | | | |

Z—R$^1$ is phenyl; R$^{3a}$ and R$^{3b}$ are H; A is C(R$^{3c}$)=CH; R$^4$ and R$^5$ are H; a is 1; R$^2$ is 2-chloro-5-thiazolyl

| R$^{3c}$ | R$^{3c}$ | R$^{3c}$ | R$^{3c}$ | R$^{3c}$ | R$^{3c}$ | R$^{3c}$ |
|---|---|---|---|---|---|---|
| Cl | HO | Me | OMe | CH=CH$_2$ | OPh | 3-F-2-pyridinyl |
| Br | C(O)Me | Et | OEt | C≡CH | NMe$_2$ | 4-Me-3-pyridinyl |
| cyano | CO$_2$Et | i-Pr | OCF$_3$ | CF$_3$ | NHCHO | 2-cyano-4-pyridinyl |
| Ph | C(O)NMe$_2$ | c-Pr | SMe | | | |

Z—R$^1$ is phenyl; R$^{3a}$ and R$^{3b}$ are H; A is CH=C(R$^{3d}$); R$^4$ and R$^5$ are H; a is 1; R$^2$ is 2-chloro-5-thiazolyl

| R$^{3d}$ | R$^{3d}$ | R$^{3d}$ | R$^{3d}$ | R$^{3d}$ | R$^{3d}$ |
|---|---|---|---|---|---|
| CHO | Me | OMe | CH=CH$_2$ | OPh | 3-F-2-pyridinyl |
| C(O)Me | Et | OEt | C≡CH | NMe$_2$ | 4-Me-3-pyridinyl |
| CO$_2$Et | i-Pr | OCF$_3$ | CF$_3$ | NHCHO | 2-cyano-4-pyridinyl |
| C(O)NMe$_2$ | c-Pr | SMe | cyano | Ph | |

Z—R$^1$ is phenyl; R$^{3b}$ is H; A is O; R$^4$ and R$^5$ are H; a is 1; R$^2$ is 2-chloro-5-thiazolyl

| R$^{3a}$ | R$^{3a}$ | R$^{3a}$ | R$^{3a}$ | R$^{3a}$ | R$^{3a}$ | R$^{3a}$ |
|---|---|---|---|---|---|---|
| F | CHO | Me | OMe | CH=CH$_2$ | OPh | 3-F-2-pyridinyl |
| Cl | C(O)Me | Et | OEt | C≡CH | NMe$_2$ | 4-Me-3-pyridinyl |
| Br | CO$_2$Et | i-Pr | OCF$_3$ | CF$_3$ | NHCHO | 2-cyano-4-pyridinyl |
| cyano | C(O)NMe$_2$ | c-Pr | SMe | Ph | | |

Z—R$^1$ is phenyl; R$^{3b}$ is H; A is S; R$^4$ and R$^5$ are H; a is 1; R$^2$ is 2-chloro-5-thiazolyl

| R$^{3a}$ | R$^{3a}$ | R$^{3a}$ | R$^{3a}$ | R$^{3a}$ | R$^{3a}$ | R$^{3a}$ |
|---|---|---|---|---|---|---|
| F | CHO | Me | OMe | CH=CH$_2$ | OPh | 3-F-2-pyridinyl |
| Cl | C(O)Me | Et | OEt | C≡CH | NMe$_2$ | 4-Me-3-pyridinyl |
| Br | CO$_2$Et | i-Pr | OCF$_3$ | CF$_3$ | NHCHO | 2-cyano-4-pyridinyl |
| cyano | C(O)NMe$_2$ | c-Pr | SMe | Ph | | |

Z—R$^1$ is phenyl; R$^{3b}$ is H; A is NMe; R$^4$ and R$^5$ are H; a is 1; R$^2$ is 2-chloro-5-thiazolyl

| R$^{3a}$ | R$^{3a}$ | R$^{3a}$ | R$^{3a}$ | R$^{3a}$ | R$^{3a}$ | R$^{3a}$ |
|---|---|---|---|---|---|---|
| F | CHO | Me | OMe | CH=CH$_2$ | OPh | 3-F-2-pyridinyl |
| Cl | C(O)NMe | Et | OEt | C≡CH | NMe$_2$ | 4-Me-3-pyridinyl |
| Br | CO$_2$Et | i-Pr | OCF$_3$ | CF$_3$ | NHCHO | 2-cyano-4-pyridinyl |
| cyano | C(O)NMe$_2$ | c-Pr | SMe | Ph | | |

TABLE 19-continued

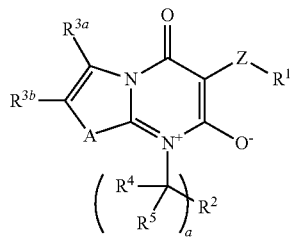

Z—R¹ is phenyl; R³ᵃ and R³ᵇ are H; A is NR³ᵉ; R⁴ and R⁵ are H; a is a 1; R² is 2-chloro-5-thiazolyl

| R³ᵉ | R³ᵉ | R³ᵉ | R³ᵉ | R³ᵉ | R³ᵉ | R³ᵉ |
|---|---|---|---|---|---|---|
| cyano | C(O)Me | i-Pr | OMe | CH=CH₂ | OPh | 3-F-2-pyridinyl |
| NMe₂ | CO₂Et | c-Pr | OEt | C≡CH | Ph | 4-Me-3-pyridinyl |
| CHO | C(O)NMe₂ | OCF₃ | CF₃ | | | 2-cyano-4-pyridinyl |

Z—R¹ is 2-fluorophenyl; R³ᵇ is H; A is CH=CMe; R⁴ and R⁵ are H; a is 1; R² is 2-chloro-5-thiazolyl

| R³ᵃ | R³ᵃ | R³ᵃ | R³ᵃ | R³ᵃ | R³ᵃ | R³ᵃ |
|---|---|---|---|---|---|---|
| H | CHO | Me | OMe | CH=CH₂ | OPh | 3-F-2-pyridinyl |
| Cl | C(O)Me | Et | OEt | C≡CH | NMe₂ | 4-Me-3-pyridinyl |
| Br | CO₂Et | i-Pr | OCF₃ | CF₃ | NHCHO | 2-cyano-4-pyriidnyl |
| cyano | C(O)NMe₂ | c-Pr | SMe | Ph | | |

Z—R¹ is 2-fluorophenyl; R³ᵃ is H; A is CH=CMe; R⁴ and R⁵ are H; a is 1; R² is 2-chloro-5-thiazolyl

| R³ᵇ | R³ᵇ | R³ᵇ | R³ᵇ | R³ᵇ | R³ᵇ | R³ᵇ |
|---|---|---|---|---|---|---|
| Cl | CHO | Me | OMe | CH=CH₂ | OPh | 3-F-2-pyridinyl |
| Br | C(O)Me | Et | OEt | C≡CH | NMe₂ | 4-Me-3-pyridinyl |
| cyano | CO₂Et | i-Pr | OCF₃ | CF₃ | NHCHO | 2-cyano-4-pyridinyl |
| Ph | C(O)NMe₂ | c-Pr | SMe | | | |

Z—R¹ is 2-fluorophenyl; R³ᵃ and R³ᵇ are H; A is C(R³ᶜ)=CH; R⁴ and R⁵ are H; a is 1; R² is 2-chloro-5-thiazolyl

| R³ᶜ | R³ᶜ | R³ᶜ | R³ᶜ | R³ᶜ | R³ᶜ | R³ᶜ |
|---|---|---|---|---|---|---|
| Cl | CHO | Me | OMe | CH=CH₂ | OPh | 3-F-2-pyridinyl |
| Br | C(O)Me | Et | OEt | C≡CH | NMe₂ | 4-Me-3-pyridinyl |
| cyano | CO₂Et | i-Pr | OCF₃ | CF₃ | NHCHO | 2-cyano-4-pyriidnyl |
| Ph | C(O)NMe₂ | c-Pr | SMe | | | |

Z—R¹ is 2-fluorophenyl; R³ᵃ and R³ᵇ are H; A is CH=C(R³ᵈ); R⁴ and R⁵ are H; a is 1; R² is 2-chloro-5-thiazolyl

| R³ᵈ | R³ᵈ | R³ᵈ | R³ᵈ | R³ᵈ | R³ᵈ |
|---|---|---|---|---|---|
| CHO | Me | OMe | CH=CH₂ | OPh | 3-F-2-pyridinyl |
| C(O)Me | Et | OEt | C≡CH | NMe₂ | 4-Me-3-pyridinyl |
| CO₂Et | i-Pr | OCF₃ | CF₃ | NHCHO | 2-cyano-4-pyridinyl |
| C(O)NMe₂ | c-Pr | SMe | cyano | Ph | |

Z—R¹ is 2-fluorophenyl; R³ᵇ is H; A is O; R⁴ and R⁵ are H; a is 1; R² is 2-chloro-5-thiazolyl

| R³ᵃ | R³ᵃ | R³ᵃ | R³ᵃ | R³ᵃ | R³ᵃ | R³ᵃ |
|---|---|---|---|---|---|---|
| F | CHO | Me | OMe | CH=CH₂ | OPh | 3-F-2-pyridinyl |
| Cl | C(O)Me | Et | OEt | C≡CH | NMe₂ | 4-Me-3-pyidinyl |
| Br | CO₂Et | i-Pr | OCF₃ | CF₃ | NHCHO | 2-cyano-4-pyridinyl |
| cyano | C(O)NMe₂ | c-Pr | SMe | Ph | | |

Z—R¹ is 2-fluorophenyl; R³ᵇ is H; A is S; R⁴ and R⁵ are H; a is 1; R² is 2-chloro-5-thiazolyl

| R³ᵃ | R³ᵃ | R³ᵃ | R³ᵃ | R³ᵃ | R³ᵃ | R³ᵃ |
|---|---|---|---|---|---|---|
| F | HO | Me | OMe | CH=CH₂ | OPh | 3-F-2-pyridinyl |
| Cl | C(O)Me | Et | OEt | C≡CH | NMe₂ | 4-Me-3-pyridinyl |
| Br | CO₂Et | i-Pr | OCF₃ | CF₃ | NHCHO | 2-cyano-4-pyriidnyl |
| cyano | C(O)NMe₂ | c-Pr | SMe | Ph | | |

TABLE 19-continued

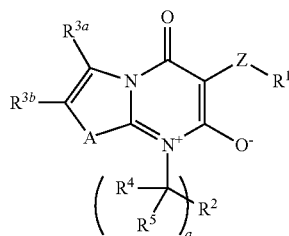

Z—R$^1$ is 2-fluorophenyl; R$^{3b}$ is H; A is NMe: R$^4$ and R$^5$ are H; a is 1; R$^2$ is 2-chloro-5-thiazolyl

| R$^{3a}$ | R$^{3a}$ | R$^{3a}$ | R$^{3a}$ | R$^{3a}$ | R$^{3a}$ | R$^{3a}$ |
|---|---|---|---|---|---|---|
| F | CHO | Me | OMe | CH=CH$_2$ | OPh | 3-F-2-pyridinyl |
| Cl | C(O)Me | Et | OEt | C≡CH | NMe$_2$ | 4-Me-3-pyridinyl |
| Br | CO$_2$Et | i-Pr | OCF$_3$ | CF$_3$ | NHCHO | 2-cyano-4-pyriidnyl |
| cyano | C(O)NMe$_2$ | c-Pr | SMe | Ph | | |

Z—R$^1$ is 2-fluorophenyl; R$^{3a}$ and R$^{3b}$ are H; A is NR$^{3e}$; R$^4$ and R$^5$ are H; a is 1; R$^2$ is 2-chloro-5-thiazolyl

| R$^{3e}$ | R$^{3e}$ | R$^{3e}$ | R$^{3e}$ | R$^{3e}$ | R$^{3e}$ | R$^{3e}$ |
|---|---|---|---|---|---|---|
| cyano | C(O)Me | i-Pr | OMe | CH=CH$_2$ | OPh | 3-F-2-pyridinyl |
| NMe$_2$ | CO$_2$Et | c-Pr | OEt | C≡CH | Ph | 4-Me-3-pyridinyl |
| CHO | C(O)NMe$_2$ | OCF$_3$ | CF$_3$ | | | 2-cyano-4-pyridinyl |

Z—R$^1$ is 3,5-dichlorophenyl; R$^{3b}$ is H; A is CH=CMe; R$^4$ and R$^5$ are H; a is 1; R$^2$ is 2-chloro-5-thiazolyl

| R$^{3a}$ | R$^{3a}$ | R$^{3a}$ | R$^{3a}$ | R$^{3a}$ | R$^{3a}$ | R$^{3a}$ |
|---|---|---|---|---|---|---|
| H | CHO | Me | OMe | CH=CH$_2$ | OPh | 3-F-2-pyridinyl |
| Cl | C(O)Me | Et | OEt | C≡CH | NMe$_2$ | 4-Me-3-pyridinyl |
| Br | CO$_2$Et | i-Pr | OCF$_3$ | CF$_3$ | NHCHO | 2-cyano-4-pyridinyl |
| cyano | C(O)NMe$_2$ | c-Pr | SMe | Ph | | |

Z—R$^1$ is 3,5-dichlorophenyl; R$^{3a}$ is H; A is CH=CMe; R$^4$ and R$^5$ are H; a is 1; R$^2$ is 2-chloro-5-thiazolyl

| R$^{3b}$ | R$^{3b}$ | R$^{3b}$ | R$^{3b}$ | R$^{3b}$ | R$^{3b}$ | R$^{3b}$ |
|---|---|---|---|---|---|---|
| Cl | CHO | Me | OMe | CH=CH$_2$ | OPh | 3-F-2-pyridinyl |
| Br | C(O)Me | Et | OEt | C≡CH | NMe$_2$ | 4-Me-3-pyridinyl |
| cyano | CO$_2$Et | i-Pr | OCF$_3$ | CF$_3$ | NHCHO | 2-cyano-4-pyridinyl |
| Ph | C(O)NMe$_2$ | c-Pr | SMe | | | |

Z—R$^1$ is 3,5-dichlorophenyl; R$^{3a}$ and R$^{3b}$ are H; A is C(R$^{3c}$)=CH; R$^4$ and R$^5$ are H; a is 1; R$^2$ is 2-chloro-5-thiazolyl

| R$^{3c}$ | R$^{3c}$ | R$^{3c}$ | R$^{3c}$ | R$^{3c}$ | R$^{3c}$ | R$^{3c}$ |
|---|---|---|---|---|---|---|
| Cl | CHO | Me | OMe | CH=CH$_2$ | OPh | 3-F-2-pyridinyl |
| Br | C(O)Me | Et | OEt | C≡CH | NMe$_2$ | 4-Me-3-pyridinyl |
| cyano | CO$_2$Et | i-Pr | OCF$_3$ | CF$_3$ | NHCHO | 2-cyano-4-pyriidnyl |
| Ph | C(O)NMe$_2$ | c-Pr | SMe | | | |

Z—R$^1$ is 3,5-dichlorophenyl; R$^{3a}$ and R$^{3b}$ are H; A is CH=C(R$^{3d}$); R$^4$ and R$^5$ are H; a is 1; R$^2$ is 2-chloro-5-thiazolyl

| R$^{3d}$ | R$^{3d}$ | R$^{3d}$ | R$^{3d}$ | R$^{3d}$ | R$^{3d}$ |
|---|---|---|---|---|---|
| CHO | Me | OMe | CH=CH$_2$ | OPh | 3-F-2-pyridinyl |
| C(O)Me | Et | OEt | C≡CH | NMe$_2$ | 4-Me-3-pyridinyl |
| CO$_2$Et | i-Pr | OCF$_3$ | CF$_3$ | NHCHO | 2-cyano-4-pyriidnyl |
| C(O)NMe$_2$ | c-Pr | SMe | cyano | Ph | |

Z—R$^1$ is 3,5-dichlorophenyl; R$^{3b}$ is H; A is O; R$^4$ and R$^5$ are H; a is 1; R$^2$ is 2-chloro-5-thiazolyl

| R$^{3a}$ | R$^{3a}$ | R$^{3a}$ | R$^{3a}$ | R$^{3a}$ | R$^{3a}$ | R$^{3a}$ |
|---|---|---|---|---|---|---|
| F | CHO | Me | OMe | CH=CH$_2$ | OPh | 3-F-2-pyridinyl |
| Cl | C(O)Me | Et | OEt | C≡CH | NMe$_2$ | 4-Me-3-pyridinyl |
| Br | CO$_2$Et | i-Pr | OCF$_3$ | CF$_3$ | NHCHO | 2-cyano-4-pyridinyl |
| cyano | C(O)NMe$_2$ | c-Pr | SMe | Ph | | |

TABLE 19-continued

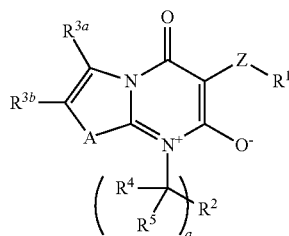

Z—R¹ is 3,5-dichlorophenyl; R³ᵇ is H; A is S; R⁴ and R⁵ are H; a is 1; R² is 2-chloro-5-thiazolyl

| R³ᵃ | R³ᵃ | R³ᵃ | R³ᵃ | R³ᵃ | R³ᵃ | R³ᵃ |
|---|---|---|---|---|---|---|
| F | CHO | Me | OMe | CH=CH₂ | OPh | 3-F-2-pyridinyl |
| Cl | C(O)Me | Et | OEt | C≡CH | NMe₂ | 4-Me-3-pyiridinyl |
| Br | CO₂Et | i-Pr | OCF₃ | CF₃ | NHCHO | 2-cyano-4-pyridinyl |
| cyano | C(O)NMe₂ | c-Pr | SMe | Ph | | |

Z—R¹ is 3,5-dichlorophenyl; R³ᵇ is H; A is NMe; R⁴ and R⁵ are H; a is 1; R² is 2-chloro-5-thiazolyl

| R³ᵃ | R³ᵃ | R³ᵃ | R³ᵃ | R³ᵃ | R³ᵃ | R³ᵃ |
|---|---|---|---|---|---|---|
| F | CHO | Me | OMe | CH=CH₂ | OPh | 3-F-2-pyridiyl |
| Cl | C(O)Me | Et | OEt | C≡CH | NMe₂ | 4-Me-3-pyridinyl |
| Br | CO₂Et | i-Pr | OCF₃ | CF₃ | NHCHO | 2-cyano-4-pyriidnyl |
| cyano | C(O)NMe₂ | c-Pr | SMe | Ph | | |

Z—R¹ is 3,5-dichlorophenyl; R³ᵃ and R³ᵇ are H; A is NR³ᵉ; R⁴ and R⁵ are H; a is 1; R² is 2-chloro-5-thiazolyl

| R³ᵉ | R³ᵉ | R³ᵉ | R³ᵉ | R³ᵉ | R³ᵉ | R³ᵉ |
|---|---|---|---|---|---|---|
| cyano | C(O)Me | i-Pr | OMe | CH=CH₂ | OPh | 3-F-2-pyridinyl |
| NMe₂ | CO₂Et | c-Pr | OEt | C≡CH | Ph | 4-Me-3-pyridinyl |
| CHO | C(O)NMe₂ | OCF₃ | CF₃ | | | 2-cyano-4-pyridinyl |

Z—R¹ is 3-(trifluoromethyl)phenyl; R³ᵇ is H; A is CH=CMe; R⁴ and R⁵ are H; a is 1; R² is 2-chloro-5-thiazolyl

| R³ᵃ | R³ᵃ | R³ᵃ | R³ᵃ | R³ᵃ | R³ᵃ | R³ᵃ |
|---|---|---|---|---|---|---|
| H | CHO | Me | OMe | CH=CH₂ | OPh | 3-F-2-pyridinyl |
| Cl | C(O)Me | Et | OEt | C≡CH | NMe₂ | 4-Me-3-pyridinyl |
| Br | CO₂Et | i-Pr | OCF₃ | CF₃ | NHCHO | 2-cyano-4-pyriidnyl |
| cyano | C(O)NMe₂ | c-Pr | SMe | Ph | | |

Z—R¹ is 3-(trifluoromethyl)phenyl; R³ᵃ is H; A is CH=CMe; R⁴ and R⁵ are H; a is 1; R² is 2-chloro-5-thiazolyl

| R³ᵇ | R³ᵇ | R³ᵇ | R³ᵇ | R³ᵇ | R³ᵇ | R³ᵇ |
|---|---|---|---|---|---|---|
| Cl | CHO | Me | OMe | CH=CH₂ | OPh | 3-F-2-pyridinyl |
| Br | C(O)Me | Et | OEt | C≡CH | NMe₂ | 4-Me-3-pyridinyl |
| cyano | CO₂Et | i-Pr | OCF₃ | CF₃ | NHCHO | 2-cyano-4-pyridinyl |
| Ph | C(O)NMe₂ | c-Pr | SMe | | | |

Z—R¹ is 3-(trifluoromethyl)phenyl; R³ᵃ and R³ᵇ are H; A is C(R³ᶜ)=CH; R⁴ and R⁵ are H; a is 1; R² is 2-chloro-5-thiazolyl

| R³ᶜ | R³ᶜ | R³ᶜ | R³ᶜ | R³ᶜ | R³ᶜ | R³ᶜ |
|---|---|---|---|---|---|---|
| Cl | CHO | Me | OMe | CH=CH₂ | OPh | 3-F-2-pyridinyl |
| Br | C(O)Me | Et | OEt | C≡CH | NMe₂ | 4-Me-3-pyridinyl |
| cyano | CO₂Et | i-Pr | OCF₃ | CF₃ | NHCHO | 2-cyano-4-pyridinyl |
| Ph | C(O)NMe₂ | c-Pr | SMe | | | |

Z—R¹ is 3-(trifluoromethyl)phenyl; R³ᵃ and R³ᵇ are H; A is CH=C(R³ᵈ); R⁴ and R⁵ are H; a is 1; R² is 2-chloro-5-thiazolyl

| R³ᵈ | R³ᵈ | R³ᵈ | R³ᵈ | R³ᵈ | R³ᵈ |
|---|---|---|---|---|---|
| CHO | Me | OMe | CH=CH₂ | OPh | 3-F-2-pyridinyl |
| C(O)Me | Et | OEt | C≡CH | NMe₂ | 4-Me-3-pyridinyl |
| CO₂Et | i-Pr | OCF₃ | CF₃ | NHCHO | 2-cyano-4-pyridinyl |
| C(O)NMe₂ | c-Pr | SMe | cyano | Ph | |

TABLE 19-continued

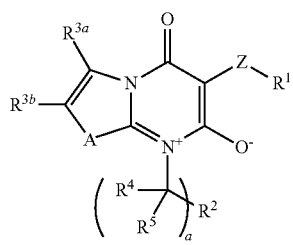

Z—R¹ is 3-(trifluoromethyl)phenyl; R³ᵇ is H; A is O; R⁴ and R⁵ are H; a is 1;
R² is 2-chloro-5-thiazolyl

| R³ᵃ | R³ᵃ | R³ᵃ | R³ᵃ | R³ᵃ | R³ᵃ | R³ᵃ |
|---|---|---|---|---|---|---|
| F | CHO | Me | OMe | CH=CH₂ | OPh | 3-F-2-pyridinyl |
| Cl | C(O)Me | Et | OEt | C≡CH | NMe₂ | 4-Me-3-pyridinyl |
| Br | CO₂Et | i-Pr | OCF₃ | CF₃ | NHCHO | 2-cyano-4-pyridinyl |
| cyano | C(O)NMe₂ | c-Pr | SMe | Ph | | |

Z—R¹ is 3-(trifluoromethyl)phenyl; R³ᵇ is H; A is S; R⁴ and R⁵ are H; a is 1;
R² is 2-chloro-5-thiazolyl

| R³ᵃ | R³ᵃ | R³ᵃ | R³ᵃ | R³ᵃ | R³ᵃ | Rᵃ |
|---|---|---|---|---|---|---|
| F | CHO | Me | OMe | CH=CH₂ | OPh | 3-F-2-pyridinyl |
| Cl | C(O)Me | Et | OEt | C≡CH | NMe₂ | 4-Me-3-pyridinyl |
| Br | CO₂Et | i-Pr | OCF₃ | CF₃ | NHCHO | 2-cyano-4-pyridinyl |
| cyano | C(O)NMe₂ | c-Pr | SMe | Ph | | |

Z—R¹ is 3-(trifluoromethyl)phenyl; R³ᵇ is H; A is NMe; R⁴ and R⁵ are H; a is 1;
R² is 2-chloro-5-thiazolyl

| R³ᵃ | R³ᵃ | R³ᵃ | R³ᵃ | R³ᵃ | R³ᵃ | R³ᵃ |
|---|---|---|---|---|---|---|
| F | CHO | Me | OMe | CH=CH₂ | OPh | 3-F-2-pyridinyl |
| Cl | C(O)Me | Et | OEt | C≡CH | NMe₂ | 4-Me-3-pyridinyl |
| Br | CO₂Et | i-Pr | OCF₃ | CF₃ | NHCHO | 2-cyano-4-pyriidnyl |
| cyano | C(O)NMe₂ | c-Pr | SMe | Ph | | |

Z—R¹ is 3-(trifluoromethyl)phenyl; R³ᵃ and R³ᵇ are H; A is NR³ᵉ; R⁴ and R⁵ are H; a is 1;
R² is 2-chloro-5-thiazolyl

| R³ᵉ | R³ᵉ | R³ᵉ | R³ᵉ | R³ᵉ | R³ᵉ | R³ᵉ |
|---|---|---|---|---|---|---|
| cyano | C(O)Me | i-Pr | OMe | CH=CH₂ | OPh | 3-F-2-pyridinyl |
| NMe₂ | CO₂Et | C-Pr | OEt | C≡CH | Ph | 4-Me-3-pyridinyl |
| CHO | C(O)NMe₂ | OCF₃ | CF₃ | | | 2-cyano-4-pyridinyl |

Z—R¹ is 3-(2-chloro-4-(trifluoromethyl)phenyl)phenyl; R³ᵇ is H; A is CH=CMe; R⁴ and R⁵ are H;
a is 1; R² is 2-chloro-5-thiazolyl

| R³ᵃ | R³ᵃ | R³ᵃ | R³ᵃ | R³ᵃ | R³ᵃ | R³ᵃ |
|---|---|---|---|---|---|---|
| H | CHO | Me | OMe | CH=CH₂ | OPh | 3-F-2-pyridinyl |
| Cl | C(O)Me | Et | OEt | C≡CH | NMe₂ | 4-Me-3-pyridinyl |
| Br | CO₂Et | i-Pr | OCF₃ | CF₃ | NHCHO | 2-cyano-4-pyridinyl |
| cyano | C(O)NMe₂ | c-Pr | SMe | Ph | | |

Z—R¹ is 3-(2-chloro-4-(trifluoromethyl)phenyl)phenyl; R³ᵃ is H; A is CH=CMe; R⁴ and R⁵ are H;
a is 1; R² is 2-chloro-5-thiazolyl

| R³ᵇ | R³ᵇ | R³ᵇ | R³ᵇ | R³ᵇ | R³ᵇ | R³ᵇ |
|---|---|---|---|---|---|---|
| Cl | CHO | Me | OMe | CH=CH₂ | OPh | 3-F-2-pyridinyl |
| Br | C(O)Me | Et | OEt | C≡CH | NMe₂ | 4-Me-3-pyridinyl |
| cyano | CO₂Et | i-Pr | OCF₃ | CF | NHCHO | 2-cyano-4-pyridinyl |
| Ph | C(O)NMe₂ | c-Pr | SMe | | | |

Z—R¹ is 3-(2-chloro-4-(trifluoromethyl)phenyl)phenyl; R³ᵃ and R³ᵇ are H; A is C(R³ᶜ)=CH;
R⁴ and R⁵ are H; a is 1; R² is 2-chloro-5-thiazolyl

| R³ᶜ | R³ᶜ | R³ᶜ | R³ᶜ | R³ᶜ | R³ᶜ | R³ᶜ |
|---|---|---|---|---|---|---|
| Cl | CHO | Me | OMe | CH=CH₂ | OPh | 3-F-2-pyridinyl |
| Br | C(O)Me | Et | OEt | C≡CH | NMe₂ | 4-Me-3-pyridinyl |

TABLE 19-continued

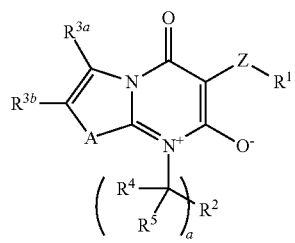

| cyano | $CO_2Et$ | i-Pr | $OCF_3$ | $CF_3$ | NHCHO | 2-cyano-4-pyridinyl |
| Ph | $C(O)NMe_2$ | c-Pr | SMe | | | |

Z—$R^1$ is 3-(2-chloro-4-(trifluoromethyl)phenyl)phenyl; $R^{3a}$ and $R^{3b}$ are H; A is CH=C($R^{3d}$);
$R^4$ and $R^5$ are H; a is 1; $R^2$ is 2-chloro-5-thiazolyl

| $R^{3d}$ | $R^{3d}$ | $R^{3d}$ | $R^{3d}$ | $R^{3d}$ | $R^{3d}$ |
|---|---|---|---|---|---|
| CHO | Me | OMe | $CH=CH_2$ | OPh | 3-F-2-pyridinyl |
| C(O)Me | Et | OEt | C≡CH | $NMe_2$ | 4-Me-3-pyridinyl |
| $CO_2Et$ | i-Pr | $OCF_3$ | $CF_3$ | NHCHO | 2-cyano-4-pyridinyl |
| $C(O)NMe_2$ | c-Pr | SMe | cyano | Ph | |

Z—$R^1$ is 3-(2-chloro-4-(trifluoromethyl)phenyl)phenyl; $R^{3b}$ is H; A is O; $R^4$ and $R^5$ are H; a is 1;
$R^2$ is 2-chloro-5-thiazolyl

| $R^{3a}$ | $R^{3a}$ | $R^{3a}$ | $R^{3a}$ | $R^{3a}$ | $R^{3a}$ | $R^{3a}$ |
|---|---|---|---|---|---|---|
| F | CHO | Me | OMe | $CH=CH_2$ | OPh | 3-F-2-pyridinyl |
| Cl | C(O)Me | Et | OEt | C≡CH | $NMe_2$ | 4-Me-3-pyridinyl |
| Br | $CO_2Et$ | i-Pr | $OCF_3$ | $CF_3$ | NHCHO | 2-cyano-4-pyridinyl |
| cyano | $C(O)NMe_2$ | c-Pr | SMe | Ph | | |

Z—$R^1$ is 3-(2-chloro-4-(trifluoromethyl)phenyl)phenyl; $R^{3b}$ is H; A is S; $R^4$ and $R^5$ are H; a is 1;
$R^2$ is 2-chloro-5-thiazolyl

| $R^{3a}$ | $R^{3a}$ | $R^{3a}$ | $R^{3a}$ | $R^{3a}$ | $R^{3a}$ | $R^{3a}$ |
|---|---|---|---|---|---|---|
| F | CHO | Me | OMe | $CH=CH_2$ | OPh | 3-F-2-pyridinyl |
| Cl | C(O)Me | Et | OEt | C≡CH | $NMe_2$ | 4-Me-3-pyridinyl |
| Br | $CO_2Et$ | i-Pr | $OCF_3$ | $CF_3$ | NHCHO | 2-cyano-4-pyriidnyl |
| cyano | $C(O)NMe_2$ | c-Pr | SMe | Ph | | |

Z—$R^1$ is 3-(2-chloro-4-(trifluoromethyl)phenyl)phenyl; $R^{3b}$ is H; A is NMe; $R^4$ and $R^5$ are H; a is 1;
$R^2$ is 2-chloro-5-thiazolyl

| $R^{3a}$ | $R^{3a}$ | $R^{3a}$ | $R^{3a}$ | $R^{3a}$ | $R^{3a}$ | $R^{3a}$ |
|---|---|---|---|---|---|---|
| F | CHO | Me | OMe | $CH=CH_2$ | OPh | 3-F-2-pyridinyl |
| Cl | C(O)Me | Et | OEt | C≡CH | $NMe_2$ | 4-Me-3-pyridinyl |
| Br | $CO_2Et$ | i-Pr | $OCF_3$ | $CF_3$ | NHCHO | 2-cyano-4-pyridinyl |
| cyano | $C(O)NMe_2$ | c-Pr | SMe | Ph | | |

Z—$R^1$ is 3-(2-chloro-4-(trifluoromethyl)phenyl)phenyl; $R^{3a}$ and $R^{3b}$ are H; A is $NR^{3e}$;
$R^4$ and $R^5$ are H; a is 1; $R^2$ is 2-chloro-5-thiazolyl

| $R^{3e}$ | $R^{3e}$ | $R^{3e}$ | $R^{3e}$ | $R^{3e}$ | $R^{3e}$ | $R^{3e}$ |
|---|---|---|---|---|---|---|
| cyano | C(O)Me | i-Pr | OMe | $CH=CH_2$ | OPh | 3-F-2-pyridinyl |
| $NMe_2$ | $CO_2Et$ | c-Pr | OEt | C≡CH | Ph | 4-Me-3-pyridinyl |
| CHO | $C(O)NMe_2$ | $OCF_3$ | $CF_3$ | | | 2-cyano-4-pyridinyl |

TABLE 20

[Structure: fused bicyclic heterocycle with substituents O, Z—R¹, A, N⁺, O⁻, CH(R²)]

| ZR¹ | ZR¹ | ZR¹ | ZR¹ | ZR¹ |
|---|---|---|---|---|
| A is NCH₂CHF₂; R² is 2-chloro-5-thiazolyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| A is NCH₂CHF₂; R² is 2-methyl-5-thiazolyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| A is NCH₂CHF₂; R² is 5-thiazolyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| A is NCH₂CHF₂; R² is CF₃ | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| A is NCH₂CHF₂; R² is 6-chloro-3-pyridinyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| A is NCH₂CHF₂; R² is 6-fluoro-3-pyridinyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| A is NCH₂CHF₂; R² is 1-methyl-4-pyrazolyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| A is NEt; R² is 2-chloro-5-thiazolyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| A is NEt; R² is 2-methyl-5-thiazolyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| A is NEt; R² is 5-thiazolyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| A is NEt; R² is CF₃ | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| A is NEt; R² is 6-chloro-3-pyridinyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me'3Ph |
| 3-CN—Ph | C(O)Ph | CO₂Et | 3,5-diCl—Ph | 3-(2-Cl-4-CF₃—Ph)Ph |
| A is NEt; R² is 6-fluoro-3-pyridinyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |

TABLE 20-continued

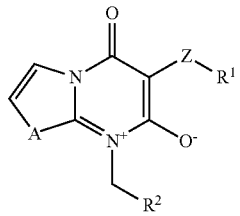

| ZR¹ | ZR¹ | ZR¹ | ZR¹ | ZR¹ |
|---|---|---|---|---|
| \multicolumn{5}{c}{A is NEt; R² is 1-methyl-4-pyrazolyl} ||||| 
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{A is NCH₂CF₃; R² is H} |||||
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{A is NCH₂(6-chloro-3-pyridinyl); R² is H} |||||
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{A is NCH₂(6-fluoro-3-pyridinyl); R² is H} |||||
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{A is NCH₂(2-chloro-5-thiazolyl); R² is H} |||||
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{A is NCH₂CF₃; R² is Me} |||||
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{A is NCH₂(6-chloro-3-pyridinyl); R² is Me} |||||
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{A is NCH₂(6-fluoro-3-pyridinyl); R² is Me} |||||
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{A is NCH₂(2-chloro-5-thiazolyl); R² is Me} |||||
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |

TABLE 21

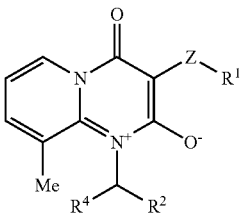

| ZR¹ | ZR¹ | ZR¹ | Zr¹ | Zr¹ |
|---|---|---|---|---|
| \multicolumn{5}{c}{R⁴ is F; R² is 2-chloro-5-thiazolyl} |||||
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMehd 2—Ph | 3-Me—Ph |
| 3-CN—Ph | C(O)Ph | CO₂Et | 3,5-diCl—Ph | 3-(2-Cl-4-CF₂—Ph)Ph |

TABLE 21-continued

| ZR¹ | ZR¹ | ZR¹ | ZR¹ | Zr¹ |
|---|---|---|---|---|
| \multicolumn{5}{c}{R⁴ is F; R² is 2-methyl-5-thiazolyl} |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{R⁴ is F; R² is 5-thiazolyl} |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{R⁴ is F; R² is CF₃} |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{R⁴ is F; R² is 6-chloro-3-pyridinyl} |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{R⁴ is F; R² is 6-fluoro-3-pyridinyl} |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| \multicolumn{5}{c}{R⁴ is F; R² is 1-methyl-4-pyrazolyl} |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |

TABLE 22

| R⁴ | R⁴ | R⁴ | R⁴ | R⁴ | R⁴ | R⁴ |
|---|---|---|---|---|---|---|
| \multicolumn{7}{c}{R⁵ is H} |
| Cl | CHO | Et | OMe | CH=CH₂ | OPh | 3-F-2-pyridinyl |
| Br | C(O)Me | i-Pr | OEt | C≡CH | NMe₂ | 4-Me-3-pyridinyl |
| cyano | CO₂Et | c-Pr | OCF₃ | SMe | NHCHO | 2-cyano-4-pyridinyl |
| Ph | C(O)NMe₂ | CF₃ | | | | |
| \multicolumn{7}{c}{R⁵ is Me} |
| Cl | CHO | Et | OMe | CH=CH₂ | OPh | 3-F-2-pyridinyl |
| Br | C(O)Me | i-Pr | OEt | C≡CH | NMe₂ | 4-Me-3-pyridinyl |
| cyano | CO₂Et | c-Pr | OCF₃ | SMe | NHCHO | 2-cyano-4-pyridinyl |
| Ph | C(O)NMe₂ | CF₃ | | | | pyridinyl |

TABLE 22-continued

| R⁴ | R⁴ | R⁴ | R⁴ | R⁴ | R⁴ | R⁴ |
|---|---|---|---|---|---|---|
| Ph | C(O)NMe₂ | CF₃ | | | | pyridinyl |
| \multicolumn{7}{c}{R⁵ is c-Pr} |
| Cl | CHO | Et | OMe | CH=CH₂ | OPh | 3-F-2-pyridinyl |
| Br | C(O)Me | i-Pr | OEt | C≡CH | NMe₂ | 4-Me-3-pyridinyl |
| cyano | CO₂Et | c-Pr | OCF₃ | SMe | NHCHO | 2-cyano-4-pyridinyl |
| Ph | C(O)NMe₂ | CF₃ | | | | |

TABLE 23

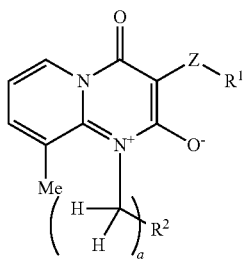

| $ZR^1$ | $ZR^1$ | $ZR^1$ | $ZR^1$ | $ZR^1$ |
|---|---|---|---|---|
| \multicolumn{5}{c}{a is 2; $R^2$ is 2-chloro-5-thiazolyl} |
| Ph | 3-MeO—Ph | 3-CF$_3$—Ph | 3-CF$_3$O—Ph | 3-Cl, 5-CF$_3$—Ph |
| 2-F—Ph | C(O)CF$_3$ | 3-CO$_2$Et—Ph | 3-C(O)NMe$_2$—Ph | 3-Me—Ph |
| 3-CN—Ph | C(O)Ph | CO$_2$Et | 3,5-diCl—Ph | 3-(2-Cl-4-CF$_3$—Ph)Ph |
| \multicolumn{5}{c}{a is 2; $R^2$ is 2-methyl-5-thiazolyl} |
| Ph | 3-MeO—Ph | 3-CF$_3$—Ph | 3-CF$_3$O—Ph | 3-Cl, 5-CF$_3$—Ph |
| 2-F—Ph | C(O)CF$_3$ | 3-CO$_2$Et—Ph | 3-C(O)NMe$_2$—Ph | 3-Me—Ph |
| 3-CN—Ph | C(O)Ph | CO$_2$Et | 3,5-diCl—Ph | 3-(2-Cl-4-CF$_3$—Ph)Ph |
| \multicolumn{5}{c}{a is 2; $R^2$ is 5-thiazolyl} |
| Ph | 3-MeO—Ph | 3-CF$_3$—Ph | 3-CF$_3$O—Ph | 3-Cl, 5-CF |
| 2-F—Ph | C(O)CF$_3$ | 3-CO$_2$Et—Ph | 3-C(O)NMe$_2$—Ph | 3-Me—Ph |
| 3-CN—Ph | C(O)Ph) | CO$_2$Et | 3,5-diCl—Ph | 3-(2-Cl-4-CF$_3$—Ph)Ph |
| \multicolumn{5}{c}{a is 2; $R^2$ is 2-fluoro-5-thiazolyl} |
| Ph | 3-MeO—Ph | 3-CF$_3$—Ph | 3-CF$_3$O—Ph | 3-Cl, 5-CF$_3$—Ph |
| 2-F—Ph | C(O)CF$_3$ | 3-CO$_2$Et—Ph | 3-C(O)NMe$_2$—Ph | 3-Me—Ph |
| 3-CN—Ph | C(O)Ph | CO$_2$Et | 3,5-diCl—Ph | 3-(2-Cl-4-CF$_3$—Ph)Ph |
| \multicolumn{5}{c}{a is 2; $R^2$ is 5-pyrimidinyl} |
| Ph | 3-MeO—Ph | 3-CF$_3$—Ph | 3-CF$_3$O—Ph | 3-Cl, 5-CF$_3$—Ph |
| 2-F—Ph | C(O)CF$_3$ | 3-CO$_2$Et—Ph | 3-C(O)NMe$_2$—Ph | 3-Me—Ph |
| 3-CN—Ph | C(O)Ph | CO$_2$Et | 3,5-diCl—Ph | 3-(2-Cl-4-CF$_3$—Ph)Ph |
| \multicolumn{5}{c}{a is 2; $R^2$ is 2-methyl-5-pyrimidinyl} |
| Ph | 3-MeO—Ph | 3-CF$_3$—Ph | 3-CF$_3$O—Ph | 3-Cl, 5-CF$_3$—Ph |
| 2-F—Ph | C(O)CF$_3$ | 3-CO$_2$Et—Ph | 3-C(O)NMe$_2$—Ph | 3-Me—Ph |
| 3-CN—Ph | C(O)Ph | CO$_2$Et | 3,5-diCl—Ph | 3-(2-Cl-4-CF$_3$—Ph)Ph |
| \multicolumn{5}{c}{a is 2; $R^2$ is CF$_3$} |
| Ph | 3-MeO—Ph | 3-CF$_3$—Ph | 3-CF$_3$O—Ph | 3-Cl, 5-CF$_3$—Ph |
| 2-F—Ph | C(O)CF$_3$ | 3-CO$_2$Et—Ph | 3-C(O)NMe$_2$—Ph | 3-Me—Ph |
| 3-CN—Ph | C(O)Ph | CO$_2$Et | 3,5-diCl—Ph | 3-(2-Cl-4-CF$_3$—Ph)Ph |
| \multicolumn{5}{c}{a is 2; $R^2$ is 6-chloro-3-pyridinyl} |
| Ph | 3-MeO—Ph | 3-CF$_3$—Ph | 3-CF$_3$O—Ph | 3-Cl, 5-CF$_3$—Ph |
| 2-F—Ph | C(O)CF$_3$ | 3-CO$_2$Et—Ph | 3-C(O)NMe$_2$—Ph | 3-Me—Ph |
| 3-CN—Ph | C(O)Ph | CO$_2$Et | 3,5-diCl—Ph | 3-(2-Cl-4-CF$_3$—Ph)Ph |
| \multicolumn{5}{c}{a is 2; $R^2$ is 6-fluoro-3-pyridinyl} |
| Ph | 3-MeO—Ph | 3-CF$_3$—Ph | 3-CF$_3$O—Ph | 3-Cl, 5-CF$_3$—Ph |
| 2-F—Ph | C(O)CF$_3$ | 3-CO$_2$Et—Ph | 3-C(O)NMe$_2$—Ph | 3-Me—Ph |
| 3-CN—Ph | C(O)Ph | CO$_2$Et | 3,5-diCl—Ph | 3-(2-Cl-4-CF$_3$—Ph)Ph |
| \multicolumn{5}{c}{a is 2; $R^2$ is 1-methyl-4-pyrazolyl} |
| Ph | 3-MeO—Ph | 3-CF$_3$—Ph | 3-CF$_3$O—Ph | 3-Cl, 5-CF$_3$—Ph |
| 2-F—Ph | C(O)CF$_3$ | 3-CO$_2$Et—Ph | 3-C(O)NMe$_2$—Ph | 3-Me—Ph |
| 3-CN—Ph | C(O)Ph | CO$_2$Et | 3,5-diCl—Ph | 3-(2-Cl-4-CF$_3$—Ph)Ph |
| \multicolumn{5}{c}{a is 3; $R^2$ is 2-chloro-5-thiazolyl} |
| Ph | 3-MeO—Ph | 3-CF$_3$—Ph | 3-CF$_3$O—Ph | 3-Cl, 5-CF$_3$—Ph |
| 2-F—Ph | C(O)CF$_3$ | 3-CO$_2$Et—Ph | 3-C(O)NMe$_2$—Ph | 3-Me—Ph |
| 3-CN—Ph | C(O)Ph | CO$_2$Et | 3,5-diCl—Ph | 3-(2-Cl-4-CF$_3$—Ph)Ph |
| \multicolumn{5}{c}{a is 3; $R^2$ is 2-methyl-5-thiazolyl} |
| Ph | 3-MeO—Ph | 3-CF$_3$—Ph | 3-CF$_3$O—Ph | 3-Cl, 5-CF$_3$—Ph |
| 2-F—Ph | C(O)CF$_3$ | 3-CO$_2$Et—Ph | 3-C(O)NMe$_2$—Ph | 3-Me—Ph |
| 3-CN—Ph | C(O)Ph | CO$_2$Et | 3,5-diCl—Ph | 3-(2-Cl-4-CF$_3$—Ph)Ph |
| \multicolumn{5}{c}{a is 3; $R^2$ is 5-thiazolyl} |
| Ph | 3-MeO—Ph | 3-CF$_3$—Ph | 3-CF$_3$O—Ph | 3-Cl, 5-CF$_3$—Ph |
| 2-F—Ph | C(O)CF$_3$ | 3-CO$_2$Et—Ph | 3-C(O)NMe$_2$—Ph | 3-Me—Ph |
| 3-CN—Ph | C(O)Ph | CO$_2$Et | 3,5-diCl—Ph | 3-(2-Cl-4-CF$_3$—Ph)Ph |

TABLE 23-continued

[Structure: pyrido-pyrimidinone core with Me at 9-position, Z-R¹ substituent at 3-position, O⁻ at 2-position, and N⁺ bearing a -(CH₂)ₐ-R² group with stereochemistry indicated]

| ZR¹ | ZR¹ | ZR¹ | ZR¹ | ZR¹ |
|---|---|---|---|---|
| a is 3; R² is CF₃ | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| a is 3; R² is 6-chloro-3-pyridinyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| a is 3; R² is 6-fluoro-3-pyridinyl | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |
| a is 3; R² is 1-methyl-4-pyrazolyl) | | | | |
| Ph | 3-MeO—Ph | 3-CF₃—Ph | 3-CF₃O—Ph | 3-Cl, 5-CF₃—Ph |
| 2-F—Ph | C(O)CF₃ | 3-CO₂Et—Ph | 3-C(O)NMe₂—Ph | 3-Me—Ph |
| 3-CN—Ph | C(O)Ph | CO₂Et | 3,5-diCl—Ph | 3-(2-Cl-4-CF₃—Ph)Ph |

TABLE 24

[Structure: pyrido-pyrimidinone core with Me at 9-position, phenyl (with numbered positions 2–6 and R substituent) at 3-position, O⁻ at 2-position, N⁺ bearing -CH₂R²]

| R² | R² | R² | R² | R² | R² | R² |
|---|---|---|---|---|---|---|
| R is 2-F | | | | | | |
| cyano | C(O)Me | Et | CH₂OMe | CH=CH₂ | OPh | 3-F-2-pyridinyl |
| CHO | CO₂Et | i-Pr | CH₂OEt | C≡CH | CH₂NMe₂ | 4-Me-3-pyridinyl |
| Ph | C(O)NMe₂ | c-Pr | CH₂OCF₃ | CH₂SMe | CH₂NHCHO | 2-cyano-4-pyridinyl |
| R is 3-Me | | | | | | |
| cyano | C(O)Me | Et | CH₂OMe | CH=CH₂ | OPh | 3-F-2-pyridinyl |
| CHO | CO₂Et | i-Pr | CH₂OEt | C≡CH | CH₂NMe₂ | 4-Me-3-pyridinyl |
| Ph | C(O)NMe₂ | c-Pr | CH₂OCF₃ | CH₂SMe | CH₂NHCHO | 2-cyano-4-pyridinyl |
| R is 3-CN | | | | | | |
| cyano | C(O)Me | Et | CH₂OMe | CH=CH₂ | OPh | 3-F-2-pyridinyl |
| CHO | CO₂Et | i-Pr | CH₂OEt | C≡CH | CH₂NMe₂ | 4-Me-3-pyridinyl |
| Ph | C(O)NMe₂ | c-Pr | CH₂OCF₃ | CH₂SMe | CH₂NHCHO | 2-cyano-4-pyridinyl |
| R is 3-OMe | | | | | | |
| cyano | C(O)Me | Et | CH₂OMe | CH=CH₂ | OPh | 3-F-2-pyridinyl |
| CHO | CO₂Et | i-Pr | CH₂OEt | C≡CH | CH₂NMe₂ | 4-Me-3-pyridinyl |
| Ph | C(O)NMe₂ | c-Pr | CH₂OCF₃ | CH₂SMe | CH₂NHCHO | 2-cyano-4-pyridinyl |

TABLE 24-continued

[Structure: pyrido-pyrimidinone with Me group, N+-CH2-R2, and phenyl with R substituent at positions 2-6]

| R² | R² | R² | R² | R² | R² | R² |
|---|---|---|---|---|---|---|
| \multicolumn{7}{c}{R is 3-CF₃} |

| R² | R² | R² | R² | R² | R² | R² |
|---|---|---|---|---|---|---|
| cyano | C(O)Me | Et | CH₂OMe | CH=CH₂ | OPh | 3-F-2-pyridinyl |
| CHO | CO₂Et | i-Pr | CH₂OEt | C≡CH | CH₂NMe₂ | 4-Me-3-pyridinyl |
| Ph | C(O)NMe₂ | c-Pr | CH₂OCF₃ | CH₂SMe | CH₂NHCHO | 2-cyano-4-pyridinyl |

R is 3-Cl, 5-Cl

| cyano | C(O)Me | Et | CH₂OMe | CH=CH₂ | OPh | 3-F-2-pyridinyl |
| CHO | CO₂Et | i-Pr | CH₂OEt | C≡CH | CH₂NMe₂ | 4-Me-3-pyridinyl |
| Ph | C(O)NMe₂ | c-Pr | CH₂OCF₃ | CH₂SMe | CH₂NHCHO | 2-cyano-4-pyridinyl |

R is 3-(2-chloro-4-(trifluoromethyl)phenyl)

| cyano | C(O)Me | Et | CH₂OMe | CH=CH₂ | OPh | 3-F-2-pyridinyl |
| CHO | CO₂Et | i-Pr | CH₂OEt | C≡CH | CH₂NMe₂ | 4-Me-3-pyridinyl |
| Ph | C(O)NMe₂ | c-Pr | CH₂OCF₃ | CH₂SMe | CH₂NHCHO | 2-cyano-4-pyridinyl |

TABLE 25

[Structure: pyrido-pyrimidinone with Me, N+-CH2-thiazol-5-yl (2-R-thiazole), phenyl with Rᵃ]

| R | R | R | R | R | R | R |
|---|---|---|---|---|---|---|

Rᵃ is 2-F

| cyano | C(O)Me | Et | OMe | CH=CH₂ | OPh | 3-F-2-pyridinyl |
| CHO | CO₂Et | i-Pr | OEt | C≡CH | NMe₂ | 4-Me-3-pyridinyl |
| Ph | C(O)NMe₂ | c-Pr | OCF₃ | SMe | NHCHO | 2-cyano-4-pyridinyl |
| CF₃ | | | | | | |

Rᵃ is 3-Me

| cyano | C(O)Me | Et | OMe | CH=CH₂ | OPh | 3-F-2-pyridinyl |
| CHO | CO₂Et | i-Pr | OEt | C≡CH | NMe₂ | 4-Me-3-pyridinyl |
| Ph | C(O)NMe₂ | c-Pr | OCF₃ | SMe | NHCHO | 2-cyano-4-pyridinyl |
| CF₃ | | | | | | |

Rᵃ is 3-CN

| cyano | C(O)Me | Et | OMe | CH=CH₂ | OPh | 3-F-2-pyridinyl |
| CHO | CO₂Et | i-Pr | OEt | C≡CH | NMe₂ | 4-Me-3-pyridinyl |
| Ph | C(O)NMe₂ | c-Pr | OCF₃ | SMe | NHCHO | 2-cyano-4-pyridinyl |
| CF₃ | | | | | | |

Rᵃ is 3-OMe

| cyano | C(O)Me | Et | OMe | CH=CH₂ | OPh | 3-F-2-pyridinyl |
| CHO | CO₂Et | i-Pr | OEt | C≡CH | NMe₂ | 4-Me-3-pyridinyl |
| Ph | C(O)NMe₂ | c-Pr | OCF₃ | SMe | NHCHO | 2-cyano-4-pyridinyl |
| CF₃ | | | | | | |

TABLE 25-continued

[Structure: same as TABLE 25]

| R | R | R | R | R | R | R |
|---|---|---|---|---|---|---|

Rᵃ is 3-CF₃

| cyano | C(O)Me | Et | OMe | CH=CH₂ | OPh | 3-F-2-pyridinyl |
| CHO | CO₂Et | i-Pr | OEt | C≡CH | NMe₂ | 4-Me-3-pyridinyl |
| Ph | C(O)NMe₂ | c-Pr | OCF₃ | SMe | NHCHO | 2-cyano-4-pyridinyl |
| CF₃ | | | | | | |

Rᵃ is 3-Cl, 5-Cl

| cyano | C(O)Me | Et | OMe | CH=CH₂ | OPh | 3-F-2-pyridinyl |
| CHO | CO₂Et | i-Pr | OEt | C≡CH | NMe₂ | 4-Me-3-pyridinyl |
| Ph | C(O)NMe₂ | c-Pr | OCF₃ | SMe | NHCHO | 2-cyano-4-pyridinyl |
| CF₃ | | | | | | |

Rᵃ is 3-(2-chloro-4-(trifluoromethyl)phenyl)

| cyano | C(O)Me | Et | OMe | CH=CH₂ | OPh | 3-F-2-pyridinyl |
| CHO | CO₂Et | i-Pr | OEt | C≡CH | NMe₂ | 4-Me-3-pyridinyl |
| Ph | C(O)NMe₂ | c-Pr | OCF₃ | SMe | NHCHO | 2-cyano-4-pyridinyl |
| CF₃ | | | | | | |

TABLE 26

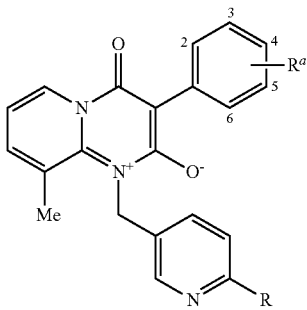

| R | R | R | R | R | R | R |
|---|---|---|---|---|---|---|
| $R^a$ is 2-F | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | | | | | | |
| $R^a$ is 3-Me | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | | | | | | |
| $R^a$ is 3-CN | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | | | | | | |
| $R^a$ is 3-OMe | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | | | | | | |
| $R^a$ is 3-CF$_3$ | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | | | | | | |
| $R^a$ is 3-Cl, 5-Cl | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | | | | | | |
| $R^a$ is 3-(2-chloro-4-(trifluoromethyl)phenyl) | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | | | | | | |

TABLE 27

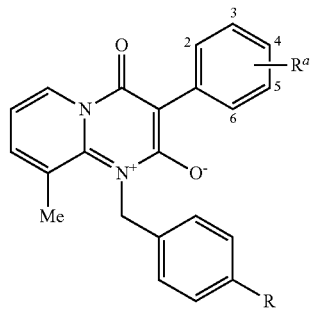

| R | R | R | R | R | R | R |
|---|---|---|---|---|---|---|
| $R^a$ is 2-F | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | Me | Cl | Br | | | |
| $R^a$ is 3-Me | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | Me | Cl | Br | | | |
| $R^a$ is 3-CN | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | Me | Cl | Br | | | |
| $R^a$ is 3-OMe | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | Me | Cl | Br | | | |
| $R^a$ is 3-CF$_3$ | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | Me | Cl | Br | | | |
| $R^a$ is 3-Cl, 5-Cl | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | Me | Cl | Br | | | |
| $R^a$ is 3-(2-chloro-4-(trifluoromethyl)phenyl) | | | | | | |
| cyano | C(O)Me | Et | OMe | CH=CH$_2$ | OPh | 3-F-2-pyridinyl |
| CHO | CO$_2$Et | i-Pr | OEt | C≡CH | NMe$_2$ | 4-Me-3-pyridinyl |
| Ph | C(O)NMe$_2$ | c-Pr | OCF$_3$ | SMe | NHCHO | 2-cyano-4-pyridinyl |
| CF$_3$ | Me | Cl | Br | | | |

TABLE 28

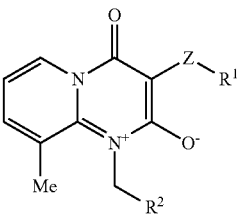

| ZR¹ | ZR¹ | ZR¹ | ZR¹ | ZR¹ | ZR¹ |
|---|---|---|---|---|---|
| R² is 2-chloro-5-thiazolyl | | | | | |
| Cl | Br | I | cyano | 4-CF₃-2-thiazolyl | 2-CF₃-5-thiazolyl |
| F | C(O)NMe₂ | NMe₂ | NHCHO | 5-CF₃-2-thiazolyl | 4-CF₃-5-thiazolyl |
| CF₃ | c-Pr-2-(c-Pr) | Et | i-Pr | 2-CF₃-4-thiazolyl | 1-Me-5-CF₃-2-imidazolyl |
| Me | CH=CH₂ | C≡CH | 2-thienyl | 5-CF₃-4-thiazolyl | 1-Me-4-CF₃-2-imidazolyl |
| c-Pr | C(O)CF₃ | C(O)Ph | 3-thienyl | C(O)(2-F—Ph) | C(O)(3,5-diCl—Ph) |
| C(O)Me | CHO | CO₂Et | | C(O)(3-CF₃—Ph) | C(O)(3-(2-Cl-4-CF₃—Ph)Ph) |
| R² is 6-chloro-3-pyridinyl | | | | | |
| Cl | Br | I | cyano | 4-CF₃-2-thiazolyl | 2-CF₃-5-thiazolyl |
| F | C(O)NMe₂ | NMe₂ | NHCHO | 5-CF₃-2-thiazolyl | 4-CF₃-5-thiazolyl |
| CF₃ | c-Pr-2-(c-Pr) | Et | i-Pr | 2-CF₃-4-thiazolyl | 1-Me-5-CF₃-2-imidazolyl |
| Me | CH=CH₂ | C≡CH | 2-thienyl | 5-CF₃-4-thiazolyl | 1-Me-4-CF₃-2-imidazolyl |
| c-Pr | C(O)CF₃ | C(O)Ph | 3-thienyl | C(O)(2-F—Ph) | C(O)(3,5-diCl—Ph) |
| C(O)Me | CHO | CO₂Et | | C(O)(3-CF₃—Ph) | C(O)(3-(2-Cl-4-CF₃—Ph)Ph) |
| R² is 6-fluoro-3-pyridinyl | | | | | |
| Cl | Br | I | cyano | 4-CF₃-2-thiazolyl | 2-CF₃-5-thiazolyl |
| F | C(O)NMe₂ | NMe₂ | NHCHO | 5-CF₃-2-thiazolyl | 4-CF₃-5-thiazolyl |
| CF₃ | c-Pr-2-(c-Pr) | Et | i-Pr | 2-CF₃-4-thiazolyl | 1-Me-5-CF₃-2-imidazolyl |
| Me | CH=CH₂ | C≡CH | 2-thienyl | 5-CF₃-4-thiazolyl | 1-Me-4-CF₃-2-imidazolyl |
| c-Pr | C(O)CF₃ | C(O)Ph | 3-thienyl | C(O)(2-F—Ph) | C(O)(3,5-diCl—Ph) |
| C(O)Me | CHO | CO₂Et | | C(O)(3-CF₃—Ph) | C(O)(3-(2-Cl-4-CF₃—Ph)Ph) |
| R² is 5-pyrimidinyl | | | | | |
| Cl | Br | I | cyano | 4-CF₃-2-thiazolyl | 2-CF₃-5-thiazolyl |
| F | C(O)NMe₂ | NMe₂ | NHCHO | 5-CF₃-2-thiazolyl | 4-CF₃-5-thiazolyl |
| CF₃ | c-Pr-2-(c-Pr) | Et | i-Pr | 2-CF₃-4-thiazolyl | 1-Me-5-CF₃-2-imidazolyl |
| Me | CH=CH₂ | C≡CH | 2-thienyl | 5-CF₃-4-thiazolyl | 1-Me-4-CF₃-2-imidazolyl |
| c-Pr | C(O)CF₃ | C(O)Ph | 3-thienyl | C(O)(2-F—Ph) | C(O)(3,5-diCl—Ph) |
| C(O)Me | CHO | CO₂Et | | C(O)(3-CF₃—Ph) | C(O)(3-(2-Cl-4-CF₃—Ph)Ph) |
| R² is 2-methyl-5-pyrimidinyl | | | | | |
| Cl | Br | I | cyano | 4-CF₃-2-thiazolyl | 2-CF₃-5-thiazolyl |
| F | C(O)NMe₂ | NMe₂ | NHCHO | 5-CF₃-2-thiazolyl | 4-CF₃-5-thiazolyl |
| CF₃ | c-Pr-2-(c-Pr) | Et | i-Pr | 2-CF₃-4-thiazolyl | 1-Me-5-CF₃-2-imidazolyl |
| Me | CH=CH₂ | C≡CH | 2-thienyl | 5-CF₃-4-thiazolyl | 1-Me-4-CF₃-2-imidazolyl |
| c-Pr | C(O)CF₃ | C(O)Ph | 3-thienyl | C(O)(2-F—Ph) | C(O)(3,5-diCl—Ph) |
| C(O)Me | CHO | CO₂Et | | C(O)(3-CF₃—Ph) | C(O)(3-(2-Cl-4-CF₃—Ph)Ph) |

TABLE 29

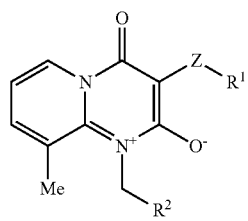

| R¹ | R¹ | R¹ | R¹ |
|---|---|---|---|
| Z is a direct bond; R² is 2-chloro-5-thiazolyl | | | |
| CH=CH(Ph) | CH=CH(2-F—Ph) | CH=CH(3-F—Ph) | CH=CH(4-F—Ph) |
| CH=CH(2-Me—Ph) | CH=CH(3-Me—Ph) | CH=CH(4-Me—Ph) | CH=CH(2-CF₃—Ph) |
| CH=CH(3-CF₃O—Ph) | CH=CH(4-CF₃O—Ph) | CH=CH(Me) | CH=CH(Et) |
| CH=CH(c-Pr-2-(c-Pr)) | CH=CH(C(O)Me) | CH=CH(CO₂Et) | CH=CH(C(O)NMe₂) |
| CH=CH(2-MeO—Ph) | CH=CH(3-CF₃—Ph) | CH=CH(i-Pr) | CH=CH(4-MeO—Ph) |

TABLE 29-continued

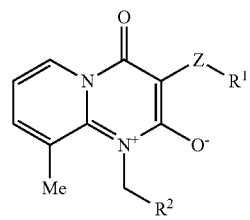

| | | | |
|---|---|---|---|
| CH=CH(3-MeO—Ph) | CH=CH(4-CF₃—Ph) | CH=CH(c-Pr) | CH=CH(2-CF₃O—Ph) |
| CH=CH(CF₃) | CH=CH(3,5-diCl—Ph) | | CH=CH(3-(2-Cl-4-CF₃—Ph)Ph) |

Z is a direct bond; $R^2$ is 6-chloro-3-pyridinyl

| | | | |
|---|---|---|---|
| CH=CH(Ph) | CH=CH(2-F—Ph) | CH=CH(3-F—Ph) | CH=CH(4-F—Ph) |
| CH=CH(2-Me—Ph) | CH=CH(3-Me—Ph) | CH=CH(4-Me—Ph) | CH=CH(2-CF₃—Ph) |
| CH=CH(3-CF₃O—Ph) | CH=CH(4-CF₃O—Ph) | CH=CH(Me) | CH=CH(Et) |
| CH=CH(c-Pr-2-(c-Pr)) | CH=CH(C(O)Me) | CH=CH(CO₂Et) | CH=CH(C(O)NMe₂) |
| CH=CH(2-MeO—Ph) | CH=CH(3-CF₃—Ph) | CH=CH(i-Pr) | CH=CH(4-MeO—Ph) |
| CH=CH(3-MeO—Ph) | CH=CH(4-CF₃—Ph) | CH=CH(c-Pr) | CH=CH(2-CF₃O—Ph) |
| CH=CH(CF₃) | CH=CH(3,5-diCl—Ph) | | CH=CH(3-(2-Cl-4-CF₃—Ph)Ph) |

Z is a direct bond; $R^2$ is 6-fluoro-3-pyridinyl

| | | | |
|---|---|---|---|
| CH=CH(Ph) | CH=CH(2-F—Ph) | CH=CH(3-F—Ph) | CH=CH(4-F—Ph) |
| CH=CH(2-Me—Ph) | CH=CH(3-Me—Ph) | CH=CH(4-Me—Ph) | CH=CH(2-CF₃—Ph) |
| CH=CH(3-CF₃O—Ph) | CH=CH(4-CF₃O—Ph) | CH=CH(Me) | CH=CH(Et) |
| CH=CH(c-Pr-2-(c-Pr)) | CH=CH(C(O)Me) | CH=CH(CO₂Et) | CH=CH(C(O)NMe₂) |
| CH=CH(2-MeO—Ph) | CH=CH(3-CF₃—Ph) | CH=CH(i-Pr) | CH=CH(4-MeO—Ph) |
| CH=CH(3-MeO—Ph) | CH=CH(4-CF₃—Ph) | CH=CH(c-Pr) | CH=CH(2-CF₃O—Ph) |
| CH=CH(CF₃) | CH=CH(3,5-diCl—Ph) | | CH=CH(3-(2-Cl-4-CF₃—Ph)Ph) |

Z is a direct bond; $R^2$ is 5-pyrimidinyl

| | | | |
|---|---|---|---|
| CH=CH(Ph) | CH=CH(2-F—Ph) | CH=CH(3-F—Ph) | CH=CH(4-F—Ph) |
| CH=CH(2-Me—Ph) | CH=CH(3-Me—Ph) | CH=CH(4-Me—Ph) | CH=CH(2-CF₃—Ph) |
| CH=CH(3-CF₃O—Ph) | CH=CH(4-CF₃O—Ph) | CH=CH(Me) | CH=CH(Et) |
| CH=CH(c-Pr-2-(c-Pr)) | CH=CH(C(O)Me) | CH=CH(CO₂Et) | CH=CH(C(O)NMe₂) |
| CH=CH(2-MeO—Ph) | CH=CH(3-CF₃—Ph) | CH=CH(i-Pr) | CH=CH(4-MeO—Ph) |
| CH=CH(3-MeO—Ph) | CH=CH(4-CF₃—Ph) | CH=CH(c-Pr) | CH=CH(2-CF₃O—Ph) |
| CH=CH(CF₃) | CH=CH(3,5-diCl—Ph) | | CH=CH(3-(2-Cl-4-CF₃—Ph)Ph) |

Z is a direct bond; $R^2$ is 2-methyl-5-pyrimidinyl

| | | | |
|---|---|---|---|
| CH=CH(Ph) | CH=CH(2-F—Ph) | CH=CH(3-F—Ph) | CH=CH(4-F—Ph) |
| CH=CH(2-Me—Ph) | CH=CH(3-Me—Ph) | CH=CH(4-Me—Ph) | CH=CH(2-CF₃—Ph) |
| CH=CH(3-CF₃O—Ph) | CH=CH(4-CF₃O—Ph) | CH=CH(Me) | CH=CH(Et) |
| CH=CH(c-Pr-2-(c-Pr)) | CH=CH(C(O)Me) | CH=CH(CO₂Et) | CH=CH(C(O)NMe₂) |
| CH=CH(2-MeO—Ph) | CH=CH(3-CF₃—Ph) | CH=CH(i-Pr) | CH=CH(4-MeO—Ph) |
| CH=CH(3-MeO—Ph) | CH=CH(4-CF₃—Ph) | CH=CH(c-Pr) | CH=CH(2-CF₃O—Ph) |
| CH=CH(CF₃) | CH=CH(3,5-diCl—Ph) | | CH=CH(3-(2-Cl-4-CF₃—Ph)Ph) |

Z is a direct bond; $R^2$ is 2-chloro-5-thiazolyl

| | | | |
|---|---|---|---|
| C≡CPh | C≡C(2-F—Ph) | C≡C(3-F—Ph) | C≡C(4-F—Ph) |
| C≡C(2-Me—Ph) | C≡C(3-Me—Ph) | C≡C(4-Me—Ph) | C≡C(2-CF₃—Ph) |
| C≡C(3-CF₃O—Ph) | C≡C(4-CF₃O—Ph) | C≡CMe | C≡CEt |
| C≡C(c-Pr-2-(c-Pr)) | C≡CC(O)Me | C≡CCO₂Et | C≡CC(O)NMe₂ |
| C≡C(2-MeO—Ph) | C≡C(3-CF₃—Ph) | C≡C(i-Pr) | C≡C(3-MeO—Ph) |
| C≡C(4-CF₃—Ph) | C≡C(c-Pr) | C≡C(4-MeO—Ph) | C≡C(2-CF₃O—Ph) |
| C≡CCF₃ | | C≡C(3,5-diCl—Ph) | C≡C(3-(2-Cl-4-CF₃—Ph)Ph) |

Z is a direct bond; $R^2$ is 6-chloro-3-pyridinyl

| | | | |
|---|---|---|---|
| C≡CPh | C≡C(2-F—Ph) | C≡C(3-F—Ph) | C≡C(4-F—Ph) |
| C≡C(2-Me—Ph) | C≡C(3-Me—Ph) | C≡C(4-Me—Ph) | C≡C(2-CF₃—Ph) |
| C≡C(3-CF₃O—Ph) | C≡C(4-CF₃O—Ph) | C≡CMe | C≡CEt |
| C≡C(c-Pr-2-(c-Pr)) | C≡CC(O)Me | C≡CCO₂Et | C≡CC(O)NMe₂ |
| C≡C(2-MeO—Ph) | C≡C(3-CF₃—Ph) | C≡C(i-Pr) | C≡C(3-MeO—Ph) |
| C≡C(4-CF₃—Ph) | C≡C(c-Pr) | C≡C(4-MeO—Ph) | C≡C(2-CF₃O—Ph) |
| C≡CCF₃ | | C≡C(3,5-diCl—Ph) | C≡C(3-(2-Cl-4-CF₃—Ph)Ph) |

Z is a direct bond; $R^2$ is 6-fluoro-3-pyridinyl

| | | | |
|---|---|---|---|
| C≡CPh | C≡C(2-F—Ph) | C≡C(3-F—Ph) | C≡C(4-F—Ph) |
| C≡C(2-Me—Ph) | C≡C(3-Me—Ph) | C≡C(4-Me—Ph) | C≡C(2-CF₃—Ph) |
| C≡C(3-CF₃O—Ph) | C≡C(4-CF₃O—Ph) | C≡CMe | C≡CEt |
| C≡C(c-Pr-2-(c-Pr)) | C≡CC(O)Me | C≡CCO₂Et | C≡CC(O)NMe₂ |
| C≡C(2-MeO—Ph) | C≡C(3-CF₃—Ph) | C≡C(i-Pr) | C≡C(3-MeO—Ph) |
| C≡C(4-CF₃—Ph) | C≡C(c-Pr) | C≡C(4-MeO—Ph) | C≡C(2-CF₃O—Ph) |
| C≡CCF₃ | | C≡C(3,5-diCl—Ph) | C≡C(3-(2-Cl-4-CF₃—Ph)Ph) |

Z is a direct bond; $R^2$ is 5-pyrimidinyl

| | | | |
|---|---|---|---|
| C≡CPh | C≡C(2-F—Ph) | C≡C(3-F—Ph) | C≡C(4-F—Ph) |
| C≡C(2-Me—Ph) | C≡C(3-Me—Ph) | C≡C(4-Me—Ph) | C≡C(2-CF₃—Ph) |

TABLE 29-continued

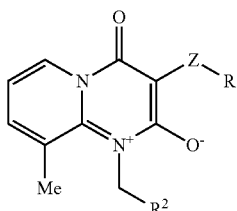

| | | | | | |
|---|---|---|---|---|---|
| C≡C(3-CF₃O—Ph) | C≡C(4-CF₃O—Ph) | C≡CMe | | C≡CEt | |
| C≡C(c-Pr-2-(c-Pr)) | C≡CC(O)Me | C≡CCO₂Et | | C≡CC(O)NMe₂ | |
| C≡C(2-MeO—Ph) | C≡C(3-CF₃—Ph) | C≡C(i-Pr) | | C≡C(3-MeO—Ph) | |
| C≡C(4-CF₃—Ph) | C≡C(c-Pr) | C≡C(4-MeO—Ph) | | C≡C(2-CF₃O—Ph) | |
| C≡CCF₃ | | C≡C(3,5-diCl—Ph) | | C≡C(3-(2-Cl-4-CF₃—Ph)Ph) | |

Z is a direct bond; R² is 2-methyl-5-pyrimidinyl

| | | | | | |
|---|---|---|---|---|---|
| C≡CPh | C≡C(2-F—Ph) | C≡C(3-F—Ph) | | C≡C(4-F—Ph) | |
| C≡C(2-Me—Ph) | C≡C(3-Me—Ph) | C≡C(4-Me—Ph) | | C≡C(2-CF₃—Ph) | |
| C≡C(3-CF₃O—Ph) | C≡C(4-CF₃O—Ph) | C≡CMe | | C≡CEt | |
| C≡C(c-Pr-2-(c-Pr)) | C≡CC(O)Me | C≡CCO₂Et | | C≡CC(O)NMe₂ | |
| C≡C(2-MeO—Ph) | C≡C(3-CF₃—Ph) | C≡C(i-Pr) | | C≡C(3-MeO—Ph) | |
| C≡C(4-CF₃—Ph) | C≡C(c-Pr) | C≡C(4-MeO—Ph) | | C≡C(2-CF₃O—Ph) | |
| C≡CCF₃ | | C≡C(3,5-diCl—Ph) | | C≡C(3-(2-Cl-4-CF₃—Ph)Ph) | |

| R¹ | R¹ | R¹ | R¹ | R¹ | R¹ |
|---|---|---|---|---|---|

Z is O; R² is 2-chloro-5-thiazolyl

| Ph | 2-F—Ph | 3-F—Ph | 4-F—Ph | 2-MeO—Ph | 4-MeO—Ph |
|---|---|---|---|---|---|
| 2-Me—Ph | 3-Me—Ph | 4-Me—Ph | 2-CF₃—Ph | 3-CF₃—Ph | 2-CF₃O—Ph |
| 3-CF₃O—Ph | 4-CF₃O—Ph | Me | Et | i-Pr | CF₃ |
| c-Pr-2-(c-Pr) | C(O)Me | CO₂Et | C(O)NMe₂ | 3,5-diCl—Ph | 3-(2-Cl-4-CF₃—Ph)Ph |
| c-Pr | 3-MeO—Ph | 4-CF₃—Ph | | | |

Z is O; R² is 6-chloro-3-pyridinyl

| Ph | 2-F—Ph | 3-F—Ph | 4-F—Ph | 2-MeO—Ph | 4-MeO—Ph |
|---|---|---|---|---|---|
| 2-Me—Ph | 3-Me—Ph | 4-Me—Ph | 2-CF₃—Ph | 3-CF₃—Ph | 2-CF₃O—Ph |
| 3-CF₃O—Ph | 4-CF₃O—Ph | Me | Et | i-Pr | CF₃ |
| c-Pr-2-(c-Pr) | C(O)Me | CO₂Et | C(O)NMe₂ | 3,5-diCl—Ph | 3-(2-Cl-4-CF₃—Ph)Ph |
| c-Pr | 3-MeO—Ph | 4-CF₃—Ph | | | |

Z is O; R² is 6-fluoro-3-pyridinyl

| Ph | 2-F—Ph | 3-F—Ph | 4-F—Ph | 2-MeO—Ph | 4-MeO—Ph |
|---|---|---|---|---|---|
| 2-Me—Ph | 3-Me—Ph | 4-Me—Ph | 2-CF₃—Ph | 3-CF₃—Ph | 2-CF₃O—Ph |
| 3-CF₃O—Ph | 4-CF₃O—Ph | Me | Et | i-Pr | CF₃ |
| c-Pr-2-(c-Pr) | C(O)Me | CO₂Et | C(O)NMe₂ | 3,5-diCl—Ph | 3-(2-Cl-4-CF₃—Ph)Ph |
| c-Pr | 3-MeO—Ph | 4-CF₃—Ph | | | |

Z is O; R² is 5-pyrimidinyl

| Ph | 2-F—Ph | 3-F—Ph | 4-F—Ph | 2-MeO—Ph | 4-MeO—Ph |
|---|---|---|---|---|---|
| 2-Me—Ph | 3-Me—Ph | 4-Me—Ph | 2-CF₃—Ph | 3-CF₃—Ph | 2-CF₃O—Ph |
| 3-CF₃O—Ph | 4-CF₃O—Ph | Me | Et | i-Pr | CF₃ |
| c-Pr-2-(c-Pr) | C(O)Me | CO₂Et | C(O)NMe₂ | 3,5-diCl—Ph | 3-(2-Cl-4-CF₃—Ph)Ph |
| c-Pr | 3-MeO—Ph | 4-CF₃—Ph | | | |

Z is O; R² is 2-methyl-5-pyrimidinyl

| Ph | 2-F—Ph | 3-F—Ph | 4-F—Ph | 2-MeO—Ph | 4-MeO—Ph |
|---|---|---|---|---|---|
| 2-Me—Ph | 3-Me—Ph | 4-Me—Ph | 2-CF₃—Ph | 3-CF₃—Ph | 2-CF₃O—Ph |
| 3-CF₃O—Ph | 4-CF₃O—Ph | Me | Et | i-Pr | CF₃ |
| c-Pr-2-(c-Pr) | C(O)Me | CO₂Et | C(O)NMe₂ | 3,5-diCl—Ph | 3-(2-Cl-4-CF₃—Ph)Ph |
| c-Pr | 3-MeO—Ph | 4-CF₃—Ph | | | |

Z is NMe; R² is 2-chloro-5-thiazolyl

| Ph | 2-F—Ph | 3-F—Ph | 4-F—Ph | 2-MeO—Ph | 4-MeO—Ph |
|---|---|---|---|---|---|
| 2-Me—Ph | 3-Me—Ph | 4-Me—Ph | 2-CF₃—Ph | 3-CF₃—Ph | 2-CF₃O—Ph |
| 3-CF₃O—Ph | 4-CF₃O—Ph | Me | Et | i-Pr | CF₃ |
| c-Pr-2-(c-Pr) | C(O)Me | CO₂Et | C(O)NMe₂ | 3,5-diCl—Ph | 3-(2-Cl-4-CF₃—Ph)Ph |
| c-Pr | 3-MeO—Ph | 4-CF₃—Ph | | | |

Z is NMe; R² is 6-chloro-3-pyridinyl

| Ph | 2-F—Ph | 3-F—Ph | 4-F—Ph | 2-MeO—Ph | 4-MeO—Ph |
|---|---|---|---|---|---|
| 2-Me—Ph | 3-Me—Ph | 4-Me—Ph | 2-CF₃—Ph | 3-CF₃—Ph | 2-CF₃O—Ph |
| 3-CF₃O—Ph | 4-CF₃O—Ph | Me | Et | i-Pr | CF₃ |
| c-Pr-2-(c-Pr) | C(O)Me | CO₂Et | C(O)NMe₂ | 3,5-diCl—Ph | 3-(2-Cl-4-CF₃—Ph)Ph |
| c-Pr | 3-MeO—Ph | 4-CF₃—Ph | | | |

TABLE 29-continued

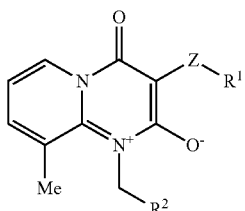

| | | | | | |
|---|---|---|---|---|---|
| Z is NMe; $R^2$ is 6-fluoro-3-pyridinyl | | | | | |
| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF$_3$—Ph | 3-CF$_3$—Ph | 2-CF$_3$O—Ph |
| 3-CF$_3$O—Ph | 4-CF$_3$O—Ph | Me | Et | i-Pr | CF$_3$ |
| c-Pr-2-(c-Pr) | C(O)Me | CO$_2$Et | C(O)NMe$_2$ | 3,5-diCl—Ph | 3-(2-Cl-4-CF$_3$—Ph)Ph |
| c-Pr | 3-MeO—Ph | 4-CF$_3$—Ph | | | |
| Z is NMe; $R^2$ is 5-pyrimidinyl | | | | | |
| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF$_3$—Ph | 3-CF$_3$—Ph | 2-CF$_3$O—Ph |
| 3-CF$_3$O—Ph | 4-CF$_3$O—Ph | Me | Et | i-Pr | CF$_3$ |
| c-Pr-2-(c-Pr) | C(O)Me | CO$_2$Et | C(O)NMe$_2$ | 3,5-diCl—Ph | 3-(2-Cl-4-CF$_3$—Ph)Ph |
| c-Pr | 3-MeO—Ph | 4-CF$_3$—Ph | | | |
| Z is NMe; $R^2$ is 2-methyl-5-pyrimidinyl | | | | | |
| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF$_3$—Ph | 3-CF$_3$—Ph | 2-CF$_3$O—Ph |
| 3-CF$_3$O—Ph | 4-CF$_3$O—Ph | Me | Et | i-Pr | CF$_3$ |
| c-Pr-2-(c-Pr) | C(O)Me | CO$_2$Et | C(O)NMe$_2$ | 3,5-diCl—Ph | 3-(2-Cl-4-CF$_3$—Ph)Ph |
| c-Pr | 3-MeO—Ph | 4-CF$_3$—Ph | | | |
| Z is C(O); $R^2$ is 2-chloro-5-thiazolyl | | | | | |
| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF$_3$—Ph | 3-CF$_3$—Ph | 2-CF$_3$O—Ph |
| 3-CF$_3$O—Ph | 4-CF$_3$O—Ph | Me | Et | i-Pr | CF$_3$ |
| c-Pr-2-(c-Pr) | C(O)Me | CO$_2$Et | C(O)NMe$_2$ | 3,5-diCl—Ph | 3-(2-Cl-4-CF$_3$—Ph)Ph |
| c-Pr | 3-MeO—Ph | 4-CF$_3$—Ph | | | |
| Z is C(O); $R^2$ is 6-chloro-3-pyridinyl | | | | | |
| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF$_3$—Ph | 3-CF$_3$—Ph | 2-CF$_3$O—Ph |
| 3-CF$_3$O—Ph | 4-CF$_3$O—Ph | Me | Et | i-Pr | CF$_3$ |
| c-Pr-2-(c-Pr) | C(O)Me | CO$_2$Et | C(O)NMe$_2$ | 3,5-diCl—Ph | 3-(2-Cl-4-CF$_3$—Ph)Ph |
| c-Pr | 3-MeO—Ph | 4-CF$_3$—Ph | | | |
| Z is C(O); $R^2$ is 6-fluoro-3-pyridinyl | | | | | |
| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF$_3$—Ph | 3-CF$_3$—Ph | 2-CF$_3$O—Ph |
| 3-CF$_3$O—Ph | 4-CF$_3$O—Ph | Me | Et | i-Pr | CF$_3$ |
| c-Pr-2-(c-Pr) | C(O)Me | CO$_2$Et | C(O)NMe$_2$ | 3,5-diCl—Ph | 3-(2-Cl-4-CF$_3$—Ph)Ph |
| c-Pr | 3-MeO—Ph | 4-CF$_3$—Ph | | | |
| Z is C(O); $R^2$ is 5-pyrimidinyl | | | | | |
| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF$_3$—Ph | 3-CF$_3$—Ph | 2-CF$_3$O—Ph |
| 3-CF$_3$O—Ph | 4-CF$_3$O—Ph | Me | Et | i-Pr | CF$_3$ |
| c-Pr-2-(c-Pr) | C(O)Me | CO$_2$Et | C(O)NMe$_2$ | 3,5-diCl—Ph | 3-(2-Cl-4-CF$_3$—Ph)Ph |
| c-Pr | 3-MeO—Ph | 4-CF$_3$—Ph | | | |
| Z is C(O); $R^2$ is 2-methyl-5-pyrimidinyl | | | | | |
| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF$_3$—Ph | 3-CF$_3$—Ph | 2-CF$_3$O—Ph |
| 3-CF$_3$O—Ph | 4-CF$_3$O—Ph | Me | Et | i-Pr | CF$_3$ |
| c-Pr-2-(c-Pr) | C(O)Me | CO$_2$Et | C(O)NMe$_2$ | 3,5-diCl—Ph | 3-(2-Cl-4-CF$_3$—Ph)Ph |
| c-Pr | 3-MeO—Ph | 4-CF$_3$—Ph | | | |
| Z is C(O)NMe; $R^2$ is 2-chloro-5-thiazolyl | | | | | |
| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF$_3$—Ph | 3-CF$_3$—Ph | 2-CF$_3$O—Ph |
| 3-CF$_3$O—Ph | 4-CF$_3$O—Ph | Me | Et | i-Pr | CF$_3$ |
| c-Pr-2-(c-Pr) | C(O)Me | CO$_2$Et | C(O)NMe$_2$ | 3,5-diCl—Ph | 3-(2-Cl-4-CF$_3$—Ph)Ph |
| c-Pr | 3-MeO—Ph | 4-CF$_3$—Ph | | | |
| Z is C(O)NMe; $R^2$ is 6-chloro-3-pyridinyl | | | | | |
| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF$_3$—Ph | 3-CF$_3$—Ph | 2-CF$_3$O—Ph |
| 3-CF$_3$O—Ph | 4-CF$_3$O—Ph | Me | Et | i-Pr | CF$_3$ |

TABLE 29-continued

[Structure: pyrido-pyrimidinone core with 8-Me, N-CH2R2, C3-ZR1, C2-O⁻, C4=O]

| c-Pr-2-(c-Pr) | C(O)Me | CO₂Et | C(O)NMe₂ | 3,5-diCl—Ph | 3-(2-Cl-4-CF₃—Ph)Ph |
| c-Pr | 3-MeO—Ph | 4-CF₃—Ph | | | |

Z is C(O)NMe; R² is 6-fluoro-3-pyridinyl

| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF₃—Ph | 3-CF₃—Ph | 2-CF₃O—Ph |
| 3-CF₃O—Ph | 4-CF₃O—Ph | Me | Et | i-Pr | CF₃ |
| c-Pr-2-(c-Pr) | C(O)Me | CO₂Et | C(O)NMe₂ | 3,5-diCl—Ph | 3-(2-Cl-4-CF₃—Ph)Ph |
| c-Pr | 3-MeO—Ph | 4-CF₃—Ph | | | |

Z is C(O)NMe; R² is 5-pyrimidinyl

| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF₃—Ph | 3-CF₃—Ph | 2-CF₃O—Ph |
| 3-CF₃O—Ph | 4-CF₃O—Ph | Me | Et | i-Pr | CF₃ |
| c-Pr-2-(c-Pr) | C(O)Me | CO₂Et | C(O)NMe₂ | 3,5-diCl—Ph | 3-(2-Cl-4-CF₃—Ph)Ph |
| c-Pr | 3-MeO—Ph | 4-CF₃—Ph | | | |

Z is C(O)NMe; R² is 2-methyl-5-pyrimidinyl

| Ph | 2-F—Ph | 3-F—Ph | 4-F—Ph | 2-MeO—Ph | 4-MeO—Ph |
| 2-Me—Ph | 3-Me—Ph | 4-Me—Ph | 2-CF₃—Ph | 3-CF₃—Ph | 2-CF₃O—Ph |
| 3-CF₃O—Ph | 4-CF₃O—Ph | Me | Et | i-Pr | CF₃ |
| c-Pr-2-(c-Pr) | C(O)Me | CO₂Et | C(O)NMe₂ | 3,5-diCl—Ph | 3-(2-Cl-4-CF₃—Ph)Ph |
| c-Pr | 3-MeO—Ph | 4-CF₃—Ph | | | |

TABLE 30

[Structure: pyrido-pyrimidinone core with 8-Me, N-CH2R2, C3-(3-biphenyl-3'-R), C2-O⁻, C4=O]

| R | R | R | R | R | R |
|---|---|---|---|---|---|
| R² is 2-chloro-5-thiazolyl | | | | | |
| Br | CH₂F | O—i-Pr | SCF₃ | C(O)NHMe | 6-Cl-3-pyridinyl |
| I | CHF₂ | OCH₂CH=CH₂ | SCHF₂ | C(O)NMe₂ | 6-F-3-pyridinyl |
| Me | OMe | OCH₂C≡CH | S(O)CF₃ | C(=NOMe)Me | N-Me-4-pyrazolyl |
| Et | OEt | O—c-Pr | SO₂CF₃ | CH=CH₂ | 3-Me-5-isoxazolyl |
| c-Pr | O—n-Pr | OCHF₂ | CO₂Me | C≡CH | 6-(6-Cl-3-pyridinyl)-3-pyridinyl |
| Ph | OPh | SCF₃ | CO₂Et | 3-ClPh | 4-CF₃-2-thiazolyl |
| | | | | | 1-Me-4-CF₃-2-imidazolyl |
| R² is 6-chloro-3-pyridinyl | | | | | |
| Br | CH₂F | O—i-Pr | SCF₃ | C(O)NHMe | 6-Cl-3-pyridinyl |
| I | CHF₂ | OCH₂CH=CH₂ | SCHF₂ | C(O)NMe₂ | 6-F-3-pyridinyl |
| Me | OMe | OCH₂C≡CH | S(O)CF₃ | C(=NOMe)Me | N-Me-4-pyrazolyl |
| Et | OEt | O—c-Pr | SO₂CF₃ | CH=CH₂ | 3-Me-5-isoxazolyl |
| c-Pr | O—n-Pr | OCHF₂ | CO₂Me | C≡CH | 6-(6-Cl-3-pyridinyl)-3-pyridinyl |
| Ph | OPh | SCF₃ | CO₂Et | 3-ClPh | 4-CF₃-2-thiazolyl |
| | | | | | 1-Me-4-CF₃-2-imidazolyl |
| R² is 6-fluoro-3-pyridinyl | | | | | |
| Br | CH₂F | O—i-Pr | SCF₃ | C(O)NHMe | 6-Cl-3-pyridinyl |
| I | CHF₂ | OCH₂CH=CH₂ | SCHF₂ | C(O)NMe₂ | 6-F-3-pyridinyl |
| Me | OMe | OCH₂C≡CH | S(O)CF₃ | C(=NOMe)Me | N-Me-4-pyrazolyl |
| Et | OEt | O—c-Pr | SO₂CF₃ | CH=CH₂ | 3-Me-5-isoxazolyl |
| c-Pr | O—n-Pr | OCHF₂ | CO₂Me | C≡CH | 6-(6-Cl-3-pyridinyl)-3-pyridinyl |

TABLE 30-continued

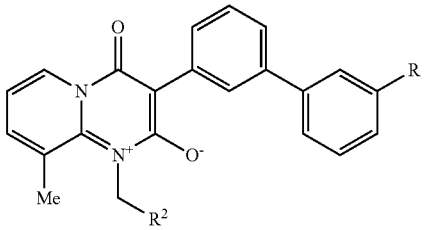

| R | R | R | R | R | R |
|---|---|---|---|---|---|
| Ph | OPh | SCF$_3$ | CO$_2$Et | 3-ClPh | 4-CF$_3$-2-thiazolyl |
|  |  |  |  |  | 1-Me-4-CF$_3$-2-imidazolyl |
| R$^2$ is 5-pyrimidinyl |

| R | R | R | R | R | R |
|---|---|---|---|---|---|
| Br | CH$_2$F | O—i-Pr | SCF$_3$ | C(O)NHMe | 6-Cl-3-pyridinyl |
| I | CHF$_2$ | OCH$_2$CH=CH$_2$ | SCHF$_2$ | C(O)NMe$_2$ | 6-F-3-pyridinyl |
| Me | OMe | OCH$_2$C≡CH | S(O)CF$_3$ | C(=NOMe)Me | N-Me-4-pyrazolyl |
| Et | OEt | O—c-Pr | SO$_2$CF$_3$ | CH=CH$_2$ | 3-Me-5-isoxazolyl |
| c-Pr | O—n-Pr | OCHF$_2$ | CO$_2$Me | C≡CH | 6-(6-Cl-3-pyridinyl)-3-pyridinyl |
| Ph | OPh | SCF$_3$ | CO$_2$Et | 3-ClPh | 4-CF$_3$-2-thiazolyl |
|  |  |  |  |  | 1-Me-4-CF$_3$-2-imidazolyl |

R$^2$ is 2-methyl-5-pyrimidinyl

| R | R | R | R | R | R |
|---|---|---|---|---|---|
| Br | CH$_2$F | O—i-Pr | SCF$_3$ | C(O)NHMe | 6-Cl-3-pyridinyl |
| I | CHF$_2$ | OCH$_2$CH=CH$_2$ | SCHF$_2$ | C(O)NMe$_2$ | 6-F-3-pyridinyl |
| Me | OMe | OCH$_2$C≡CH | S(O)CF$_3$ | C(=NOMe)Me | N-Me-4-pyrazolyl |
| Et | OEt | O—c-Pr | SO$_2$CF$_3$ | CH=CH$_2$ | 3-Me-5-isoxazolyl |
| c-Pr | O—n-Pr | OCHF$_2$ | CO$_2$Me | C≡CH | 6-(6-Cl-3-pyridinyl)-3-pyridinyl |
| Ph | OPh | SCF$_3$ | CO$_2$Et | 3-ClPh | 4-CF$_3$-2-thiazolyl |
|  |  |  |  |  | 1-Me-4-CF$_3$-2-imidazolyl |

TABLE 31

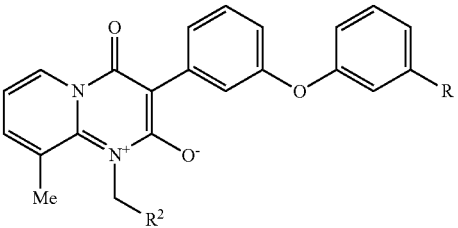

| R | R | R | R | R | R |
|---|---|---|---|---|---|

R$^2$ is 2-chloro-5-thiazolyl

| R | R | R | R | R | R |
|---|---|---|---|---|---|
| H | c-Pr | O—i-Pr | SCF$_3$ | C(O)NHMe | 3-ClPh |
| F | CF$_3$ | OCH$_2$CH=CH$_2$ | SCHF$_2$ | C(O)NMe$_2$ | 6-Cl-3-pyridinyl |
| Cl | CH$_2$F | OCH$_2$C≡CH | S(O)CF$_3$ | C(=NOMe)Me | 6-F-3-pyridinyl |
| Br | CHF$_2$ | O—c-Pr | SO$_2$CF$_3$ | CH=CH$_2$ | N-Me-4-pyrazolyl |
| I | OMe | OCF$_3$ | CO$_2$Me | C≡CH | 3-Me-5-isoxazolyl |
| Me | OEt | OCHF$_2$ | CO$_2$Et | Ph | 6-(6-Cl-3-pyridinyl)-3-pyridinyl |
| Et | O—n-Pr | SCF$_3$ | cyano | OPh | 4-CF$_3$-2-thiazolyl |
|  |  |  |  |  | 1-Me-4-CF$_3$-2-imidazolyl |

R$^2$ is 6-chloro-3-pyridinyl

| R | R | R | R | R | R |
|---|---|---|---|---|---|
| H | c-Pr | O—i-Pr | SCF$_3$ | C(O)NHMe | 3-ClPh |
| F | CF$_3$ | OCH$_2$CH=CH$_2$ | SCHF$_2$ | C(O)NMe$_2$ | 6-Cl-3-pyridinyl |
| Cl | CH$_2$F | OCH$_2$C≡CH | S(O)CF$_3$ | C(=NOMe)Me | 6-F-3-pyridinyl |
| Br | CHF$_2$ | O—c-Pr | SO$_2$CF$_3$ | CH=CH$_2$ | N-Me-4-pyrazolyl |
| I | OMe | OCF$_3$ | CO$_2$Me | C≡CH | 3-Me-5-isoxazolyl |
| Me | OEt | OCHF$_2$ | CO$_2$Et | Ph | 6-(6-Cl-3-pyridinyl)-3-pyridinyl |
| Et | O—n-Pr | SCF$_3$ | cyano | OPh | 4-CF$_3$-2-thiazolyl |
|  |  |  |  |  | 1-Me-4-CF$_3$-2-imidazolyl |

R$^2$ is 6-fluoro-3-pyridinyl

| R | R | R | R | R | R |
|---|---|---|---|---|---|
| H | c-Pr | O—i-Pr | SCF$_3$ | C(O)NHMe | 3-ClPh |
| F | CF$_3$ | OCH$_2$CH=CH$_2$ | SCHF$_2$ | C(O)NMe$_2$ | 6-Cl-3-pyridinyl |
| Cl | CH$_2$F | OCH$_2$C≡CH | S(O)CF$_3$ | C(=NOMe)Me | 6-F-3-pyridinyl |

TABLE 31-continued

[Structure: pyrido-pyrimidinone core with 9-Me substituent, N-CH2-R2, and a 3-(3-phenoxyphenyl) substituent where the distal phenyl bears R]

| R | R | R | R | R | R |
|---|---|---|---|---|---|
| Br | CHF₂ | O—c-Pr | SO₂CF₃ | CH=CH₂ | N-Me-4-pyrazolyl |
| I | OMe | OCF₃ | CO₂Me | C≡CH | 3-Me-5-isoxazolyl |
| Me | OEt | OCHF₂ | CO₂Et | Ph | 6-(6-Cl-3-pyridinyl)-3-pyridinyl |
| Et | O—n-Pr | SCF₃ | cyano | OPh | 4-CF₃-2-thiazolyl |
|   |   |   |   |   | 1-Me-4-CF₃-2-imidazolyl |

R² is 5-pyrimidinyl

| R | R | R | R | R | R |
|---|---|---|---|---|---|
| H | c-Pr | O—i-Pr | SCF₃ | C(O)NHMe | 3-ClPh |
| F | CF₃ | OCH₂CH=CH₂ | SCHF₂ | C(O)NMe₂ | 6-Cl-3-pyridinyl |
| Cl | CH₂F | OCH₂C≡CH | S(O)CF₃ | C(=NOMe)Me | 6-F-3-pyridinyl |
| Br | CHF₂ | O—c-Pr | SO₂CF₃ | CH=CH₂ | N-Me-4-pyrazolyl |
| I | OMe | OCF₃ | CO₂Me | C≡CH | 3-Me-5-isoxazolyl |
| Me | OEt | OCHF₂ | CO₂Et | Ph | 6-(6-Cl-3-pyridinyl)-3-pyridinyl |
| Et | O—n-Pr | SCF₃ | cyano | OPh | 4-CF₃-2-thiazolyl |
|   |   |   |   |   | 1-Me-4-CF₃-2-imidazolyl |

R² is 2-methyl-5-pyrimidinyl

| R | R | R | R | R | R |
|---|---|---|---|---|---|
| H | c-Pr | O—i-Pr | SCF₃ | C(O)NHMe | 3-ClPh |
| F | CF₃ | OCH₂CH=CH₂ | SCHF₂ | C(O)NMe₂ | 6-Cl-3-pyridinyl |
| Cl | CH₂F | OCH₂C≡CH | S(O)CF₃ | C(=NOMe)Me | 6-F-3-pyridinyl |
| Br | CHF₂ | O—c-Pr | SO₂CF₃ | CH=CH₂ | N-Me-4-pyrazolyl |
| I | OMe | OCF₃ | CO₂Me | C≡CH | 3-Me-5-isoxazolyl |
| Me | OEt | OCHF₂ | CO₂Et | Ph | 6-(6-Cl-3-pyridinyl)-3-pyridinyl |
| Et | O—n-Pr | SCF₃ | cyano | OPh | 4-CF₃-2-thiazolyl |
|   |   |   |   |   | 1-Me-4-CF₃-2-imidazolyl |

TABLE 32

[Structure: pyrido-pyrimidinone core with 9-Me and N-CH2-R2, 3-substituent is a terphenyl (3,3'-biphenyl-4''-R)]

| R | R | R | R | R | R |
|---|---|---|---|---|---|

R² is 2-chloro-5-thiazolyl

| R | R | R | R | R | R |
|---|---|---|---|---|---|
| H | c-Pr | O—i-Pr | SCF₃ | C(O)NHMe | 3-ClPh |
| F | CF₃ | OCH₂CH=CH₂ | SCHF₂ | C(O)NMe₂ | 6-Cl-3-pyridinyl |
| Cl | CH₂F | OCH₂=CH | S(O)CF₃ | C(=NOMe)Me | 6-F-3-pyridinyl |
| Br | CHF₂ | O—c-Pr | SO₂CF₃ | CH=CH₂ | N-Me-4-pyrazolyl |
| I | OMe | OCF₃ | CO₂Me | C≡CH | 3-Me-5-isoxazolyl |
| Me | OEt | OCHF₂ | CO₂Et | Ph | 6-(6-Cl-3-pyridinyl)-3-pyridinyl |
| Et | O—n-Pr | SCF₃ | cyano | OPh | 4-CF₃-2-thiazolyl |
|   |   |   |   |   | 1-Me-4-CF₃-2-imidazolyl |

R² is 6-chloro-3-pyridinyl

| R | R | R | R | R | R |
|---|---|---|---|---|---|
| H | c-Pr | O—i-Pr | SCF₃ | C(O)NHMe | 3-ClPh |
| F | CF₃ | OCH₂CH=CH₂ | SCHF₂ | C(O)NMe₂ | 6-Cl-3-pyridinyl |
| Cl | CH₂F | OCH₂=CH | S(O)CF₃ | C(=NOMe)Me | 6-F-3-pyridinyl |
| Br | CHF₂ | O—c-Pr | SO₂CF₃ | CH=CH₂ | N-Me-4-pyrazolyl |
| I | OMe | OCF₃ | CO₂Me | C≡CH | 3-Me-5-isoxazolyl |
| Me | OEt | OCHF₂ | CO₂Et | Ph | 6-(6-Cl-3-pyridinyl)-3-pyridinyl |
| Et | O—n-Pr | SCF₃ | cyano | OPh | 4-CF₃-2-thiazolyl |
|   |   |   |   |   | 1-Me-4-CF₃-2-imidazolyl |

TABLE 32-continued

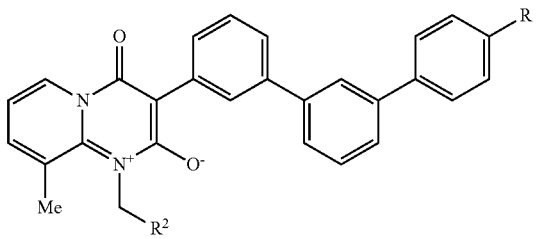

| R | R | R | R | R | R |
|---|---|---|---|---|---|
| $R^2$ is 6-fluoro-3-pyridinyl | | | | | |
| H  | c-Pr  | O—i-Pr        | $SCF_3$    | C(O)NHMe    | 3-ClPh |
| F  | $CF_3$ | $OCH_2CH=CH_2$ | $SCHF_2$  | $C(O)NMe_2$ | 6-Cl-3-pyridinyl |
| Cl | $CH_2F$ | $OCH_2=CH$   | $S(O)CF_3$ | C(=NOMe)Me  | 6-F-3-pyridinyl |
| Br | $CHF_2$ | O—c-Pr       | $SO_2CF_3$ | $CH=CH_2$   | N-Me-4-pyrazolyl |
| I  | OMe   | $OCF_3$       | $CO_2Me$   | C≡CH        | 3-Me-5-isoxazolyl |
| Me | OEt   | $OCHF_2$      | $CO_2Et$   | Ph          | 6-(6-Cl-3-pyridinyl)-3-pyridinyl |
| Et | O—n-Pr | $SCF_3$      | cyano      | OPh         | 4-$CF_3$-2-thiazolyl |
|    |       |               |            |             | 1-Me-4-$CF_3$-2-imidazolyl |
| $R^2$ is 5-pyrimidinyl | | | | | |
| H  | c-Pr  | O—i-Pr        | $SCF_3$    | C(O)NHMe    | 3-ClPh |
| F  | $CF_3$ | $OCH_2CH=CH_2$ | $SCHF_2$  | $C(O)NMe_2$ | 6-Cl-3-pyridinyl |
| Cl | $CH_2F$ | $OCH_2=CH$   | $S(O)CF_3$ | C(=NOMe)Me  | 6-F-3-pyridinyl |
| Br | $CHF_2$ | O—c-Pr       | $SO_2CF_3$ | $CH=CH_2$   | N-Me-4-pyrazolyl |
| I  | OMe   | $OCF_3$       | $CO_2Me$   | C≡CH        | 3-Me-5-isoxazolyl |
| Me | OEt   | $OCHF_2$      | $CO_2Et$   | Ph          | 6-(6-Cl-3-pyridinyl)-3-pyridinyl |
| Et | O—n-Pr | $SCF_3$      | cyano      | OPh         | 4-$CF_3$-2-thiazolyl |
|    |       |               |            |             | 1-Me-4-$CF_3$-2-imidazolyl |
| $R^2$ is 2-methyl-5-pyrimidinyl | | | | | |
| H  | c-Pr  | O—i-Pr        | $SCF_3$    | C(O)NHMe    | 3-ClPh |
| F  | $CF_3$ | $OCH_2CH=CH_2$ | $SCHF_2$  | $C(O)NMe_2$ | 6-Cl-3-pyridinyl |
| Cl | $CH_2F$ | $OCH_2=CH$   | $S(O)CF_3$ | C(=NOMe)Me  | 6-F-3-pyridinyl |
| Br | $CHF_2$ | O—c-Pr       | $SO_2CF_3$ | $CH=CH_2$   | N-Me-4-pyrazolyl |
| I  | OMe   | $OCF_3$       | $CO_2Me$   | C≡CH        | 3-Me-5-isoxazolyl |
| Me | OEt   | $OCHF_2$      | $CO_2Et$   | Ph          | 6-(6-Cl-3-pyridinyl)-3-pyridinyl |
| Et | O—n-Pr | $SCF_3$      | cyano      | OPh         | 4-$CF_3$-2-thiazolyl |
|    |       |               |            |             | 1-Me-4-$CF_3$-2-imidazolyl |

A compound of this invention will generally be used as an invertebrate pest control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g, oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids can be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which are branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents,* annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention can also contain formulation auxiliaries and additives, known to those skilled in the art as formulation aids (some of which can be considered to also function as solid diluents, liquid diluents or surfactants). Such formulation auxiliaries and additives can control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all formulations are prepared in conventional ways. Compound numbers refer to compounds in Index Tables A-E. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
| --- | --- |
| compound 30 | 98.5% |
| silica aerogel | 0.5% |
| synthetic amorphous fine silica | 1.0% |

Example B

| Wettable Powder | |
| --- | --- |
| compound 50 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
| --- | --- |
| compound 113 | 10.0% |
| attapulgite granules (low volatile matter, 0.71/0.30 mm; U.S.S. No. 25-50 sieves) | 90.0% |

Example D

| Extruded Pellet | |
| --- | --- |
| compound 191 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| compound 231 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| compound 254 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Seed Treatment

| | |
|---|---|
| compound 289 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

Fertilizer Stick

| | |
|---|---|
| compound 352 | 2.50% |
| pyrrolidone-styrene copolymer | 4.80% |
| tristyrylphenyl 16-ethoxylate | 2.30% |
| talc | 0.80% |
| corn starch | 5.00% |
| slow-release fertilizer | 36.00% |
| kaolin | 38.00% |
| water | 10.60% |

Example I

Suspension Concentrate

| | |
|---|---|
| compound 30 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

Emulsion in Water

| | |
|---|---|
| compound 50 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example K

Oil Dispersion

| | |
|---|---|
| compound 30 | 25% |
| polyoxyethylene sorbitol hexaoleate | 15% |
| organically modified bentonite clay | 2.5% |
| fatty acid methyl ester | 57.5% |

Example L

Suspoemulsion

| | |
|---|---|
| compound 50 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Compounds of this invention exhibit activity against a wide spectrum of invertebrate pests. These pests include invertebrates inhabiting a variety of environments such as, for example, plant foliage, roots, soil, harvested crops or other foodstuffs, building structures or animal integuments. These pests include, for example, invertebrates feeding on foliage (including leaves, stems, flowers and fruits), seeds, wood, textile fibers or animal blood or tissues, and thereby causing injury or damage to, for example, growing or stored agronomic crops, forests, greenhouse crops, ornamentals, nursery crops, stored foodstuffs or fiber products, or houses or other structures or their contents, or being harmful to animal health or public health. Those skilled in the art will appreciate that not all compounds are equally effective against all growth stages of all pests.

These present compounds and compositions are thus useful agronomically for protecting field crops from phytophagous invertebrate pests, and also nonagronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compounds and compositions may interact synergistically with traits introduced by genetic engineering or modified by mutagenesis, thus enhancing phenotypic expression or effectiveness of the traits or increasing the invertebrate pest control effectiveness of the present compounds and compositions. In particular, the present compounds and compositions may interact synergistically with the phenotypic expression of proteins or other natural products toxic to invertebrate pests to provide greater-than-additive control of these pests.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Examples of agronomic or nonagronomic invertebrate pests include eggs, larvae and adults of the order Lepidoptera, such as armyworms, cutworms, loopers, and heliothines in the family Noctuidae (e.g., pink stem borer (*Sesamia inferens* Walker), corn stalk borer (*Sesamia nonagrioides* Lefebvre), southern armyworm (*Spodoptera eridania* Cramer), fall armyworm (*Spodoptera fugiperda* J. E. Smith), beet armyworm (*Spodoptera exigua* Hübner), cotton leafworm (*Spodoptera littoralis* Boisduval), yellowstriped armyworm (*Spodoptera ornithogalli* Guenée), black cutworm (*Agrotis ipsilon* Hufnagel), velvetbean caterpillar (*Anticarsia gemmatalis* Hübner), green fruitworm (*Lithophane antennata* Walker), cabbage armyworm (*Barathra brassicae* Linnaeus), soybean looper (*Pseudoplusia includens* Walker), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: *Crambinae*) such as sod worm (*Herpetogramma licarsisalis* Walker), sugarcane stem borer (*Chilo infuscatellus* Snellen), tomato small borer (*Neoleucinodes elegantalis* Guenée), green leafroller (*Cnaphalocerus medinalis*), grape leaffolder (*Desmia funeralis* Hübner), melon worm (*Diaphania nitidalis* Stoll), cabbage center grub (*Helluala hydralis* Guenée), yellow stem borer (*Scirpophaga incertulas* Walker), early shoot borer (*Scirpophaga infuscatellus* Snellen), white stem borer (*Scirpophaga innotata* Walker), top shoot borer (*Scirpophaga nivella* Fabricius), dark-headed rice borer (*Chilo polychrysus* Meyrick), cabbage cluster caterpillar (*Crocidolomia binotalis* English)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), citrus false codling moth (*Cryptophlebia leucotreta* Meyrick), citrus borer (*Ecdytolopha aurantiana* Lima), redbanded leafroller (*Argyrotaenia velutinana* Walker), obliquebanded leafroller (*Choristoneura rosaceana* Harris), light brown apple moth (*Epiphyas postvittana* Walker), European grape berry moth (*Eupoecilia ambiguella* Hübner), apple bud moth (*Pandemis pyrusana* Kearfott), omnivorous leafroller (*Platynota stultana* Walsingham), barred fruit-tree tortrix (*Pandemis cerasana* Hübner), apple brown tortrix (*Pandemis heparana* Denis & Schiffermüller)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus), peach fruit borer (*Carposina niponensis* Walsingham), peach twig borer (*Anarsia lineatella* Zeller), potato tuberworm (*Phthorimaea operculella* Zeller), spotted teniform leafminer (*Lithocolletis blancardella* Fabricius), Asiatic apple leafminer (*Lithocolletis ringoniella* Matsumura), rice leaffolder (*Lerodea eufala* Edwards), apple leafminer (*Leucoptera scitella* Zeller)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)), smoky brown cockroach (*Periplaneta fuliginosa* Service), Australian Cockroach (*Periplaneta australasiae* Fabr.), lobster cockroach (*Nauphoeta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)), annual bluegrass weevil (*Listronotus maculicollis* Dietz), bluegrass billbug (*Sphenophorus parvulus* Gyllenhal), hunting billbug (*Sphenophorus venatus vestitus*), Denver billbug (*Sphenophorus cicatristriatus*

Fahraeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scarabaeidae (e.g., Japanese beetle (*Popillia japonica* Newman), oriental beetle (*Anomala orientalis* Waterhouse, *Exomala orientalis* (Waterhouse) Baraud), northern masked chafer (*Cyclocephala borealis* Arrow), southern masked chafer (*Cyclocephala immaculata* Olivier or *C. lurida* Bland), dung beetle and white grub (*Aphodius* spp.), black turfgrass ataenius (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae.

In addition, agronomic and nonagronomic pests include: eggs, adults and larvae of the order Dermaptera including earwigs from the family Forficulidae (e.g., European earwig (*Forficula auricularia* Linnaeus), black earwig (*Chelisoches morio* Fabricius)); eggs, immatures, adults and nymphs of the orders Hemiptera and Homoptera such as, plant bugs from the family Miridae, cicadas from the family Cicadidae, leafhoppers (e.g. *Empoasca* spp.) from the family Cicadellidae, bed bugs (e.g., *Cimex lectularius* Linnaeus) from the family Cimicidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae squash bugs from the family Coreidae, and red bugs and cotton stainers from the family Pyrrhocoridae.

Agronomic and nonagronomic pests also include: eggs, larvae, nymphs and adults of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae; ticks in the family Ixodidae, commonly known as hard ticks (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and ticks in the family Argasidae, commonly known as soft ticks (e.g., relapsing fever tick (*Ornithodoros turicata*), common fowl tick (*Argas radiatus*)); scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. diferentialis* Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); eggs, adults and immatures of the order Diptera including leafminers (e.g., *Liriomyza* spp. such as serpentine vegetable leafminer (*Liriomyza sativae* Blanchard)), midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, adults and immatures of the order Thysanoptera including onion thrips (*Thrips tabaci* Lindeman), flower thrips (*Frankliniella* spp.), and other foliar feeding thrips; insect pests of the order Hymenoptera including ants of the Family Formicidae including the Florida carpenter ant (*Camponotus floridanus* Buckley), red carpenter ant (*Camponotus ferrugineus* Fabricius), black carpenter ant (*Camponotus pennsylvanicus* De Geer), white-footed ant (*Technomyrmex albipes* fr. Smith), big headed ants (*Pheidole* sp.), ghost ant (*Tapinoma melanocephalum* Fabricius); Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster) and odorous house ant (*Tapinoma sessile* Say). Other Hymenoptera including bees (including carpenter bees), hornets, yellow jackets, wasps, and sawflies (*Neodiprion* spp.; *Cephus* spp.); insect pests of the order Isoptera including termites in the Termitidae (e.g., *Macrotermes* sp., *Odontotermes obesus* Rambur), Kalotermitidae (e.g., *Cryptotermes* sp.), and Rhinotermitidae (e.g., *Reticulitermes* sp., *Coptotermes* sp., *Heterotermes tenuis* Hagen) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus* Linnaeus), chicken body louse (*Menacanthus stramineus* Nitzsch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis*

Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus).

Examples of invertebrate pests of stored grain include larger grain borer (*Prostephanus truncatus*), lesser grain borer (*Rhyzopertha dominica*), rice weevil (*Stiophilus oryzae*), maize weevil (*Stiophilus zeamais*), cowpea weevil (*Callosobruchus maculatus*), red flour beetle (*Tribolium castaneum*), granary weevil (*Stiophilus granarius*), Indian meal moth (*Plodia interpunctella*), Mediterranean flour beetle (*Ephestia kuhniella*) and flat or rusty grain beetle (*Cryptolestis ferrugineus*).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenée (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)).

Compounds of the invention also have significant activity on members from the order Homoptera including: *Acyrthosiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compounds of this invention may also have activity on members from the order Hemiptera including: *Acrosternum hilare* Say (green stink bug), *Anasa tristis* De Geer (squash bug), *Blissus leucopterus leucopterus* Say (chinch bug), *Cimex lectularius* Linnaeus (bed bug) *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrips), *Scirthothrips citri* Moulton (citrus thrips), *Sericothrips variabilis* Beach (soybean thrips), and *Thrips tabaci* Lindeman (onion thrips); and the order Coleoptera (e.g., *Leptinotarsa decemlineata* Say (Colorado potato beetle), *Epilachna varivestis* Mulsant (Mexican bean beetle) and wireworms of the genera *Agriotes*, *Athous* or *Limonius*).

Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Note that some contemporary classification systems place Homoptera as a suborder within the order Hemiptera.

Of note is use of compounds of this invention for controlling potato leafhopper (*Empoasca fabae*). Of note is use of compounds of this invention for controlling corn planthopper (*Peregrinus maidis*). Of note is use of compounds of this invention for controlling cotton melon aphid (*Aphis gossypii*). Of note is use of compounds of this invention for controlling green peach aphid (*Myzus persicae*). Of note is use of compounds of this invention for controlling diamondback moth (*Plutella xylostella*). Of note is use of compounds of this invention for controlling fall armyworm (*Spodoptera frugiperda*).

Of note is use of compounds of this invention for controlling southern green stink bug (*Nezara viridula*), western tarnished plant bug (*Lygus hesperus*), rice water weevil (*Lissorhoptrus oryzophilus*), rice brown planthopper (*Nilaparvata lugens*), rice green leafhopper (*Nephotettix virescens*) and striped rice borer (*Chilo suppressalis*).

Compounds of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula 1, an N-oxide, or salt thereof, at least one additional component selected from the group consisting of surfactants, solid diluents and liquid diluents, and at least one additional biologically active compound or agent. For mixtures of the present invention, the other biologically active compounds or agents can be formulated together with the present compounds, including the compounds of Formula 1, to form a premix, or the other biologically active compounds or agents can be formulated separately from the present compounds, including the compounds of Formula 1, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, amidoflumet, amitraz, avermectin, azadirachtin, azinphos-methyl, bensultap, bifenthrin, bifenazate, bistrifluron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, meperfluthrin, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, sulfoxaflor, tebufenozide, tebufenpyrad, teflubenzuron, tefluthrin, terbufos, tetrachlorvinphos, tetramethrin, tetramethylfluthrin, thiacloprid, thiamethoxam, thiodicarb, thiosultapsodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, amitraz, avermectin, azadirachtin, bensultap, bifenthrin, buprofezin, cadusafos, carbaryl, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultapsodium, tralomethrin, triazamate, triflumuron, *Bacillus thuringiensis* delta-endotoxins, all strains of *Bacillus thuringiensis* and all strains of *Nucleo polyhydrosis* viruses.

One embodiment of biological agents for mixing with compounds of this invention include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than the compound of Formula 1. In certain instances, a combination with at least one other invertebrate pest control active ingredient having a similar spectrum of control but a different site of action will be particularly advantageous for resistance management. Thus, a composition of the present invention can further comprise a biologically effective amount of at least one additional invertebrate pest control active ingredient having a similar spectrum of control but belonging to a different chemical class or having a different site of action. These additional biologically active compounds or agents include, but are not limited to, sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-gated chloride channel antagonists such as avermectin or blockers such as ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; molting inhibitors and ecdysone agonists such as azadirachtin, methoxyfenozide and tebufenozide; ryanodine receptor ligands such as ryanodine, anthranilic diamides such as chlorantraniliprole, cyantraniliprole and flubendiamide; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin or endosulfan; pyrethroids; carbamates; insecticidal ureas; and biological agents including nucleopolyhedro viruses (NPV), members of *Bacillus thuringiensis*, encapsulated delta-endotoxins of *Bacillus thuringiensis*, and other naturally occurring or genetically modified insecticidal viruses.

Further examples of biologically active compounds or agents with which compounds of this invention can be formulated are: fungicides such as 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, fluxapyroxad, folpet, fosetyl-aluminum, fthalide, fuberidazole, furalaxyl, furametpyr, hexaconazole, hymexazole, guazatine, imazalil, imibenconazole, iminoctadine, iodicarb, ipconazole, iprobenfos, iprodione, iprovalicarb, isoconazole, isoprothiolane, isotianil, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penflufen, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pyrametostrobin, pyraoxystrobin, pryazophos, pyrifenox, pyrimethanil, pyrifenox, pyriofenone, pyrolnitrine, pyroquilon, quinconazole, quinoxyfen, quintozene, silthiofam, simeconazole, spiroxamine, streptomycin, sulfur, tebuconazole, tebufloquin, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimorphamide, tricyclazole, trifloxystrobin, triforine, triticonazole, uniconazole, validamycin, valifenalate, vinclozolin, zineb, ziram, and zoxamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

Of note are fungicides and compositions comprising fungicides such as 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, azoxystrobin, copper hydroxide, cymoxanil, cyproconazole, difenoconazole, famoxadone, fenoxanil, ferimzone, flusilazole, flutolanil, fthalide, furametpyr, hexaconazole, isoprothiolane, isotianil, kasugamycin, mancozeb, metominostrobin, orysastrobin, pencycuron, penthiopyrad, picoxystrobin, probenazole, propiconazole, proquinazid, pyroquilon, simeconazole, tiadinil, tricyclazole, trifloxystrobin and validamycin.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Compounds of this invention and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U. K., 2003 and *The BioPesticide Manual, 2$^{nd}$ Edition*, L. G. Copping, Ed., British Crop Protection Council, Farnham, Surrey, U. K., 2001.

For embodiments where one or more of these various mixing partners are used, the weight ratio of these various mixing partners (in total) to the compound of Formula 1, an N-oxide, or salt thereof, is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of invertebrate pests controlled beyond the spectrum controlled by the compound of Formula 1 alone.

Table A lists specific combinations of a compound of Formula 1 with other invertebrate pest control agents illustrative of the mixtures, compositions and methods of the present invention. The first column of Table A lists the specific invertebrate pest control agents (e.g., "Abamectin" in the first line). The second column of Table A lists the mode of action (if known) or chemical class of the invertebrate pest control agents. The third column of Table A lists embodiment(s) of ranges of weight ratios for rates at which a compound of Formula 1 can be applied relative to an invertebrate pest control agent (e.g., "50:1 to 1:50" of a compound of Formula 1 relative to abamectin by weight). Thus, for example, the first line of Table A specifically discloses the combination of a compound of Formula 1 with abamectin can be applied in a weight ratio between 50:1 to 1:50. The remaining lines of Table A are to be construed similarly. Of further note Table A lists specific combinations of a compound of Formula 1 with other invertebrate pest control agents illustrative of the mixtures, compositions and methods of the present invention and includes additional embodiments of weight ratio ranges for application rates.

TABLE A

| Invertebrate Pest Control Agent | Mode of Action or Chemical Class | Typical Weight Ratio |
| --- | --- | --- |
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyantraniliprole | ryanodine receptor ligands | 100:1 to 1:120 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |

TABLE A-continued

| Invertebrate Pest Control Agent | Mode of Action or Chemical Class | Typical Weight Ratio |
| --- | --- | --- |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

Of note is the composition of the present invention wherein the at least one additional biologically active compound or agent is selected from the Invertebrate Pest Control Agents listed in Table A above.

The weight ratios of a compound, including a compound of Formula 1, an N-oxide, or salt thereof, to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Tables B1 to B81 are embodiments of specific compositions comprising a compound of Formula 1 (compound numbers (Cmpd. No.) refer to compounds in Index Tables A-E) and an additional invertebrate pest control agent.

TABLE B1

| Mixture No. | Cmpd. No. | and | Invertebrate Pest Control Agent |
| --- | --- | --- | --- |
| B1-1 | 1 | and | Abamectin |
| B1-2 | 1 | and | Acetamiprid |
| B1-3 | 1 | and | Amitraz |
| B1-4 | 1 | and | Avermectin |
| B1-5 | 1 | and | Azadirachtin |
| B1-5a | 1 | and | Bensultap |
| B1-6 | 1 | and | Beta-cyfluthrin |
| B1-7 | 1 | and | Bifenthrin |
| B1-8 | 1 | and | Buprofezin |
| B1-9 | 1 | and | Cartap |
| B1-10 | 1 | and | Chlorantraniliprole |
| B1-11 | 1 | and | Chlorfenapyr |
| B1-12 | 1 | and | Chlorpyrifos |
| B1-13 | 1 | and | Clothianidin |
| B1-14 | 1 | and | Cyantraniliprole |
| B1-15 | 1 | and | Cyfluthrin |
| B1-16 | 1 | and | Cyhalothrin |
| B1-17 | 1 | and | Cypermethrin |
| B1-18 | 1 | and | Cyromazine |
| B1-19 | 1 | and | Deltamethrin |
| B1-20 | 1 | and | Dieldrin |
| B1-21 | 1 | and | Dinotefuran |
| B1-22 | 1 | and | Diofenolan |
| B1-23 | 1 | and | Emamectin |
| B1-24 | 1 | and | Endosulfan |
| B1-25 | 1 | and | Esfenvalerate |
| B1-26 | 1 | and | Ethiprole |
| B1-27 | 1 | and | Fenothiocarb |
| B1-28 | 1 | and | Fenoxycarb |

TABLE B1-continued

| Mixture No. | Cmpd. No. | and | Invertebrate Pest Control Agent |
|---|---|---|---|
| B1-29 | 1 | and | Fenvalerate |
| B1-30 | 1 | and | Fipronil |
| B1-31 | 1 | and | Flonicamid |
| B1-32 | 1 | and | Flubendiamide |
| B1-33 | 1 | and | Flufenoxuron |
| B1-34 | 1 | and | Hexaflumuron |
| B1-35 | 1 | and | Hydramethylnon |
| B1-36 | 1 | and | Imidacloprid |
| B1-37 | 1 | and | Indoxacarb |
| B1-38 | 1 | and | Lambda-cyhalothrin |
| B1-39 | 1 | and | Lufenuron |
| B1-40 | 1 | and | Metaflumizone |
| B1-41 | 1 | and | Methomyl |
| B1-42 | 1 | and | Methoprene |
| B1-43 | 1 | and | Methoxyfenozide |
| B1-44 | 1 | and | Nitenpyram |
| B1-45 | 1 | and | Nithiazine |
| B1-46 | 1 | and | Novaluron |
| B1-47 | 1 | and | Oxamyl |
| B1-48 | 1 | and | Phosmet |
| B1-49 | 1 | and | Pymetrozine |
| B1-50 | 1 | and | Pyrethrin |
| B1-51 | 1 | and | Pyridaben |
| B1-52 | 1 | and | Pyridalyl |
| B1-53 | 1 | and | Pyriproxyfen |
| B1-54 | 1 | and | Ryanodine |
| B1-55 | 1 | and | Spinetoram |
| B1-56 | 1 | and | Spinosad |
| B1-57 | 1 | and | Spirodiclofen |
| B1-58 | 1 | and | Spiromesifen |
| B1-59 | 1 | and | Spirotetramat |
| B1-60 | 1 | and | Tebufenozide |
| B1-61 | 1 | and | Thiacloprid |
| B1-62 | 1 | and | Thiamethoxam |
| B1-63 | 1 | and | Thiodicarb |
| B1-64 | 1 | and | Thiosultap-sodium |
| B1-65 | 1 | and | Tolfenpyrad |
| B1-66 | 1 | and | Tralomethrin |
| B1-67 | 1 | and | Triazamate |
| B1-68 | 1 | and | Triflumuron |
| B1-69 | 1 | and | *Bacillus thuringiensis* |
| B1-70 | 1 | and | *Bacillus thuringiensis* delta-endotoxin |
| B1-71 | 1 | and | NPV (e.g., Gemstar) |

Table B2

Table B2 is identical to Table B1, except that each reference to compound 1 in the column headed "Cmpd. No." is replaced by a reference to compound 18. For example, the first mixture in Table B2 is designated B2-1 and is a mixture of compound 18 and the additional invertebrate pest control agent abamectin.

Table B3

Table B3 is identical to Table B1, except that each reference to compound 1 in the column headed "Cmpd. No." is replaced by a reference to compound 19. For example, the first mixture in Table B3 is designated B3-1 and is a mixture of compound 19 and the additional invertebrate pest control agent abamectin.

Table B4

Table B4 is identical to Table B1, except that each reference to compound 1 in the column headed "Cmpd. No." is replaced by a reference to compound 20. For example, the first mixture in Table B4 is designated B4-1 and is a mixture of compound 20 and the additional invertebrate pest control agent abamectin.

Table B5

Table B5 is identical to Table B1, except that each reference to compound 1 in the column headed "Cmpd. No." is replaced by a reference to compound 21. For example, the first mixture in Table B5 is designated B5-1 and is a mixture of compound 21 and the additional invertebrate pest control agent abamectin.

Table B6

Table B6 is identical to Table B1, except that each reference to compound 1 in the column headed "Cmpd. No." is replaced by a reference to compound 23. For example, the first mixture in Table B6 is designated B6-1 and is a mixture of compound 23 and the additional invertebrate pest control agent abamectin.

Table B7

Table B7 is identical to Table B1, except that each reference to compound 1 in the column headed "Cmpd. No." is replaced by a reference to compound 26. For example, the first mixture in Table B7 is designated B7-1 and is a mixture of compound 26 and the additional invertebrate pest control agent abamectin.

Table B8

Table B8 is identical to Table B1, except that each reference to compound 1 in the column headed "Cmpd. No." is replaced by a reference to compound 29. For example, the first mixture in Table B8 is designated B8-1 and is a mixture of compound 29 and the additional invertebrate pest control agent abamectin.

Table B9

Table B9 is identical to Table B1, except that each reference to compound 1 in the column headed "Cmpd. No." is replaced by a reference to compound 30. For example, the first mixture in Table B9 is designated B9-1 and is a mixture of compound 30 and the additional invertebrate pest control agent abamectin.

Table B10

Table B10 is identical to Table B1, except that each reference to compound 1 in the column headed "Cmpd. No." is replaced by a reference to compound 33. For example, the first mixture in Table B10 is designated B10-1 and is a mixture of compound 33 and the additional invertebrate pest control agent abamectin.

Table B11

Table B11 is identical to Table B1, except that each reference to compound 1 in the column headed "Cmpd. No." is replaced by a reference to compound 36. For example, the first mixture in Table B11 is designated B11-1 and is a mixture of compound 36 and the additional invertebrate pest control agent abamectin.

Table B12

Table B12 is identical to Table B1, except that each reference to compound 1 in the column headed "Cmpd. No." is replaced by a reference to compound 37. For example, the first mixture in Table B12 is designated B12-1 and is a mixture of compound 37 and the additional invertebrate pest control agent abamectin.

Table B13

Table B13 is identical to Table B1, except that each reference to compound 1 in the column headed "Cmpd. No." is replaced by a reference to compound 40. For example, the first mixture in Table B13 is designated B13-1 and is a mixture of compound 40 and the additional invertebrate pest control agent abamectin.

Table B14

Table B14 is identical to Table B1, except that each reference to compound 1 in the column headed "Cmpd. No." is replaced by a reference to compound 44. For example, the first mixture in Table B14 is designated B14-1 and is a mixture of compound 44 and the additional invertebrate pest control agent abamectin.

Table B15

Table B15 is identical to Table B1, except that each reference to compound 1 in the column headed "Cmpd. No." is replaced by a reference to compound 47. For example, the first mixture in Table B15 is designated B15-1 and is a mixture of compound 47 and the additional invertebrate pest control agent abamectin.

Table B16

Table B16 is identical to Table B1, except that each reference to compound 1 in the column headed "Cmpd. No." is replaced by a reference to compound 49. For example, the first mixture in Table B16 is designated B16-1 and is a mixture of compound 49 and the additional invertebrate pest control agent abamectin.

Table B17

Table B17 is identical to Table B1, except that each reference to compound 1 in the column headed "Cmpd. No." is replaced by a reference to compound 50. For example, the first mixture in Table B17 is designated B17-1 and is a mixture of compound 50 and the additional invertebrate pest control agent abamectin.

Table B18

Table B18 is identical to Table B1, except that each reference to compound 1 in the column headed "Cmpd. No." is replaced by a reference to compound 51. For example, the first mixture in Table B18 is designated B18-1 and is a mixture of compound 51 and the additional invertebrate pest control agent abamectin.

Table B19

Table B19 is identical to Table B1, except that each reference to compound 1 in the column headed "Cmpd. No." is replaced by a reference to compound 52. For example, the first mixture in Table B19 is designated B2-1 and is a mixture of compound 52 and the additional invertebrate pest control agent abamectin.

Table B20

Table B20 is identical to Table B1, except that each reference to compound 1 in the column headed "Cmpd. No." is replaced by a reference to compound 53. For example, the first mixture in Table B20 is designated B20-1 and is a mixture of compound 53 and the additional invertebrate pest control agent abamectin.

Table B21

Table B21 is identical to Table B1, except that each reference to compound 1 in the column headed "Cmpd. No." is replaced by a reference to compound 56. For example, the first mixture in Table B21 is designated B21-1 and is a mixture of compound 56 and the additional invertebrate pest control agent abamectin.

Table B22

Table B22 is identical to Table B1, except that each reference to compound 1 in the column headed "Cmpd. No." is replaced by a reference to compound 57. For example, the first mixture in Table B22 is designated B22-1 and is a mixture of compound 57 and the additional invertebrate pest control agent abamectin.

Table B23

Table B23 is identical to Table B1, except that each reference to compound 1 in the column headed "Cmpd. No." is replaced by a reference to compound 58. For example, the first mixture in Table B23 is designated B23-1 and is a mixture of compound 58 and the additional invertebrate pest control agent abamectin.

Table B24

Table B24 is identical to Table B1, except that each reference to compound 1 in the column headed "Cmpd. No." is replaced by a reference to compound 59. For example, the first mixture in Table B24 is designated B24-1 and is a mixture of compound 59 and the additional invertebrate pest control agent abamectin.

Table B25

Table B25 is identical to Table B1, except that each reference to compound 1 in the column headed "Cmpd. No." is replaced by a reference to compound 60. For example, the first mixture in Table B25 is designated B25-1 and is a mixture of compound 60 and the additional invertebrate pest control agent abamectin.

Table B26

Table B26 is identical to Table B1, except that each reference to compound 1 in the column headed "Cmpd. No." is replaced by a reference to compound 62. For example, the first mixture in Table B26 is designated B26-1 and is a mixture of compound 62 and the additional invertebrate pest control agent abamectin.

Table B27

Table B27 is identical to Table B1, except that each reference to compound 1 in the column headed "Cmpd. No." is replaced by a reference to compound 63. For example, the first mixture in Table B27 is designated B27-1 and is a mixture of compound 63 and the additional invertebrate pest control agent abamectin.

Table B28

Table B28 is identical to Table B1, except that each reference to compound 1 in the column headed "Cmpd. No." is replaced by a reference to compound 65. For example, the first mixture in Table B28 is designated B28-1 and is a mixture of compound 65 and the additional invertebrate pest control agent abamectin.

Table B29

Table B29 is identical to Table B1, except that each reference to compound 1 in the column headed "Cmpd. No." is replaced by a reference to compound 71. For example, the first mixture in Table B29 is designated B29-1 and is a mixture of compound 71 and the additional invertebrate pest control agent abamectin.

Table B30

Table B30 is identical to Table B1, except that each reference to compound 1 in the column headed "Cmpd. No." is replaced by a reference to compound 74. For example, the first mixture in Table B30 is designated B30-1 and is a mixture of compound 74 and the additional invertebrate pest control agent abamectin.

Table B31

Table B31 is identical to Table B1, except that each reference to compound 1 in the column headed "Cmpd. No." is replaced by a reference to compound 77. For example, the first mixture in Table B31 is designated B31-1 and is a mixture of compound 77 and the additional invertebrate pest control agent abamectin.

Table B32

Table B32 is identical to Table B1, except that each reference to compound 1 in the column headed "Cmpd. No." is replaced by a reference to compound 79. For example, the first mixture in Table B32 is designated B32-1 and is a mixture of compound 79 and the additional invertebrate pest control agent abamectin.

Table B33

Table B33 is identical to Table B1, except that each reference to compound 1 in the column headed "Cmpd. No." is replaced by a reference to compound 80. For example, the first mixture in Table B33 is designated B33-1 and is a mixture of compound 80 and the additional invertebrate pest control agent abamectin.

Table B34

Table B34 is identical to Table B1, except that each reference to compound 1 in the column headed "Cmpd. No." is replaced by a reference to compound 81. For example, the first mixture in Table B34 is designated B34-1 and is a mixture of compound 81 and the additional invertebrate pest control agent abamectin.

Table B35

Table B35 is identical to Table B1, except that each reference to compound 1 in the column headed "Cmpd. No." is replaced by a reference to compound 82. For example, the first mixture in Table B35 is designated B35-1 and is a mixture of compound 82 and the additional invertebrate pest control agent abamectin.

Table B36

Table B36 is identical to Table B1, except that each reference to compound 1 in the column headed "Cmpd. No." is replaced by a reference to compound 83. For example, the first mixture in Table B36 is designated B36-1 and is a mixture of compound 83 and the additional invertebrate pest control agent abamectin.

Table B37

Table B37 is identical to Table B1, except that each reference to compound 1 in the column headed "Cmpd. No." is replaced by a reference to compound 84. For example, the first mixture in Table B37 is designated B37-1 and is a mixture of compound 84 and the additional invertebrate pest control agent abamectin.

Table B38

Table B38 is identical to Table B1, except that each reference to compound 1 in the column headed "Cmpd. No." is replaced by a reference to compound 85. For example, the first mixture in Table B38 is designated B38-1 and is a mixture of compound 85 and the additional invertebrate pest control agent abamectin.

Table B39

Table B39 is identical to Table B1, except that each reference to compound 1 in the column headed "Cmpd. No." is replaced by a reference to compound 86. For example, the first mixture in Table B39 is designated B39-1 and is a mixture of compound 86 and the additional invertebrate pest control agent abamectin.

Table B40

Table B40 is identical to Table B1, except that each reference to compound 1 in the column headed "Cmpd. No." is replaced by a reference to compound 87. For example, the first mixture in Table B40 is designated B40-1 and is a mixture of compound 87 and the additional invertebrate pest control agent abamectin.

Table B41

Table B41 is identical to Table B1, except that each reference to compound 1 in the column headed "Cmpd. No." is replaced by a reference to compound 89. For example, the first mixture in Table B41 is designated B41-1 and is a mixture of compound 89 and the additional invertebrate pest control agent abamectin.

Table B42

Table B42 is identical to Table B1, except that each reference to compound 1 in the column headed "Cmpd. No." is replaced by a reference to compound 99. For example, the first mixture in Table B42 is designated B42-1 and is a mixture of compound 99 and the additional invertebrate pest control agent abamectin.

Table B43

Table B43 is identical to Table B1, except that each reference to compound 1 in the column headed "Cmpd. No." is replaced by a reference to compound 102. For example, the first mixture in Table B43 is designated B43-1 and is a mixture of compound 102 and the additional invertebrate pest control agent abamectin.

Table B44

Table B44 is identical to Table B1, except that each reference to compound 1 in the column headed "Cmpd. No." is replaced by a reference to compound 113. For example, the first mixture in Table B44 is designated B44-1 and is a mixture of compound 113 and the additional invertebrate pest control agent abamectin.

Table B45

Table B45 is identical to Table B1, except that each reference to compound 1 in the column headed "Cmpd. No." is replaced by a reference to compound 118. For example, the first mixture in Table B45 is designated B45-1 and is a mixture of compound 118 and the additional invertebrate pest control agent abamectin.

Table B46

Table B46 is identical to Table B1, except that each reference to compound 1 in the column headed "Cmpd. No." is replaced by a reference to compound 125. For example, the first mixture in Table B46 is designated B46-1 and is a mixture of compound 125 and the additional invertebrate pest control agent abamectin.

Table B47

Table B47 is identical to Table B1, except that each reference to compound 1 in the column headed "Cmpd. No." is replaced by a reference to compound 137. For example, the first mixture in Table B47 is designated B47-1 and is a mixture of compound 137 and the additional invertebrate pest control agent abamectin.

Table B48

Table B43 is identical to Table B1, except that each reference to compound 1 in the column headed "Cmpd. No." is replaced by a reference to compound 183. For example, the first mixture in Table B48 is designated B48-1 and is a mixture of compound 183 and the additional invertebrate pest control agent abamectin.

Table B49

Table B49 is identical to Table B1, except that each reference to compound 1 in the column headed "Cmpd. No." is replaced by a reference to compound 190. For example, the first mixture in Table B49 is designated B49-1 and is a mixture of compound 190 and the additional invertebrate pest control agent abamectin.

Table B50

Table B50 is identical to Table B1, except that each reference to compound 1 in the column headed "Cmpd. No." is replaced by a reference to compound 191. For example, the first mixture in Table B50 is designated B50-1 and is a mixture of compound 191 and the additional invertebrate pest control agent abamectin.

Table B51

Table B51 is identical to Table B1, except that each reference to compound 1 in the column headed "Cmpd. No." is replaced by a reference to compound 196. For example, the first mixture in Table B51 is designated B51-1 and is a mixture of compound 196 and the additional invertebrate pest control agent abamectin.

Table B52

Table B52 is identical to Table B1, except that each reference to compound 1 in the column headed "Cmpd. No." is replaced by a reference to compound 229. For example, the first mixture in Table B52 is designated B52-1 and is a mixture of compound 229 and the additional invertebrate pest control agent abamectin.

Table B53

Table B53 is identical to Table B1, except that each reference to compound 1 in the column headed "Cmpd. No." is replaced by a reference to compound 231. For example, the first mixture in Table B53 is designated B53-1 and is a mixture of compound 231 and the additional invertebrate pest control agent abamectin.

Table B54

Table B54 is identical to Table B1, except that each reference to compound 1 in the column headed "Cmpd. No." is replaced by a reference to compound 254. For example, the first mixture in Table B54 is designated B54-1 and is a mixture of compound 254 and the additional invertebrate pest control agent abamectin.

Table B55

Table B55 is identical to Table B1, except that each reference to compound 1 in the column headed "Cmpd. No." is replaced by a reference to compound 257. For example, the first mixture in Table B55 is designated B55-1 and is a mixture of compound 257 and the additional invertebrate pest control agent abamectin.

Table B56

Table B56 is identical to Table B1, except that each reference to compound 1 in the column headed "Cmpd. No." is replaced by a reference to compound 272. For example, the first mixture in Table B56 is designated B56-1 and is a mixture of compound 272 and the additional invertebrate pest control agent abamectin.

Table B57

Table B57 is identical to Table B1, except that each reference to compound 1 in the column headed "Cmpd. No." is replaced by a reference to compound 289. For example, the first mixture in Table B57 is designated B57-1 and is a mixture of compound 289 and the additional invertebrate pest control agent abamectin.

Table B58

Table B58 is identical to Table B1, except that each reference to compound 1 in the column headed "Cmpd. No." is replaced by a reference to compound 296. For example, the first mixture in Table B58 is designated B58-1 and is a mixture of compound 296 and the additional invertebrate pest control agent abamectin.

Table B59

Table B59 is identical to Table B1, except that each reference to compound 1 in the column headed "Cmpd. No." is replaced by a reference to compound 299. For example, the first mixture in Table B59 is designated B59-1 and is a mixture of compound 299 and the additional invertebrate pest control agent abamectin.

Table B60

Table B60 is identical to Table B1, except that each reference to compound 1 in the column headed "Cmpd. No." is replaced by a reference to compound 307. For example, the first mixture in Table B60 is designated B60-1 and is a mixture of compound 307 and the additional invertebrate pest control agent abamectin.

Table B61

Table B61 is identical to Table B1, except that each reference to compound 1 in the column headed "Cmpd. No." is replaced by a reference to compound 308. For example, the first mixture in Table B61 is designated B61-1 and is a mixture of compound 308 and the additional invertebrate pest control agent abamectin.

Table B62

Table B62 is identical to Table B1, except that each reference to compound 1 in the column headed "Cmpd. No." is replaced by a reference to compound 315. For example, the first mixture in Table B62 is designated B62-1 and is a mixture of compound 315 and the additional invertebrate pest control agent abamectin.

Table B63

Table B63 is identical to Table B1, except that each reference to compound 1 in the column headed "Cmpd. No." is replaced by a reference to compound 343. For example, the first mixture in Table B63 is designated B63-1 and is a mixture of compound 343 and the additional invertebrate pest control agent abamectin.

Table B64

Table B64 is identical to Table B1, except that each reference to compound 1 in the column headed "Cmpd. No." is replaced by a reference to compound 344. For example, the first mixture in Table B64 is designated B64-1 and is a mixture of compound 344 and the additional invertebrate pest control agent abamectin.

Table B65

Table B65 is identical to Table B1, except that each reference to compound 1 in the column headed "Cmpd. No." is replaced by a reference to compound 352. For example, the first mixture in Table B65 is designated B65-1 and is a mixture of compound 352 and the additional invertebrate pest control agent abamectin.

Table B66

Table B66 is identical to Table B1, except that each reference to compound 1 in the column headed "Cmpd. No." is replaced by a reference to compound 363. For example, the first mixture in Table B66 is designated B66-1 and is a mixture of compound 363 and the additional invertebrate pest control agent abamectin.

Table B67

Table B67 is identical to Table B1, except that each reference to compound 1 in the column headed "Cmpd. No." is replaced by a reference to compound 364. For example, the first mixture in Table B67 is designated B67-1 and is a mixture of compound 364 and the additional invertebrate pest control agent abamectin.

Table B68

Table B68 is identical to Table B1, except that each reference to compound 1 in the column headed "Cmpd. No." is replaced by a reference to compound 368. For example, the first mixture in Table B68 is designated B68-1 and is a mixture of compound 368 and the additional invertebrate pest control agent abamectin.

Table B69

Table B69 is identical to Table B1, except that each reference to compound 1 in the column headed "Cmpd. No." is replaced by a reference to compound 381. For example, the first mixture in Table B69 is designated B69-1 and is a mixture of compound 381 and the additional invertebrate pest control agent abamectin.

Table B70

Table B70 is identical to Table B1, except that each reference to compound 1 in the column headed "Cmpd. No." is replaced by a reference to compound 385. For example, the first mixture in Table B70 is designated B70-1 and is a mixture of compound 385 and the additional invertebrate pest control agent abamectin.

Table B71

Table B71 is identical to Table B1, except that each reference to compound 1 in the column headed "Cmpd. No." is replaced by a reference to compound 421. For example, the first mixture in Table B71 is designated B71-1 and is a mixture of compound 421 and the additional invertebrate pest control agent abamectin.

Table B72

Table B72 is identical to Table B1, except that each reference to compound 1 in the column headed "Cmpd. No." is replaced by a reference to compound 433. For example, the first mixture in Table B72 is designated B72-1 and is a mixture of compound 433 and the additional invertebrate pest control agent abamectin.

Table B73

Table B73 is identical to Table B1, except that each reference to compound 1 in the column headed "Cmpd. No." is replaced by a reference to compound 435. For example, the first mixture in Table B73 is designated B73-1 and is a mixture of compound 435 and the additional invertebrate pest control agent abamectin.

Table B74

Table B74 is identical to Table B1, except that each reference to compound 1 in the column headed "Cmpd. No." is replaced by a reference to compound 448. For example, the first mixture in Table B74 is designated B74-1 and is a mixture of compound 448 and the additional invertebrate pest control agent abamectin.

Table B75

Table B75 is identical to Table B1, except that each reference to compound 1 in the column headed "Cmpd. No." is replaced by a reference to compound 449. For example, the first mixture in Table B75 is designated B75-1 and is a mixture of compound 449 and the additional invertebrate pest control agent abamectin.

Table B76

Table B76 is identical to Table B1, except that each reference to compound 1 in the column headed "Cmpd. No." is replaced by a reference to compound 450. For example, the first mixture in Table B76 is designated B76-1 and is a mixture of compound 450 and the additional invertebrate pest control agent abamectin.

Table B77

Table B77 is identical to Table B1, except that each reference to compound 1 in the column headed "Cmpd. No." is replaced by a reference to compound 451. For example, the first mixture in Table B77 is designated B77-1 and is a mixture of compound 451 and the additional invertebrate pest control agent abamectin.

Table B78

Table B78 is identical to Table B1, except that each reference to compound 1 in the column headed "Cmpd. No." is replaced by a reference to compound 462. For example, the first mixture in Table B78 is designated B78-1 and is a mixture of compound 462 and the additional invertebrate pest control agent abamectin.

Table B79

Table B79 is identical to Table B1, except that each reference to compound 1 in the column headed "Cmpd. No." is replaced by a reference to compound 482. For example, the first mixture in Table B79 is designated B79-1 and is a mixture of compound 482 and the additional invertebrate pest control agent abamectin.

Table B80

Table B80 is identical to Table B1, except that each reference to compound 1 in the column headed "Cmpd. No." is replaced by a reference to compound 490. For example, the first mixture in Table B80 is designated B80-1 and is a mixture of compound 490 and the additional invertebrate pest control agent abamectin.

Table B81

Table B81 is identical to Table B1, except that each reference to compound 1 in the column headed "Cmpd. No." is replaced by a reference to compound 493. For example, the first mixture in Table B81 is designated B81-1 and is a mixture of compound 493 and the additional invertebrate pest control agent abamectin.

The specific mixtures listed in Tables B1 to B81 typically combine a compound of Formula 1 with the other invertebrate pest agent in the ratios specified in Table A.

Listed below in Tables C1 to C81 are embodiments of specific compositions comprising a compound of Formula 1 (compound numbers (Cmpd. No.) refer to compounds in Index Tables A-E) and an additional fungicide.

TABLE C1

| Mixture No. | Cmpd. No. | and | Fungicide |
|---|---|---|---|
| C1-1 | 1 | and | Probenazole |
| C1-2 | 1 | and | Tiadinil |
| C1-3 | 1 | and | Isotianil |
| C1-4 | 1 | and | Pyroquilon |
| C1-5 | 1 | and | Metominostrobin |
| C1-6 | 1 | and | Flutolanil |
| C1-7 | 1 | and | Validamycin |
| C1-8 | 1 | and | Furametpyr |
| C1-9 | 1 | and | Pencycuron |
| C1-10 | 1 | and | Simeconazole |
| C1-11 | 1 | and | Orysastrobin |
| C1-12 | 1 | and | Trifloxystrobin |
| C1-13 | 1 | and | Isoprothiolane |
| C1-14 | 1 | and | Azoxystrobin |
| C1-15 | 1 | and | Tricyclazole |
| C1-16 | 1 | and | Hexaconazole |
| C1-17 | 1 | and | Difenoconazole |
| C1-18 | 1 | and | Cyproconazole |
| C1-19 | 1 | and | Propiconazole |
| C1-20 | 1 | and | Fenoxanil |
| C1-21 | 1 | and | Ferimzone |
| C1-22 | 1 | and | Fthalide |
| C1-23 | 1 | and | Kasugamycin |
| C1-24 | 1 | and | Picoxystrobin |
| C1-25 | 1 | and | Penthiopyrad |
| C1-26 | 1 | and | Famoxadone |
| C1-27 | 1 | and | Cymoxanil |
| C1-28 | 1 | and | Proquinazid |
| C1-29 | 1 | and | Flusilazole |
| C1-30 | 1 | and | Mancozeb |
| C1-31 | 1 | and | Copper hydroxide |
| C1-32 | 1 | and | (a) |

(a) 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone

Table C2

Table C2 is identical to Table C1, except that each reference to compound 1 in the column headed "Cmpd. No."

is replaced by a reference to compound 18. For example, the first mixture in Table C2 is designated C2-1 and is a mixture of compound 18 and the additional fungicide probenazole.

Table C3

Table C3 is identical to Table C1, except that each reference to compound 1 in the column headed "Cmpd. No." is replaced by a reference to compound 19. For example, the first mixture in Table C3 is designated C3-1 and is a mixture of compound 19 and the additional fungicide probenazole.

Table C4

Table C4 is identical to Table C1, except that each reference to compound 1 in the column headed "Cmpd. No." is replaced by a reference to compound 20. For example, the first mixture in Table C4 is designated C4-1 and is a mixture of compound 20 and the additional fungicide probenazole.

Table C5

Table C5 is identical to Table C1, except that each reference to compound 1 in the column headed "Cmpd. No." is replaced by a reference to compound 21. For example, the first mixture in Table C5 is designated C5-1 and is a mixture of compound 21 and the additional fungicide probenazole.

Table C6

Table C6 is identical to Table C1, except that each reference to compound 1 in the column headed "Cmpd. No." is replaced by a reference to compound 23. For example, the first mixture in Table C6 is designated C6-1 and is a mixture of compound 23 and the additional fungicide probenazole.

Table C7

Table C7 is identical to Table C1, except that each reference to compound 1 in the column headed "Cmpd. No." is replaced by a reference to compound 26. For example, the first mixture in Table C7 is designated C7-1 and is a mixture of compound 26 and the additional fungicide probenazole.

Table C8

Table C8 is identical to Table C1, except that each reference to compound 1 in the column headed "Cmpd. No." is replaced by a reference to compound 29. For example, the first mixture in Table C8 is designated C8-1 and is a mixture of compound 29 and the additional fungicide probenazole.

Table C9

Table C9 is identical to Table C1, except that each reference to compound 1 in the column headed "Cmpd. No." is replaced by a reference to compound 30. For example, the first mixture in Table C9 is designated C9-1 and is a mixture of compound 30 and the additional fungicide probenazole.

Table C10

Table C10 is identical to Table C1, except that each reference to compound 1 in the column headed "Cmpd. No." is replaced by a reference to compound 33. For example, the first mixture in Table C10 is designated C10-1 and is a mixture of compound 33 and the additional fungicide probenazole.

Table C11

Table C11 is identical to Table C1, except that each reference to compound 1 in the column headed "Cmpd. No." is replaced by a reference to compound 36. For example, the first mixture in Table C11 is designated C11-1 and is a mixture of compound 36 and the additional fungicide probenazole.

Table C12

Table C12 is identical to Table C1, except that each reference to compound 1 in the column headed "Cmpd. No." is replaced by a reference to compound 37. For example, the first mixture in Table C12 is designated C12-1 and is a mixture of compound 37 and the additional fungicide probenazole.

Table C13

Table C13 is identical to Table C1, except that each reference to compound 1 in the column headed "Cmpd. No." is replaced by a reference to compound 40. For example, the first mixture in Table C13 is designated C13-1 and is a mixture of compound 40 and the additional fungicide probenazole.

Table C14

Table C14 is identical to Table C1, except that each reference to compound 1 in the column headed "Cmpd. No." is replaced by a reference to compound 44. For example, the first mixture in Table C14 is designated C14-1 and is a mixture of compound 44 and the additional fungicide probenazole.

Table C15

Table C15 is identical to Table C1, except that each reference to compound 1 in the column headed "Cmpd. No." is replaced by a reference to compound 47. For example, the first mixture in Table C15 is designated C15-1 and is a mixture of compound 47 and the additional fungicide probenazole.

Table C16

Table C16 is identical to Table C1, except that each reference to compound 1 in the column headed "Cmpd. No." is replaced by a reference to compound 49. For example, the first mixture in Table C16 is designated C16-1 and is a mixture of compound 49 and the additional fungicide probenazole.

Table C17

Table C17 is identical to Table C1, except that each reference to compound 1 in the column headed "Cmpd. No." is replaced by a reference to compound 50. For example, the first mixture in Table C17 is designated C17-1 and is a mixture of compound 50 and the additional fungicide probenazole.

Table C18

Table C18 is identical to Table C1, except that each reference to compound 1 in the column headed "Cmpd. No." is replaced by a reference to compound 51. For example, the first mixture in Table C18 is designated C18-1 and is a mixture of compound 51 and the additional fungicide probenazole.

Table C19

Table C19 is identical to Table C1, except that each reference to compound 1 in the column headed "Cmpd. No." is replaced by a reference to compound 52. For example, the first mixture in Table C19 is designated C19-1 and is a mixture of compound 52 and the additional fungicide probenazole.

Table C20

Table C20 is identical to Table C1, except that each reference to compound 1 in the column headed "Cmpd. No." is replaced by a reference to compound 53. For example, the first mixture in Table C20 is designated C20-1 and is a mixture of compound 53 and the additional fungicide probenazole.

Table C21

Table C21 is identical to Table C1, except that each reference to compound 1 in the column headed "Cmpd. No." is replaced by a reference to compound 56. For example, the first mixture in Table C21 is designated C21-1 and is a mixture of compound 56 and the additional fungicide probenazole.

Table C22

Table C22 is identical to Table C1, except that each reference to compound 1 in the column headed "Cmpd. No." is replaced by a reference to compound 57. For example, the first mixture in Table C22 is designated C22-1 and is a mixture of compound 57 and the additional fungicide probenazole.

Table C23

Table C23 is identical to Table C1, except that each reference to compound 1 in the column headed "Cmpd. No." is replaced by a reference to compound 58. For example, the first mixture in Table C23 is designated C23-1 and is a mixture of compound 58 and the additional fungicide probenazole.

Table C24

Table C24 is identical to Table C1, except that each reference to compound 1 in the column headed "Cmpd. No." is replaced by a reference to compound 59. For example, the first mixture in Table C24 is designated C24-1 and is a mixture of compound 59 and the additional fungicide probenazole.

Table C25

Table C25 is identical to Table C1, except that each reference to compound 1 in the column headed "Cmpd. No." is replaced by a reference to compound 60. For example, the first mixture in Table C25 is designated C25-1 and is a mixture of compound 60 and the additional fungicide probenazole.

Table C26

Table C26 is identical to Table C1, except that each reference to compound 1 in the column headed "Cmpd. No." is replaced by a reference to compound 62. For example, the first mixture in Table C26 is designated C26-1 and is a mixture of compound 62 and the additional fungicide probenazole.

Table C27

Table C27 is identical to Table C1, except that each reference to compound 1 in the column headed "Cmpd. No." is replaced by a reference to compound 63. For example, the first mixture in Table C27 is designated C27-1 and is a mixture of compound 63 and the additional fungicide probenazole.

Table C28

Table C28 is identical to Table C1, except that each reference to compound 1 in the column headed "Cmpd. No." is replaced by a reference to compound 65. For example, the first mixture in Table C28 is designated C28-1 and is a mixture of compound 65 and the additional fungicide probenazole.

Table C29

Table C29 is identical to Table C1, except that each reference to compound 1 in the column headed "Cmpd. No." is replaced by a reference to compound 71. For example, the first mixture in Table C29 is designated C29-1 and is a mixture of compound 71 and the additional fungicide probenazole.

Table C30

Table C30 is identical to Table C1, except that each reference to compound 1 in the column headed "Cmpd. No." is replaced by a reference to compound 74. For example, the first mixture in Table C30 is designated C30-1 and is a mixture of compound 74 and the additional fungicide probenazole.

Table C31

Table C31 is identical to Table C1, except that each reference to compound 1 in the column headed "Cmpd. No." is replaced by a reference to compound 77. For example, the first mixture in Table C31 is designated C31-1 and is a mixture of compound 77 and the additional fungicide probenazole.

Table C32

Table C32 is identical to Table C1, except that each reference to compound 1 in the column headed "Cmpd. No." is replaced by a reference to compound 79. For example, the first mixture in Table C32 is designated C32-1 and is a mixture of compound 79 and the additional fungicide probenazole.

Table C33

Table C33 is identical to Table C1, except that each reference to compound 1 in the column headed "Cmpd. No." is replaced by a reference to compound 80. For example, the first mixture in Table C33 is designated C33-1 and is a mixture of compound 80 and the additional fungicide probenazole.

Table C34

Table C34 is identical to Table C1, except that each reference to compound 1 in the column headed "Cmpd. No." is replaced by a reference to compound 81. For example, the first mixture in Table C34 is designated C34-1 and is a mixture of compound 81 and the additional fungicide probenazole.

Table C35

Table C35 is identical to Table C1, except that each reference to compound 1 in the column headed "Cmpd. No." is replaced by a reference to compound 82. For example, the first mixture in Table C35 is designated C35-1 and is a mixture of compound 82 and the additional fungicide probenazole.

Table C36

Table C36 is identical to Table C1, except that each reference to compound 1 in the column headed "Cmpd. No." is replaced by a reference to compound 83. For example, the first mixture in Table C36 is designated C36-1 and is a mixture of compound 83 and the additional fungicide probenazole.

Table C37

Table C37 is identical to Table C1, except that each reference to compound 1 in the column headed "Cmpd. No." is replaced by a reference to compound 84. For example, the first mixture in Table C37 is designated C37-1 and is a mixture of compound 84 and the additional fungicide probenazole.

Table C38

Table C38 is identical to Table C1, except that each reference to compound 1 in the column headed "Cmpd. No." is replaced by a reference to compound 85. For example, the first mixture in Table C38 is designated C38-1 and is a mixture of compound 85 and the additional fungicide probenazole.

Table C39

Table C39 is identical to Table C1, except that each reference to compound 1 in the column headed "Cmpd. No." is replaced by a reference to compound 86. For example, the first mixture in Table C39 is designated C39-1 and is a mixture of compound 86 and the additional fungicide probenazole.

Table C40

Table C40 is identical to Table C1, except that each reference to compound 1 in the column headed "Cmpd. No." is replaced by a reference to compound 87. For example, the first mixture in Table C40 is designated C40-1 and is a mixture of compound 87 and the additional fungicide probenazole.

Table C41

Table C41 is identical to Table C1, except that each reference to compound 1 in the column headed "Cmpd. No." is replaced by a reference to compound 89. For example, the first mixture in Table C41 is designated C41-1 and is a mixture of compound 89 and the additional fungicide probenazole.

Table C42

Table C42 is identical to Table C1, except that each reference to compound 1 in the column headed "Cmpd. No." is replaced by a reference to compound 99. For example, the first mixture in Table C42 is designated C42-1 and is a mixture of compound 99 and the additional fungicide probenazole.

Table C43

Table C43 is identical to Table C1, except that each reference to compound 1 in the column headed "Cmpd. No." is replaced by a reference to compound 102. For example, the first mixture in Table C43 is designated C43-1 and is a mixture of compound 102 and the additional fungicide probenazole.

Table C44

Table C44 is identical to Table C1, except that each reference to compound 1 in the column headed "Cmpd. No." is replaced by a reference to compound 113. For example, the first mixture in Table C44 is designated C44-1 and is a mixture of compound 113 and the additional fungicide probenazole.

Table C45

Table C45 is identical to Table C1, except that each reference to compound 1 in the column headed "Cmpd. No." is replaced by a reference to compound 118. For example, the first mixture in Table C45 is designated C45-1 and is a mixture of compound 118 and the additional fungicide probenazole.

Table C46

Table C46 is identical to Table C1, except that each reference to compound 1 in the column headed "Cmpd. No." is replaced by a reference to compound 125. For example, the first mixture in Table C46 is designated C46-1 and is a mixture of compound 125 and the additional fungicide probenazole.

Table C47

Table C47 is identical to Table C1, except that each reference to compound 1 in the column headed "Cmpd. No." is replaced by a reference to compound 137. For example, the first mixture in Table C47 is designated C47-1 and is a mixture of compound 137 and the additional fungicide probenazole.

Table C48

Table C43 is identical to Table C1, except that each reference to compound 1 in the column headed "Cmpd. No." is replaced by a reference to compound 183. For example, the first mixture in Table C48 is designated C48-1 and is a mixture of compound 183 and the additional fungicide probenazole.

Table C49

Table C49 is identical to Table C1, except that each reference to compound 1 in the column headed "Cmpd. No." is replaced by a reference to compound 190. For example, the first mixture in Table C49 is designated C49-1 and is a mixture of compound 190 and the additional fungicide probenazole.

Table C50

Table C50 is identical to Table C1, except that each reference to compound 1 in the column headed "Cmpd. No." is replaced by a reference to compound 191. For example, the first mixture in Table C50 is designated C50-1 and is a mixture of compound 191 and the additional fungicide probenazole.

Table C51

Table C51 is identical to Table C1, except that each reference to compound 1 in the column headed "Cmpd. No." is replaced by a reference to compound 196. For example, the first mixture in Table C51 is designated C51-1 and is a mixture of compound 196 and the additional fungicide probenazole.

Table C52

Table C52 is identical to Table C1, except that each reference to compound 1 in the column headed "Cmpd. No." is replaced by a reference to compound 229. For example, the first mixture in Table C52 is designated C52-1 and is a mixture of compound 229 and the additional fungicide probenazole.

Table C53

Table C53 is identical to Table C1, except that each reference to compound 1 in the column headed "Cmpd. No." is replaced by a reference to compound 231. For example, the first mixture in Table C53 is designated C53-1 and is a mixture of compound 231 and the additional fungicide probenazole.

Table C54

Table C54 is identical to Table C1, except that each reference to compound 1 in the column headed "Cmpd. No." is replaced by a reference to compound 254. For example, the first mixture in Table C54 is designated C54-1 and is a mixture of compound 254 and the additional fungicide probenazole.

Table C55

Table C55 is identical to Table C1, except that each reference to compound 1 in the column headed "Cmpd. No." is replaced by a reference to compound 257. For example, the first mixture in Table C55 is designated C55-1 and is a mixture of compound 257 and the additional fungicide probenazole.

Table C56

Table C56 is identical to Table C1, except that each reference to compound 1 in the column headed "Cmpd. No." is replaced by a reference to compound 272. For example, the first mixture in Table C56 is designated C56-1 and is a mixture of compound 272 and the additional fungicide probenazole.

Table C57

Table C57 is identical to Table C1, except that each reference to compound 1 in the column headed "Cmpd. No." is replaced by a reference to compound 289. For example, the first mixture in Table C57 is designated C57-1 and is a mixture of compound 289 and the additional fungicide probenazole.

Table C58

Table C58 is identical to Table C1, except that each reference to compound 1 in the column headed "Cmpd. No." is replaced by a reference to compound 296. For example, the first mixture in Table C58 is designated C58-1 and is a mixture of compound 296 and the additional fungicide probenazole.

Table C59

Table C59 is identical to Table C1, except that each reference to compound 1 in the column headed "Cmpd. No." is replaced by a reference to compound 299. For example, the first mixture in Table C59 is designated C59-1 and is a mixture of compound 299 and the additional fungicide probenazole.

Table C60

Table C60 is identical to Table C1, except that each reference to compound 1 in the column headed "Cmpd. No." is replaced by a reference to compound 307. For example, the first mixture in Table C60 is designated C60-1 and is a mixture of compound 307 and the additional fungicide probenazole.

Table C61

Table C61 is identical to Table C1, except that each reference to compound 1 in the column headed "Cmpd. No." is replaced by a reference to compound 308. For example, the first mixture in Table C61 is designated C61-1 and is a mixture of compound 308 and the additional fungicide probenazole.

Table C62

Table C62 is identical to Table C1, except that each reference to compound 1 in the column headed "Cmpd. No." is replaced by a reference to compound 315. For example, the first mixture in Table C62 is designated C62-1 and is a mixture of compound 315 and the additional fungicide probenazole.

Table C63

Table C63 is identical to Table C1, except that each reference to compound 1 in the column headed "Cmpd. No." is replaced by a reference to compound 343. For example, the first mixture in Table C63 is designated C63-1 and is a mixture of compound 343 and the additional fungicide probenazole.

Table C64

Table C64 is identical to Table C1, except that each reference to compound 1 in the column headed "Cmpd. No." is replaced by a reference to compound 344. For example, the first mixture in Table C64 is designated C64-1 and is a mixture of compound 344 and the additional fungicide probenazole.

Table C65

Table C65 is identical to Table C1, except that each reference to compound 1 in the column headed "Cmpd. No." is replaced by a reference to compound 352. For example, the first mixture in Table C65 is designated C65-1 and is a mixture of compound 352 and the additional fungicide probenazole.

Table C66

Table C66 is identical to Table C1, except that each reference to compound 1 in the column headed "Cmpd. No." is replaced by a reference to compound 363. For example, the first mixture in Table C66 is designated C66-1 and is a mixture of compound 363 and the additional fungicide probenazole.

Table C67

Table C67 is identical to Table C1, except that each reference to compound 1 in the column headed "Cmpd. No." is replaced by a reference to compound 364. For example, the first mixture in Table C67 is designated C67-1 and is a mixture of compound 364 and the additional fungicide probenazole.

Table C68

Table C68 is identical to Table C1, except that each reference to compound 1 in the column headed "Cmpd. No." is replaced by a reference to compound 368. For example, the first mixture in Table C68 is designated C68-1 and is a mixture of compound 368 and the additional fungicide probenazole.

Table C69

Table C69 is identical to Table C1, except that each reference to compound 1 in the column headed "Cmpd. No." is replaced by a reference to compound 381. For example, the first mixture in Table C69 is designated C69-1 and is a mixture of compound 381 and the additional fungicide probenazole.

Table C70

Table C70 is identical to Table C1, except that each reference to compound 1 in the column headed "Cmpd. No." is replaced by a reference to compound 385. For example, the first mixture in Table C70 is designated C70-1 and is a mixture of compound 385 and the additional fungicide probenazole.

Table C71

Table C71 is identical to Table C1, except that each reference to compound 1 in the column headed "Cmpd. No." is replaced by a reference to compound 421. For example, the first mixture in Table C71 is designated C71-1 and is a mixture of compound 421 and the additional fungicide probenazole.

Table C72

Table C72 is identical to Table C1, except that each reference to compound 1 in the column headed "Cmpd. No." is replaced by a reference to compound 433. For example, the first mixture in Table C72 is designated C72-1 and is a mixture of compound 433 and the additional fungicide probenazole.

Table C73

Table C73 is identical to Table C1, except that each reference to compound 1 in the column headed "Cmpd. No." is replaced by a reference to compound 435. For example, the first mixture in Table C73 is designated C73-1 and is a mixture of compound 435 and the additional fungicide probenazole.

Table C74

Table C74 is identical to Table C1, except that each reference to compound 1 in the column headed "Cmpd. No." is replaced by a reference to compound 448. For example, the first mixture in Table C74 is designated C74-1 and is a mixture of compound 448 and the additional fungicide probenazole.

Table C75

Table C75 is identical to Table C1, except that each reference to compound 1 in the column headed "Cmpd. No." is replaced by a reference to compound 449. For example, the first mixture in Table C75 is designated C75-1 and is a mixture of compound 449 and the additional fungicide probenazole.

Table C76

Table C76 is identical to Table C1, except that each reference to compound 1 in the column headed "Cmpd. No." is replaced by a reference to compound 450. For example, the first mixture in Table C76 is designated C76-1 and is a mixture of compound 450 and the additional fungicide probenazole.

Table C77

Table C77 is identical to Table C1, except that each reference to compound 1 in the column headed "Cmpd. No." is replaced by a reference to compound 451. For example, the first mixture in Table C77 is designated C77-1 and is a mixture of compound 451 and the additional fungicide probenazole.

Table C78

Table C78 is identical to Table C1, except that each reference to compound 1 in the column headed "Cmpd. No." is replaced by a reference to compound 462. For example, the first mixture in Table C78 is designated C78-1 and is a mixture of compound 462 and the additional fungicide probenazole.

Table C79

Table C79 is identical to Table C1, except that each reference to compound 1 in the column headed "Cmpd. No." is replaced by a reference to compound 482. For example, the first mixture in Table C79 is designated C79-1 and is a mixture of compound 482 and the additional fungicide probenazole.

Table C80

Table C80 is identical to Table C1, except that each reference to compound 1 in the column headed "Cmpd. No." is replaced by a reference to compound 490. For example, the first mixture in Table C80 is designated C80-1 and is a mixture of compound 490 and the additional fungicide probenazole.

Table C81

Table C81 is identical to Table C1, except that each reference to compound 1 in the column headed "Cmpd. No." is replaced by a reference to compound 493. For example, the first mixture in Table C81 is designated C81-1 and is a mixture of compound 493 and the additional fungicide probenazole.

Invertebrate pests are controlled in agronomic and nonagronomic applications by applying one or more compounds of this invention, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and a biologically effective amount of at least one additional biologically active compound or agent. Examples of suitable compositions comprising a compound of the invention and a biologically effective amount of at least one additional biologically active compound or agent include granular compositions wherein the additional active compound is present on the same granule as the compound of the invention or on granules separate from those of the compound of the invention.

Embodiments of the method of this invention include contacting the environment. Of note is the method wherein the environment is a plant. Also of note is the method wherein the environment is an animal. Also of note is the method wherein the environment is a seed.

To achieve contact with a compound or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling an invertebrate pest comprising contacting the invertebrate pest or its environment with a biologically effective amount of a compound of the present invention or with a composition comprising a biologically effective amount of a compound of the present invention. Of further note is this method wherein the environment is soil and the composition is applied to the soil as a soil drench formulation. Of further note is that compounds of this invention are also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compounds of this invention can also be impregnated into materials for fabricating invertebrate control devices (e.g., insect netting).

Compounds of this invention are also useful in seed treatments for protecting seeds from invertebrate pests. In the context of the present disclosure and claims, treating a seed means contacting the seed with a biologically effective amount of a compound of this invention, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as Bacillus thuringiensis toxin or those expressing herbicide resistance such as glyphosate acetyltransferase, which provides resistance to glyphosate.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1, an N-oxide, or salt thereof, and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects,* 1994 BCPC Mongraph No. 57, and references listed therein.

The treated seed typically comprises a compound of the present invention in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this invention can be incorporated into a bait composition that is consumed by an invertebrate pest or used within a device such as a trap, bait station, and the like. Such a bait composition can be in the form of granules which comprise (a) active ingredients, namely a biologically effective amount of a compound of Formula 1 an N-oxide, or salt thereof; (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The compounds of this invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present invention. Combinations with spray oils, spray oil concentrates, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as needed for application. Of note is a spray composition comprising a biologically effective amount of a compound or a composition of the present invention and a carrier. One embodiment of such a spray composition comprises a biologically effective amount of a compound or a composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

Nonagronomic uses refer to invertebrate pest control in the areas other than fields of crop plants. Nonagronomic uses of the present compounds and compositions include control of invertebrate pests in stored grains, beans and other foodstuffs, and in textiles such as clothing and carpets. Nonagronomic uses of the present compounds and compositions also include invertebrate pest control in ornamental plants, forests, in yards, along roadsides and railroad rights of way, and on turf such as lawns, golf courses and pastures. Nonagronomic uses of the present compounds and compositions also include invertebrate pest control in houses and other buildings which may be occupied by humans and/or companion, farm, ranch, zoo or other animals. Nonagronomic uses of the present compounds and compositions also include the control of pests such as termites that can damage wood or other structural materials used in buildings.

Nonagronomic uses of the present compounds and compositions also include protecting human and animal health by controlling invertebrate pests that are parasitic or transmit infectious diseases. The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. Compounds and compositions of the present invention are particularly suitable for combating external parasitic or disease transmitting pests. Compounds and compositions of the present invention are suitable for systemic and/or non-systemic control of infestation or infection by parasites on animals.

Compounds and compositions of the present invention are suitable for combating parasites that infest animal subjects including those in the wild, livestock and agricultural working animals such as cattle, sheep, goats, horses, pigs, donkeys, camels, bison, buffalos, rabbits, hens, turkeys, ducks, geese and bees (e.g., raised for meat, milk, butter, eggs, fur, leather, feathers and/or wool). By combating parasites, fatalities and performance reduction (in terms of meat, milk, wool, skins, eggs, honey, etc.) are reduced, so that applying a composition comprising a compound of the present invention allows more economic and simple husbandry of animals.

Compounds and compositions of the present invention are especially suitable for combating parasites that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, bison, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the inventive compounds can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws, and parrots raised for the pet or collector market, among others.

For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of invertebrate parasitic pests controlled by administering a parasiticidally effective amount of a compound of this invention to an animal to be protected include ectoparasites (arthropods, acarines, etc) and endoparasites (helminths, e.g., nematodes, trematodes, cestodes, acanthocephalans, etc.).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the Helminths, the group of worms described as nematodes causes widespread and at times serious infection in various species of animals. Nematodes that are contemplated to be treated by the compounds of this invention and by the inventive methods include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria.*

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris.* Certain of these, such as Nematodirus, *Cooperia* and *Oesophagostomum* attack primarily the intestinal tract while others, such as *Haemonchus* and *Ostertagia,* are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the compounds of this invention and by the inventive methods include, without limitation, the following genera: *Alaria, Fasciola, Nanophyetus, Opisthorchis, Paragonimus* and *Schistosoma.*

Cestodes that are contemplated to be treated by the compounds of this invention and by the inventive methods include, without limitation, the following genera: *Diphyllobothrium, Diplydium, Spirometra* and *Taenia.*

The most common genera of parasites of the gastrointestinal tract of humans are *Ancylostoma, Necator, Ascaris, Strongyloides, Trichinella, Capillaria, Trichuris* and *Enterobius.* Other medically important genera of parasites which are found in the blood or other tissues and organs outside the gastrointestinal tract are the filarial worms such as *Wuchereria, Brugia, Onchocerca* and *Loa,* as well as *Dracunculus* and extra intestinal stages of the intestinal worms *Strongyloides* and *Trichinella.*

Numerous other Helminth genera and species are known to the art, and are also contemplated to be treated by the compounds of the invention. These are enumerated in great detail in *Textbook of Veterinary Clinical Parasitology, Volume 1, Helminths,* E. J. L. Soulsby, F. A. Davis Co., Philadelphia, Pa.; *Helminths, Arthropods and Protozoa,* (6th *Edition of Monnig's Veterinary Helminthology and Entomology*), E. J. L. Soulsby, The Williams and Wilkins Co., Baltimore, Md.

It is also contemplated that the inventive compounds are effective against a number of ectoparasites of animals, e.g., arthropod ectoparasites of mammals and birds although it is also recognized that some arthropods can be endoparasites as well.

Thus, insect and acarine pests include, e.g., biting insects, such as flies and mosquitoes, mites, ticks, lice, fleas, true bugs, parasitic maggots, and the like.

Adult flies include, e.g., the horn fly or *Haematobia irritans,* the horse fly or *Tabanus* spp., the stable fly or *Stomoxys calcitrans,* the black fly or *Simulium* spp., the deer fly or *Chrysops* spp., the louse fly or *Melophagus ovinus,* the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax,* the cattle grub or *Hypoderma* spp., the fleeceworm and the *Gastrophilus* of horses. Mosquitoes include, for example, *Culex* spp., *Anopheles* spp., and *Aedes* spp.

Mites include Mesostigmata spp. e.g., mesostigmatids such as the chicken mite, *Dermanyssus gallinae*; itch or scab mites such as Sarcoptidae spp. for example, *Sarcoptes scabiei*; mange mites such as Psoroptidae spp. including

*Chorioptes bovis* and *Psoroptes ovis*; chiggers e.g., Trombiculidae spp. for example the North American chigger, *Trombicula alfreddugesi*.

Ticks include, e.g., soft-bodied ticks including Argasidae spp. for example *Argas* spp. and *Ornithodoros* spp.; hard-bodied ticks including Ixodidae spp., for example *Rhipicephalus sanguineus, Dermacentor variabilis, Dermacentor andersoni, Amblyomma americanum, Ixodes scapularis* and *Boophilus* spp.

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., Cimicidae or e.g., the common bed bug (*Cimex lectularius*); Triatominae spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other arthropod pests and ectoparasites are known to the art, and are also contemplated to be treated by the compounds of the invention. These are enumerated in great detail in *Medical and Veterinary Entomology*, D. S. Kettle, John Wiley & Sons, New York and Toronto; *Control of Arthropod Pests of Livestock: A Review of Technology*, R. O. Drummand, J. E. George, and S. E. Kunz, CRC Press, Boca Raton, Fla.

The compounds and compositions of this invention may also be effective against a number of protozoa endoparasites of animals, such as those summarized by Table 1, as follows.

TABLE 1

Exemplary Parasitic Protozoa and Associated Human Diseases

| Phylum | Subphylum | Representative Genera | Human Disease or Disorder |
|---|---|---|---|
| Sarcomastigophora (with flagella, pseudopodia, or both) | Mastigophora (Flagella) | *Leishmania* | Visceral, cutaneous and mucocutaneous Infection |
| | | *Trypansoma* | Sleeping sickness Chagas' disease |
| | | *Giardia* | Diarrhea |
| | | *Trichomonas* | Vaginitis |
| | Sarcodina (pseudopodia) | *Entamoeba* | Dysentery, liver Abscess |
| | | *Dientamoeba* | Colitis |
| | | *Naegleria* and *Acanthamoeba* | Central nervous system and corneal ulcers |
| Apicomplexa (apical complex) | | *Babesia* | Babesiesis |
| | | *Plasmodium* | Malaria |
| | | *Isospora* | Diarrhea |
| | | *Sarcocystis* | Diarrhea |
| | | *Cryptosporidum* | Diarrhea |
| | | *Toxoplasma* | Toxoplasmosis |
| | | *Eimeria* | Chicken coccidiosis |
| Microspora | | *Enterocytozoon* | Diarrhea |
| Ciliaphora (with cilia) | | *Balantidium* | Dysentery |
| Unclassified | | *Pneumocystis* | Pneumonia |

In particular, the compounds of this invention are effective against ectoparasites including fleas such as *Ctenocephalides felis* (cat flea) and *Ctenocephalides canis* (dog flea).

The compounds of this invention may also be effective against other ectoparasites including flies such as *Haematobia* (*Lyperosia*) *irritans* (horn fly), *Stomoxys calcitrans* (stable fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus instestinalis, Gastrophilus haemorrhoidalis* and *Gastrophilus naslis*; lice such as *Bovicola* (*Damalinia*) *bovis, Bovicola equi, Haematopinus asini, Felicola subrostratus, Heterodoxus spiniger, Lignonathus setosus* and *Trichodectes canis*; keds such as *Melophagus ovinus*; mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites); and ticks such as *Ixodes* spp., *Boophilus* spp., *Rhipicephalus* spp., *Amblyomma* spp., *Dermacentor* spp., *Hyalomma* spp. and *Haemaphysalis* spp.

Biologically active compounds or agents useful in the compositions of the present invention include the organophosphate pesticides. This class of pesticides has very broad activity as insecticides and, in certain instances, anthelmintic activity. Organophosphate pesticides include, e.g., dicrotophos, terbufos, dimethoate, diazinon, disulfoton, trichlorfon, azinphos-methyl, chlorpyrifos, malathion, oxydemeton-methyl, methamidophos, acephate, ethyl parathion, methyl parathion, mevinphos, phorate, carbofenthion and phosalone. It is also contemplated to include combinations of the inventive methods and compounds with carbamate type pesticides, including, e.g., carbaryl, carbofuran, aldicarb, molinate, methomyl, carbofuran, etc., as well as combinations with the organochlorine type pesticides. It is further contemplated to include combinations with biological pesticides, including repellents, the pyrethrins (as well as synthetic variations thereof, e.g., allethrin, resmethrin, permethrin, tralomethrin), and nicotine, that is often employed as an acaricide. Other contemplated combinations are with miscellaneous pesticides including: *bacillus thuringensis*, chlorobenzilate, formamidines (e.g., amitraz), copper compounds (e.g., copper hydroxide and cupric oxychloride sulfate), cyfluthrin, cypermethrin, dicofol, endosulfan, esenfenvalerate, fenvalerate, lambda-cyhalothrin, methoxychlor and sulfur.

Of note are additional biologically active compounds or agents selected from art-known anthelmintics, such as, for example, avermectins (e.g., ivermectin, moxidectin, milbemycin), benzimidazoles (e.g., albendazole, triclabendazole), salicylanilides (e.g., closantel, oxyclozanide), substituted phenols (e.g., nitroxynil), pyrimidines (e.g., pyrantel), imidazothiazoles (e.g., levamisole) and praziquantel.

Other biologically active compounds or agents useful in the compositions of the present invention can be selected from Insect Growth Regulators (IGRs) and Juvenile Hormone Analogues (JHAs) such as diflubenzuron, triflumuron, fluazuron, cyromazine, methoprene, etc., thereby providing both initial and sustained control of parasites (at all stages of insect development, including eggs) on the animal subject, as well as within the environment of the animal subject.

Of note are biologically active compounds or agents useful in the compositions of the present invention selected from the antiparasitic class of avermectin compounds. As stated above, the avermectin family of compounds is a series of very potent antiparasitic agents known to be useful against a broad spectrum of endoparasites and ectoparasites in mammals.

A notable compound for use within the scope of the present invention is ivermectin. Ivermectin is a semi-synthetic derivative of avermectin and is generally produced as a mixture of at least 80% 22,23-dihydroavermectin $B_{1a}$ and less than 20% 22,23-dihydroavermectin $B_{1b}$. Ivermectin is disclosed in U.S. Pat. No. 4,199,569.

Abamectin is an avermectin that is disclosed as Avermectin $B_{1a}/B_{1b}$ in U.S. Pat. No. 4,310,519. Abamectin contains at least 80% of avermectin $B_{1a}$ and not more than 20% of avermectin $B_{1b}$.

Another notable avermectin is Doramectin, also known as 25-cyclohexyl-avermectin $B_1$. The structure and preparation of Doramectin is disclosed in U.S. Pat. No. 5,089,480.

Another notable avermectin is Moxidectin. Moxidectin, also known as LL-F28249 alpha, is known from U.S. Pat. No. 4,916,154.

Another notable avermectin is Selamectin. Selamectin is 25-cyclohexyl-25-de(1-methylpropyl)-5-deoxy-22,23-dihydro-5-(hydroxyimino)-avermectin $B_1$ monosaccharide.

Milbemycin, or B41, is a substance which is isolated from the fermentation broth of a Milbemycin producing strain of *Streptomyces*. The microorganism, the fermentation conditions and the isolation procedures are more fully described in U.S. Pat. No. 3,950,360 and U.S. Pat. No. 3,984,564.

Emamectin (4"-deoxy-4"-epi-methylaminoavermectin $B_1$), which can be prepared as described in U.S. Pat. No. 5,288,710 or U.S. Pat. No. 5,399,717, is a mixture of two homologues, 4"-deoxy-4"-epi-methylaminoavermectin $B_{1a}$ and 4"-deoxy-4"-epi-methylaminoavermectin $B_{1b}$. Preferably, a salt of Emamectin is used. Non-limiting examples of salts of Emamectin which can be used in the present invention include the salts described in U.S. Pat. No. 5,288,710, e.g., salts derived from benzoic acid, substituted benzoic acid, benzenesulfonic acid, citric acid, phosphoric acid, tartaric acid, maleic acid, and the like. Most preferably, the Emamectin salt used in the present invention is Emamectin benzoate.

Eprinomectin is chemically known as 4"-epi-acetylamino-4"-deoxy-avermectin $B_1$. Eprinomectin was specifically developed to be used in all cattle classes and age groups. It was the first avermectin to show broad-spectrum activity against both endo- and ecto-parasites while also leaving minimal residues in meat and milk. It has the additional advantage of being highly potent when delivered topically.

The composition of the present invention optionally comprises combinations of one or more of the following antiparasite compounds: imidazo[1,2-b]pyridazine compounds as described by U.S. application Ser. No. 11/019,597, filed on Dec. 22, 2004, and published on Aug. 18, 2005 as US 2005-0182059A1; 1-(4-mono and di-halomethylsulphonylphenyl)-2-acylamino-3-fluoropropanol compounds, as described by U.S. application Ser. No. 11/018,156, filed on Dec. 21, 2004, now U.S. Pat. No. 7,361,689; trifluoromethanesulfonanilide oxime ether derivatives, as described by U.S. application Ser. No. 11/231,423, filed on Sep. 21, 2005, now U.S. Pat. No. 7,312,248; and n-[(phenyloxy)phenyl]-1,1,1-trifluoromethanesulfonamide and n-[(phenylsulfanyl) phenyl]-1,1,1-trifluoromethanesulfonamide derivatives, as described by U.S. Provisional Application Ser. No. 60/688, 898, filed on Jun. 9, 2005, and published as US 2006-0281695A1 on Dec. 14, 2006.

The compositions of the present invention can also further comprise a flukicide. Suitable flukicides include, for example, triclabendazole, fenbendazole, albendazole, Clorsulon and oxibendazole. It will be appreciated that the above combinations can further include combinations of antibiotic, antiparasitic and anti-fluke active compounds.

In addition to the above combinations, it is also contemplated to provide combinations of the inventive methods and compounds, as described herein, with other animal health remedies such as trace elements, anti-inflammatories, anti-infectives, hormones, dermatological preparations, including antiseptics and disinfectants, and immunobiologicals such as vaccines and antisera for the prevention of disease.

For example, such antinfectives include one or more antibiotics that are optionally co-administered during treatment using the inventive compounds or methods, e.g., in a combined composition and/or in separate dosage forms. Art-known antibiotics suitable for this purpose include, for example, those listed herein below.

One useful antibiotic is Florfenicol, also known as D-(threo)-1-(4-methylsulfonylphenyl)-2-dichloroacetamido-3-fluoro-1-propanol. Another notable antibiotic compound is D-(threo)-1-(4-methylsulfonylphenyl)-2-difluoroacetamido-3-fluoro-1-propanol. Another useful antibiotic is Thiamphenicol. Processes for the manufacture of these antibiotic compounds, and intermediates useful in such processes, are described in U.S. Pat. No. 4,311,857; U.S. Pat. No. 4,582,918; U.S. Pat. No. 4,973,750; U.S. Pat. No. 4,876,352; U.S. Pat. No. 5,227,494; U.S. Pat. No. 4,743,700; U.S. Pat. No. 5,567,844; U.S. Pat. No. 5,105,009; U.S. Pat. No. 5,382,673; U.S. Pat. No. 5,352,832; and U.S. Pat. No. 5,663,361. Other florfenicol analogs and/or prodrugs have been disclosed and such analogs also can be used in the compositions and methods of the present invention (see e.g., U.S. Patent Application Publication No: 2004/0082553, now U.S. Pat. No. 7,041,670, and U.S. patent application Ser. No. 11/016,794, now U.S. Pat. No. 7,153,842).

Another useful antibiotic compound is Tilmicosin. Tilmicosin is a macrolide antibiotic that is chemically defined as 20-dihydro-20-deoxy-20-(cis-3,5-dimethylpiperidin-1-yl)-desmycosin and which is reportedly disclosed in U.S. Pat. No. 4,820,695.

Another useful antibiotic for use in the present invention is tulathromycin. Tulathromycin is also identified as (2R, 3S,4R,5R,8R,10R,11R,12S,13S,14R) 13-[(2,6-dideoxy-3-C-methyl-3-O-methyl-4-C-[(propylamino)methyl]-alpha-L-ribo-hexopyranosyl]-oxy]-2-ethyl-3,4,10-trihydroxy-3,5,8, 10,12,14-hexamethyl-11-[[3,4,6-trideoxy-3-(dimethyl-amino)-beta-D-xylo-hexopyranosyl]oxy]-1-oxa-6-azacyclopentadecan-15-one. Tulathromycin can be prepared in accordance with the procedures set forth in U.S. Patent Publication No. 2003/0064939 A1.

Further antibiotics for use in the present invention include the cephalosporins such as, for example, ceftiofur, cefquinome, etc. The concentration of the cephalosporin in the formulation of the present invention optionally varies between about 1 mg/mL to 500 mg/mL.

Another useful antibiotic includes the fluoroquinolones, such as, for example, enrofloxacin, danofloxacin, difloxacin, orbifloxacin and marbofloxacin. Enrofloxacin is typically administered in a concentration of about 100 mg/mL. Danofloxacin is typically administered at a concentration of about 180 mg/mL.

Other useful macrolide antibiotics include compounds from the class of ketolides, or, more specifically, the azalides. Such compounds are described in, for example, U.S. Pat. No. 6,514,945, U.S. Pat. No. 6,472,371, U.S. Pat.

No. 6,270,768, U.S. Pat. No. 6,437,151, U.S. Pat. No. 6,271,255, U.S. Pat. No. 6,239,112, U.S. Pat. No. 5,958,888, U.S. Pat. No. 6,339,063 and U.S. Pat. No. 6,054,434.

Other useful antibiotics include the tetracyclines, particularly chlortetracycline and oxytetracycline. Other antibiotics may include β-lactams such as penicillins, e.g., penicillin, ampicillin, amoxicillin, or a combination of amoxicillin with clavulanic acid or other beta lactamase inhibitors.

Nonagronomic applications in the veterinary sector are by conventional means such as by enteral administration in the form of, for example, tablets, capsules, drinks, drenching preparations, granulates, pastes, boli, feed-through procedures, or suppositories; or by parenteral administration, such as by injection (including intramuscular, subcutaneous, intravenous, intraperitoneal) or implants; by nasal administration; by topical administration, for example, in the form of immersion or dipping, spraying, washing, coating with powder, or application to a small area of the animal, and through articles such as neck collars, ear tags, tail bands, limb bands or halters which comprise compounds or compositions of the present invention.

Any of the compounds of the present invention, or a suitable combination of such compounds, may be administered directly to the animal subject and/or indirectly by applying it to the local environment in which the animal dwells (such as bedding, enclosures, or the like). Direct administration includes contacting the skin, fur or feathers of a subject animal with the compounds, or by feeding or injecting the compounds into the animal.

The compounds of the present invention may be administered in a controlled release form, e.g., in a subcutaneous slow release formulation, or in the form of a controlled release device affixed to an animal such as a fleacollar. Collars for the controlled release of an insecticide agent for long term protection against flea infestation in a companion animal are art-known, and are described, for example, by U.S. Pat. No. 3,852,416, U.S. Pat. No. 4,224,901, U.S. Pat. No. 5,555,848 and U.S. Pat. No. 5,184,573.

Typically a parasiticidal composition according to the present invention comprises a mixture of a compound of Formula 1, an N-oxide, or salt thereof, with one or more pharmaceutically or veterinarily acceptable carriers comprising excipients and auxiliaries selected with regard to the intended route of administration (e.g., oral, topical or parenteral administration such as injection) and in accordance with standard practice. In addition, a suitable carrier is selected on the basis of compatibility with the one or more active ingredients in the composition, including such considerations as stability relative to pH and moisture content. Therefore of note is a composition for protecting an animal from an invertebrate parasitic pest comprising a parasitically effective amount of a compound of the invention and at least one carrier.

For parenteral administration including intravenous, intramuscular and subcutaneous injection, a compound of the present invention can be formulated in suspension, solution or emulsion in oily or aqueous vehicles, and may contain adjuncts such as suspending, stabilizing and/or dispersing agents. The compounds of the present invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the present invention may also be formulated as a depot preparation. Such long acting formulations may be administered by implantation (for example, subcutaneously or intramuscularly) or by intramuscular or subcutaneous injection. The compounds of the present invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the present invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

Compounds of the present invention have been discovered to have favorable pharmacokinetic and pharmacodynamic properties providing systemic availability from oral administration and ingestion. Therefore after ingestion by the animal to be protected, parasiticidally effective concentrations of compounds of the invention in the bloodstream protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, a compound of the present invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., crosslinked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

The compounds of Formula 1 may also be formulated in rectal compositions such as suppositories or retention enemas, using, e.g., conventional suppository bases such as cocoa butter or other glycerides.

Formulations for topical administration are typically in the form of a powder, cream, suspension, spray, emulsion, foam, paste, aerosol, ointment, salve or gel. More typically a topical formulation is a water-soluble solution, which can be in the form of a concentrate that is diluted before use. Parasiticidal compositions suitable for topical administration typically comprise a compound of the present invention and one or more topically suitable carriers. In applications of a parasiticidal composition topically to the exterior of an animal as a line or spot (i.e. "spot-on" treatment), the active ingredient migrates over the surface of the animal to cover most or all of its external surface area. As a result, the treated animal is particularly protected from invertebrate pests that feed off the epidermis of the animal such as ticks, fleas and lice. Therefore formulations for topical localized administration often comprise at least one organic solvent to facilitate transport of the active ingredient over the skin and/or penetration into the epidermis of the animal. Carriers in such formulations include propylene glycol, paraffins, aromatics, esters such as isopropyl myristate, glycol ethers, alcohols such as ethanol, n-propanol, 2-octyl dodecanol or oleyl alcohol; solutions in esters of monocarboxylic acids, such as isopropyl myristate, isopropyl palmitate, lauric acid oxalic ester, oleic acid oleyl ester, oleic acid decyl ester, hexyl laurate, oleyl oleate, decyl oleate, caproic acid esters of saturated fatty alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or solutions of esters of aliphatic acids, e.g., glycols. It may be advantageous for a crystallization inhibitor or a dispersant known from the pharmaceutical or cosmetic industry also to be present.

A pour-on formulation may also be prepared for control of parasites in an animal of agricultural worth. The pour-on formulations of this invention can be in the form of a liquid, powder, emulsion, foam, paste, aerosol, ointment, salve or gel. Typically, the pour-on formulation is liquid. These pour-on formulations can be effectively applied to sheep, cattle, goats, other ruminants, camelids, pigs and horses. The pour-on formulation is typically applied by pouring in one or several lines or in a spot-on the dorsal midline (back) or shoulder of an animal. More typically, the formulation is applied by pouring it along the back of the animal, following the spine. The formulation can also be applied to the animal by other conventional methods, including wiping an impregnated material over at least a small area of the animal, or applying it using a commercially available applicator, by means of a syringe, by spraying or by using a spray race. The pour-on formulations include a carrier and can also include one or more additional ingredients. Examples of suitable additional ingredients are stabilizers such as antioxidants, spreading agents, preservatives, adhesion promoters, active solubilisers such as oleic acid, viscosity modifiers, UV blockers or absorbers, and colourants. Surface active agents, including anionic, cationic, non-ionic and ampholytic surface active agents, can also be included in these formulations.

The formulations of this invention typically include an antioxidant, such as BHT (butylated hydroxytoluene). The antioxidant is generally present in amounts of at 0.1-5% (wt/vol). Some of the formulations require a solubilizer, such as oleic acid, to dissolve the active agent, particularly if spinosad is used. Common spreading agents used in these pour-on formulations are: IPM, IPP, caprylic/capric acid esters of saturated $C_{12}$-$C_{18}$ fatty alcohols, oleic acid, oleyl ester, ethyl oleate, triglycerides, silicone oils and DPM. The pour-on formulations of this invention are prepared according to known techniques. Where the pour-on is a solution, the parasiticide/insecticide is mixed with the carrier or vehicle, using heat and stirring where required. Auxiliary or additional ingredients can be added to the mixture of active agent and carrier, or they can be mixed with the active agent prior to the addition of the carrier. If the pour-on is an emulsion or suspension, these formulations are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

For agronomic applications, the rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

In general for veterinary use, a compound of Formula 1, an N-oxide, or salt thereof, is administered in a parasiticidally effective amount to an animal to be protected from invertebrate parasite pests. A parasiticidally effective amount is the amount of active ingredient needed to achieve an observable effect diminishing the occurrence or activity of the target invertebrate parasite pest. One skilled in the art will appreciate that the parasitically effective dose can vary for the various compounds and compositions of the present invention, the desired parasitical effect and duration, the target invertebrate pest species, the animal to be protected, the mode of application and the like, and the amount needed to achieve a particular result can be determined through simple experimentation.

For oral administration to homeothermic animals, the daily dosage of a compound of the present invention typically ranges from about 0.01 mg/kg to about 100 mg/kg, more typically from about 0.5 mg/kg to about 100 mg/kg, of animal body weight. For topical (e.g., dermal) administration, dips and sprays typically contain from about 0.5 ppm to about 5000 ppm, more typically from about 1 ppm to about 3000 ppm, of a compound of the present invention.

Representative compounds of this invention prepared by the methods described herein are shown in Index Tables A-E. See Index Table F for $^1$H NMR data. For mass spectral data (AP$^+$ (M+1)), the numerical value reported is the molecular weight of the parent molecular ion (M) formed by addition of H$^+$ (molecular weight of 1) to the molecule to give a M+1 peak observed by mass spectrometry using atmospheric pressure chemical ionization (AP$^+$). The alternate molecular ion peaks (e.g., M+2 or M+4) that occur with compounds containing multiple halogens are not reported. The variable "R$^A$" in Index Tables A-C represents one or a combination of substituents as listed in Index Tables A-C.

The following abbreviations are used in the Index Tables which follow: Cmpd means Compound, Me is methyl, Et is ethyl, i-Pr is isopropyl, n-Bu is normal-butyl, t-Bu is tertiary-butyl, Ph is phenyl, CHO is formyl, Ac is acetyl (i.e. C(O)CH$_3$) and SO$_2$Me is methyl sulfonyl.

Fragments X-1 through X-6 shown below are referred to in the Index Tables. The wavy line denotes the attachment point of the fragment to the remainder of the molecule.

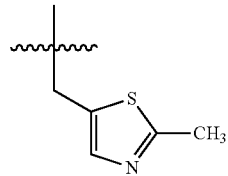

X-6

INDEX TABLE A

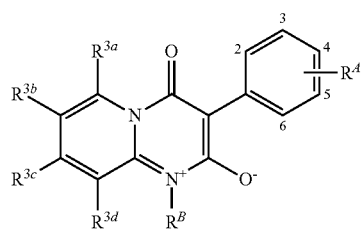

| Cmpd | R$^A$ | R$^B$ | R$^{3a}$ | R$^{3b}$ | R$^{3c}$ | R$^{3d}$ | AP+ (M + 1) |
|---|---|---|---|---|---|---|---|
| 1 | 3-OCF$_3$ | X-2 | H | H | H | Br | 532 |
| 2 | H | Pr | H | CH$_3$ | H | H | 295 |
| 3 | H | Pr | H | H | CH$_3$ | H | 295 |
| 4 | H | Pr | CH$_3$ | H | H | H | 295 |
| 5 | H | Pr | H | cyano | H | H | 306 |
| 6 | H | Pr | Cl | H | H | H | 315 |
| 8 | H | Pr | H | H | H | Cl | 315 |
| 9 | H | X-1 | F | H | H | H | 382 |
| 10 | 4-F | X-1 | F | H | H | H | 400 |
| 11 | 3-OCF$_3$ | X-1 | F | H | H | H | 466 |
| 12 | 3-OCF$_3$ | X-1 | F | H | H | H | 418 |
| 13 | 3-OCF$_3$ | X-1 | H | F | H | F | * |
| 14 | 2-F, 4-F | X-1 | H | F | H | F | * |
| 15 | 4-F | X-1 | H | F | H | F | * |
| 16 | H | CH$_2$CF$_3$ | H | H | H | OH | * |
| 17 | 4-F | CH$_2$CF$_3$ | H | H | H | OH | 355 |
| 18 | 3-CF$_3$ | X-2 | H | H | H | Br | 516 |
| 19 | 3-Br | X-2 | H | H | H | Br | 558 |
| 20 | 3-Cl, 5-CF$_3$ | X-2 | H | H | H | Br | 550 |
| 21 | 2-F, 3-Cl, 5-CF$_3$ | X-2 | H | H | H | Br | 600 |
| 22 | 3-OCF$_3$ | X-2 | H | H | H | cyano | 479 |
| 23 | 3-OCF$_3$ | X-2 | H | H | H | Cl | 488 |
| 24 | 3-OCF$_3$ | X-2 | H | H | OCH$_3$ | H | 484 |
| 25 | 3-OCF$_3$ | X-2 | H | OCH$_3$ | H | H | 484 |
| 26 | 3-OCF$_3$ | X-2 | H | H | H | CH$_3$ | 468 |
| 27 | 3-OCF$_3$ | X-2 | H | H | Br | H | 532 |
| 28 | 3-CF$_3$ | X-2 | H | H | Br | H | 516 |
| 29 | 3-CF$_3$ | X-2 | H | H | H | CH$_3$ | 452 |
| 30 | 2-F | X-2 | H | H | H | CH$_3$ | 402 |
| 31 | 2-F | X-2 | H | H | Br | H | 466 |
| 32 | 2-F | X-2 | H | H | OCH$_3$ | H | 418 |
| 33 | 3-Cl, 5-OCF$_3$ | X-2 | H | H | H | Br | 566 |
| 34 | H | X-2 | H | H | CH$_3$ | H | 384 |
| 35 | H | X-2 | H | H | Cl | H | 404 |
| 54 | 3-OCF$_3$ | X-2 | CH$_3$ | H | H | H | 468 |
| 55 | 2-F | X-2 | CH$_3$ | H | H | H | 402 |
| 61 | 3-OCF$_3$ | X-2 | H | Br | H | CH$_3$ | 546 |
| 63 | 2-F, 3-CF$_3$ | X-2 | H | Br | H | CH$_3$ | 470 |
| 430 | 2-F | X-2 | H | I | H | H | 514 |

* See Index Table F for $^1$H NMR data.

INDEX TABLE B

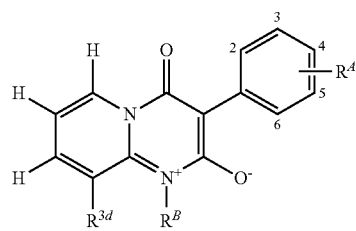

| Cmpd | $R^A$ | $R^B$ | $R^{3d}$ | m.p. (° C.) | AP+ (M + 1) |
|---|---|---|---|---|---|
| 36 | 3-Cl, 5-OCF$_3$ | X-2 | CH$_3$ | | 502 |
| 37 | 2-F, 6-F | X-2 | CH$_3$ | | 420 |
| 38 | 2-F | X-1 | CH$_3$ | | 396 |
| 39 | 3-OCF$_3$ | X-1 | CH$_3$ | | 462 |
| 40 | 3-SCF$_3$ | X-2 | CH$_3$ | | 484 |
| 41 | 2-F | X-2 | OCH$_3$ | | 418 |
| 42 | H | X-3 | CH$_3$ | | * |
| 43 | 3-OCF$_3$ | X-3 | CH$_3$ | | * |
| 44 | 2-F | X-3 | CH$_3$ | | * |
| 45 | 3-CF$_3$ | X-3 | CH$_3$ | | * |
| 46 | 2-F, 6-F | X-3 | CH$_3$ | | * |
| 47 | H | X-2 | CH$_3$ | | 383 |
| 48 | 2-OCH$_3$, 5-OCH$_3$ | X-2 | CH$_3$ | | 443 |
| 49 | 2-F, 5-CF$_3$ | X-2 | CH$_3$ | | 470 |
| 50 | 4-F | X-2 | CH$_3$ | | 402 |
| 51 | 3-OCF$_3$ | X-2 | OCH$_3$ | | 484 |
| 52 | 2-F, 5-CF$_3$ | X-2 | OCH$_3$ | | 486 |
| 53 | 2-OCH$_3$, 5-OCF$_3$ | X-2 | CH$_3$ | | 498 |
| 56 | 2-OCH$_3$ | X-2 | CH$_3$ | | 414 |
| 57 | 2-F, 3-Cl, 5-CF$_3$ | X-2 | CH$_3$ | | 504 |
| 58 | 4-SCF$_3$ | X-2 | CH$_3$ | | 484 |
| 59 | 2-F, 4-F | X-2 | CH$_3$ | | 420 |
| 60 | 2-F, 3-Cl | X-2 | CH$_3$ | | 436 |
| 62 | 3-OCH$_3$ | X-2 | CH$_3$ | | 414 |
| 64 | 3-SCF$_3$ | X-4 | CH$_3$ | | 462 |
| 65 | 3-I | X-2 | CH$_3$ | | 510 |
| 66 | 2-F, 3-CF$_3$ | X-2 | OCH$_3$ | | 486 |
| 67 | 3-I | X-2 | CH$_3$ | | 476 |
| 68 | 3-OCF$_3$ | X-2 | Ph | | 530 |
| 69 | 3-OCH$_3$ | X-2 | Ph | | 476 |
| 70 | 3-OCF$_3$ | X-5 | CH$_3$ | | 434 |
| 71 | 3-OCF$_3$ | X-6 | CH$_3$ | | 448 |
| 72 | 3-OCF$_3$ | X-4 | CH$_3$ | | 446 |
| 73 | 3-CF$_3$ | X-5 | CH$_3$ | | 418 |
| 74 | 3-CF$_3$ | X-6 | CH$_3$ | | 432 |
| 75 | 3-CF$_3$ | X-4 | CH$_3$ | | 430 |
| 76 | 2-F | X-5 | CH$_3$ | | 368 |
| 77 | 2-F | X-6 | CH$_3$ | | 382 |
| 78 | 2-F | X-4 | CH$_3$ | | 380 |
| 79 | 3-Br, 5-CF$_3$ | X-2 | CH$_3$ | | 530 |
| 80 | 3-Br, 5-OCF$_3$ | X-2 | CH$_3$ | | 546 |
| 81 | 3-Cl, 5-CF$_3$ | X-2 | CH$_3$ | | 486 |
| 82 | 3-F, 5-CF$_3$ | X-2 | CH$_3$ | | 470 |
| 83 | 3-I, 5-OCH$_3$ | X-2 | CH$_3$ | | 540 |
| 84 | 3-Br | X-2 | CH$_3$ | | 462 |
| 101 | 3-(C≡CH) | X-2 | CH$_3$ | | 408 |
| 102 | 3-(CH=CH$_2$) | X-2 | CH$_3$ | | 410 |
| 103 | 2-Cl, 5-CF$_3$ | X-2 | CH$_3$ | | 486 |
| 104 | 2-F, 3-OCH$_3$ | X-2 | CH$_3$ | | 432 |
| 105 | 4-Cl | X-2 | CH$_3$ | | 418 |
| 106 | 3,4-(—OCH$_2$O—) | X-2 | CH$_3$ | | 428 |
| 107 | 3-CF$_3$ | CH$_2$CF$_3$ | CH$_3$ | | 403 |
| 108 | 2-OCH$_3$, 3-F, 5-F | X-2 | CH$_3$ | | 450 |
| 109 | 2-OCH$_3$, 3-OCH$_3$, | X-2 | CH$_3$ | | 444 |
| 110 | 3-F, 4-F, 5-F | X-2 | CH$_3$ | | 438 |
| 111 | 2-F, 4-OCH$_3$ | X-2 | CH$_3$ | | 432 |
| 112 | 3-OCH$_3$, 4-F | X-2 | CH$_3$ | | 432 |
| 113 | 3-Cl, 5-Cl | X-2 | CH$_3$ | | 452 |
| 114 | 3-OCH$_3$, 4-OCH$_3$ | X-2 | CH$_3$ | | 444 |
| 115 | 4-OCH$_3$ | X-2 | CH$_3$ | | 414 |
| 116 | 2-OCH$_3$, 4-OCH$_3$ | X-2 | CH$_3$ | | 444 |
| 117 | 3-F, 4-OCH$_3$ | X-2 | CH$_3$ | | 432 |
| 118 | 3-Cl | X-2 | CH$_3$ | | 418 |
| 119 | 3-F, 4-F | X-2 | CH$_3$ | | 420 |
| 120 | 3-CF$_3$, 4-F | X-2 | CH$_3$ | | 470 |

INDEX TABLE B-continued

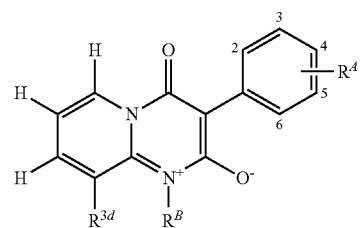

| Cmpd | $R^A$ | $R^B$ | $R^{3d}$ | m.p. (° C.) | AP+ (M + 1) |
|---|---|---|---|---|---|
| 121 | 2-OCH$_3$, 5-CF$_3$ | X-2 | CH$_3$ | | 482 |
| 122 | 3-CH$_3$ | X-2 | CH$_3$ | | 398 |
| 123 | 3-CH$_2$CH$_3$ | X-2 | CH$_3$ | | 412 |
| 124 | 2-OCH$_3$, 5-F | X-2 | CH$_3$ | | 432 |
| 125 | 2-F, 3-F | X-2 | CH$_3$ | | 420 |
| 126 | 2-OCH$_3$, 5-Br | X-2 | CH$_3$ | | 492 |
| 127 | 2-F, 5-Cl | X-2 | CH$_3$ | | 436 |
| 128 | 3-OCF$_3$, 4-Cl | X-2 | CH$_3$ | | 502 |
| 129 | 2-OCH$_3$, 5-Cl | X-2 | CH$_3$ | | 448 |
| 130 | 2-Cl, 5-Cl | X-2 | CH$_3$ | | 452 |
| 131 | 3-Cl, 5-CF$_3$ | X-2 | OCH$_3$ | | 502 |
| 132 | 3-OCH$_3$, 5-OCH$_3$ | X-2 | CH$_3$ | | 444 |
| 133 | 3-Cl, 5-CF$_3$ | X-6 | CH$_3$ | | 466 |
| 134 | 2-Cl, 3-Cl | X-2 | CH$_3$ | | 452 |
| 135 | 3-OCH$_2$CH$_3$ | X-2 | CH$_3$ | | 428 |
| 136 | 3-OCF$_3$ | X-2 | CH$_2$CH$_3$ | | 482 |
| 152 | 2-OCH$_2$CH$_3$ | X-2 | CH$_3$ | | 428 |
| 153 | H | X-2 | CH=CH$_2$ | | 396 |
| 154 | 3-CF$_3$ | X-2 | CH=CH$_2$ | | 464 |
| 155 | 2-F | X-2 | CH=CH$_2$ | | 414 |
| 156 | 3-CF$_3$ | CH$_2$(1-methyl-4-imidazolyl) | CH$_3$ | | 415 |
| 157 | 2-F, 5-Br | X-2 | CH$_3$ | | 480 |
| 158 | 3-F, 4-Cl | X-2 | CH$_3$ | | 436 |
| 159 | 3-F | X-2 | CH$_3$ | | 402 |
| 160 | 3,5-diF | X-2 | CH$_3$ | | 420 |
| 161 | 2-F, 4-Cl | X-2 | CH$_3$ | | 436 |
| 162 | 3,4-diCl | X-2 | CH$_3$ | | 452 |
| 163 | 3-Br, 5-F | X-2 | CH$_3$ | | 480 |
| 164 | 3-CH$_3$, 4-Cl | X-2 | CH$_3$ | | 432 |
| 165 | 2,5-diF | X-2 | CH$_3$ | | 420 |
| 166 | 2-Cl, 4-F | X-2 | CH$_3$ | | 436 |
| 167 | 3-CH$_3$, 5-CF$_3$ | X-2 | CH$_3$ | | 466 |
| 168 | 3-CH$_3$, 5-Cl | X-2 | CH$_3$ | | 462 |
| 169 | 2-CH$_3$, 4-Br | X-2 | CH$_3$ | | 476 |
| 170 | 3-Br, 4-F | X-2 | CH$_3$ | | 480 |
| 173 | 3-OCF$_3$, 4-F | X-2 | CH$_3$ | | 486 |
| 179 | 2-F | X-2 | CH$_2$CH$_3$ | | 416 |
| 180 | 3-OCH$_2$CH$_3$, 5-OCH$_2$CH$_3$ | X-2 | CH$_3$ | | 440 |
| 181 | 2-CH$_3$, 5-Cl | X-2 | CH$_3$ | | 432 |
| 182 | 2-OCH$_3$, 5-CH$_3$ | X-2 | CH$_3$ | | 428 |
| 183 | 2-F, 5-CH$_3$ | X-2 | CH$_3$ | | 416 |
| 185 | H | X-2 | Cl | | 404 |
| 186 | 2-F | X-2 | Cl | | 421 |
| 187 | 3-C(CH$_3$)$_3$ | X-2 | CH$_3$ | | 440 |
| 188 | 3-Cl, 5-CF$_3$ | X-2 | CH$_2$CH$_3$ | | 500 |
| 192 | 3-(4-chlorophenyl) | X-2 | CH$_2$CH$_3$ | | 508 |
| 196 | 2-F, 3-CH$_3$ | X-2 | CH$_3$ | | 416 |
| 197 | 2-OCH$_3$, 3-CH$_3$ | X-2 | CH$_3$ | | 428 |
| 198 | 3-Br | X-2 | CH$_2$CH$_3$ | | 476 |
| 202 | 3-(4-chlorophenyl) | X-2 | OCH$_3$ | | 510 |
| 203 | 3-CH$_2$CH$_2$CH$_3$ | X-2 | CH$_3$ | | 426 |
| 204 | 2-CH$_3$ | X-2 | CH$_3$ | | 398 |
| 205 | 4-CH$_3$ | X-2 | CH$_3$ | | 398 |
| 206 | 2-Cl | X-2 | CH$_3$ | | * |
| 212 | 2-F | X-2 | I | | 514 |
| 213 | 2-F | X-2 | CH$_2$F | | 420 |
| 216 | H | X-2 | CH$_2$F | | 402 |
| 217 | 3-CF$_3$ | X-2 | CH$_2$F | | 470 |
| 218 | H | X-2 | I | | * |
| 223 | 4-F | X-2 | OCH$_3$ | | 418 |
| 224 | 2-nitro | X-2 | CH$_3$ | | * |
| 225 | 2-nitro, 5-CF$_3$ | X-2 | CH$_3$ | | * |
| 226 | H | X-2 | CH$_2$OC(O)CH$_3$ | | * |
| 227 | 3-CH$_3$, 5-CH$_3$ | X-2 | CH$_3$ | | 411 |

INDEX TABLE B-continued

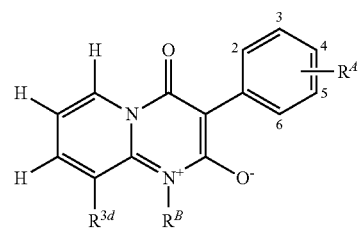

| Cmpd | $R^A$ | $R^B$ | $R^{3d}$ | m.p. (° C.) | AP+ (M + 1) |
|---|---|---|---|---|---|
| 228 | 3-Cl, 4-F | X-2 | $CH_3$ | | 436 |
| 234 | 3-cyano, 4-F | X-2 | $CH_3$ | | 428 |
| 235 | 3-Br, 5-$CH_3$ | X-2 | $CH_3$ | | 476 |
| 236 | 4-cyano | X-2 | $CH_3$ | | 409 |
| 237 | 4-nitro | X-2 | $CH_3$ | | * |
| 240 | 3-cyano, 5-$CF_3$ | X-2 | $CH_3$ | | 477 |
| 241 | 3-$CH(CH_3)_2$ | X-2 | $CH_3$ | | 426 |
| 243 | 3-$Si(CH_2CH_3)_3$ | X-2 | $CH_3$ | | 498 |
| 244 | 3-$Si(CH_3)_3$ | X-2 | $CH_3$ | | 456 |
| 249 | 3-$OSi(CH(CH_3)_2)_3$ | X-2 | $CH_3$ | | 556 |
| 257 | 3-Br, 5-Cl | X-2 | $CH_3$ | | 496 |
| 265 | 3-$CH_3$, 5-$Si(CH_3)_3$ | X-2 | $CH_3$ | | 470 |
| 266 | 3-$OCH_3$, 5-$C(O)OCH_3$ | X-2 | $CH_3$ | | 472 |
| 268 | 3-cyano, 5-$OCH_3$ | X-2 | $CH_3$ | | 539 |
| 296 | 3-Br, 5-cyano | X-2 | $CH_3$ | | 487 |
| 297 | 3-F, 5-cyano | X-2 | $CH_3$ | | 427 |
| 298 | 3-Cl, 5-cyano | X-2 | $CH_3$ | | 443 |
| 304 | 3-cyano, 5-$CH_3$ | X-2 | $CH_3$ | | 423 |
| 310 | 2-I | X-2 | $CH_3$ | | 510 |
| 311 | 3-cyano | X-2 | $CH_3$ | | 409 |
| 312 | 2-cyano | X-2 | $CH_3$ | | 409 |
| 324 | 2-F, 5-cyano | X-2 | $CH_3$ | | 427 |
| 335 | 3,5-diCl, 4-F | X-2 | $CH_3$ | | * |
| 339 | 3-$C(O)OCH_3$ | X-2 | $CH_3$ | | 442 |
| 342 | 2-Cl, 5-Br | X-2 | $CH_3$ | | 496 |
| 348 | H | 2-methyl-1-imidazolyl | $CH_3$ | | * |
| 349 | H | 4-methyl-1-imidazolyl | $CH_3$ | | * |
| 350 | H | 2,4-dimethyl-1-imidazolyl | $CH_3$ | | 361 |
| 351 | 3-Cl, 5-$C(O)OCH_3$ | X-2 | $CH_3$ | | 476 |
| 353 | 3-Br, 4-$CH_3$ | X-2 | $CH_3$ | | 475 |
| 354 | 3-(2-chloro-4-(trifluoromethyl)phenyl) | X-2 | $OCH_3$ | | 578 |
| 355 | 3-(2-fluoro-4-(trifluoromethyl)phenyl) | X-2 | $OCH_3$ | | 562 |
| 370 | H | 1-imidazolyl | | | 333 |
| 373 | 3-$C(O)CH_3$ | X-2 | $CH_3$ | | 426 |
| 380 | 3-$CF_3$, 5-$C(O)OCH_3$ | X-2 | $CH_3$ | | 510 |
| 382 | 3-cyclopropyl | X-2 | $CH_3$ | | 424 |
| 389 | 3,5-diCl | $CH_2CH_2CH_2OCH_3$ | $CH_3$ | | 393 |
| 390 | H | $CH_2CH_2CH_2OCH_3$ | $CH_3$ | 107-109 | |
| 392 | 2-F | $CH_2CH_2CH_2OCH_3$ | | 109-110 | |
| 395 | 3-Cl, 5-F | X-2 | $CH_3$ | | 436 |
| 396 | 4-$C(O)OCH_3$ | X-2 | $CH_3$ | | 442 |
| 397 | 4-$C(O)CH_3$ | X-2 | $CH_3$ | | 426 |
| 403 | 3-F, 5-$CF_3$ | X-2 | $OCH_3$ | | 486 |
| 404 | 3-Cl, 5-$OCH_3$ | X-2 | $CH_3$ | | 448 |
| 405 | 3-$CH_3$, 4-F | X-2 | $CH_3$ | | 416 |
| 406 | H | 3-methyl-5-isoxazolyl | $CH_3$ | 109-111 | |
| 413 | 4-(2-chloro-4-(trifluoromethyl)phenyl) | X-2 | $CH_3$ | | 562 |
| 414 | 4-I | X-2 | $CH_3$ | | 510 |
| 415 | 4-(2-chloro-4-fluorophenyl) | X-2 | $CH_3$ | | 512 |
| 416 | 4-(3-chloro-5-(trifluoromethyl)phenyl) | X-2 | $CH_3$ | | 562 |
| 417 | 2-F | $CH_2$(3-tetrahydrofuranyl) | $CH_3$ | | 354 |
| 420 | 4-(3-chloro-4-(trifluoromethyl)phenyl | X-2 | $CH_3$ | | 564 |
| 423 | 2-(2-chloro-4-(trifluoromethyl)phenyl | X-2 | $CH_3$ | | 562 |

INDEX TABLE B-continued

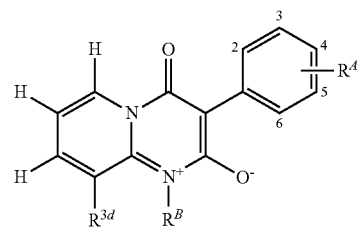

| Cmpd | $R^A$ | $R^B$ | $R^{3d}$ | m.p. (° C.) | AP+ (M + 1) |
|---|---|---|---|---|---|
| 424 | 3-F, 5-OCH$_3$ | X-2 | CH$_3$ | | 432 |
| 425 | 3-Cl, 5-I | X-2 | CH$_3$ | | 544 |
| 426 | 3-OCH$_3$, 5-CF$_3$ | X-2 | CH$_3$ | | 482 |
| 428 | 2-(2-chloro-4-fluorophenyl) | X-2 | CH$_3$ | | 512 |
| 436 | H | CH$_2$(3-tetrahydrofuranyl) | CH$_3$ | 208-211 | |
| 439 | 3-(C(CH$_3$)=NOCH$_3$) | X-2 | CH$_3$ | | 455 |
| 442 | 3-Cl, 5-F | X-2 | OCH$_3$ | | 452 |
| 445 | 3-(2-chloro-4-(trifluoromethyl)phenyl) | CH$_2$CH$_2$CH$_2$OCH$_3$ | CH$_3$ | 144-146 | |
| 446 | 3,5-diCl | CH$_2$(3-tetrahydrofuranyl) | CH$_3$ | >300 | |
| 452 | 2-OCH$_3$, 5-CN | X-2 | CH$_3$ | | 439 |
| 453 | 3-(C(CH$_3$)=NOCH$_2$CH$_3$) | X-2 | CH$_3$ | | 469 |
| 458 | 3-thienyl | X-2 | CH$_3$ | | 466 |
| 459 | 3-OCF$_3$ | CH$_2$(3-tetrahydrofuranyl) | CH$_3$ | | 420 |
| 460 | 3-OCF$_3$ | CH$_2$CH$_2$CH$_2$OCH$_3$ | CH$_3$ | | 408 |
| 463 | 3-(2,4-dimethylphenyl) | X-2 | CH$_3$ | | 504 |
| 469 | 2-F | CH$_2$(3-methyl-5-isoxazolyl) | CH$_3$ | 162-164 | |
| 470 | 3-(2-chloro-4-(trifluoromethyl)phenyl) | CH$_2$(3-methyl-2-isoxazolyl | CH$_3$ | 181-182 | |
| 471 | 3,5-diCl | CH$_2$(3-methyl-5-isoxazolyl | CH$_3$ | 184-186 | |
| 472 | H | CH$_2$CF$_3$ | CH$_3$ | 138-140 | |
| 473 | 2-F | CH$_2$CF$_3$ | CH$_3$ | 188-190 | |
| 475 | H | CH$_2$(5-thiazolyl) | CH$_3$ | 174-176 | |
| 476 | 3,5-diCl | CH$_2$(5-thiazolyl) | CH$_3$ | 200-201 | |
| 477 | 3-(2-chloro-4-(trifluoromethyl)phenyl) | CH$_2$(5-thiazolyl) | CH$_3$ | 107-109 | |
| 478 | H | CH$_2$(2-methyl-5-thiazolyl) | CH$_3$ | 164-166 | |
| 479 | 3-(2-chloro-4-(trifluoromethyl)phenyl) | CH$_2$(2-methyl-5-thiazolyl) | CH$_3$ | 199-200 | |
| 480 | 3-(2-chloro-4-(trifluoromethyl)phenyl), 4-F | X-2 | OCH$_3$ | | 596 |
| 481 | 3-Cl, 5-(4-chloro-2-fluorophenyl) | X-2 | OCH$_3$ | | 562 |
| 486 | 3-Cl, 4-Br | X-2 | CH$_3$ | | 498 |
| 487 | 3-CF$_3$, 4-Br | X-2 | CH$_3$ | | 531 |
| 488 | 2-F, 3-Cl, 4-Br | X-2 | CH$_3$ | | * |
| 494 | H | CH$_2$(2-chloro-4-(trifluoromethyl)-5-thiazolyl) | CH$_3$ | | 452 |
| 495 | 3-CH$_3$, 5-OCH$_3$ | X-2 | CH$_3$ | | 429 |
| 496 | 3-F, 5-I | X-2 | CH$_3$ | | 582 |
| 497 | 3-CH$_3$, 5-I | X-2 | CH$_3$ | | 524 |
| 498 | 3-CH$_3$, 5-F | X-2 | CH$_3$ | | 416 |

* See Index Table F for $^1$H NMR data.

INDEX TABLE C

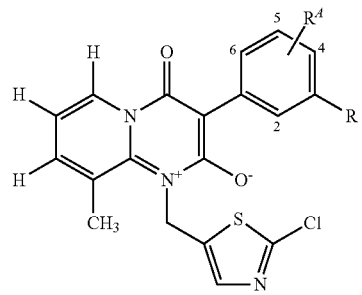

| Cmpd | $R^A$ | R | m.p. (° C.) | AP+ (M + 1) |
|---|---|---|---|---|
| 85 | H | 3-(trifluoromethoxy)phenyl | | 544 |
| 86 | H | 2,5-difluorophenyl | | 496 |
| 87 | 5-OCF$_3$ | 6-chloro-3-pyridinyl | | 579 |
| 88 | H | 2,3-dichlorophenyl | | 528 |
| 89 | H | 2,4-dichlorophenyl | | 528 |
| 90 | H | 5-cyano-2-ethoxyphenyl | | 515 |
| 137 | H | 4-(trifluoromethyl)phenyl | | 528 |
| 138 | H | 5-chloro-2-fluorophenyl | | 512 |
| 139 | H | 2,5-dichlorophenyl | | 528 |
| 140 | H | 4-chlorophenyl | | 494 |
| 150 | H | 3-chloro-4-(trifluoromethyl)phenyl | | 562 |
| 151 | H | 2-chloro-5-fluorophenyl | | 512 |
| 174 | 5-OCH$_3$ | 4-chlorophenyl | | 524 |
| 175 | H | —O-(4-fluorophenyl) | | 494 |
| 176 | H | —O-(2-fluorophenyl) | | 494 |
| 177 | H | —O-(3-fluorophenyl) | | 494 |
| 178 | 5-F | 4-chlorophenyl | | 512 |
| 184 | H | —O-(phenyl) | | 476 |
| 189 | H | 2-chloro-4-fluorophenyl | | 510 |
| 190 | H | 4-chloro-2-fluorophenyl | | 512 |
| 191 | H | 2-chloro-4-(trifluoromethyl)phenyl | | 562 |
| 193 | H | 4-bromophenyl | | 538 |
| 194 | H | 4-methylphenyl | | 474 |
| 195 | H | 4-fluorophenyl | | 478 |
| 199 | H | 2-methyl-4-chlorophenyl | | 508 |
| 200 | H | 3-chlorophenyl | | 494 |
| 201 | H | 3-chloro-4-fluorophenyl | | 512 |
| 207 | H | 4-chloro-3-fluorophenyl | | 512 |
| 208 | 4-F | 4-chlorophenyl | | 512 |
| 209 | 4-F | 4-chloro-2-fluorophenyl | | 530 |
| 210 | 6-OCH$_3$ | 4-chlorophenyl | | 523 |
| 211 | 6-OCH$_3$ | 4-chloro-2-fluorophenyl | | 542 |
| 214 | 6-F | 4-chloro-2-fluorophenyl | | 530 |
| 215 | 6-F | 4-chlorophenyl | | 512 |
| 219 | H | —O-(2,5-dichlorophenyl) | | 544 |
| 220 | H | —O-(4-chlorophenyl) | | 510 |
| 221 | H | —O-(4-methoxyphenyl) | | 506 |
| 222 | H | —O-(4-cyanophenyl) | | 501 |
| 229 | H | 2-fluoro-4-(trifluoromethyl)phenyl | | 546 |
| 230 | H | 4-bromo-2-fluorophenyl | | 558 |
| 231 | H | 2-fluoro-5-(trifluoromethoxy)phenyl | | 562 |
| 232 | H | 4-chloro-2-methoxyphenyl | | 524 |
| 233 | H | 5-cyano-2-fluorophenyl | | 504 |
| 238 | 4-OCH$_3$ | 4-chloro-2-fluorophenyl | | 542 |
| 239 | 4-OCH$_3$ | 4-chlorophenyl | | 524 |
| 246 | 5-CH$_3$ | 6-(trifluoromethyl)-3-pyridinyl | | 543 |
| 247 | H | 3-cyano-4-fluorophenyl | | 503 |
| 248 | H | 2,4-difluorophenyl | | 496 |
| 250 | 6-OCH$_3$ | 2-chloro-4-fluorophenyl | | 542 |
| 251 | 4-F | 2-chloro-4-fluorophenyl | | 530 |
| 252 | H | —O-(4-bromophenyl) | | 554 |
| 253 | H | —O-(2-chloro-4-fluorophenyl) | | 528 |
| 255 | H | 2-methylphenyl | | 474 |
| 256 | 5-Cl | 4-chlorophenyl | | 528 |
| 258 | H | —C(O)(4-chlorophenyl) | | 523 |
| 259 | H | —CH$_2$(4-chlorophenyl) | | 509 |
| 262 | 5-Cl | 2,4-dichlorophenyl | | 562 |
| 263 | 5-F | 4-(trifluoromethyl)phenyl | | 546 |
| 264 | 5-Cl | 4-(trifluoromethyl)phenyl | | 562 |
| 269 | H | phenyl | | 460 |
| 270 | 6-F | 4-fluorophenyl | | 496 |
| 271 | H | 3,5-difluorophenyl | | 496 |
| 272 | H | 2-methyl-4-(trifluoromethyl)phenyl | | 542 |
| 273 | 5-Cl | 6-(trifluoromethyl)-3-pyridinyl | | 563 |
| 276 | 5-CF$_3$ | 4-chloro-2-methylphenyl | | 576 |
| 277 | H | 3-chloro-5-(trifluoromethyl)phenyl | | 564 |
| 278 | 4-CH$_3$ | 2-chloro-4-(trifluoromethyl)phenyl | | 576 |
| 279 | 5-CF$_3$ | 6-chloro-3-pyridinyl | | 563 |
| 285 | H | 4-chloro-2-(trifluoromethyl)phenyl | | 567 |
| 286 | 5-CF$_3$ | 4-chlorophenyl | | 567 |
| 287 | H | —S-(4-(trifluoromethyl)phenyl) | | 561 |
| 289 | 4-F | 2-chloro-4-(trifluoromethyl)phenyl | | 580 |
| 290 | 4-F | 6-(trifluoromethyl)-3-pyridinyl | | 547 |
| 291 | 4-F | 2,4-dichlorophenyl | | 546 |
| 299 | 6-F | 6-(trifluoromethyl)-3-pyridinyl | | 547 |
| 300 | 6-F | 4-(trifluoromethyl)phenyl | | 546 |
| 301 | 6-Cl | 4-(trifluoromethyl)phenyl | | 562 |
| 302 | 6-Cl | 6-(trifluoromethyl)-3-pyridinyl | | 563 |
| 305 | 4-Cl | 4-(trifluoromethyl)phenyl | | 562 |
| 306 | 4-Cl | 6-(trifluoromethyl)-3-pyridinyl | | 563 |
| 307 | H | 2,6-dichloro-3-pyridinyl | | 529 |
| 308 | 5-Cl | 2,6-dichloro-3-pyridinyl | | 563 |
| 315 | H | 4,6-dichlorophenyl-3-pyridinyl | | 531 |
| 316 | 4-CH$_3$ | 4-(trifluoromethyl)phenyl | | 542 |
| 317 | 4-CH$_3$ | 6-(trifluoromethyl)-3-pyridinyl | | 543 |
| 318 | 6-CH$_3$ | 6-(trifluoromethyl)-3-pyridinyl | | 543 |
| 319 | 6-CH$_3$ | 2-chloro-4-(trifluoromethyl)phenyl | | 576 |
| 320 | 6-CH$_3$ | 4-(trifluoromethyl)phenyl | | 542 |
| 321 | 4-OCH$_3$ | 2-chloro-4-(trifluoromethyl)phenyl | | 592 |
| 322 | 6-OCH$_3$ | 4-(trifluoromethyl)phenyl | | 558 |
| 323 | 6-OCH$_3$ | 2-chloro-4-(trifluoromethyl)phenyl | | 592 |
| 325 | H | 4-cyanophenyl | | 485 |
| 326 | H | 4-chloro-2-cyanophenyl | | 519 |
| 327 | H | 4-carbomethoxy-2-chlorophenyl | | 535 |
| 328 | 6-Cl | 2-methyl-4-(trifluoromethyl)phenyl | | 576 |
| 329 | 4-OCH$_3$ | 4-(trifluoromethyl)phenyl | | 558 |
| 330 | 4-F | 3-chloro-5-(trifluoromethyl)phenyl | | 580 |
| 336 | 4-OCH$_3$ | 2-fluoro-4-(trifluoromethyl)phenyl | | 576 |
| 337 | H | 3-bromo-5-fluorophenyl | | 556 |
| 338 | 4-CN | 2-chloro-4-(trifluoromethyl)phenyl | | 587 |
| 343 | 6-F | 2-chloro-4-(trifluoromethyl)phenyl | | 580 |
| 344 | 4-Cl | 2-chloro-4-(trifluoromethyl)phenyl | | 596 |
| 345 | 4-OCH$_3$ | 6-(trifluoromethyl)-3-pyridinyl | | 559 |
| 346 | 4-CH$_3$ | 4-chloro-2-fluorophenyl | | 526 |
| 347 | H | 3-chloro-5-fluorophenyl | | 512 |
| 352 | 5-CH$_3$ | 2-chloro-4-(trifluoromethyl)phenyl | | 576 |
| 362 | H | 4-(methylthio)phenyl | | 506 |
| 363 | 4-F | 2-fluoro-4-(trifluoromethyl)phenyl | | 564 |
| 364 | 4-F | 2-methyl-4-(trifluoromethyl)phenyl | | 560 |
| 365 | 4-F | 4-chloro-2-methylphenyl | | 526 |
| 366 | H | 2,4-dimethylphenyl | | 488 |
| 367 | H | 2-chloro-5-(trifluoromethyl)phenyl | | 562 |
| 368 | 4-F | 4-chloro-2-(trifluoromethyl)phenyl | | 580 |
| 369 | 4-Cl | 4-chloro-2-fluorophenyl | | 546 |
| 374 | 4-F | 2-fluoro-5-(trifluoromethoxy)phenyl | | 580 |
| 375 | H | 2,4-bis(trifluoromethyl)phenyl | | 596 |
| 376 | 4-OCH$_3$ | 4-chloro-2-(trifluoromethyl)phenyl | | 592 |
| 377 | 4-OCH$_3$ | 2-methyl-4-(trifluoromethyl)phenyl | | 572 |
| 378 | 4-OCH$_3$ | 4-chloro-2-methylphenyl | | 538 |
| 381 | 5-CH$_3$ | 4-chloro-2-fluorophenyl | | 526 |
| 384 | H | 6-chloro-2-fluoro-3-pyridinyl | | 513 |
| 385 | 4-CH$_3$ | 2-chloro-4-(trifluoromethyl)phenyl | | 560 |

INDEX TABLE C-continued

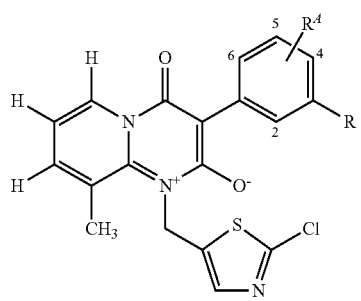

| Cmpd | $R^A$ | R | m.p. (° C.) | AP+ (M + 1) |
|---|---|---|---|---|
| 386 | 4-OCH$_3$ | 4-chloro-3-fluorophenyl | | 542 |
| 387 | 4-F | 4-chloro-3-fluorophenyl | | 530 |
| 388 | 4-F | 3-chloro-4-(trifluoromethyl)phenyl | | 580 |
| 398 | 4-OCH$_3$ | 2-fluoro-5-(trifluoromethoxy)phenyl | | 592 |
| 399 | 4-F | 2,6-dichloro-3-pyridinyl | | 547 |
| 400 | H | 3-chloro-4-(trifluoromethyl)phenyl | | 562 |
| 401 | 5-Cl | 2-chloro-4-(trifluoromethyl)phenyl | | 596 |
| 402 | 5-Cl | 4-chloro-2-fluorophenyl | | 546 |
| 407 | 5-Cl | 2-methyl-4-(trifluoromethyl)phenyl | | 576 |
| 408 | 5-Cl | 2-fluoro-5-(trifluoromethyl)phenyl | | 596 |
| 409 | 4-CH$_3$ | 2-fluoro-5-(trifluoromethoxy)phenyl | | 576 |
| 410 | 5-Cl | 2-fluoro-4-(trifluoromethyl)phenyl | | 580 |
| 411 | 4-CH$_3$ | 4-chloro-2-(trifluoromethyl)phenyl | | 576 |
| 412 | 5-CF$_3$ | 2-chloro-4-(trifluoromethyl)phenyl | | 630 |
| 421 | 6-F | 2-fluoro-4-(trifluoromethyl)phenyl | | 564 |
| 422 | 6-OCH$_3$ | 2-fluoro-4-(trifluoromethyl)phenyl | | 576 |
| 427 | 4-F | 2-chloro-5-(trifluoromethyl)phenyl | | 580 |
| 429 | 4-CH$_3$ | 2-chloro-5-(trifluoromethyl)phenyl | | 576 |
| 431 | 4-OCH$_3$ | 2-chloro-5-(trifluoromethyl)phenyl | | 592 |
| 432 | 6-F | 2-methyl-4-(trifluoromethyl)phenyl | | 560 |
| 433 | 5-F | 2-chloro-4-(trifluoromethyl)phenyl | | 580 |
| 434 | 5-F | 2-chloro-4-(trifluoromethyl)phenyl | | 580 |
| 435 | 5-F | 2-methyl-4-(trifluoromethyl)phenyl | | 560 |
| 437 | H | 4-chloro-3-cyanophenyl | | 519 |
| 438 | H | 4-cyano-2-fluorophenyl | | 503 |
| 440 | 4-CH$_3$ | 2-methyl-4-(trifluoromethyl)phenyl | | 556 |
| 441 | 5-F | 4-chloro-2-fluorophenyl | | 530 |
| 443 | 4-F | 2,4-bis(trifluoromethyl)phenyl | | 614 |
| 448 | 4-OCH$_3$ | 2-fluoro-5-(trifluoromethyl)phenyl | | 576 |
| 449 | H | 2-fluoro-5-(trifluoromethyl)phenyl | | 546 |
| 450 | 4-F | 2-fluoro-5-(trifluoromethyl)phenyl | | 564 |
| 451 | 5-OCH$_3$ | 2-chloro-4-(trifluoromethyl)phenyl | | 592 |
| 457 | H | 4-fluoro-2-(trifluoromethyl)phenyl | | 546 |
| 462 | 5-CN | 2-chloro-4-(trifluoromethyl)phenyl | | 587 |
| 464 | H | 2-ethoxy-6-(trifluoromethyl)-3-pyridinyl | | 572 |
| 467 | H | 2-chloro-6-(trifluoromethyl)-3-pyridinyl | | 563 |
| 468 | 5-Cl | 2-fluoro-5-(trifluoromethyl)phenyl | | 566 |
| 474 | H | 2-chloro-4-(trifluoromethyl)phenyl | 154-155 | |
| 482 | 4-Cl | 2-methyl-4-(trifluoromethyl)phenyl | | 576 |
| 483 | 4-CH$_3$ | 2-fluoro-5-(trifluoromethyl)phenyl | | 560 |
| 484 | 4-CH$_3$ | 2,4-bis(trifluoromethyl)phenyl | | 610 |
| 485 | 5-F | 2-fluoro-4-(trifluoromethyl)phenyl | | 564 |
| 489 | 4-OCH$_3$ | 2,4-bis(trifluoromethyl)phenyl | | 676 |
| 490 | 5-OCH$_3$ | 2-fluoro-4-(trifluoromethyl)phenyl | | 576 |
| 491 | 5-OCH$_3$ | 4-chloro-2-fluorophenyl | | 542 |
| 493 | 5-CN | 4-chloro-2-fluorophenyl | | 537 |
| 499 | 5-Cl | 4,6-dichloro-3-pyridinyl | | 563 |
| 500 | 5-F | 2-fluoro-5-(trifluoromethyl)phenyl | | 564 |
| 501 | 4-F | 4-fluoro-2-(trifluoromethyl)phenyl | | 564 |

INDEX TABLE D

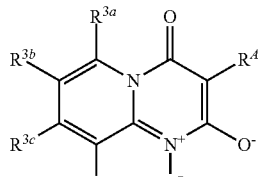

$R^B$ is X-2, $R^{3a}$, $R^{3b}$ and $R^{3c}$ are H, $R^{3d}$ is CH$_3$

| Cmpd | $R^A$ | m.p. (° C.) | AP+ (M + 1) |
|---|---|---|---|
| 242 | SCF$_3$ | | * |
| 245 | CH$_2$CH$_2$CH$_2$CH$_3$ | | 364 |
| 254 | 2-(4-(trifluoromethyl)phenyl)-4-pyridinyl | | 529 |
| 260 | 2-(4-chlorophenoxy)-4-pyrimidinyl | | * |
| 261 | 2-bromo-4-pyridinyl | | 463 |
| 267 | 2-(4-(trifluoromethyl)phenyl)-4-pyrimidinyl | | 530 |
| 274 | 2-chloro-6-(trifluoromethyl)-4-pyridinyl | | 486 |
| 275 | CH$_3$ | | * |
| 280 | CH(CH$_3$)$_2$ | | * |
| 281 | CH$_2$C$_6$H$_5$ | | * |
| 282 | CH$_2$CH$_3$ | | * |
| 283 | CH(CH$_3$)CH$_2$CH$_3$ | | 378 |
| 284 | C(CH$_3$)$_3$ | | 364 |
| 288 | 2,6-dichloro-4-pyridinyl | | 455 |
| 292 | CH$_2$CH(CH$_3$)$_2$ | | * |
| 293 | CH$_2$CH$_2$CH$_2$CH$_3$ | | * |
| 294 | CH$_2$CH$_2$CH$_3$ | | * |
| 295 | CH$_2$CH=CH$_2$ | | * |
| 303 | CH$_2$CH=CHC$_6$H$_5$ | | 424 |
| 309 | 1-naphthalenyl | 162-165 | |
| 313 | 8-methyl-1-naphthalenyl | 252-253 | |
| 314 | 2-naphthalenyl | 211-214 | |
| 331 | 5-bromo-3-pyridinyl | | * |
| 341 | CH=CHCH$_2$CH$_3$ | | 362 |
| 358 | CH$_2$C≡CH | | * |
| 359 | 6-chloro-3-pyridinyl | | * |
| 360 | 2-(2-chloro-4-(trifluoromethyl)phenyl)-4-pyridinyl | | 563 |
| 361 | CH$_2$C≡CCH$_3$ | | * |
| 371 | H | | 308 |
| 379 | 6-methyl-3-pyridinyl | | 399 |
| 383 | cis-CH$_2$CH=CHCH$_3$ | | * |
| 393 | 5-methyl-3-pyridinyl | | 399 |
| 394 | 5-ethyl-3-pyridinyl | | 413 |
| 418 | 6-fluoro-3-pyridinyl | | 403 |
| 419 | 2-chloro-3-pyridinyl | | 419 |
| 444 | 3-cyano-3-pyridinyl | | 410 |
| 447 | 6-(4-(trifluoromethyl)phenyl)-3-pyridinyl | | 529 |
| 454 | 2-thienyl | | 390 |
| 455 | 3-thienyl | | 390 |
| 456 | 1-(2,6-dichloro-4-(trifluoromethyl)phenyl-4-pyrazolyl) | | 586 |
| 461 | 2-(2-chloro-4-(trifluoromethyl)phenyl)-3-pyridinyl | | 563 |
| 465 | 4-bromo-2-thienyl | | 468 |
| 492 | 4-(2-chloro-4-(trifluoromethyl)phenyl-2-thienyl | | 568 |

* See Index Table F for $^1$H NMR data.

INDEX TABLE E

| Cmpd | Structure | m.p. (°C.) | AP+ (M + 1) |
|---|---|---|---|
| 91 | 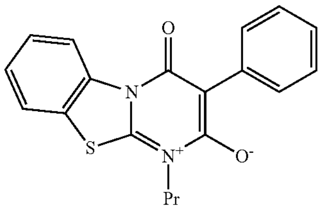 | | 337 |
| 92 | 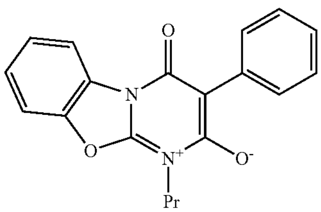 | | 321 |
| 93 | 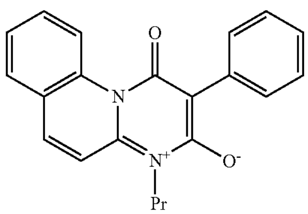 | | 331 |
| 94 | 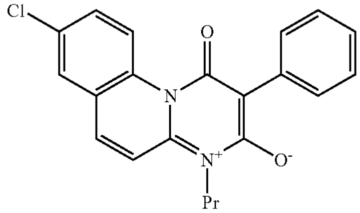 | | 365 |
| 95 | 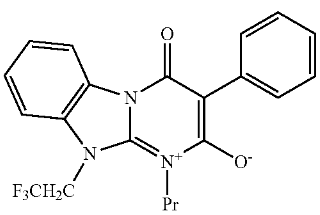 | | 402 |
| 96 | 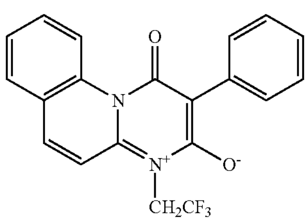 | | * |

INDEX TABLE E-continued

| Cmpd | Structure | m.p. (°C.) | AP+ (M + 1) |
|---|---|---|---|
| 97 | 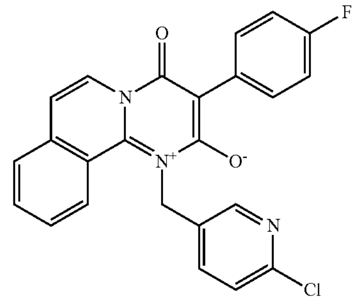 [SMILES: O=c1c(-c2ccc(F)cc2)c([O-])[n+](Cc2ccc(Cl)nc2)c2c3ccccc3ccn12] | | 432 |
| 98 | 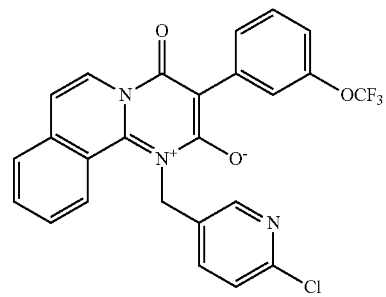 [SMILES: O=c1c(-c2cccc(OC(F)(F)F)c2)c([O-])[n+](Cc2ccc(Cl)nc2)c2c3ccccc3ccn12] | | * |
| 99 | 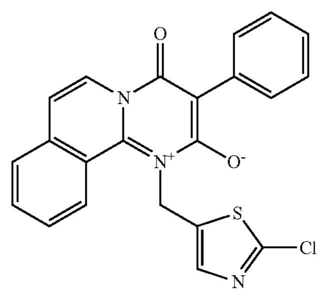 [SMILES: O=c1c(-c2ccccc2)c([O-])[n+](Cc2cnc(Cl)s2)c2c3ccccc3ccn12] | | 420 |
| 100 | 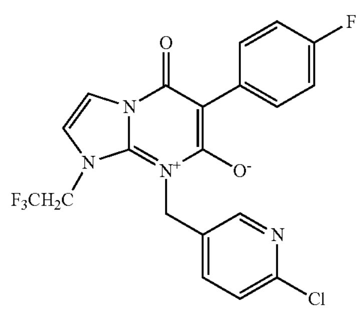 | | 452 |
| 171 | 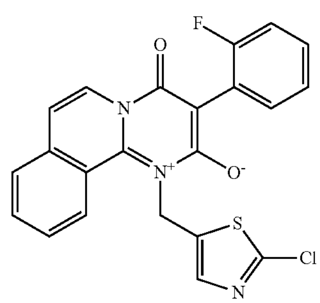 [SMILES: O=c1c(-c2ccccc2F)c([O-])[n+](Cc2cnc(Cl)s2)c2c3ccccc3ccn12] | | 438 |

INDEX TABLE E-continued

| Cmpd | Structure | m.p. (°C.) | AP+ (M+1) |
|---|---|---|---|
| 172 | 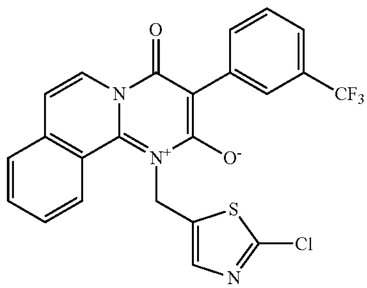 [SMILES: O=c1c(-c2cccc(C(F)(F)F)c2)c([O-])[n+](Cc2cnc(Cl)s2)c2c3ccccc3ccn12] | | 487 |
| 333 | 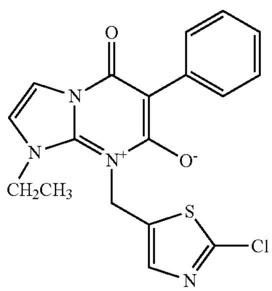 [SMILES: CCn1ccn2c(=O)c(-c3ccccc3)c([O-])[n+](Cc3cnc(Cl)s3)c12] | | 387 |
| 334 | 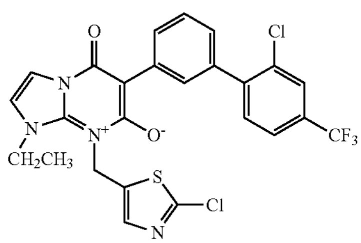 [SMILES: CCn1ccn2c(=O)c(-c3cccc(-c4ccc(C(F)(F)F)cc4Cl)c3)c([O-])[n+](Cc3cnc(Cl)s3)c12] | | 565 |
| 340 | 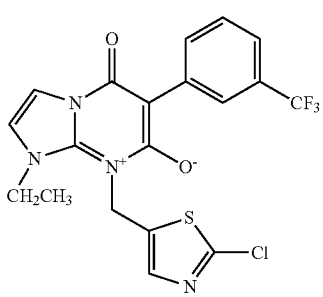 [SMILES: CCn1ccn2c(=O)c(-c3cccc(C(F)(F)F)c3)c([O-])[n+](Cc3cnc(Cl)s3)c12] | | 455 |
| 356 | 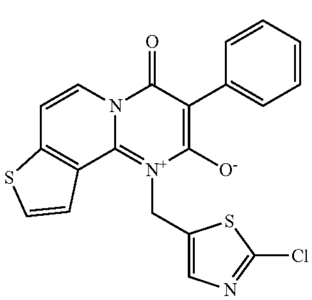 [SMILES: O=c1c(-c2ccccc2)c([O-])[n+](Cc2cnc(Cl)s2)c2c3ccsc3ccn12] | 224-226 | |
| 357 | 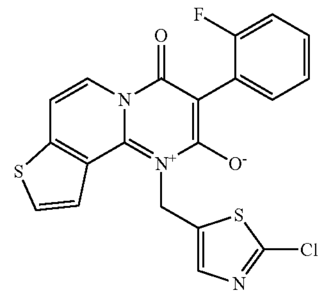 [SMILES: O=c1c(-c2ccccc2F)c([O-])[n+](Cc2cnc(Cl)s2)c2c3ccsc3ccn12] | 235-236 | |
| 391 | 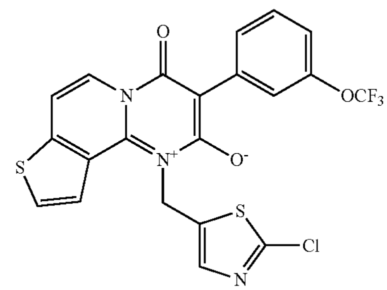 [SMILES: O=c1c(-c2cccc(OC(F)(F)F)c2)c([O-])[n+](Cc2cnc(Cl)s2)c2c3ccsc3ccn12] | | 510 |

\* See Index Table F for ¹H NMR data.

INDEX TABLE F

| Cmpd No. | ¹H NMR Data[a, b] |
|---|---|
| 13 | δ 9.47 (s, 1H), 8.39 (s, 1H), 7.80-7.85 (m, 2H), 7.74 (s, 1H), 7.65 (s, 1H), 7.43 (t, 1H), 7.32 (d, 1H), 7.14 (d, 1H), 5.75 (br s, 2H). |
| 14 | δ 9.43 (s, 1H), 8.39 (s, 1H), 7.76-7.85 (m, 2H), 7.74 (s, 1H), 7.65 (s, 1H), 7.43 (t, 1H), 7.32 (d, 1H), 7.14 (d, 1H), 5.75 (br s, 2H). |
| 15 | δ 9.47 (s, 1H), 8.39 (s, 1H), 7.73-7.83 (m, 3H), 7.64 (dd, 1H), 7.30 (d, 1H), 7.11 (t, 2H), 5.75 (br s, 2H). |
| 16 | δ (CD₃OD) 9.85 (D, 1H), 7.56 (d, 2H), 7.49 (d, 1H), 7.32-7.38 (m, 3H), 7.22 (t, 1H), 6.2 (br s, 2H). |
| 42 | δ (acetone-d₆) 9.46 (d, 1H), 9.04 (s, 1H), 8.81 (s, 2H), 8.23 (d, 1H), 7.86 (d, 2H), 7.53 (t, 1H), 7.26 (t, 2H), 7.11 (t, 1H), 5.65 (s, 2H), 2.68 (s, 3H). |
| 43 | δ (acetone-d₆) 9.47 (d, 1H), 9.05 (s, 1H), 8.83 (s, 2H), 8.27 (d, 1H), 8.02-8.04 (m, 2H), 7.57 (t, 1H), 7.38 (t, 1H), 7.06 (d, 1H), 5.66 (s, 2H), 2.69 (s, 3H). |
| 44 | δ (acetone-d₆) 9.41 (d, 1H), 9.04 (s, 1H), 8.79 (s, 2H), 8.24 (d, 1H), 7.53 (m, 2H), 7.26 (m, 1H), 7.04-7.12 (m, 2H), 5.65 (s, 2H), 2.68 (s, 3H). |
| 45 | δ (acetone-d₆) 9.46 (d, 1H), 9.05 (s, 1H), 8.83 (s, 2H), 8.37 (s, 1H), 8.26 (d, 1H), 8.24 (d, 1H), 7.58 (t, 1H), 7.43-7.51 (m, 2H), 5.67 (s, 2H), 2.69 (s, 3H). |
| 46 | δ (acetone-d₆) 9.39 (d, 1H), 9.04 (s, 1H), 8.79 (s, 2H), 8.28 (d, 1H), 7.56 (t, 1H), 7.34 (t, 1H), 6.96 (t, 2H), 5.67 (s, 2H), 2.72 (s, 3H). |
| 96 | δ 9.42 (d, 1H), 8.3 (d, 1H), 7.73-7.9 (m, 4H), 7.68 (t, 1H), 7.39-7.48 (m, 3H), 7.26 (m, 1H). |

INDEX TABLE F-continued

| Cmpd No. | $^1$H NMR Data$^{a, b}$ |
|---|---|
| 98 | δ 9.31 (d, 1H), 8.43 (d, 1H), 8.22 (s, 1H), 7.97 (dd, 2H), 7.80-7.85 (m, 2H), 7.72 (dd, 1H), 7.61 (2s, 2H), 7.38 (dd, 2H), 7.07 (d, 1H), 5.72 (br s, 2H). |
| 206 | δ (DMSO-d$_6$) 9.27 (d, 1H), 8.29 (d, 1H), 7.76 (s, 1H), 7.56 (t, 1H), 7.48 (dd, 1H), 7.41 (dd, 1H), 7.31-7.36 (m, 2H), 5.46 (s, 2H) 2.73 (s, 3H). |
| 218 | δ 9.59 (d, 1H), 9.04 (d, 1H), 7.84 (d, 2H), 7.62 (s, 1H), 7.40 (dd, 1H), 7.30 (dd, 2H), 7.15 (dd, 1H), 6.07 (s, 2H). |
| 224 | δ (acetone-d$_6$) 8.96 (d, 1H), 8.00 (s, 1H), 7.69-8.00 (m, 4H), 7.26 (t, 1H), 6.91 (t, 1H), 5.61 (s, 2H), 2.55 (s, 3H). |
| 225 | δ (acetone-d$_6$) 9.41 (d, 1H), 8.39 (d, 1H), 8.28 (s, 1H), 8.12 (d, 1H), 7.82 (d, 1H), 7.71 (s, 1H), 7.65 (t, 1H), 5.65 (s, 2H) 2.93 (s, 3H). |
| 226 | δ 9.65 (d, 1H), 8.40 (d, 1H), 7.77 (d, 2H), 7.58 (s, 1H), 7.40 (dd, 3H), 7.25 (dd, 1H), 5.62 (s, 2H), 5.39 (s, 2H), 2.24 (s, 3H). |
| 237 | δ (acetone-d$_6$) 9.44 (d, 1H), 8.34-8.37 (m, 2H), 8.14-8.21 (m, 3H), 7.74 (s, 1H), 7.62 (t, 1H), 5.66 (s, 2H), 2.91 (s, 3H). |
| 242 | δ (acetone-d$_6$) 9.31 (d, 1H), 8.40 (d, 1H), 7.67 (s, 1H), 7.61 t, 1H), 5.58 (s, 2H), 2.81 (s, 3H). |
| 260 | δ (DMSO-d$_6$) 9.24 (d, 1H), 8.53 (d, 1H), 8.40 (t, 1H), 8.16 (d, 1H), 7.99 (s, 1H), 7.57 (t, 2H), 7.46 (d, 2H), 7.37 (d, 2H), 5.59 (s, 2H). |
| 275 | δ 9.48 (d, 1H), 7.94 (d, 1H), 7.42 (s, 1H), 7.33 (dd, 1H), 5.60 (s, 2H), 2.80 (s, 3H), 2.14 (s, 3H). |
| 280 | δ 9.45 (d, 1H), 7.90 (d, 1H), 7.41 (s, 1H), 7.30 (dd, 1H), 5.56 (s, 2H), 3.42 (m, 1H), 2.78 (s, 3H), 1.34 (d, 6H). |
| 281 | δ 9.45 (d, 1H), 7.90 (d, 1H), 7.49 (d, 2H), 7.39 (s, 1H), 7.24 (dd, 1 H), 7.22 (dd, 2H), 7.14 (dd, 1 H), 5.58 (s, 2H), 3.96 (s, 2H), 2.76 (s, 3H). |
| 282 | δ 9.48 (d, 1H), 7.92 (d, 1H), 7.42 (s, 1H), 7.29 (dd, 1H), 5.59 (s, 2H), 2.8 (s, 3H), 2.67 (q, 2H), 1.18 (t, 3H). |
| 292 | δ 9.46 (d, 1H), 7.92 (d, 1H), 7.40 (s, 1H), 7.31 (dd, 1H), 5.60 (s, 2H), 2.80 (s, 3H), 2.50 (d, 2H), 2.04 (m, 1H) 0.96 (d, 6H). |
| 293 | δ 9.48 (d, 1H), 7.93 (d, 1H), 7.42 (s, 1H), 7.34 (dd, 1H), 5.58 (s, 2H), 2.80 (s, 2H), 2.64 (d, 2H), 1.60 (m, 2H), 1.39 (m, 2H), 0.90 (t, 3H). |
| 294 | δ 9.48 (d, 1H), 7.93 (d, 1H), 7.42 (s, 1H) 7.31 (dd, 1H), 5.58 (s, 2H), 2.80 (s, 3H), 2.62 (m, 2H), 1.62 (m, 2H), 1.00 (t, 3H). |
| 295 | δ 9.48(d, 1H), 7.94 (d, 1H), 7.41 (s, 1H), 7.32 (dd, 1H), 6.02 (m, 1H), 5.60 (s, 2H), 5.21 (d 1H), 5.03 (d, 1H), 3.40 (d, 2H), 2.80 (s, 3H). |
| 331 | δ (acetone-d$_6$) 9.47 (d, 1H), 9.21 (s, 1H), 8.60 (s, 1H), 8.42 (s, 1H), 8.38 (d, 1H), 7.73 (s, 1H), 7.60 (t, 1H), 5.63 (s, 2H), 2.91 (s, 3H). |
| 335 | δ (acetone-d$_6$) 9.46 (d, 1H), 7.99 (d, 1H), 7.82 (s, 1H), 7.37 (t, 1H), 7.23 (s, 2H), 5.56 (s, 2H) 2.73 (s, 3H). |
| 348 | δ (DMSO-d$_6$) 9.33 (d, 1H), 8.32 (d, 1H), 7.63 (d, 2H), 7.54 (s, 1H), 7.28 (t, 2H), 7.14 (t, 1H), 7.00 (s, 1H), 6.70 (s, 1H), 6.24 (s, 2H), 2.61 (s, 3H), 2.26 (s, 3H). |
| 349 | δ (DMSO-d$_6$) 9.32 (d, 1H), 8.30 (d, 1H), 7.71-7.65 (m, 2H), 7.60 (t, 2H), 7.30 (t, 2H), 7.16 (t, 1H), 6.86 (s, 1H), 6.28 (s, 2H), 2.61 (s, 3H), 2.02 (s, 3H). |
| 358 | δ 9.48 (d, 1H), 7.97 (d, 1H), 7.42 (s, 1H), 7.36 (dd, 1H), 5.60 (s, 2H), 3.57 (s, 2H), 2.80 (s, 3H), 1.97 (s, 1H). |
| 359 | δ (DMSO-d$_6$) 9.37 (d, 1H), 8.84 (s, 1H), 8.32-8.27 (m, 2H), 7.78 (s, 1H), 7.59 (t, 1H), 7.49 (d, 1H), 5.44 (s, 2H), 2.70 (s, 3H). |
| 361 | δ 9.47 (d, 1H), 7.96 (d, 1H), 7.42 (s, 1H), 7.35 (dd, 1H), 5.59 (s, 2H), 3.50 (q, 2H), 2.80 (s, 3H), 1.77 (t, 3H). |
| 383 | δ 9.46 (d, 1H), 7.92 (d, 1H), 7.40 (s, 1H), 7.31 (dd, 1H), 5.60 (m, 4H), 3.40 (d, 2H), 2.80 (s, 3H), 1.83 (d, 3H). |
| 488 | δ (methanol-d$_4$) 9.37 (d, 1H), 8.29 (d, 1H), 7.63 (s, 1H), 7.57-7.56 (m, 2H), 7.54-7.50 (m, 1H), 5.60 (s, 2H), 2.81 (s, 3H). |

$^a$$^1$H NMR data are in ppm downfield from tetramethylsilane. CDCl$_3$ solution unless indicated otherwise; "acetone-d$_6$" is CD$_3$C(=O)CD$_3$. Couplings are designated by (s)-singlet, (d)-doublet, (t)-triplet, (m)-multiplet, (dd)-doublet of doublets, (br s)-broad singlet.
$^b$$^1$H NMR spectra of compounds wherein R$^2$ is CH$_2$CF$_3$ often do not show peaks corresponding to the C$\underline{H}_2$CF$_3$ protons.

The following Tests demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. Compound numbers refer to compounds in Index Tables A-E.

BIOLOGICAL EXAMPLES OF THE INVENTION

Test A

For evaluating control of diamondback moth (*Plutella xylostella*) the test unit consisted of a small open container with a 12-14-day-old radish plant inside. This was pre-infested with ~50 neonate larvae that were dispensed into the test unit via corn cob grits using a bazooka inoculator. The larvae moved onto the test plant after being dispensed into the test unit.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc. Greeley, Colo., USA). The formulated compounds were applied in 1 mL of liquid through a SUJ2 atomizer nozzle with ⅛ JJ custom body (Spraying Systems Co., Wheaton, Ill., USA) positioned 1.27 cm (0.5 inches) above the top of each test unit. Test compounds were sprayed at 50 ppm and/or 10 ppm, and replicated three times. After spraying of the formulated test compound, each test unit was allowed to dry for 1 h and then a black, screened cap was placed on top. The test units were held for 6 days in a growth chamber at 25° C. and 70% relative humidity. Plant feeding damage was then visually assessed based on foliage consumed.

Of the compounds of Formula 1 tested at 50 ppm, the following provided very good to excellent levels of control efficacy (40% or less feeding damage and/or 100% mortality): 1, 18, 19, 20, 21, 23, 26, 28, 29, 30, 33, 36, 37, 39, 40, 41, 43, 47, 48, 49, 50, 51, 52, 53, 54, 56, 57, 58, 59, 60, 62, 63, 65, 66, 67, 70, 71, 72, 73, 74, 75, 77, 79, 80, 81, 82, 83, 84, 85, 86, 87, 88, 89, 90, 99, 101, 102, 103, 104, 105, 106, 107, 108, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 150, 151, 152, 153, 154, 155, 156, 157, 158, 159, 160, 161, 162, 163, 164, 165, 166, 167, 168, 169, 170, 172, 173, 174, 175, 176, 177, 178, 179, 180, 181, 182, 183, 184, 186, 187, 188, 189, 190, 191, 192, 193, 194, 195, 196, 198, 199, 200, 201, 202, 203, 204, 205, 206, 207, 208, 209, 210, 211, 212, 214, 215, 217, 218, 219, 220, 221, 222, 223, 225, 227, 228, 229, 230, 231, 232, 235, 236, 237, 238, 239, 240, 241, 242, 244, 245, 246, 248, 250, 251, 252, 253, 254, 255, 256, 257, 258, 259, 261, 262, 263, 264, 265, 266, 267, 268, 269, 270, 271, 272, 273, 274, 275, 276, 277, 278, 279, 280, 281, 282, 283, 285, 286, 287, 288, 289, 290, 291, 292, 293, 294, 295, 296, 297, 298, 299, 300, 301, 302, 304, 305, 306, 307, 308, 309, 310, 311, 312, 314, 315, 316, 317, 318, 319 and 334.

Of the compounds of Formula 1 tested at 10 ppm, the following provided very good to excellent levels of control efficacy (40% or less feeding damage and/or 100% mortality): 1, 18, 20, 21, 23, 26, 29, 30, 33, 36, 37, 39, 40, 41, 47, 48, 49, 50, 51, 52, 53, 54, 56, 57, 58, 59, 60, 62, 63, 65, 66, 70, 71, 72, 73, 74, 79, 80, 81, 82, 83, 84, 85, 86, 89, 90, 99, 101, 102, 103, 104, 105, 106, 110, 111, 112, 113, 114, 115, 117, 118, 119, 120, 121, 122, 123, 124, 125, 126, 127, 128, 129, 130, 131, 132, 133, 134, 135, 136, 137, 138, 139, 140, 150, 151, 152, 154, 156, 157, 158, 159, 160, 161, 162, 163, 164, 165, 166, 167, 168, 169, 170, 171, 173, 175, 176, 177, 178, 179, 180, 181, 182, 183, 184, 185, 186, 187, 188, 189, 190, 191, 193, 194, 195, 196, 198, 199, 200, 201, 203, 205, 206, 207, 208, 209, 210, 211, 212, 214, 215, 216, 217, 218, 219, 220, 221, 223, 225, 227, 228, 229, 230, 231, 235, 236, 237, 238, 239, 240, 241, 242, 244, 245, 246, 248, 250, 251, 252, 253, 254, 255, 256, 257, 259, 261, 262, 263, 265, 266, 267, 269, 270, 271, 272, 273, 274, 276, 277, 278, 280, 281, 285, 286, 287, 288, 289, 290, 291, 292, 294, 295, 296, 297, 298, 299, 300, 301, 302, 304, 305, 306, 307, 308, 309, 310, 311, 312, 314, 315, 316, 317, 318, 319, 321, 322, 323, 324, 325, 326, 327, 328, 329, 330, 331, 332, 334, 335, 336, 337, 338, 339, 340, 341, 342, 343, 344, 345, 346, 347, 351, 352, 353, 354, 355, 356, 357, 359, 360, 363, 364, 365, 366, 367, 368, 369, 373, 374, 375, 376, 377, 378, 379, 380, 381, 382, 383, 384, 385, 386, 387, 388, 395, 397, 398, 399, 400, 401, 402, 403, 404, 405, 407, 408, 409, 411, 412, 414, 415, 416, 419, 421, 422, 423, 424, 425, 426, 427, 429, 431, 432, 433, 434, 435, 437, 438, 439, 440, 441, 442, 443, 445, 448, 449, 450, 451, 452, 453, 454, 455, 457, 459, 462, 464, 465, 466, 467, 468, 469, 470, 474, 475, 476, 477, 478, 479, 481, 482, 483, 484, 485, 486, 487, 488, 489, 490, 491, 492, 493, 495, 496, 497, 498, 499, 500 and 501.

Test B

For evaluating control of fall armyworm (*Spodoptera frugiperda*) the test unit consisted of a small open container with a 4-5-day-old maize (corn) plant inside. This was pre-infested (using a core sampler) with 10-15 1-day-old larvae on a piece of insect diet.

Test compounds were formulated and sprayed at 50 ppm and/or 10 ppm as described for Test A. The applications were replicated three times. After spraying, the test units were maintained in a growth chamber at 25° C. and 70% relative humidity and then visually rated as described for Test A.

Of the compounds of Formula 1 tested at 50 ppm, the following provided very good to excellent levels of control efficacy (40% or less feeding damage and/or 100% mortality): 1, 18, 19, 20, 21, 23, 26, 29, 30, 33, 36, 37, 40, 47, 49, 50, 51, 52, 53, 54, 56, 57, 58, 59, 60, 62, 63, 65, 66, 71, 74, 79, 80, 81, 82, 83, 84, 85, 86, 87, 89, 90, 101, 102, 103, 104, 105, 106, 110, 111, 112, 113, 115, 117, 118, 119, 120, 121, 122, 123, 124, 125, 126, 127, 128, 129, 130, 131, 132, 133, 134, 135, 136, 137, 138, 139, 140, 150, 151, 152, 154, 157, 158, 159, 160, 161, 162, 163, 164, 165, 166, 167, 168, 170, 171, 172, 173, 174, 175, 176, 177, 178, 179, 180, 181, 182, 183, 184, 187, 188, 189, 190, 191, 192, 193, 194, 195, 196, 198, 199, 200, 201, 202, 203, 205, 207, 208, 209, 210, 211, 214, 215, 219, 220, 221, 223, 227, 228, 229, 230, 231, 232, 235, 236, 238, 239, 240, 241, 244, 245, 246, 248, 250, 251, 252, 253, 254, 255, 256, 257, 259, 261, 262, 263, 264, 265, 266, 267, 269, 270, 271, 272, 273, 274, 276, 277, 278, 279, 281, 285, 286, 288, 289, 290, 291, 292, 294, 296, 297, 299, 300, 301, 304, 305, 306, 307, 308, 309, 310, 311, 313, 314, 315, 316, 317, 318, 319 and 334.

Of the compounds of Formula 1 tested at 10 ppm, the following provided very good to excellent levels of control efficacy (40% or less feeding damage and/or 100% mortality): 1, 18, 20, 23, 26, 29, 30, 33, 36, 40, 47, 49, 50, 51, 52, 53, 57, 58, 59, 60, 62, 63, 65, 66, 71, 79, 80, 81, 82, 83, 84, 85, 86, 89, 90, 101, 102, 103, 105, 113, 115, 118, 120, 121, 122, 123, 125, 126, 127, 128, 131, 132, 133, 134, 135, 136, 137, 138, 139, 140, 150, 151, 152, 154, 157, 158, 159, 160, 161, 162, 163, 165, 167, 168, 170, 173, 174, 175, 176, 177, 178, 180, 183, 184, 187, 189, 190, 191, 193, 194, 195, 196, 198, 199, 200, 202, 203, 207, 208, 209, 210, 211, 214, 215, 219, 220, 227, 228, 229, 230, 231, 232, 235, 238, 239, 240, 241, 244, 245, 246, 248, 250, 251, 252, 253, 254, 255, 256, 257, 261, 262, 263, 264, 265, 266, 269, 270, 271, 272, 276, 277, 278, 285, 286, 288, 289, 290, 291, 296, 297, 299, 300, 301, 305, 307, 308, 309, 313, 314, 315, 316, 317, 321, 322, 323, 325, 326, 327, 329, 330, 332, 334, 335, 336, 337, 338, 341, 343, 344, 345, 346, 347, 351, 352, 353, 354, 355, 359, 363, 364, 365, 366, 367, 368, 369, 374, 375, 376, 377, 378, 380, 381, 382, 384, 385, 386, 387, 388, 391, 395, 398, 399, 401, 402, 403, 404, 405, 407, 408, 409, 410, 411, 412, 413, 414, 415, 421, 422, 424, 425, 426, 427, 429, 431, 432, 433, 434, 435, 437, 438, 439, 440, 441, 442, 443, 448, 449, 450, 451, 453, 454, 455, 457, 458, 462, 464, 465, 466, 467, 468, 479, 480, 481, 482, 483, 484, 485, 486, 487, 489, 490, 491, 492, 493, 495, 496, 497, 498, 499, 500 and 501.

Test C

For evaluating control of green peach aphid (*Myzus persicae*) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The aphids moved onto the test plant as the leaf piece desiccated. After pre-infestation, the soil of the test unit was covered with a layer of sand.

Test compounds were formulated and sprayed at 50 ppm and/or 10 ppm as described for Test A. The applications were replicated three times. After spraying of the formulated test compound, each test unit was allowed to dry for 1 h and then a black, screened cap was placed on top. The test units were held for 6 days in a growth chamber at 19-21° C. and 50-70% relative humidity. Each test unit was then visually assessed for insect mortality.

Of the compounds of Formula 1 tested at 50 ppm, the following resulted in at least 80% mortality: 29, 30, 32, 36, 40, 45, 47, 48, 50, 53, 56, 59, 60, 62, 71, 73, 74, 79, 80, 81, 82, 83, 85, 89, 102, 103, 104, 105, 111, 112, 113, 114, 115, 117, 118, 119, 120, 121, 122, 123, 125, 131, 132, 133, 135, 156, 159, 160, 167, 168, 173, 180, 182, 183, 191, 196, 199, 203, 205, 209, 211, 227, 228, 238, 239, 240, 241, 245, 257, 261, 265, 266, 270, 272, 275, 278, 280, 282, 285, 288, 289, 291, 294, 295, 296, 299, 304, 308, 311, 312, 324, 330, 331, 333, 337, 340, 343, 357, 358, 359, 360, 361, 364, 367, 368, 369, 372, 373, 374, 376, 378, 382, 383, 393, 395, 399, 403, 404, 405, 409, 411, 412, 414, 419, 421, 424, 425, 432, 435, 438, 439, 441, 443, 453, 457, 478, 495, 498 and 499.

Of the compounds of Formula 1 tested at 10 ppm, the following resulted in at least 80% mortality: 29, 30, 36, 47, 50, 53, 59, 62, 74, 79, 80, 81, 83, 113, 115, 118, 120, 121, 122, 123, 125, 132, 133, 135, 159, 160, 168, 180, 182, 183, 227, 240, 241, 257, 266, 285, 288, 289, 294, 295, 296, 299, 304, 311, 331, 333, 359, 374, 382, 395, 405, 424, 438, 439, 453, 495 and 498.

Test D

For evaluating control of cotton melon aphid (*Aphis gossypii*) through contact and/or systemic means, the test unit consisted of a small open container with a 6-7-day-old cotton plant inside. This was pre-infested with 30-40 insects on a piece of leaf according to the cut-leaf method described for Test C, and the soil of the test unit was covered with a layer of sand.

Test compounds were formulated and sprayed at 50 ppm and/or 10 ppm as described for Test C. The applications were replicated three times. After spraying, the test units were maintained in a growth chamber and then visually rated as described for Test C.

Of the compounds of Formula 1 tested at 50 ppm, the following resulted in at least 80% mortality: 30, 36, 40, 48, 50, 53, 60, 62, 73, 74, 79, 80, 81, 82, 83, 102, 111, 115, 118, 121, 122, 123, 124, 125, 126, 129, 131, 133, 135, 159, 168, 180, 182, 183, 196, 199, 227, 235, 240, 257, 266, 275, 296, 304, 331, 333, 339, 340, 351, 373, 395, 405, 424, 425, 439, 441, 478, 495 and 498.

Of the compounds of Formula 1 tested at 10 ppm, the following resulted in at least 80% mortality: 53, 60, 62, 79, 83, 121, 122, 123, 168, 180, 182, 227, 240, 266, 296, 340, 373, 424, 495 and 498.

Test E

For evaluating control of corn planthopper (*Peregrinus maidis*) through contact and/or systemic means, the test unit consisted of a small open container with a 3-4-day-old maize plant (spike) inside. White sand was added to the top of the soil prior to application. Test compounds were formulated and sprayed at 50 ppm and/or 10 ppm, and replicated three times as described for Test A. After spraying, the test units were allowed to dry for 1 h before they were post-infested with ~15-20 nymphs (18 to 21 day old) by sprinkling them onto the sand with a salt shaker. A black, screened cap was placed on the top of each test unit, and the test units were held for 6 days in a growth chamber at 22-24° C. and 50-70% relative humidity. Each test unit was then visually assessed for insect mortality.

Of the compounds of Formula 1 tested at 50 ppm the following provided very good to excellent levels of control efficacy (80% or more mortality): 1, 21, 26, 29, 30, 36, 40, 44, 47, 48, 49, 50, 51, 52, 53, 56, 57, 59, 60, 62, 63, 65, 70, 71, 73, 74, 77, 79, 80, 81, 82, 83, 84, 85, 101, 102, 103, 105, 111, 112, 113, 114, 115, 116, 117, 118, 119, 120, 121, 122, 123, 124, 125, 126, 127, 128, 129, 130, 131, 132, 133, 134, 135, 152, 157, 158, 159, 160, 165, 167, 168, 170, 173, 180, 181, 182, 183, 189, 191, 196, 199, 203, 205, 206, 209, 212, 227, 228, 231, 235, 240, 242, 246, 254, 257, 261, 262, 272, 275, 277, 282, 288, 289, 291, 294, 295, 296, 297, 298, 299, 300, 304, 309, 311, 312, 322, 324, 330, 331, 333, 337, 339, 340, 342, 343, 344, 347, 349, 352, 355, 358, 359, 360, 361, 363, 364, 365, 368, 369, 372, 373, 374, 377, 378, 379, 382, 384, 387, 393, 394, 395, 397, 399, 404, 405, 409, 414, 419, 421, 422, 424, 425, 432, 435, 439, 443, 450, 452, 453, 454, 455, 462, 464, 467, 475, 478, 482, 495, 496, 497, 498, 499 and 501.

Of the compounds of Formula 1 tested at 10 ppm the following provided very good to excellent levels of control efficacy (80% or more mortality): 26, 29, 30, 36, 37, 47, 48, 49, 50, 53, 56, 57, 59, 60, 62, 63, 74, 79, 80, 81, 82, 84, 102, 103, 105, 112, 113, 114, 115, 118, 119, 120, 121, 122, 123, 124, 125, 126, 127, 128, 129, 130, 132, 133, 135, 152, 157, 158, 159, 160, 165, 167, 168, 170, 173, 180, 182, 183, 189, 196, 227, 235, 240, 246, 257, 275, 282, 288, 289, 295, 296, 299, 300, 304, 309, 311, 324, 331, 333, 339, 340, 342, 358, 359, 364, 373, 374, 382, 393, 395, 397, 405, 419, 424, 452, 453, 455, 467, 478, 495, 496, 498 and 499.

Test F

For evaluating control of potato leafhopper (*Empoasca fabae*) through contact and/or systemic means, the test unit consisted of a small open container with a 5-6-day-old Soleil bean plant (primary leaves emerged) inside. White sand was added to the top of the soil and one of the primary leaves was excised prior to application.

Test compounds were formulated and sprayed at 50 ppm and/or 10 ppm, and the tests were replicated three times as described for Test A. After spraying, the test units were allowed to dry for 1 h before they were post-infested with 5 potato leafhoppers (18-21-day-old adults). A black, screened cap was placed on the top of each test unit, and the test units were held for 6 days in a growth chamber at 24° C. and 70% relative humidity. Each test unit was then visually assessed for insect mortality.

Of the compounds of Formula 1 tested at 50 ppm the following provided very good to excellent levels of control efficacy (80% or more mortality): 1, 20, 21, 23, 26, 29, 30, 36, 37, 40, 41, 42, 43, 44, 45, 47, 48, 49, 50, 51, 52, 53, 56, 57, 58, 59, 60, 62, 63, 65, 66, 71, 74, 75, 77, 79, 80, 81, 82, 83, 84, 85, 89, 104, 105, 106, 107, 110, 111, 112, 113, 114, 115, 116, 117, 118, 119, 120, 121, 122, 123, 124, 125, 126, 127, 128, 129, 130, 131, 132, 134, 135, 136, 139, 140, 150, 152, 153, 155, 156, 157, 158, 159, 160, 161, 164, 165, 166, 167, 168, 169, 170, 173, 179, 180, 181, 182, 183, 186, 188, 189, 191, 193, 196, 199, 204, 205, 206, 207, 209, 210, 211, 212, 214, 215, 218, 225, 226, 227, 228, 230, 231, 235, 236, 238, 239, 240, 242, 245, 246, 250, 251, 256, 257, 261, 262, 272, 275, 276, 277, 278, 280, 282, 285, 286, 288, 289, 291, 292, 294, 295, 296, 299, 300, 301, 302, 304, 305, 306, 308, 309, 310, 311, 312, 318, 321, 322, 323, 324, 325, 327, 328, 330, 333, 336, 337, 338, 340, 342, 343, 344, 352, 354, 355, 356, 357, 358, 359, 360, 361, 363, 364, 367, 368, 369, 372, 373, 374, 375, 376, 377, 378, 382, 384, 385, 387, 388, 403, 404, 405, 407, 412, 414, 419, 421, 424, 425, 427, 432, 435, 438, 439, 440, 441, 443, 450, 457, 464, 467, 478, 482, 495, 498 and 499.

Of the compounds of Formula 1 tested at 10 ppm the following provided very good to excellent levels of control efficacy (80% or more mortality): 26, 29, 30, 36, 37, 40, 47, 48, 49, 50, 51, 52, 53, 56, 57, 59, 60, 62, 63, 65, 66, 71, 75, 79, 80, 81, 82, 83, 84, 88, 89, 102, 104, 105, 106, 111, 113, 114, 115, 116, 118, 119, 120, 121, 122, 123, 124, 125, 126, 127, 129, 130, 131, 132, 135, 152, 157, 158, 159, 160, 161, 164, 165, 166, 168, 169, 170, 173, 180, 182, 183, 189, 191, 196, 205, 206, 210, 211, 212, 214, 218, 227, 228, 231, 236, 239, 240, 245, 246, 256, 257, 262, 272, 277, 282, 285, 286, 289, 291, 295, 299, 300, 302, 309, 310, 312, 322, 323, 324, 330, 333, 342, 343, 344, 352, 354, 357, 359, 360, 364, 367, 368, 374, 375, 382, 405, 424, 434, 438, 440, 443, 478, 498 and 499.

Test G

For evaluating control of Western Flower Thrips (*Frankliniella occidentalis*) through contact and/or systemic means, the test unit consisted of a small open container with a 5-7-day-old Soleil bean plant inside.

Test compounds were formulated and sprayed at 250, 50 and/or 10 ppm, and the tests were replicated three times as described for Test A. After spraying, the test units were allowed to dry for 1 hour, and then 22-27 adult *thrips* were added to the unit. A black, screened cap was placed on the top of each test unit, and the test units were held for 7 days at 25° C. and 45-55% relative humidity.

Of the compounds of Formula 1 tested at 250 ppm, the following provided very good to excellent levels of control efficacy (30% or less plant damage and/or 100% mortality): 50, 56, 89, 121, 139, 343, 344 and 346.

Of the compounds of Formula 1 tested at 50 ppm, the following provided very good to excellent levels of control efficacy (30% or less plant damage and/or 100% mortality): 191, 199, 230, 272, 285, 289, 300, 321, 322, 343, 344, 346, 352, 360, 364, 365, 368, 369, 377, 378, 407, 409, 411, 421, 432, 435, 438, 440 and 443.

Of the compounds of Formula 1 tested at 10 ppm, the following provided very good to excellent levels of control efficacy (30% or less plant damage and/or 100%/0 mortality): 272, 289, 343, 344, 346, 364 and 369.

What is claimed is:
1. A method for controlling an invertebrate pest comprising contacting the invertebrate pest or its environment with a biologically effective amount of a compound of Formula 1 or salt thereof,

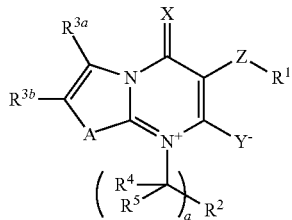

1 wherein
X is O or S;
Y is O or S;
A is $C(R^{3c})=C(R^{3d})$, provided that the $C(R^{3c})=C(R^{3d})$ moiety is oriented so the carbon atom bonded to $R^{3d}$ is connected directly to the pyrimidinium ring of Formula 1;
Z is a direct bond, O, $S(O)_n$, $NR^6$, $C(R^7)_2O$, $OC(R^7)_2$, $C(=X^1)$, $C(=X^1)E$, $EC(=X^1)$, $C(=NOR^8)$ or $C(=NN(R^6)_2)$;
$X^1$ is O, S or $NR^9$;
E is O, S or $NR^{9a}$;
$R^1$ is a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from $S(=O)_u(=NR^{24})_z$, each ring or ring system optionally substituted with up to 5 substituents independently selected from $R^{14}$;
$R^2$ is H, halogen, cyano, hydroxy, amino, nitro, OCN, SCN, CHO, C(=O)OH, C(=O)NH$_2$, C(=S)NH$_2$, SO$_2$NH$_2$, C(=O)R$^{18}$, C(=O)OR$^{18}$, NHR$^{18}$, NR$^{18}$R$^{19}$, C(=O)NR$^{21}$R$^{19}$, C(=S)NR$^{21}$R$^{19}$, SO$_2$NR$^{21}$R$^{19}$, OC(=O)R$^{21}$, OC(=O)OR$^{18}$, OC(=O)NR$^{21}$R$^{19}$, N(R$^{21}$)C(=O)R$^{21}$, N(R$^{21}$)C(=O)OR$^{19}$, N(R$^{21}$)C(=O)NR$^{21}$R$^{22}$, OSO$_2$R$^{18}$, OSO$_2$NR$^{21}$R$^{22}$, NR$^{21}$SO$_2$R$^{18}$, NR$^{21}$SO$_2$NR$^{21}$R$^{22}$ or Si(R$^{18}$R$^{19}$R$^{20}$); or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$ and Si(R$^{10}$)$_3$; or a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from $S(=O)_u(=NR^{24})_z$, each ring or ring system optionally substituted with up to 5 substituents independently selected from $R^{15}$;
$R^{3a}$, $R^{3b}$, $R^{3c}$ and $R^{3d}$ are independently H, halogen, cyano, hydroxy, amino, nitro, SF$_5$, OCN, SCN, CHO, C(=O)OH, C(=O)NH$_2$, C(=S)NH$_2$, SO$_2$NH$_2$, C(=O)R$^{18}$, C(=O)OR$^{18}$, NHR$^{18}$, NR$^{18}$R$^{19}$, C(=O)NR$^{21}$R$^{19}$, C(=S)NR$^{21}$R$^{19}$, SO$_2$NR$^{21}$R$^{19}$, OC(=O)R$^{21}$, OC(=O)OR$^{18}$, OC(=O)NR$^{21}$R$^{19}$, N(R$^{21}$)C(=O)R$^{21}$, N(R$^{21}$)C(=O)OR$^{19}$, N(R$^{21}$)C(=O)NR$^{21}$R$^{22}$, OSO$_2$R$^{18}$, OSO$_2$NR$^{21}$R$^{22}$, NR$^{21}$SO$_2$R$^{18}$, NR$^{21}$SO$_2$NR$^{21}$R$^{22}$, Si(R$^{18}$R$^{19}$R$^{20}$) or $Z^1Q^t$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from $R^{17}$; or $R^{3a}$ and $R^{3b}$, or $R^{3b}$ and $R^{3c}$, or $R^{3c}$ and $R^{3d}$ are taken together with the adjacent carbon atoms to which they are attached to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from $S(=O)_n$, each ring optionally substituted with up to 3 substituents independently selected from the group consisting of halogen, cyano, hydroxy, amino, nitro, C(=O)OH, C(=O)NH$_2$, SO$_2$NH$_2$, C$_1$-C$_4$ alkyl, C$_1$-C$_4$ haloalkyl, C$_2$-C$_4$ alkenyl, C$_2$-C$_4$ haloalkenyl, C$_2$-C$_4$ alkynyl, C$_2$-C$_4$ haloalkynyl, C$_3$-C$_7$ cycloalkyl, C$_3$-C$_7$ halocycloalkyl, C$_4$-C$_8$ alkylcycloalkyl, C$_4$-C$_8$ haloalkylcycloalkyl, C$_4$-C$_8$ cycloalkylalkyl, C$_4$-C$_8$ halocycloalkylalkyl, C$_1$-C$_6$ alkoxy, C$_1$-C$_6$ haloalkoxy, C$_2$-C$_6$ alkoxycarbonyl, C$_2$-C$_6$ haloalkoxycarbonyl, C$_2$-C$_6$ alkylcarbonyl and C$_2$-C$_6$ haloalkylcarbonyl;

each R$^4$ and R$^5$ is independently H, halogen, cyano, hydroxy, amino, nitro, OCN, SCN, CHO, C(=O)OH, C(=O)NH$_2$, C(=S)NH$_2$ or SO$_2$NH$_2$; or C$_1$-C$_6$ alkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{12}$ cycloalkylcycloalkyl, C$_5$-C$_8$ alkylcycloalkylalkyl, C$_3$-C$_6$ cycloalkenyl, C$_1$-C$_6$ alkoxy, C$_3$-C$_6$ cycloalkoxy, C$_4$-C$_8$ cycloalkylalkoxy, C$_2$-C$_6$ alkenyloxy or C$_2$-C$_6$ alkynyloxy, each unsubstituted or substituted with at least one substituent independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$ and Si(R$^{10}$)$_3$; or R$^4$ and R$^5$ are taken together with the carbon atom to which they are attached to form a 3- to 7-membered ring containing ring members selected from carbon atoms and up to 2 heteroatoms independently selected from one O, one S, and up to 2 N, wherein up to 2 carbon atom ring members are independently selected from C(=O) and C(=S) and the sulfur atom ring member is selected from S, S(O) or S(O)$_2$, said ring optionally substituted with up to 4 substituents independently selected from the group consisting of halogen, cyano and C$_1$-C$_4$ alkyl;

each R$^6$ is independently H; or C$_1$-C$_6$ alkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl, C$_3$-C$_6$ cycloalkenyl, C$_2$-C$_6$ alkylcarbonyl or C$_2$-C$_6$ alkoxycarbonyl, each unsubstituted or substituted with at least one substituent independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$ and Si(R$^{10}$)$_3$; or two R$^6$ substituents are taken together with the nitrogen atom to which they are attached to form a 3- to 7-membered ring containing ring members selected from carbon atoms and up to 2 heteroatoms independently selected from one O, one S, and up to 2 N, wherein up to 2 carbon atom ring members are independently selected from C(=O) and C(=S) and the sulfur atom ring member is selected from S, S(O) or S(O)$_2$, said ring optionally substituted with up to 4 substituents independently selected from the group consisting of halogen, cyano and C$_1$-C$_4$ alkyl;

each R$^7$ and R$^8$ is independently H; or C$_1$-C$_6$ alkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl, C$_3$-C$_6$ cycloalkenyl, C$_2$-C$_6$ alkylcarbonyl or C$_2$-C$_6$ alkoxycarbonyl, each unsubstituted or substituted with at least one substituent independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$ and Si(R$^{10}$)$_3$;

each R$^9$ is independently C$_1$-C$_6$ alkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl, C$_3$-C$_6$ cycloalkenyl, C$_2$-C$_6$ alkylcarbonyl or C$_2$-C$_6$ alkoxycarbonyl, each unsubstituted or substituted with at least one substituent independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$ and Si(R$^{10}$)$_3$;

each R$^{9a}$ is independently H; or C$_1$-C$_6$ alkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl, C$_3$-C$_6$ cycloalkenyl, C$_2$-C$_6$ alkylcarbonyl or C$_2$-C$_6$ alkoxycarbonyl, each unsubstituted or substituted with at least one substituent independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$ and Si(R$^{10}$)$_3$;

each R$^{10}$ and R$^{11}$ is independently C$_1$-C$_6$ alkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl or C$_3$-C$_6$ cycloalkenyl, each unsubstituted or substituted with at least one substituent independently selected from the group consisting of halogen, cyano, nitro, CHO, C(=O)OH, C(=O)NH$_2$, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl and C$_3$-C$_6$ trialkylsilyl; or phenyl or a 5- or 6-membered heteroaromatic ring, each unsubstituted or substituted with at least one substituent independently selected from the group consisting of C$_1$-C$_6$ alkyl, C$_1$-C$_6$ haloalkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl, C$_3$-C$_6$ cycloalkenyl, halogen, cyano, nitro, CHO, C(=O)OH, C(=O)NH$_2$, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl and C$_3$-C$_6$ trialkylsilyl;

each R$^{12}$ and R$^{13}$ is independently C$_1$-C$_6$ alkyl, C$_2$-C$_6$ alkenyl, C$_2$-C$_6$ alkynyl, C$_3$-C$_8$ cycloalkyl, C$_4$-C$_8$ alkylcycloalkyl, C$_4$-C$_8$ cycloalkylalkyl, C$_6$-C$_{10}$ cycloalkylcycloalkyl, C$_5$-C$_{10}$ alkylcycloalkylalkyl or C$_3$-C$_6$ cycloalkenyl, each unsubstituted or substituted with at least one substituent independently selected from the group consisting of halogen, cyano, nitro, CHO, C(=O)OH, C(=O)NH$_2$, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl and $C_3$-$C_6$ trialkylsilyl; or phenyl or a 5- or 6-membered heteroaromatic ring, each unsubstituted or substituted with at least one substituent independently selected from the group consisting of $C_1$-$C_6$ alkyl, $C_1$-$C_6$ haloalkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, halogen, cyano, nitro, CHO, C(=O)OH, C(=O)NH$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl; or $R^{12}$ and $R^{13}$ are taken together with the nitrogen atom to which they are attached to form a 3- to 7-membered ring containing ring members selected from carbon atoms and up to 2 heteroatoms independently selected from one O, one S, and up to 2 N, wherein up to 2 carbon atom ring members are independently selected from C(=O) and C(=S) and the sulfur atom ring member is selected from S, S(O) or S(O)$_2$, said ring optionally substituted with up to 4 substituents independently selected from the group consisting of halogen, cyano and $C_1$-$C_4$ alkyl;

each $R^{14}$ is independently halogen, cyano, hydroxy, amino, nitro, SF$_5$, OCN, SCN, CHO, C(=O)OH, C(=O)NH$_2$, C(=S)NH$_2$, SO$_2$NH$_2$, C(=O)R$^{18}$, C(=O)OR$^{18}$, NHR$^{18}$, NR$^{18}$R$^{19}$, C(=O)NR$^{21}$R$^{19}$, C(=O)NR$^{21}$NR$^{22}$R$^{23}$, C(=S)NR$^{21}$R$^{19}$, SO$_2$NR$^{21}$R$^{19}$, OC(=O)R$^{21}$, OC(=O)OR$^{18}$, OC(=O)NR$^{21}$R$^{19}$, N(R$^{21}$)C(=O)R$^{21}$, N(R$^{21}$)C(=O)OR$^{19}$, N(R$^{21}$)C(=O)NR$^{21}$R$^{22}$, OSO$_2$R$^{18}$, OSO$_2$NR$^{21}$R$^{22}$, NR$^{21}$SO$_2$R$^{18}$, NR$^{21}$SO$_2$NR$^{21}$R$^{22}$, Si(R$^{18}$R$^{19}$R$^{20}$), C(=NR$^{21}$)R$^{22}$, C(=NOR$^{21}$)R$^{22}$, C(=NNR$^{21}$R$^{22}$)R$^{23}$, C(=NN(C(=O)R$^{19}$)R$^{21}$)R$^{22}$, C(=NN(C(=O)OR$^{19}$)R$^{21}$)R$^{22}$, ON=CR$^{21}$R$^{22}$, ONR$^{21}$R$^{22}$, S(=O)(=NR$^{21}$)R$^{22}$, SO$_2$NR$^{21}$C(=O)NR$^{22}$R$^{23}$, P(=X$^2$)R$^{18}$R$^{19}$, OP(=X$^2$)R$^{18}$R$^{19}$, OP(=X$^2$)(OR$^{18}$)R$^{19}$, OP(=X$^2$)(OR$^{18}$)OR$^{19}$, N=CR$^{21}$R$^{22}$, NR$^{21}$N=CR$^{21}$R$^{22}$, NR$^{21}$NR$^{22}$R$^{23}$, NR$^{21}$C(=X$^2$)NR$^{22}$R$^{23}$, NR$^{21}$C(=NR$^{21}$)NR$^{22}$R$^{23}$, NR$^{21}$NR$^{21}$C(=X$^2$)NR$^{22}$R$^{23}$, NR$^{21}$NR$^{21}$SO$_2$NR$^{22}$R$^{23}$, $Z^1Q^t$ or $Z^1Q^tZ^1Q^t$; or $C_1$-$C_8$ alkyl, $C_2$-$C_8$ alkynyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from R$^{17}$; or two R$^{14}$ substituents on adjacent ring atoms are taken together with the adjacent ring atoms to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from S(=O)$_n$, each ring optionally substituted with up to 3 substituents independently selected from the group consisting of halogen, cyano, hydroxy, amino, nitro, C(=O)OH, C(=O)NH$_2$, SO$_2$NH$_2$, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_6$ alkoxy, $C_1$-$C_6$ haloalkoxy, $C_2$-$C_6$ alkoxycarbonyl, $C_2$-$C_6$ haloalkoxycarbonyl, $C_2$-$C_6$ alkylcarbonyl and $C_2$-$C_6$ haloalkylcarbonyl;

each $X^2$ is independently O or S;

each $Z^1$ is independently a direct bond, O, S(O)$_n$, NR$^6$, C(R$^7$)$_2$, C(R$^7$)=C(R$^7$), C≡C, C(R$^7$)$_2$O, OC(R$^7$)$_2$, C(=X$^1$), C(=X$^1$)E, EC(=X$^1$), C(=NOR$^8$) or C(=NN(R$^6$)$_2$);

each $Q^i$ is independently a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from S(=O)$_u$(=NR$^{24}$)$_z$, each ring or ring system optionally substituted with up to 4 substituents independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, OR$^{11}$, S(O)$_n$R$^{10}$, SO$_2$NR$^{12}$R$^{13}$, Si(R$^{10}$)$_3$ and R$^{16}$;

each $Q^r$ is independently a 3- to 10-membered ring or a 7- to 11-membered ring system, each ring or ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and the sulfur atom ring members are independently selected from S(=O)$_u$(=NR$^{24}$)$_z$, each ring or ring system optionally substituted with up to 5 substituents independently selected from the group consisting of halogen, cyano, nitro, CHO, C(=O)OH, C(=O)NH$_2$, C(=O)R$^{10}$, C(=O)OR$^{11}$, C(=O)NR$^{12}$R$^{13}$, C(=O)NR$^{21}$NR$^{22}$R$^{23}$, OR$^{11}$, S(O)$_n$R$^{10}$, SO$_2$NR$^{12}$R$^{13}$, S(=O)(=NR$^{21}$)R$^{22}$, Si(R$^{10}$)$_3$ and R$^{16}$;

each $R^{15}$ is independently halogen, cyano, hydroxy, amino, nitro, SF$_5$, OCN, SCN, CHO, C(=O)OH, C(=O)NH$_2$, C(=S)NH$_2$, SO$_2$NH$_2$, C(=O)R$^{18}$, C(=O)OR$^{18}$, NHR$^{18}$, NR$^{18}$R$^{19}$, C(=O)NR$^{21}$R$^{19}$, C(=O)NR$^{21}$NR$^{22}$R$^{23}$, C(=S)NR$^{21}$R$^{19}$, SO$_2$NR$^{21}$R$^{19}$, S(=O)(=NR$^{21}$)R$^{22}$, OC(=O)R$^{21}$, OC(=O)OR$^{18}$, OC(=O)NR$^{21}$R$^{19}$, N(R$^{21}$)C(=O)R$^{21}$, N(R$^{21}$)C(=O)OR$^{19}$, N(R$^{21}$)C(=O)NR$^{21}$R$^{22}$, OSO$_2$R$^{18}$, OSO$_2$NR$^{21}$R$^{22}$, NR$^{21}$SO$_2$R$^{18}$, NR$^{21}$SO$_2$NR$^{21}$R$^{22}$, Si(R$^{18}$R$^{19}$R$^{20}$) or $Z^1Q^r$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from $R^{17}$; or two $R^{15}$ substituents on adjacent ring atoms are taken together with the adjacent ring atoms to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(=O) and C(=S) and the sulfur atom ring members are independently selected from $S(=O)_n$, each ring optionally substituted with up to 3 substituents independently selected from the group consisting of halogen, cyano, hydroxy, amino, nitro, C(=O)OH, C(=O)$NH_2$, $SO_2NH_2$, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_6$ alkoxy, $C_1$-$C_6$ haloalkoxy, $C_2$-$C_6$ alkoxycarbonyl, $C_2$-$C_6$ haloalkoxycarbonyl, $C_2$-$C_6$ alkylcarbonyl and $C_2$-$C_6$ haloalkylcarbonyl;

each $R^{16}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from the group consisting of halogen, cyano, nitro, CHO, C(=O)OH, C(=O)$NH_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl; or phenyl or a 5- or 6-membered heteroaromatic ring, each unsubstituted or substituted with at least one substituent independently selected from the group consisting of $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl, $C_3$-$C_6$ cycloalkenyl, halogen, cyano, nitro, CHO, C(=O)OH, C(=O)$NH_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl and $C_3$-$C_6$ trialkylsilyl;

each $R^{17}$ is independently halogen, cyano, nitro, OH, CHO, C(=O)OH, C(=O)$NH_2$, C(=O)$R^{10}$, C(=O)$OR^{11}$, C(=O)$NR^{12}R^{13}$, $OR^{11}$, $S(O)_nR^{10}$, $SO_2NR^{12}R^{13}$, $Si(R^{10})_3$ or $Z^1Q^r$;

each $R^{18}$, $R^{19}$ and $R^{20}$ is independently $Q^r$; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{17}$;

each $R^{21}$ is independently $Q^r$ or H; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{17}$;

each $R^{22}$ and $R^{23}$ is independently $Q^r$ or H; or $C_1$-$C_6$ alkyl, $C_2$-$C_6$ alkenyl, $C_2$-$C_6$ alkynyl, $C_3$-$C_8$ cycloalkyl, $C_4$-$C_8$ alkylcycloalkyl, $C_4$-$C_8$ cycloalkylalkyl, $C_6$-$C_{10}$ cycloalkylcycloalkyl, $C_5$-$C_{10}$ alkylcycloalkylalkyl or $C_3$-$C_6$ cycloalkenyl, each unsubstituted or substituted with at least one substituent independently selected from $R^{17}$; or $R^{22}$ and $R^{23}$ are taken together with the nitrogen atom to which they are attached to form a 3- to 7-membered ring containing ring members selected from carbon atoms and up to 2 heteroatoms independently selected from one O, one S, and up to 2 N, wherein up to 2 carbon atom ring members are independently selected from C(=O) and C(=S) and the sulfur atom ring member is selected from S, S(O) or $S(O)_2$, said ring optionally substituted with up to 4 substituents independently selected from the group consisting of halogen, cyano and $C_1$-$C_4$ alkyl;

each $R^{24}$ is independently H, cyano, OCN, SCN, CHO, C(=O)OH, C(=O)$NH_2$, C(=S)$NH_2$, $SO_2NH_2$, C(=O)$R^{18}$, C(=O)$OR^{18}$, $NHR^{18}$, $NR^{18}R^{19}$, C(=O)$NR^{21}R^{19}$, C(=S)$NR^{21}R^{19}$, $SO_2NR^{21}R^{19}$, OC(=O)$R^{21}$, OC(=O)$OR^{18}$, OC(=O)$NR^{21}R^{19}$, $N(R^{21})$C(=O)$R^{21}$, $N(R^{21})$C(=O)$OR^{19}$, $N(R^{21})$C(=O)$NR^{21}R^{22}$, $OSO_2R^{18}$, $OSO_2NR^{21}R^{22}$, $NR^{21}SO_2R^{18}$, $NR^{21}SO_2NR^{21}R^{22}$, $Si(R^{18}R^{19}R^{20})$ or $Z^1Q^r$; or $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_3$-$C_8$ cycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl, each unsubstituted or substituted with at least one substituent independently selected from $R^{17}$;

a is 1, 2 or 3;

each n is independently 0, 1 or 2; and u and z in each instance of $S(=O)_u(=NR^{24})_z$ are independently 0, 1 or 2, provided that the sum of u and z in each instance of $S(=O)_u(=NR^{24})_z$ is 0, 1 or 2;

provided that when $R^{3c}$ is H or F, and $R^{3d}$ is H, F, $CF_2H$ or $CF_3$, then at least one of $R^{3a}$ or $R^{3b}$ is other than H.

2. The method of claim 1 wherein the compound of Formula 1 is selected from the group consisting of:
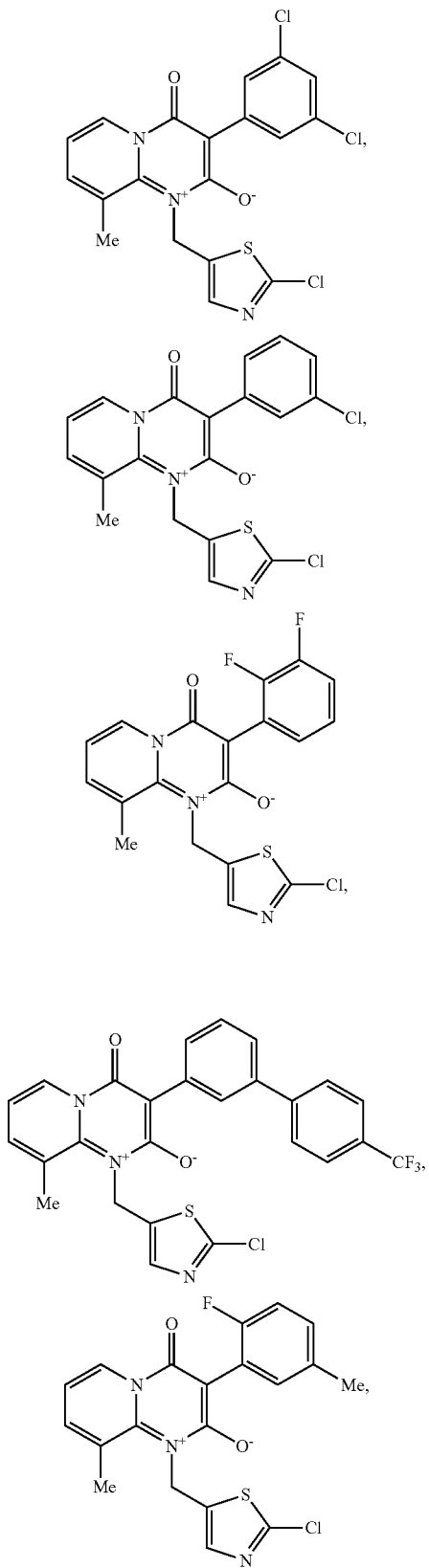
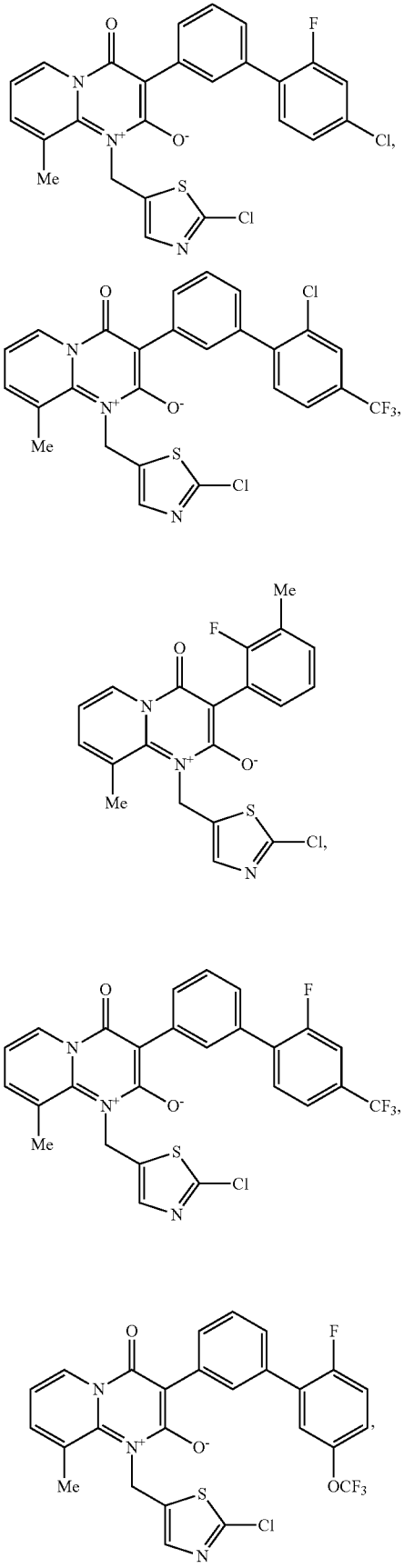

305
-continued
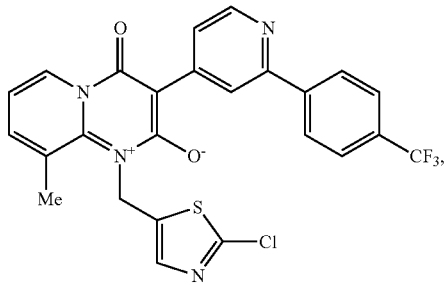
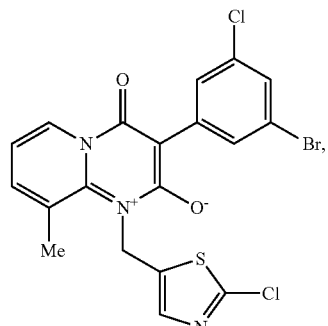
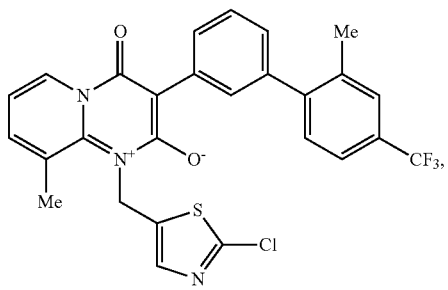
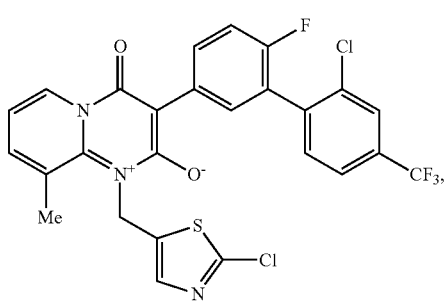
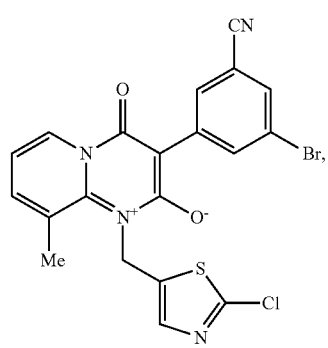
306
-continued
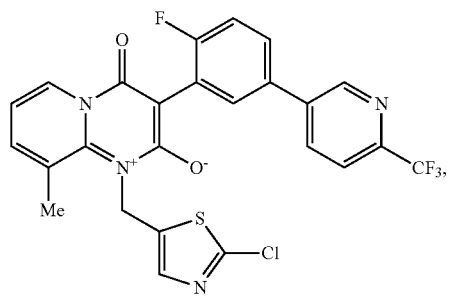
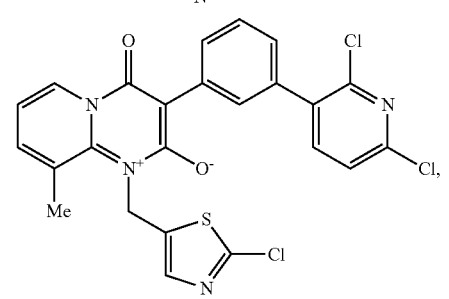
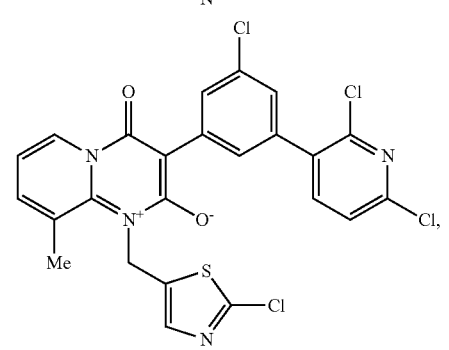
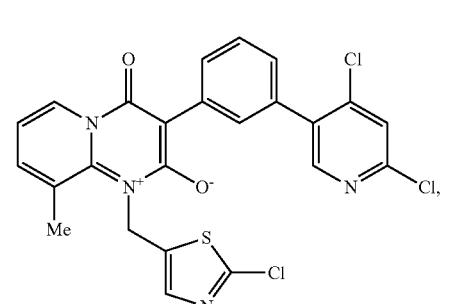
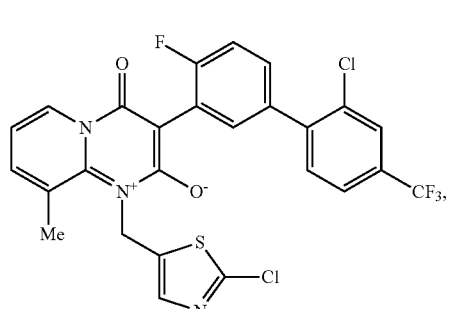

307
-continued
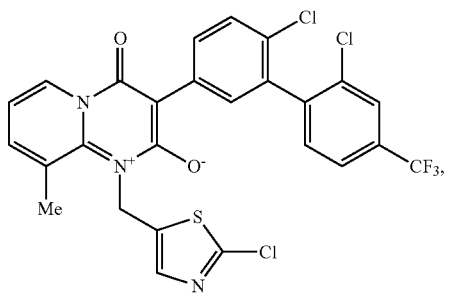
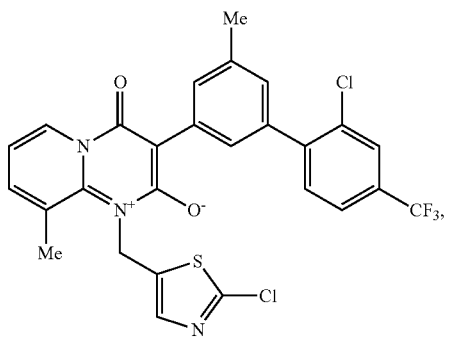
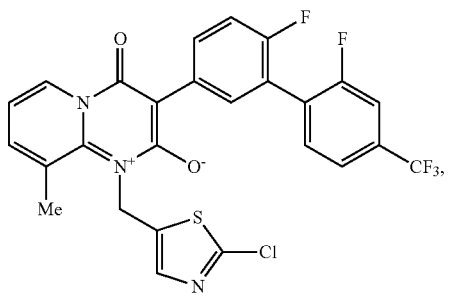
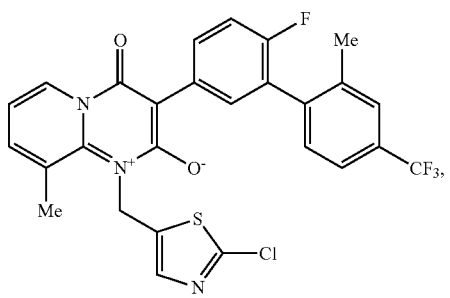
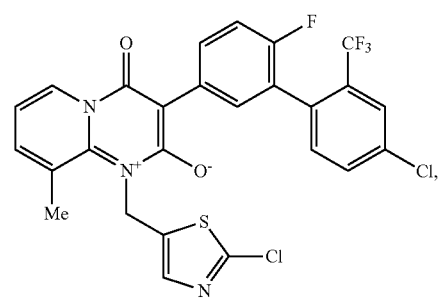
308
-continued
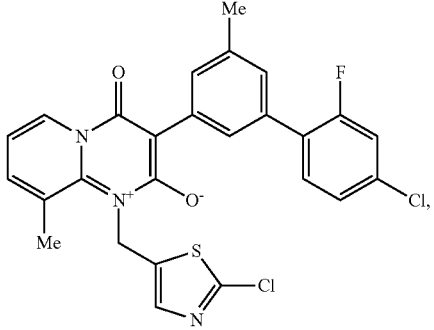
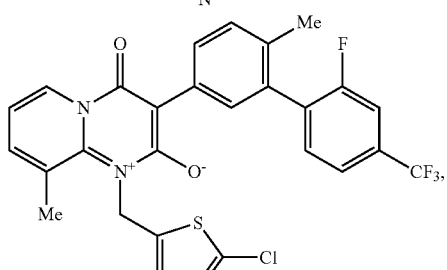
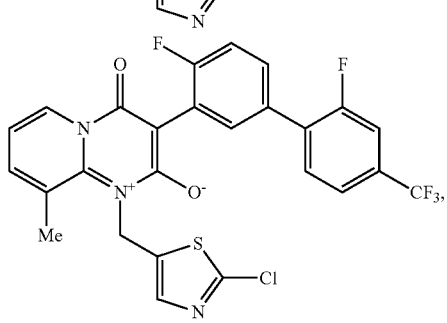
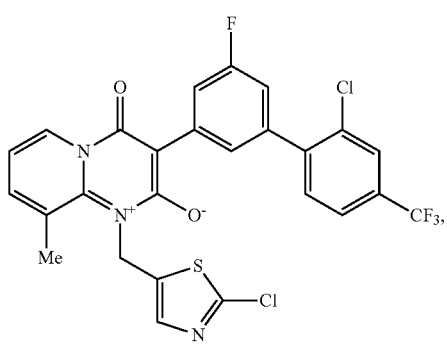
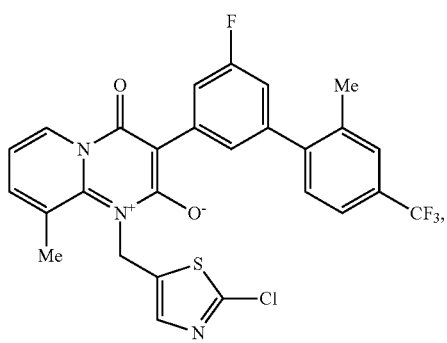

309
-continued
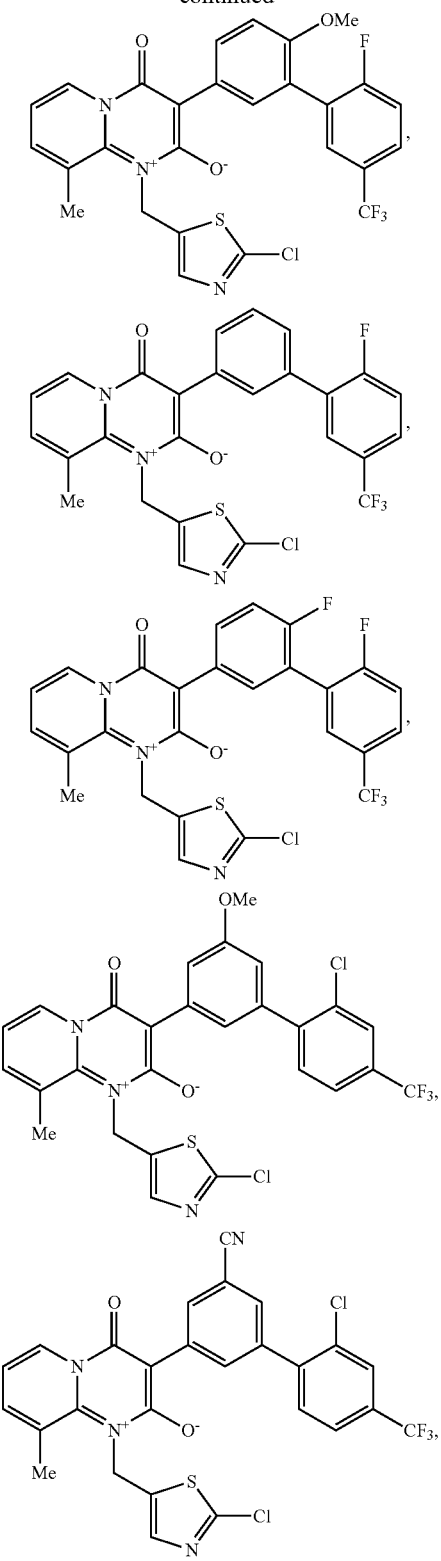
310
-continued
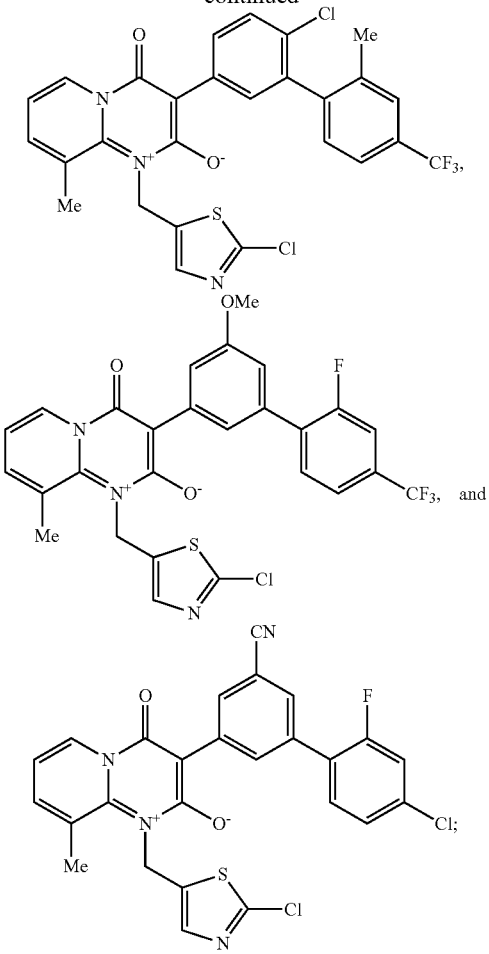
and at least one additional component selected from the group consisting of surfactants, solid diluents and liquid diluents.
3. The method of claim 2 wherein the compound of Formula 1 is
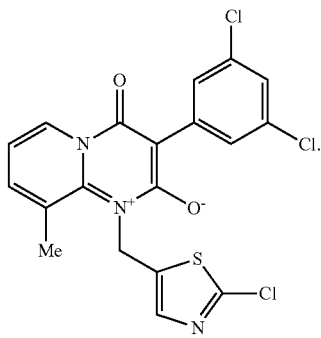 [SMILES: Cc1cccn2c(=O)c(-c3cc(Cl)cc(Cl)c3)c([O-])[n+](Cc3cnc(Cl)s3)c12]
* * * * *